(12) United States Patent
Challita-Eid et al.

(10) Patent No.: US 7,700,749 B2
(45) Date of Patent: Apr. 20, 2010

(54) NUCLEIC ACID AND CORRESPONDING PROTEIN ENTITLED 205P1B5 USEFUL IN TREATMENT AND DETECTION OF CANCER

(75) Inventors: Pia M. Challita-Eid, Encino, CA (US); Arthur B. Raitano, Los Angeles, CA (US); Mary Faris, Los Angeles, CA (US); Rene S. Hubert, Los Angeles, CA (US); Aya Jakobovits, Beverly Hills, CA (US)

(73) Assignee: Agensys, Inc., Santa Monica, CA (US)

( * ) Notice: Subject to any disclaimer, the term of this patent is extended or adjusted under 35 U.S.C. 154(b) by 687 days.

(21) Appl. No.: 10/415,014

(22) PCT Filed: Aug. 30, 2002

(86) PCT No.: PCT/US02/27760

§ 371 (c)(1), (2), (4) Date: Oct. 27, 2003

(87) PCT Pub. No.: WO03/020954

PCT Pub. Date: Mar. 13, 2003

(65) Prior Publication Data

US 2004/0110674 A1 Jun. 10, 2004

Related U.S. Application Data

(60) Provisional application No. 60/316,664, filed on Aug. 31, 2001.

(51) Int. Cl.
*C07H 21/02* (2006.01)
*C07H 21/04* (2006.01)
*C12P 21/06* (2006.01)
*C12N 5/00* (2006.01)

(52) U.S. Cl. .................... 536/23.1; 435/69.1; 435/325; 536/23.5

(58) Field of Classification Search ........................ None
See application file for complete search history.

(56) References Cited

U.S. PATENT DOCUMENTS

| 5,801,232 | A | * | 9/1998 | Elliott et al. | ............... | 536/23.5 |
| 5,981,193 | A | * | 11/1999 | Harpold et al. | .............. | 435/7.1 |
| 6,261,791 | B1 | * | 7/2001 | Reiter et al. | ................. | 435/7.9 |
| 6,440,681 | B1 | | 8/2002 | Elliott et al. | ................. | 435/7.2 |

FOREIGN PATENT DOCUMENTS

| AU | 9656247 | 1/1997 |
|----|---------|--------|
| EP | 1184390 | 3/2002 |
| EP | 1184391 | 3/2002 |
| FR | 2813499 | 3/2002 |
| JP | 60078996 | 5/1985 |
| WO | WO9010648 | 9/1990 |
| WO | WO9115602 | 10/1991 |
| WO | WO9420617 | * 9/1994 |
| WO | WO9513299 | 5/1995 |
| WO | WO9641876 | 12/1996 |
| WO | WO-99/20757 | 4/1999 |
| WO | WO9930736 | 6/1999 |
| WO | WO-01/62925 | 8/2001 |
| WO | WO0159063 | 8/2001 |
| WO | WO0171042 | 9/2001 |
| WO | WO0174833 | 10/2001 |
| WO | WO0175063 | 10/2001 |
| WO | WO0175067 | 10/2001 |
| WO | WO0188125 | 11/2001 |
| WO | WO0202639 | 1/2002 |
| WO | WO0210449 | 2/2002 |
| WO | WO0230268 | 4/2002 |
| WO | WO02059266 | 8/2002 |
| WO | WO-2004/016225 | 2/2004 |

OTHER PUBLICATIONS

International Search Report for PCT/US02/27760 mailed on Sep. 17, 2004, 5 pages.
Elliot et al., Journal of Molecular Neuroscience (1996) 7:217-228.
Schuller and Orloff, Biochemical Pharmacology (1998) 55(9):1377-1384.
Supplementary Partial European Search Report for EP 02 75 9510, mailed on Oct. 10, 2005, 5 pages.
Tarroni et al., FEBS Letters (1992) 312(1):66-70.
Boyd, Critical Reviews in Toxicology (1997) 27(3):299-318.
Stauderman et al., Journal of Pharmacology and Experimental Therapeutics (1998) 284(2):777-789.
Supplementary European Search Report for EP 02759510.7, mailed on Dec. 23, 2005, 7 pages.
First Statement of Proposed Amendments for Australian Patent Application No. 2002324842, filed on Mar. 31, 2004, 6 pages.
Examiner's First Report on Australian Patent Application No, 2002324842, mailed on Mar. 30, 2006, 2 pages.
Request to Amend a Complete Specification and Second Statement of Proposed Amendments for Australian Patent Application No. 2002324842, filed on Mar. 6, 2007, 6 pages.
Examiner's Report No. 2 for Australian Patent Application No, 2002324842, mailed on Mar. 12, 2007, 2 pages.
Request to Amend a Complete Specification and Third Statement of Proposed Amendments for Australian Patent Application No. 2002324842, filed on Apr. 23, 2007, 4 pages.
Notice of Acceptance for Australian Patent Application No. 2002324842, mailed on May 1, 2007, 3 pages.
Voluntary Amendment for Canadian Patent Application No. 2,458,915, filed on Aug. 4, 2004, 2 pages.
Voluntary Amendment for Canadian Patent Application No. 2,458,915, filed on Jul. 16, 2007, 6 pages.

(Continued)

*Primary Examiner*—Larry R. Helms
*Assistant Examiner*—Lei Yao
(74) *Attorney, Agent, or Firm*—Morrison & Foerster LLP

(57) ABSTRACT

A novel gene (designated 205P1B5) and its encoded protein are described. While 205P1B5 exhibits tissue specific expression in normal adult tissue, it is aberrantly expressed in prostrate cancer. Consequently, 205P1B5 provides a diagnostic, prognostic, prophylactic and/or therapeutic target for cancer. The 205P1B5 gene or fragment thereof, or its encoded protein or a fragment thereof, can be used to elicit an immune response.

8 Claims, 21 Drawing Sheets

OTHER PUBLICATIONS

Amendment for European Patent Application No. 02759510.7, filed on Aug. 16, 2004, 2 pages.

Amendment for European Patent Application No. 02759510.7, filed on Nov. 17, 2005, 2 pages.

Non-acceptance of Amendments Pursuant to Rules 41(1) and 86(1) EPC for European Patent Application No. 02759510.7, mailed on Dec. 6, 2005, 1 page.

Communication Pursuant to Article 96(2) EPC for European Patent Application No. 02759510.7, mailed on Nov. 29, 2007, 6 pages.

Notice of Reasons for Rejection for Japanese Patent Application No. 2003-525655, mailed on Dec. 14, 2006, 4 pages.

Notice of Final Rejection for Japanese Patent Application No. 2003-525655, mailed on Sep. 11, 2007, 3 pages.

Notice of Reasons for Rejection for Japanese Patent Application No. 2007-65917, mailed on Sep. 11, 2007, 3 pages.

Gotti, Progress in Neurobiology (2004) 74(6):363-396.

Office Action for European Patent Application No. 02 759 510.7, mailed on Jun. 10, 2009, 8 pages.

Schuller, Nature Reviews Cancer (2009) 9(3):195-205.

* cited by examiner

Figure 1

```
1    GATCTTNCCT ACCGGGGAGG GATGGATGGT TGGATACAGG TGGCTGGGCT ATTCCATCCA
61   TNTGGAAGCA CATTTGAGCC TCCAGGCTTC TCCTTGACGT CATTCCTCTC CTTCCTTGCT
121  GCAAAATGGC TCTGCACCAG CCGGCCCCCA GGAGGTCTGG CAGAGCTGAG AGCCATGGCC
181  TGNAGGGGCT CCATATGTCC CTACGCGTGC AGNAGGCAAA CAAGAAAGAC CATCCTGAGC
241  TGCTNCTGAC CCACCTCAAA CTCATTTCAT TTGGCCTGTC CTCCCTCCC
```

Figure 2

Figure 2A. The cDNA (SEQ ID NO:701) and amino acid sequence (SEQ ID NO:702) of 205P1B5 v.1. The start methionine is underlined. The open reading frame extends from nucleic acid 555-2144 including the stop codon.

```
   1 gagagaacagcgtgagcctgtgtgcttgtgtgctgagccctcatccctcctggggccag
  61 gcttgggtttcacctgcagaatcgcttgtgctgggctgcctgggctgtcctcagtggcac
 121 ctgcatgaagccgttctggctgccagagctggacagccccaggaaaacccacctctctgc
 181 agagcttgcccagctgtcccgggaagccaaatgcctctcatgtaagtcttctgctcgac
 241 ggggtgtctcctaaaccctcactcttcagcctctgtttgaccatgaaatgaagtgactga
 301 gctctattctgtacctgccactctatttctggggtgacttttgtcagctgcccagaatct
 361 ccaagccaggctggttctctgcatcctttcaatgacctgttttcttctgtaaccacaggt
 421 tcggtggtgagaggaagcctcgcagaatccagcagaatcctcacagaatccagcagcagc
 481 tctgctggggacatggtccatggtgcaacccacagcaaagccctgacctgacctcctgat
   1                                    M  G  P  S  C  P  V  F  L  S  F  T  K  L  S  L
 541 gctcaggagaagccATGGGCCCCTCCTGTCCTGTGTTCCTGTCCTTCACAAAGCTCAGCC
  17  W  W  L  L  L  T  P  A  G  G  E  E  A  K  R  P  P  P  R  A
 601 TGTGGTGGCTCCTTCTGACCCCAGCAGGTGGAGAGGAAGCTAAGCGCCCACCTCCCAGGG
  37  P  G  D  P  L  S  S  P  S  P  T  A  L  P  Q  G  G  S  H  T
 661 CTCCTGGAGACCCACTCTCCTCTCCCAGTCCCACGGCATTGCCGCAGGGAGGCTCGCATA
  57  E  T  E  D  R  L  F  K  H  L  F  R  G  Y  N  R  W  A  R  P
 721 CCGAGACTGAGGACCGGCTCTTCAAACACCTCTTCCGGGGCTACAACCGCTGGGCGCGCC
  77  V  P  N  T  S  D  V  V  I  V  R  F  G  L  S  I  A  Q  L  I
 781 CGGTGCCCAACACTTCAGACGTGGTGATTGTGCGCTTTGGACTGTCCATCGCTCAGCTCA
  97  D  V  D  E  K  N  Q  M  M  T  T  N  V  W  L  K  Q  E  W  S
 841 TCGATGTGGATGAGAAGAACCAAATGATGACCACCAACGTCTGGCTAAAACAGGAGTGGA
 117  D  Y  K  L  R  W  N  P  T  D  F  G  N  I  T  S  L  R  V  P
 901 GCGACTACAAACTGCGCTGGAACCCCACTGATTTTGGCAACATCACATCTCTCAGGGTCC
 137  S  E  M  I  W  I  P  D  I  V  L  Y  N  N  A  D  G  E  F  A
 961 CTTCTGAGATGATCTGGATCCCCGACATTGTTCTCTACAACAATGCAGATGGGGAGTTTG
 157  V  T  H  M  T  K  A  H  L  F  S  T  G  T  V  H  W  V  P  P
1021 CAGTGACCCACATGACCAAGGCCCACCTCTTCTCCACGGGCACTGTGCACTGGGTGCCCC
 177  A  I  Y  K  S  S  C  S  I  D  V  T  F  F  P  F  D  Q  Q  N
1081 CGGCCATCTACAAGAGCTCCTGCAGCATCGACGTCACCTTCTTCCCCTTCGACCAGCAGA
 197  C  K  M  K  F  G  S  W  T  Y  D  K  A  K  I  D  L  E  Q  M
1141 ACTGCAAGATGAAGTTTGGCTCCTGGACTTATGACAAGGCCAAGATCGACCTGGAGCAGA
 217  E  Q  T  V  D  L  K  D  Y  W  E  S  G  E  W  A  I  V  N  A
1201 TGGAGCAGACTGTGGACCTGAAGGACTACTGGGAGAGCGGCGAGTGGGCCATCGTCAATG
 237  T  G  T  Y  N  S  K  K  Y  D  C  C  A  E  I  Y  P  D  V  T
1261 CCACGGGCACCTACAACAGCAAGAAGTACGACTGCTGCGCCGAGATCTACCCCGACGTCA
 257  Y  A  F  V  I  R  R  L  P  L  F  Y  T  I  N  L  I  I  P  C
1321 CCTACGCCTTCGTCATCCGGCGGCTGCCGCTCTTCTACACCATCAACCTCATCATCCCCT
 277  L  L  I  S  C  L  T  V  L  V  F  Y  L  P  S  D  C  G  E  K
1381 GCCTGCTCATCTCCTGCCTCACTGTGCTGGTCTTCTACCTGCCCTCCGACTGCGGCGAGA
 297  I  T  L  C  I  S  V  L  L  S  L  T  V  F  L  L  L  I  T  E
1441 AGATCACGCTGTGCATTTCGGTGCTGCTGTCACTCACCGTCTTCCTGCTGCTCATCACTG
 317  I  I  P  S  T  S  L  V  I  P  L  I  G  E  Y  L  L  F  T  M
1501 AGATCATCCCGTCCACCTCGCTGGTCATCCCGCTCATCGGCGAGTACCTGCTGTTCACCA
 337  I  F  V  T  L  S  I  V  I  T  V  F  V  L  N  V  H  H  R  S
1561 TGATCTTCGTCACCCTGTCCATCGTCATCACCGTCTTCGTGCTCAATGTGCACCACCGCT
 357  P  S  T  H  T  M  P  H  W  V  R  G  A  L  L  G  C  V  P  R
1621 CCCCCAGCACCCACACCATGCCCCACTGGGTGCGGGGAGCCCTTCTGGGCTGTGTGCCCC
 377  W  L  L  M  N  R  P  P  P  V  E  L  C  H  P  L  R  L  K
1681 GGTGGCTTCTGATGAACCGGCCCCACCACCCGTGGAGCTCTGCCACCCCCTACGCCTGA
 397  L  S  P  S  Y  H  W  L  E  S  N  V  D  A  E  E  R  E  V  V
1741 AGCTCAGCCCCTCTTATCACTGGCTGGAGAGCAACGTGGATGCCGAGGAGAGGGAGGTGG
 417  V  E  E  D  R  W  A  C  A  G  H  V  A  P  S  V  G  T  L
1801 TGGTGGAGGAGGAGGACAGATGGGCATGTGCAGGTCATGTGGCCCCCTCTGTGGGCACCC
 437  C  S  H  G  H  L  H  S  G  A  S  G  P  K  A  E  A  L  L  Q
1861 TCTGCAGCCACGGCCACCTGCACTCTGGGGCCTCAGGTCCCAAGGCTGAGGCTCTGCTGC
 457  E  G  E  L  L  L  S  P  H  M  Q  K  A  L  E  G  V  H  Y  I
1921 AGGAGGGTGAGCTGCTGCTATCACCCCACATGCAGAAGGCACTGGAAGGTGTGCACTACA
 477  A  D  H  L  R  S  E  D  A  D  S  S  V  K  E  D  W  K  Y  V
1981 TTGCCGACCACCTGCGGTCTGAGGATGCTGACTCTTCGGTGAAGGAGGACTGGAAGTATG
 497  A  M  V  I  D  R  I  F  L  W  L  F  I  I  V  C  F  L  G  T
2041 TTGCCATGGTCATCGACAGGATCTTCCTCTGGCTGTTTATCATCGTCTGCTTCCTGGGGA
 517  I  G  L  F  L  P  P  F  L  A  G  M  I  *
```

Figure 2A-2

```
2101 CCATCGGCCTCTTTCTGCCTCCGTTCCTAGCTGGAATGATCTGActgcacctccctcgag
2161 ctggctcccagggcaaaggggagggttcttggatgtggaagggctttgaacaatgtttag
2221 atttggagatgagcccaaagtgccagggagaacagccaggtgaggtgggaggttggagag
2281 ccaggtgaggtctctgtaagtcaggctggggttgaagtttggagtctgtccgagtttgca
2341 gggtgctgagctgtatggtccagcaggggagtaataagggctcttctggaaggggaggaa
2401 gcgggaggcagggcctgcacctgatgtggaggtacagggcagatcttccctaccggggag
2461 ggatggatggttggatacaggtggctgggctattccatccatctggaagcacatttgagc
2521 ctccaggcttctccttgacgtcattcctctccttccttgctgcaaaatggctctgcacca
2581 gccggcccccaggaggtctggcagagctgagagccatggcctgcaggggctccatatgtc
2641 cctacgcgtgcagcaggcaaacaaga
```

Figure 2B. The cDNA (SEQ ID NO:703) and amino acid sequence (SEQ ID NO:704) of 205P1B5 v.2. The start methionine is underlined. The open reading frame extends from nucleic acid 555-2144 including the stop codon.

```
   1 gagagaacagcgtgagcctgtgtgcttgtgtgctgagccctcatccctcctggggccag
  61 gcttgggtttcacctgcagaatcgcttgtgctgggctgcctgggctgtcctcagtggcac
 121 ctgcatgaagccgttctggctgccagagctggacagcccaggaaaacccacctctctgc
 181 agagcttgccagctgtccccgggaagccaaatgcctctcatgtaagtcttctgctcgac
 241 ggggtgtctcctaaaccctcactcttcagcctctgtttgaccatgaaatgaagtgactga
 301 gctctattctgtacctgccactctatttctggggtgacttttgtcagctgcccagaatct
 361 ccaagccaggctggttctctgcatcctttcaatgacctgttttcttctgtaaccacaggt
 421 tcggtggtgagaggaagcctcgcagaatccagcagaatcctcacagaatccagcagcagc
 481 tctgctggggacatggtccatggtgcaacccacagcaaagccctgacctgacctcctgat
   1                   M  G  P  S  C  P  V  F  L  S  F  T  K  L  S  L
 541 gctcaggagaagccATGGGCCCCTCCTGTCCTGTGTTCCTGTCCTTCACAAAGCTCAGCC
  17  W  W  L  L  L  T  P  A  G  G  E  E  A  K  R  P  P  P  R  A
 601 TGTGGTGGCTCCTTCTGACCCCAGCAGGTGGAGAGGAAGCTAAGCGCCCACCTCCCAGGG
  37  P  G  D  P  L  S  S  P  S  P  T  A  L  P  Q  G  G  S  H  T
 661 CTCCTGGAGACCCACTCTCCTCTCCCAGTCCCACGGCATTGCCGCAGGGAGGCTCGCATA
  57  E  T  E  D  R  L  F  K  H  L  F  R  G  Y  N  R  W  A  R  P
 721 CCGAGACTGAGGACCGGCTCTTCAAACACCTCTTCCGGGGCTACAACCGCTGGGCGCGCC
  77  V  P  N  T  S  D  V  V  I  V  R  F  G  L  S  I  A  Q  L  I
 781 CGGTGCCCAACACTTCAGACGTGGTGATTGTGCGCTTTGGACTGTCCATCGCTCAGCTCA
  97  D  V  D  E  K  N  Q  M  M  T  T  N  V  W  L  K  Q  E  W  S
 841 TCGATGTGGATGAGAAGAACCAAATGATGACCACCAACGTCTGGCTAAAACAGGAGTGGA
 117  D  Y  K  L  R  W  N  P  A  D  F  G  N  I  T  S  L  R  V  P
 901 GCGACTACAAACTGCGCTGGAACCCCGCTGATTTTGGCAACATCACATCTCTCAGGGTCC
 137  S  E  M  I  W  I  P  D  I  V  L  Y  N  N  A  D  G  E  F  A
 961 CTTCTGAGATGATCTGGATCCCCGACATTGTTCTCTACAACAATGCAGATGGGGAGTTTG
 157  V  T  H  M  T  K  A  H  L  F  S  T  G  T  V  H  W  V  P  P
1021 CAGTGACCCACATGACCAAGGCCCACCTCTTCTCCACGGGCACTGTGCACTGGGTGCCCC
 177  A  I  Y  K  S  S  C  S  I  D  V  T  F  P  F  D  Q  Q  N
1081 CGGCCATCTACAAGAGCTCCTGCAGCATCGACGTCACCTTCTTCCCCTTCGACCAGCAGA
 197  C  K  M  K  F  G  S  W  T  Y  D  K  A  K  I  D  L  E  Q  M
1141 ACTGCAAGATGAAGTTTGGCTCCTGGACTTATGACAAGGCCAAGATCGACCTGGAGCAGA
 217  E  Q  T  V  D  L  K  D  Y  W  E  S  G  E  W  A  I  V  N  A
1201 TGGAGCAGACTGTGGACCTGAAGGACTACTGGGAGAGCGGCGAGTGGGCCATCGTCAATG
 237  T  G  T  Y  N  S  K  K  Y  D  C  C  A  E  I  Y  P  D  V  T
1261 CCACGGGCACCTACAACAGCAAGAAGTACGACTGCTGCGCCGAGATCTACCCCGACGTCA
 257  Y  A  F  V  I  R  R  L  P  L  F  Y  T  I  N  L  I  I  P  C
1321 CCTACGCCTTCGTCATCCGGCGGCTGCCGCTCTTCTACACCATCAACCTCATCATCCCCT
 277  L  L  I  S  C  L  T  V  L  V  F  Y  L  P  S  D  C  G  E  K
1381 GCCTGCTCATCTCCTGCCTCACTGTGCTGGTCTTCTACCTGCCCTCCGACTGCGGCGAGA
 297  I  T  L  C  I  S  V  L  L  S  L  T  V  F  L  L  L  I  T  E
1441 AGATCACGCTGTGCATTTCGGTGCTGCTGTCACTCACCGTCTTCCTGCTGCTCATCACTG
 317  I  I  P  S  T  S  L  V  I  P  L  I  G  E  Y  L  L  F  T  M
1501 AGATCATCCCGTCCACCTCGCTGGTCATCCCGCTCATCGGCGAGTACCTGCTGTTCACCA
 337  I  F  V  T  L  S  I  V  I  T  V  F  V  L  N  V  H  H  R  S
1561 TGATCTTCGTCACCCTGTCCATCGTCATCACCGTCTTCGTGCTCAATGTGCACCACCGCT
 357  P  S  T  H  T  M  P  H  W  V  R  G  A  L  L  G  C  V  P  R
1621 CCCCCAGCACCCACACCATGCCCCACTGGGTGCGGGGGGCCCTTCTGGGCTGTGTGCCCC
 377  W  L  L  M  N  R  P  P  P  P  V  E  L  C  H  P  L  R  L  K
1681 GGTGGCTTCTGATGAACCGGCCCCCACCACCCGTGGAGCTCTGCCACCCCCTACGCCTGA
 397  L  S  P  S  Y  H  W  L  E  S  N  V  D  A  E  E  R  E  V  V
1741 AGCTCAGCCCCTCTTATCACTGGCTGGAGAGCAACGTGGATGCCGAGGAGAGGGAGGTGG
 417  V  E  E  D  R  W  A  C  A  G  H  V  A  P  S  V  G  T  L
1801 TGGTGGAGGAGGAGGACAGATGGGCATGTGCAGGTCATGTGGCCCCCTCTGTGGGCACCC
 437  C  S  H  G  H  L  H  S  G  A  S  G  P  K  A  E  A  L  L  Q
1861 TCTGCAGCCACGGCCACCTGCACTCTGGGGCCTCAGGTCCCAAGGCTGAGGCTCTGCTGC
 457  E  G  E  L  L  L  S  P  H  M  Q  K  A  L  E  G  V  H  Y  I
1921 AGGAGGGTGAGCTGCTGCTATCACCCCACATGCAGAAGGCACTGGAAGGTGTGCACTACA
 477  A  D  H  L  R  S  E  D  A  D  S  S  V  K  E  D  W  K  Y  V
1981 TTGCCGACCACCTGCGGTCTGAGGATGCTGACTCTTCGGTGAAGGAGGACTGGAAGTATG
```

Figure 2B-2

```
 497      A  M  V  I  D  R  I  F  L  W  L  F  I  I  V  C  F  L  G  T
2041 TTGCCATGGTCATCGACAGGATCTTCCTCTGGCTGTTTATCATCGTCTGCTTCCTGGGGA
 517      I  G  L  F  L  P  P  F  L  A  G  M  I  *
2101 CCATCGGCCTCTTTCTGCCTCCGTTCCTAGCTGGAATGATCTGActgcacctccctcgag
2161 ctggctcccagggcaaaggggagggttcttggatgtggaagggctttgaacaatgtttag
2221 atttggagatgagcccaaagtgccagggagaacagccaggtgaggtgggaggttggagag
2281 ccaggtgaggtctctctaagtcaggctggggttgaagtttggagtctgtccgagtttgca
2341 gggtgctgagctgtatggtccagcaggggagtaataagggctcttccggaaggggaggaa
2401 gcgggaggcaggcctgcacctgatgtggaggtacaggcagatcttccctaccggggaggg
2461 atggatggttggatacaggtggctgggctattccatccatctggaagcacatttgagcct
2521 ccaggcttctccttgacgtcattcctctccttccttgctgcaaaatggctctgcaccagc
2581 cggccccaggaggtctggcagagctgagagccatggcctgcaggggctccatatgtccc
2641 tacgcgtgcagcaggcaaacaaga
```

Figure 3

Figure 3A. Amino acid sequence of 205P1B5 v.1 (SEQ ID NO:702). The 205P1B5 v.1 protein has 529 amino acids.

```
  1 MGPSCPVFLS FTKLSLWWLL LTPAGGEEAK RPPPRAPGDP LSSPSPTALP QGGSHTETED
 61 RLFKHLFRGY NRWARPVPNT SDVVIVRFGL SIAQLIDVDE KNQMMTTNVW LKQEWSDYKL
121 RWNPTDFGNI TSLRVPSEMI WIPDIVLYNN ADGEFAVTHM TKAHLFSTGT VHWVPPAIYK
181 SSCSIDVTFF PFDQQNCKMK FGSWTYDKAK IDLEQMEQTV DLKDYWESGE WAIVNATGTY
241 NSKKYDCCAE IYPDVTYAFV IRRLPLFYTI NLIIPCLLIS CLTVLVFYLP SDCGEKITLC
301 ISVLLSLTVF LLLITEIIPS TSLVIPLIGE YLLFTMIFVT LSIVITVFVL NVHHRSPSTH
361 TMPHWVRGAL LGCVPRWLLM NRPPPPVELC HPLRLKLSPS YHWLESNVDA EEREVVVEEE
421 DRWACAGHVA PSVGTLCSHG HLHSGASGPK AEALLQEGEL LLSPHMQKAL EGVHYIADHL
481 RSEDADSSVK EDWKYVAMVI DRIFLWLFII VCFLGTIGLF LPPFLAGMI
```

Figure 3B. Amino acid sequence of 205P1B5 v.2 (SEQ ID NO:704). The 205P1B5 v.2 protein has 529 amino acids.

```
  1 MGPSCPVFLS FTKLSLWWLL LTPAGGEEAK RPPPRAPGDP LSSPSPTALP QGGSHTETED
 61 RLFKHLFRGY NRWARPVPNT SDVVIVRFGL SIAQLIDVDE KNQMMTTNVW LKQEWSDYKL
121 RWNPADFGNI TSLRVPSEMI WIPDIVLYNN ADGEFAVTHM TKAHLFSTGT VHWVPPAIYK
181 SSCSIDVTFF PFDQQNCKMK FGSWTYDKAK IDLEQMEQTV DLKDYWESGE WAIVNATGTY
241 NSKKYDCCAE IYPDVTYAFV IRRLPLFYTI NLIIPCLLIS CLTVLVFYLP SDCGEKITLC
301 ISVLLSLTVF LLLITEIIPS TSLVIPLIGE YLLFTMIFVT LSIVITVFVL NVHHRSPSTH
361 TMPHWVRGAL LGCVPRWLLM NRPPPPVELC HPLRLKLSPS YHWLESNVDA EEREVVVEEE
421 DRWACAGHVA PSVGTLCSHG HLHSGASGPK AEALLQEGEL LLSPHMQKAL EGVHYIADHL
481 RSEDADSSVK EDWKYVAMVI DRIFLWLFII VCFLGTIGLF LPPFLAGMI
```

Figure 4: Alignment of 205P1B5 with cholinergic receptor, nicotinic, alpha polypeptide 2

Score = 1014 bits (2622), Expect = 0.0
Identities = 529/529 (100%), Positives = 529/529 (100%)

```
2C5P1B5: 1    MGPSCPVFLSFTKLSLWWLLLTPAGGEEAKRPPPRAPGDPLSSPSPTALPQGGSHTETED 60
              MGPSCPVFLSFTKLSLWWLLLTPAGGEEAKRPPPRAPGDPLSSPSPTALPQGGSHTETED
Sbjct:   1    MGPSCPVFLSFTKLSLWWLLLTPAGGEEAKRPPPRAPGDPLSSPSPTALPQGGSHTETED 60

2C5P1B5:61    RLFKHLFRGYNRWARPVPNTSDVVIVRFGLSIAQLIDVDEKNQMMTTNVWLKQEWSDYKL 120
              RLFKHLFRGYNRWARPVPNTSDVVIVRFGLSIAQLIDVDEKNQMMTTNVWLKQEWSDYKL
Sbjct:  61    RLFKHLFRGYNRWARPVPNTSDVVIVRFGLSIAQLIDVDEKNQMMTTNVWLKQEWSDYKL 120

2C5P1B5:121   RWNPTDFGNITSLRVPSEMIWIPDIVLYNNADGEFAVTHMTKAHLFSTGTVHWVPPAIYK 180
              RWNPTDFGNITSLRVPSEMIWIPDIVLYNNADGEFAVTHMTKAHLFSTGTVHWVPPAIYK
Sbjct: 121    RWNPTDFGNITSLRVPSEMIWIPDIVLYNNADGEFAVTHMTKAHLFSTGTVHWVPPAIYK 180

2C5P1B5:181.  SSCSIDVTFFPFDQQNCKMKFGSWTYDKAKIDLEQMEQTVDLKDYWESGEWAIVNATGTY 240
              SSCSIDVTFFPFDQQNCKMKFGSWTYDKAKIDLEQMEQTVDLKDYWESGEWAIVNATGTY
Sbjct:  181   SSCSIDVTFFPFDQQNCKMKFGSWTYDKAKIDLEQMEQTVDLKDYWESGEWAIVNATGTY 240

2C5P1B5:241   NSKKYDCCAEIYPDVTYAFVIRRLPLFYTINLIIPCLLISCLTVLVFYLPSDCGEKITLC 300
              NSKKYDCCAEIYPDVTYAFVIRRLPLFYTINLIIPCLLISCLTVLVFYLPSDCGEKITLC
Sbjct: 241    NSKKYDCCAEIYPDVTYAFVIRRLPLFYTINLIIPCLLISCLTVLVFYLPSDCGEKITLC 300

2C5P1B5:301   ISVLLSLTVFLLLITEIIPSTSLVIPLIGEYLLFTMIFVTLSIVITVFVLNVHHRSPSTH 360
              ISVLLSLTVFLLLITEIIPSTSLVIPLIGEYLLFTMIFVTLSIVITVFVLNVHHRSPSTH
Sbjct: 301    ISVLLSLTVFLLLITEIIPSTSLVIPLIGEYLLFTMIFVTLSIVITVFVLNVHHRSPSTH 360

2C5P1B5:361   TMPHWVRGALLGCVPRWLLMNRPPPPVELCHPLRLKLSPSYHWLESNVDAEEREVVVEEE 420
              TMPHWVRGALLGCVPRWLLMNRPPPPVELCHPLRLKLSPSYHWLESNVDAEEREVVVEEE
Sbjct: 361    TMPHWVRGALLGCVPRWLLMNRPPPPVELCHPLRLKLSPSYHWLESNVDAEEREVVVEEE 420

2C5P1B5:421   DRWACAGHVAPSVGTLCSHGHLHSGASGPKAEALLQEGELLLSPHMQKALEGVHYIADHL 480
              DRWACAGHVAPSVGTLCSHGHLHSGASGPKAEALLQEGELLLSPHMQKALEGVHYIADHL
Sbjct: 421    DRWACAGHVAPSVGTLCSHGHLHSGASGPKAEALLQEGELLLSPHMQKALEGVHYIADHL 480

2C5P1B5:481   RSEDADSSVKEDWKYVAMVIDRIFLWLFIIVCFLGTIGLFLPPFLAGMI 529
              RSEDADSSVKEDWKYVAMVIDRIFLWLFIIVCFLGTIGLFLPPFLAGMI
Sbjct: 481    RSEDADSSVKEDWKYVAMVIDRIFLWLFIIVCFLGTIGLFLPPFLAGMI 529
```

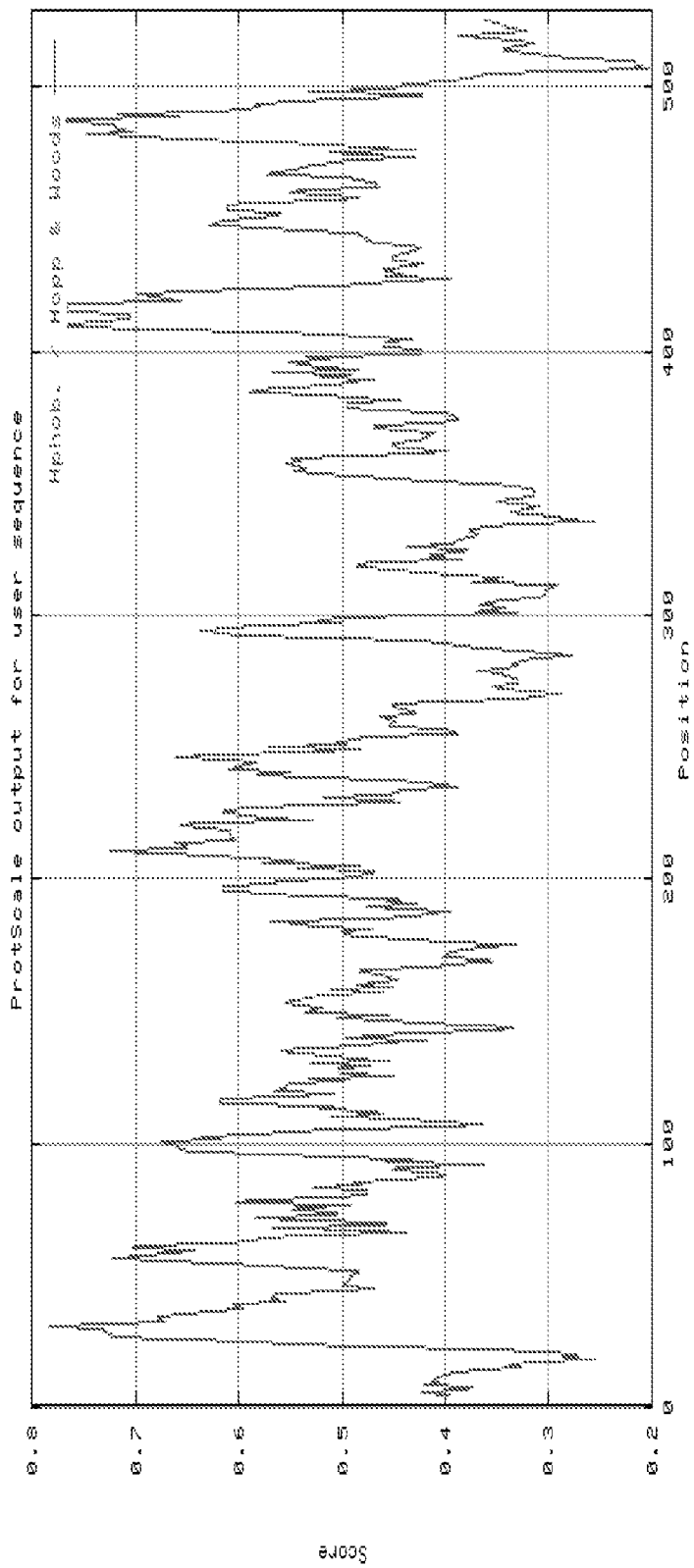
Figure 5: 205P1B5 Hydrophilicity profile
(Hopp T.P., Woods K.R., 1981. Proc. Natl. Acad. Sci. U.S.A. 78:3824-3828)

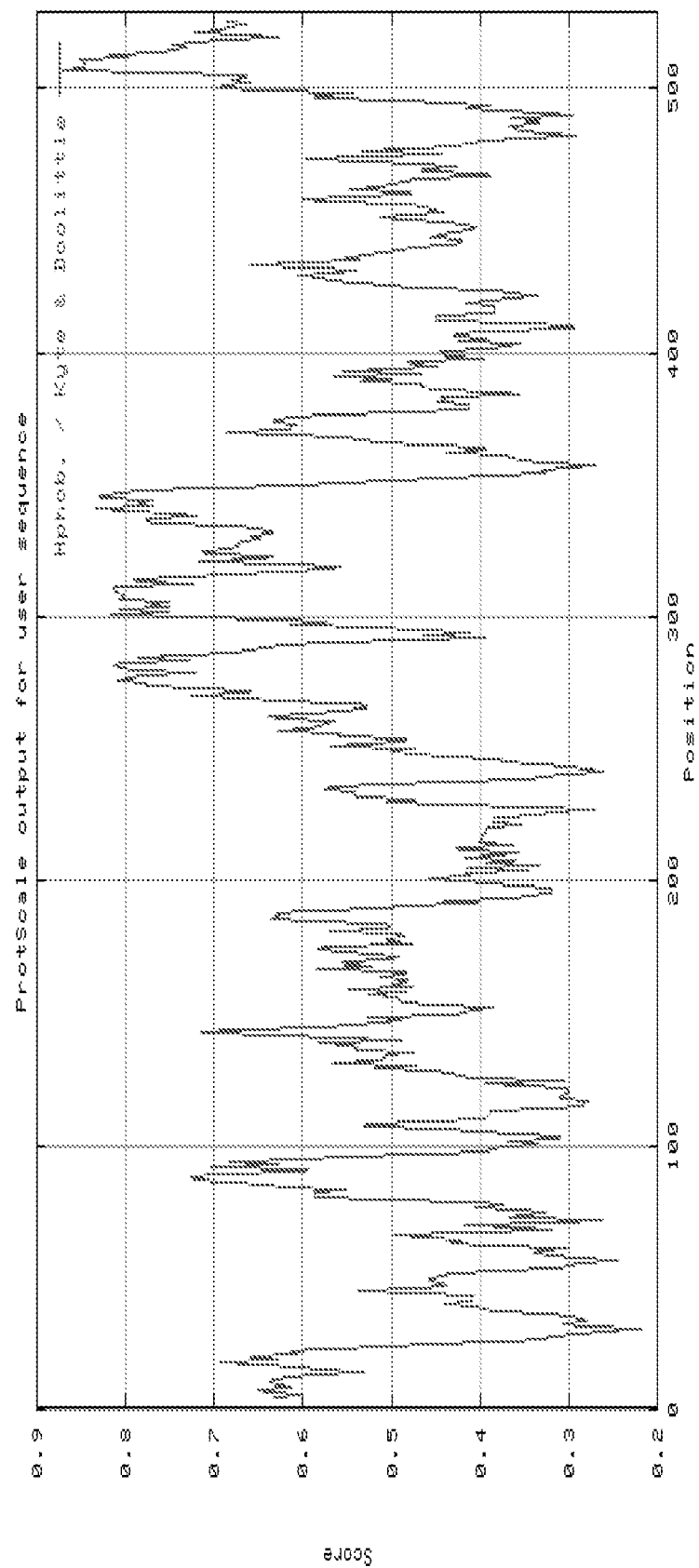
Figure 6: 205P1B5 Hydropathicity Profile
(Kyte J., Doolittle R.F., 1982. J. Mol. Biol. 157:105-132)

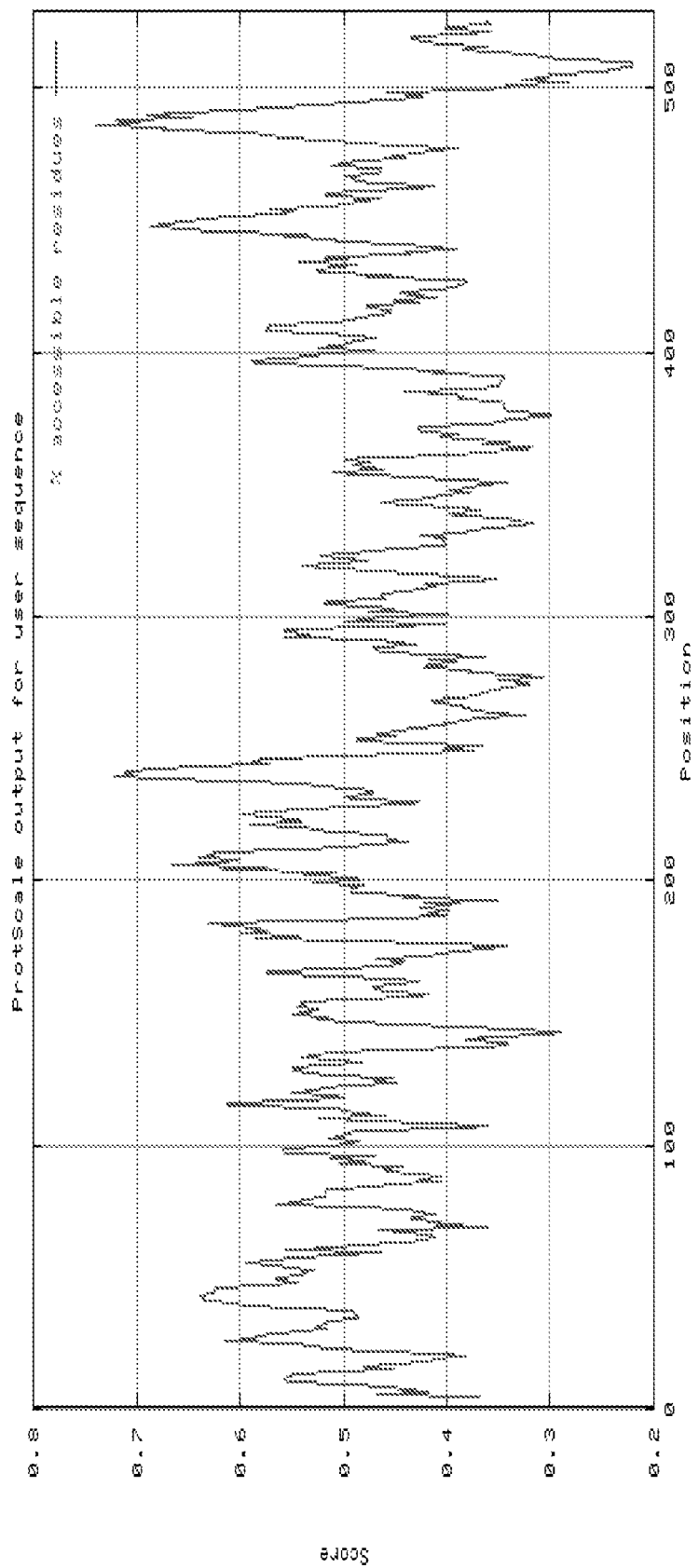
Figure 7: 205P1B5 % Accessible Residues Profile
(Janin J., 1979. Nature 277:491-492)

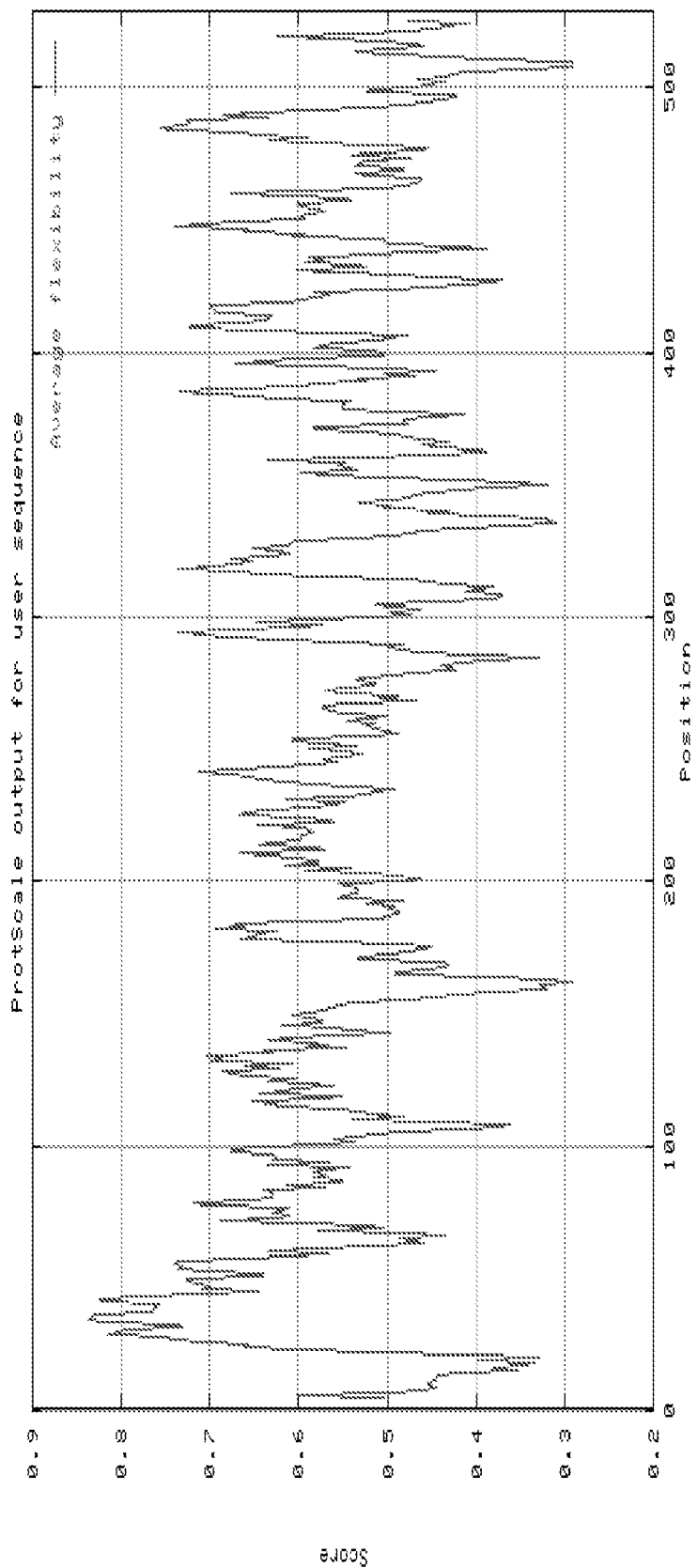
Figure 8: 205P1B5 Average Flexibility Profile
(Bhaskaran R., Ponnuswamy P.K., 1988.
Int. J. Pept. Protein Res. 32:242-255)

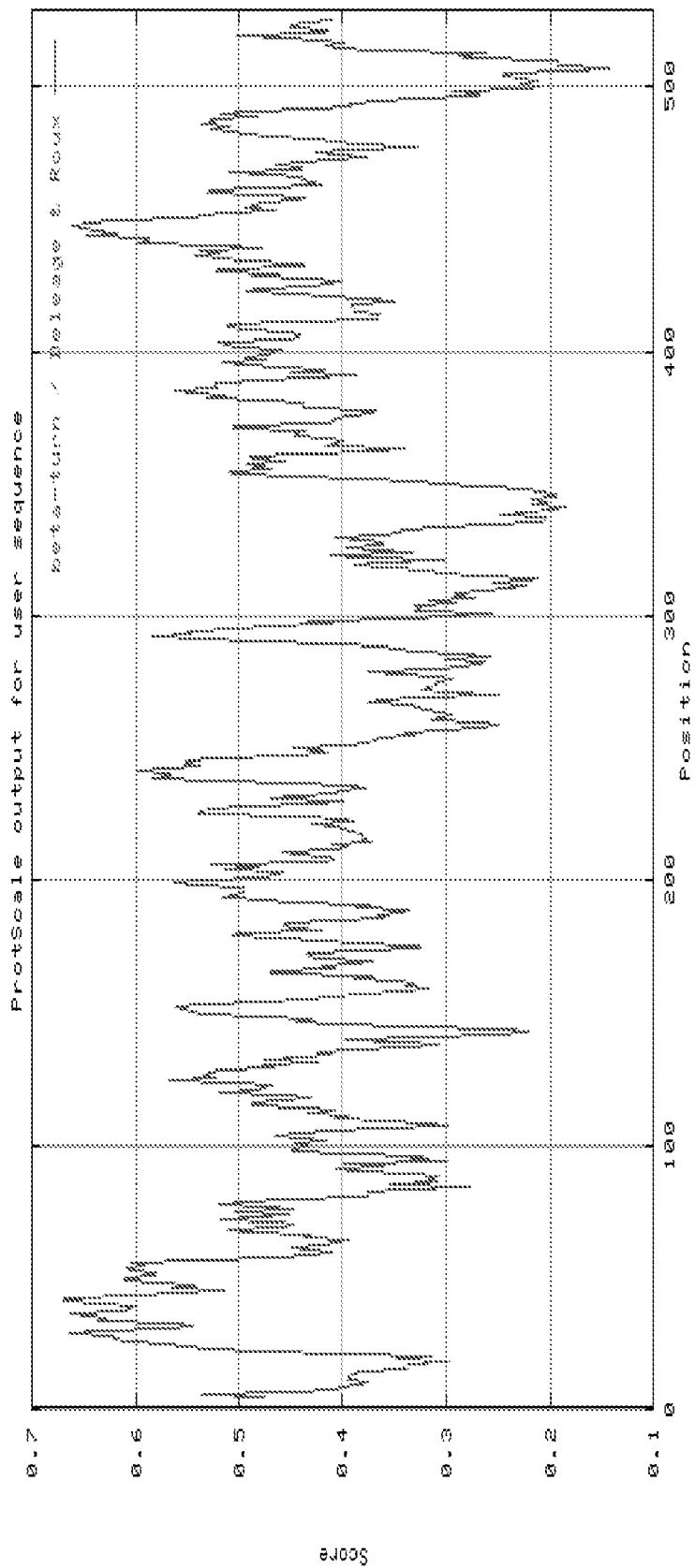
Figure 9: 205P1B5 Beta-turn Profile
(Deleage, G., Roux B. 1987. Protein Engineering 1:289-294)

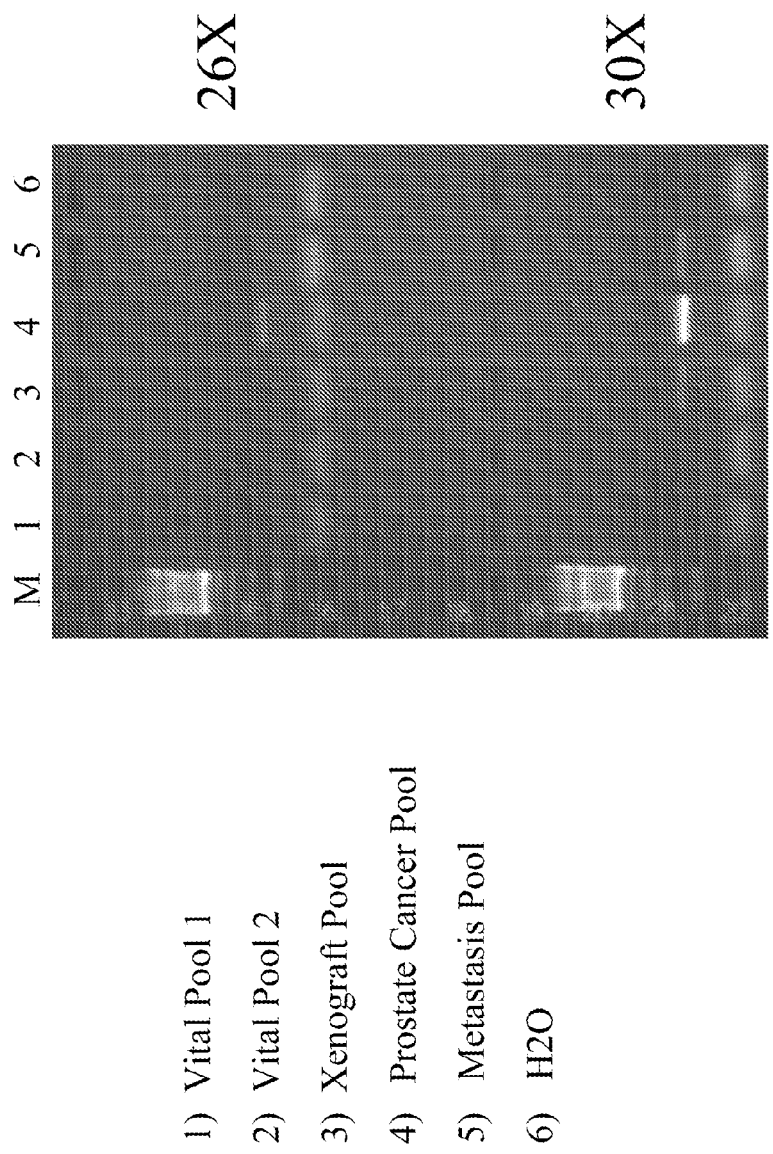
Figure 10: RT-PCR analysis of 205P1B5 expression
1) Vital Pool 1
2) Vital Pool 2
3) Xenograft Pool
4) Prostate Cancer Pool
5) Metastasis Pool
6) H2O

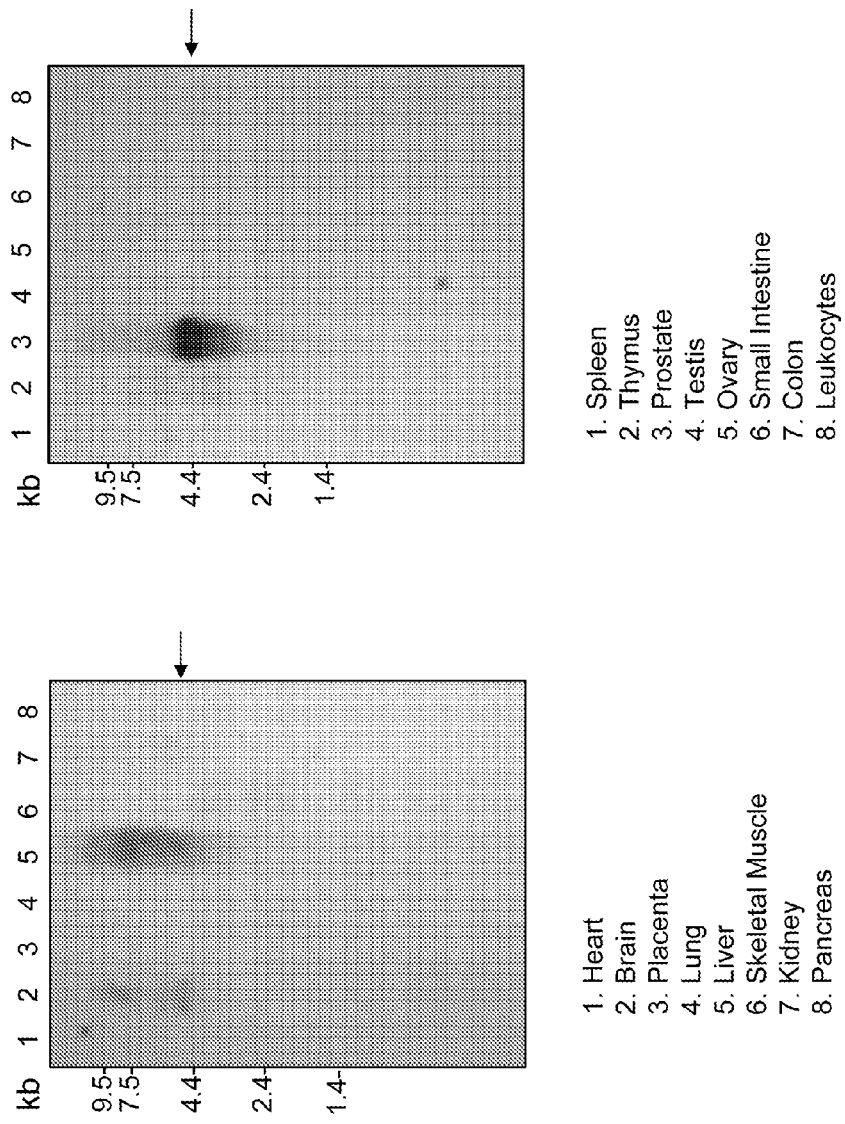
Figure 11: Expression of 205P1B5 in Normal Tissues

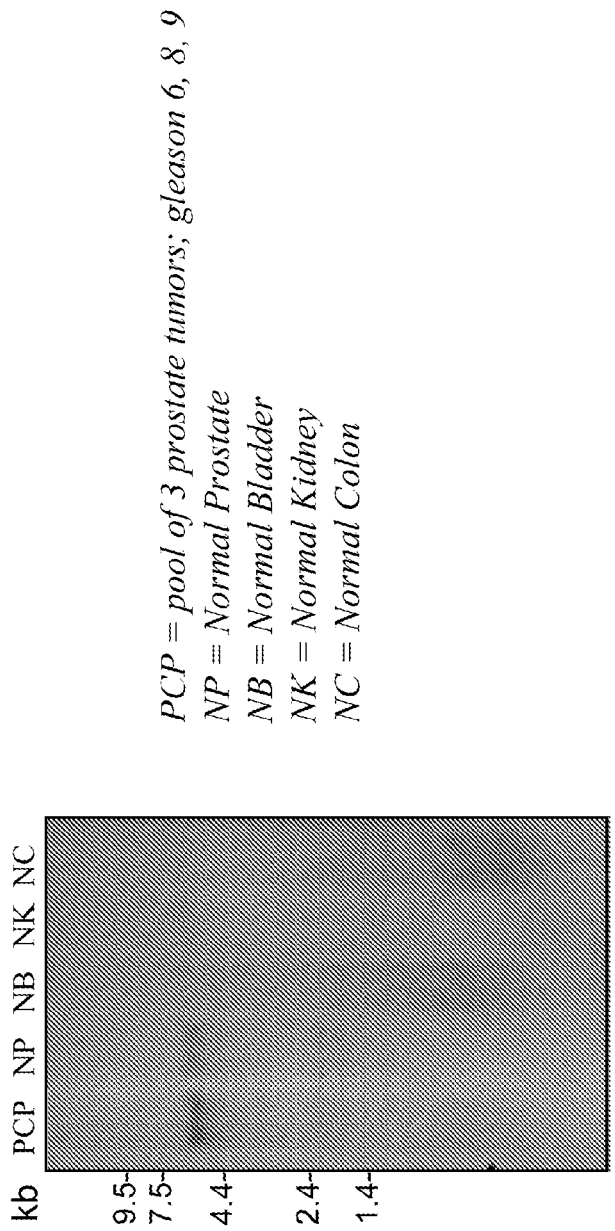
Figure 12: Expression of 205P1B5 in Human Patient Cancer Specimens

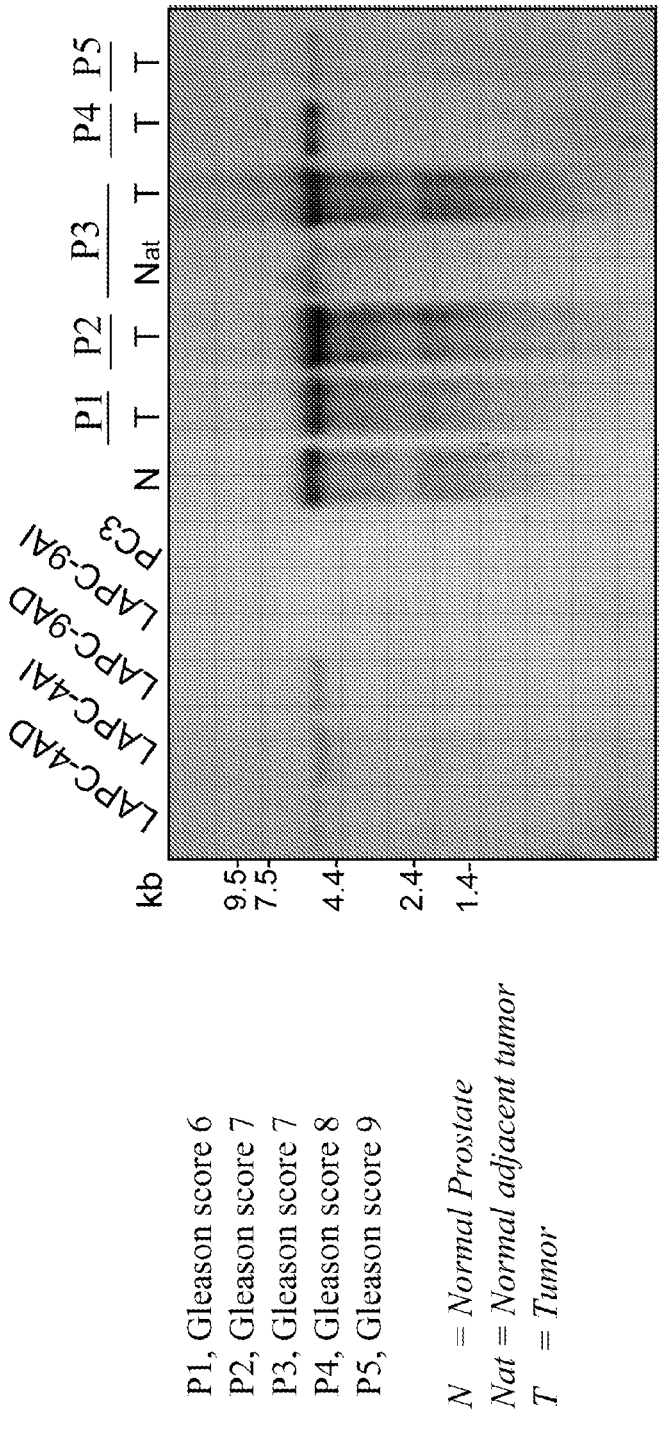
Figure 13: Expression of 205P1B5 in Prostate Cancer Xenografts and Prostate Cancer Patient Specimens
P1, Gleason score 6
P2, Gleason score 7
P3, Gleason score 7
P4, Gleason score 8
P5, Gleason score 9
N = Normal Prostate
Nat = Normal adjacent tumor
T = Tumor

Figure 14A

```
           10        20        30        40        50        60        70
            |         |         |         |         |         |         |
MGPSCPVFLSFTKLSLWWLLLTPAGGEEAKRPPPRAPGDPLSSPSPTALPQGGSHTETEDRLFKHLFRGY
cccccchhhhhhheeeeeeeccccccccccccccccccccccccccccccccchhhhhhhhhhhhhh
NRWARPVPNTSDVVIVRFGLSIAQLIDVDEKNQMMTTNVWLKQEWSDYKLRWNPTDFGNITSLRVPSEMI
hhhcccccccccceeeeeehhhhhhhhhcccccchhhhhhhcceeeccccccceeeeecccccccee
WIPDIVLYNNADGEFAVTHMTKAHLFSTGTVHWVPPAIYKSSCSIDVTFFPFDQQNCKMKFGSWTYDKAK
eecceeecccccehhhhhhhhhheeecccccccccccccceeeeccccccccccccccccccchchhh
IDLEQMEQTVDLKDYWESGEWAIVNATGTYNSKKYDCCAETYPDVTYAFVIRRLPLFYTINLIIPCLLIS
chhhhhhhcchhhhhccccceeeeeccccccccccccchccchhhhhhhccceeehhhhhhhhhhc
CLTVLVFYLPSDCGEKITLCISVLLSLTVFLLLITEIIPSTSLVIPLIGEYLLFTMIFVTLSIVITVFVL
cheeeeeecccccccccchhhhhhhhhhhhcccchhhhhhhhhhhhhhhhhhhhhhhhhhhhhheh
NVHHRSPSTHTMPHWVRGALLGCVPRWLLMNRPPPPVELCHPLRLKLSPSYHWLESNVDAEEREVVVEEE
hcccccccccccchecccchceeccccccccccccccceeeccccccccccccchhhhehhhh
DRWACAGHVAPSVGTLCSHGHLHSGASGPKAEALLQEGELLLSPHMQKALEGVHYIADHLRSEDADSSVK
hhhhhccccccchhhhhhhhhhhhhhhhhhhhccccchhhhhchhhhhcccchhehhcccccccchh
EDWKYVAMVIDRIFLWLFIIVCFLGTIGLFLPPFLAGMI
hhhhhhhhhhhhhhhhhhhhhhhhhhhhcccc
``` c: random coil (45.94%)
e: extended strand (12.67%)
h: alpha helix (41.40%)

Expression of 205P1B5 in Prostate Cancer Metastasis Specimens

Expression of 205P1B5 Enhances Proliferation of 3T3 Cells

SEQUENCE LISTING

```
<160> NUMBER OF SEQ ID NOS: 736

<210> SEQ ID NO 1
<211> LENGTH: 9
<212> TYPE: PRT
<213> ORGANISM: Homo sapiens

<400> SEQUENCE: 1

Ser Ile Asp Val Thr Phe Phe Pro Phe
 1               5

<210> SEQ ID NO 2
<211> LENGTH: 9
<212> TYPE: PRT
<213> ORGANISM: Homo sapiens

<400> SEQUENCE: 2

His Thr Glu Thr Glu Asp Arg Leu Phe
```

```
                1               5

<210> SEQ ID NO 3
<211> LENGTH: 9
<212> TYPE: PRT
<213> ORGANISM: Homo sapiens

<400> SEQUENCE: 3

Thr Ser Asp Val Val Ile Val Arg Phe
 1               5

<210> SEQ ID NO 4
<211> LENGTH: 9
<212> TYPE: PRT
<213> ORGANISM: Homo sapiens

<400> SEQUENCE: 4

Glu Thr Glu Asp Arg Leu Phe Lys His
 1               5

<210> SEQ ID NO 5
<211> LENGTH: 9
<212> TYPE: PRT
<213> ORGANISM: Homo sapiens

<400> SEQUENCE: 5

Gln Met Glu Gln Thr Val Asp Leu Lys
 1               5

<210> SEQ ID NO 6
<211> LENGTH: 9
<212> TYPE: PRT
<213> ORGANISM: Homo sapiens

<400> SEQUENCE: 6

Leu Val Ile Pro Leu Ile Gly Glu Tyr
 1               5

<210> SEQ ID NO 7
<211> LENGTH: 9
<212> TYPE: PRT
<213> ORGANISM: Homo sapiens

<400> SEQUENCE: 7

Lys Ile Asp Leu Glu Gln Met Glu Gln
 1               5

<210> SEQ ID NO 8
<211> LENGTH: 9
<212> TYPE: PRT
<213> ORGANISM: Homo sapiens

<400> SEQUENCE: 8

Ile Thr Glu Ile Ile Pro Ser Thr Ser
 1               5

<210> SEQ ID NO 9
<211> LENGTH: 9
<212> TYPE: PRT
<213> ORGANISM: Homo sapiens

<400> SEQUENCE: 9

Pro Val Glu Leu Cys His Pro Leu Arg
 1               5
```

```
<210> SEQ ID NO 10
<211> LENGTH: 9
<212> TYPE: PRT
<213> ORGANISM: Homo sapiens

<400> SEQUENCE: 10

Ala Leu Glu Gly Val His Tyr Ile Ala
1               5

<210> SEQ ID NO 11
<211> LENGTH: 9
<212> TYPE: PRT
<213> ORGANISM: Homo sapiens

<400> SEQUENCE: 11

Asp Ala Glu Glu Arg Glu Val Val Val
1               5

<210> SEQ ID NO 12
<211> LENGTH: 9
<212> TYPE: PRT
<213> ORGANISM: Homo sapiens

<400> SEQUENCE: 12

Arg Ser Glu Asp Ala Asp Ser Ser Val
1               5

<210> SEQ ID NO 13
<211> LENGTH: 9
<212> TYPE: PRT
<213> ORGANISM: Homo sapiens

<400> SEQUENCE: 13

Lys Tyr Asp Cys Cys Ala Glu Ile Tyr
1               5

<210> SEQ ID NO 14
<211> LENGTH: 9
<212> TYPE: PRT
<213> ORGANISM: Homo sapiens

<400> SEQUENCE: 14

Asn Thr Ser Asp Val Val Ile Val Arg
1               5

<210> SEQ ID NO 15
<211> LENGTH: 9
<212> TYPE: PRT
<213> ORGANISM: Homo sapiens

<400> SEQUENCE: 15

Val Thr Tyr Ala Phe Val Ile Arg Arg
1               5

<210> SEQ ID NO 16
<211> LENGTH: 9
<212> TYPE: PRT
<213> ORGANISM: Homo sapiens

<400> SEQUENCE: 16

Ile Gly Glu Tyr Leu Leu Phe Thr Met
1               5

<210> SEQ ID NO 17
```

```
<211> LENGTH: 9
<212> TYPE: PRT
<213> ORGANISM: Homo sapiens

<400> SEQUENCE: 17

Ser Cys Leu Thr Val Leu Val Phe Tyr
1               5

<210> SEQ ID NO 18
<211> LENGTH: 9
<212> TYPE: PRT
<213> ORGANISM: Homo sapiens

<400> SEQUENCE: 18

Asn Ala Asp Gly Glu Phe Ala Val Thr
1               5

<210> SEQ ID NO 19
<211> LENGTH: 9
<212> TYPE: PRT
<213> ORGANISM: Homo sapiens

<400> SEQUENCE: 19

Leu Leu Leu Ser Pro His Met Gln Lys
1               5

<210> SEQ ID NO 20
<211> LENGTH: 9
<212> TYPE: PRT
<213> ORGANISM: Homo sapiens

<400> SEQUENCE: 20

Cys Ala Glu Ile Tyr Pro Asp Val Thr
1               5

<210> SEQ ID NO 21
<211> LENGTH: 9
<212> TYPE: PRT
<213> ORGANISM: Homo sapiens

<400> SEQUENCE: 21

Val Val Glu Glu Glu Asp Arg Trp Ala
1               5

<210> SEQ ID NO 22
<211> LENGTH: 9
<212> TYPE: PRT
<213> ORGANISM: Homo sapiens

<400> SEQUENCE: 22

Lys Ala Glu Ala Leu Leu Gln Glu Gly
1               5

<210> SEQ ID NO 23
<211> LENGTH: 9
<212> TYPE: PRT
<213> ORGANISM: Homo sapiens

<400> SEQUENCE: 23

Asp Leu Glu Gln Met Glu Gln Thr Val
1               5

<210> SEQ ID NO 24
<211> LENGTH: 9
<212> TYPE: PRT
```

<213> ORGANISM: Homo sapiens

<400> SEQUENCE: 24

Pro Ser Cys Pro Val Phe Leu Ser Phe
1               5

<210> SEQ ID NO 25
<211> LENGTH: 9
<212> TYPE: PRT
<213> ORGANISM: Homo sapiens

<400> SEQUENCE: 25

Trp Ser Asp Tyr Lys Leu Arg Trp Asn
1               5

<210> SEQ ID NO 26
<211> LENGTH: 9
<212> TYPE: PRT
<213> ORGANISM: Homo sapiens

<400> SEQUENCE: 26

Ile Ser Cys Leu Thr Val Leu Val Phe
1               5

<210> SEQ ID NO 27
<211> LENGTH: 9
<212> TYPE: PRT
<213> ORGANISM: Homo sapiens

<400> SEQUENCE: 27

Leu Gln Glu Gly Glu Leu Leu Leu Ser
1               5

<210> SEQ ID NO 28
<211> LENGTH: 9
<212> TYPE: PRT
<213> ORGANISM: Homo sapiens

<400> SEQUENCE: 28

Pro Thr Asp Phe Gly Asn Ile Thr Ser
1               5

<210> SEQ ID NO 29
<211> LENGTH: 9
<212> TYPE: PRT
<213> ORGANISM: Homo sapiens

<400> SEQUENCE: 29

Ala Ile Val Asn Ala Thr Gly Thr Tyr
1               5

<210> SEQ ID NO 30
<211> LENGTH: 9
<212> TYPE: PRT
<213> ORGANISM: Homo sapiens

<400> SEQUENCE: 30

Leu Ile Asp Val Asp Glu Lys Asn Gln
1               5

<210> SEQ ID NO 31
<211> LENGTH: 9
<212> TYPE: PRT
<213> ORGANISM: Homo sapiens

```
<400> SEQUENCE: 31

Leu Cys His Pro Leu Arg Leu Lys Leu
1               5

<210> SEQ ID NO 32
<211> LENGTH: 9
<212> TYPE: PRT
<213> ORGANISM: Homo sapiens

<400> SEQUENCE: 32

Asn Val Asp Ala Glu Glu Arg Glu Val
1               5

<210> SEQ ID NO 33
<211> LENGTH: 9
<212> TYPE: PRT
<213> ORGANISM: Homo sapiens

<400> SEQUENCE: 33

Gly Cys Val Pro Arg Trp Leu Leu Met
1               5

<210> SEQ ID NO 34
<211> LENGTH: 9
<212> TYPE: PRT
<213> ORGANISM: Homo sapiens

<400> SEQUENCE: 34

Asp Val Asp Glu Lys Asn Gln Met Met
1               5

<210> SEQ ID NO 35
<211> LENGTH: 9
<212> TYPE: PRT
<213> ORGANISM: Homo sapiens

<400> SEQUENCE: 35

His Thr Met Pro His Trp Val Arg Gly
1               5

<210> SEQ ID NO 36
<211> LENGTH: 9
<212> TYPE: PRT
<213> ORGANISM: Homo sapiens

<400> SEQUENCE: 36

Ser Glu Asp Ala Asp Ser Ser Val Lys
1               5

<210> SEQ ID NO 37
<211> LENGTH: 9
<212> TYPE: PRT
<213> ORGANISM: Homo sapiens

<400> SEQUENCE: 37

Ala Thr Gly Thr Tyr Asn Ser Lys Lys
1               5

<210> SEQ ID NO 38
<211> LENGTH: 9
<212> TYPE: PRT
<213> ORGANISM: Homo sapiens

<400> SEQUENCE: 38
```

His Trp Val Pro Ala Ile Tyr Lys
1               5

<210> SEQ ID NO 39
<211> LENGTH: 9
<212> TYPE: PRT
<213> ORGANISM: Homo sapiens

<400> SEQUENCE: 39

Leu Ile Ile Pro Cys Leu Leu Ile Ser
1               5

<210> SEQ ID NO 40
<211> LENGTH: 9
<212> TYPE: PRT
<213> ORGANISM: Homo sapiens

<400> SEQUENCE: 40

Ile Trp Ile Pro Asp Ile Val Leu Tyr
1               5

<210> SEQ ID NO 41
<211> LENGTH: 9
<212> TYPE: PRT
<213> ORGANISM: Homo sapiens

<400> SEQUENCE: 41

Ser Gly Glu Trp Ala Ile Val Asn Ala
1               5

<210> SEQ ID NO 42
<211> LENGTH: 9
<212> TYPE: PRT
<213> ORGANISM: Homo sapiens

<400> SEQUENCE: 42

Asp Ser Ser Val Lys Glu Asp Trp Lys
1               5

<210> SEQ ID NO 43
<211> LENGTH: 9
<212> TYPE: PRT
<213> ORGANISM: Homo sapiens

<400> SEQUENCE: 43

Ser Ser Cys Ser Ile Asp Val Thr Phe
1               5

<210> SEQ ID NO 44
<211> LENGTH: 9
<212> TYPE: PRT
<213> ORGANISM: Homo sapiens

<400> SEQUENCE: 44

Lys Gln Glu Trp Ser Asp Tyr Lys Leu
1               5

<210> SEQ ID NO 45
<211> LENGTH: 9
<212> TYPE: PRT
<213> ORGANISM: Homo sapiens

<400> SEQUENCE: 45

Ile Pro Asp Ile Val Leu Tyr Asn Asn
1               5

<210> SEQ ID NO 46
<211> LENGTH: 9
<212> TYPE: PRT
<213> ORGANISM: Homo sapiens

<400> SEQUENCE: 46

Val Ile Asp Arg Ile Phe Leu Trp Leu
1               5

<210> SEQ ID NO 47
<211> LENGTH: 9
<212> TYPE: PRT
<213> ORGANISM: Homo sapiens

<400> SEQUENCE: 47

Cys Pro Val Phe Leu Ser Phe Thr Lys
1               5

<210> SEQ ID NO 48
<211> LENGTH: 9
<212> TYPE: PRT
<213> ORGANISM: Homo sapiens

<400> SEQUENCE: 48

Tyr Pro Asp Val Thr Tyr Ala Phe Val
1               5

<210> SEQ ID NO 49
<211> LENGTH: 9
<212> TYPE: PRT
<213> ORGANISM: Homo sapiens

<400> SEQUENCE: 49

Glu Gly Glu Leu Leu Leu Ser Pro His
1               5

<210> SEQ ID NO 50
<211> LENGTH: 9
<212> TYPE: PRT
<213> ORGANISM: Homo sapiens

<400> SEQUENCE: 50

Asp Gly Glu Phe Ala Val Thr His Met
1               5

<210> SEQ ID NO 51
<211> LENGTH: 10
<212> TYPE: PRT
<213> ORGANISM: Homo sapiens

<400> SEQUENCE: 51

His Thr Glu Thr Glu Asp Arg Leu Phe Lys
1               5                   10

<210> SEQ ID NO 52
<211> LENGTH: 10
<212> TYPE: PRT
<213> ORGANISM: Homo sapiens

<400> SEQUENCE: 52

Cys Ala Glu Ile Tyr Pro Asp Val Thr Tyr
1               5                   10

```
<210> SEQ ID NO 53
<211> LENGTH: 10
<212> TYPE: PRT
<213> ORGANISM: Homo sapiens

<400> SEQUENCE: 53

Arg Ser Glu Asp Ala Asp Ser Ser Val Lys
 1               5                  10

<210> SEQ ID NO 54
<211> LENGTH: 10
<212> TYPE: PRT
<213> ORGANISM: Homo sapiens

<400> SEQUENCE: 54

Asp Val Asp Glu Lys Asn Gln Met Met Thr
 1               5                  10

<210> SEQ ID NO 55
<211> LENGTH: 10
<212> TYPE: PRT
<213> ORGANISM: Homo sapiens

<400> SEQUENCE: 55

Glu Thr Glu Asp Arg Leu Phe Lys His Leu
 1               5                  10

<210> SEQ ID NO 56
<211> LENGTH: 10
<212> TYPE: PRT
<213> ORGANISM: Homo sapiens

<400> SEQUENCE: 56

Ile Thr Glu Ile Ile Pro Ser Thr Ser Leu
 1               5                  10

<210> SEQ ID NO 57
<211> LENGTH: 10
<212> TYPE: PRT
<213> ORGANISM: Homo sapiens

<400> SEQUENCE: 57

Glu Ile Tyr Pro Asp Val Thr Tyr Ala Phe
 1               5                  10

<210> SEQ ID NO 58
<211> LENGTH: 10
<212> TYPE: PRT
<213> ORGANISM: Homo sapiens

<400> SEQUENCE: 58

Ile Ser Cys Leu Thr Val Leu Val Phe Tyr
 1               5                  10

<210> SEQ ID NO 59
<211> LENGTH: 10
<212> TYPE: PRT
<213> ORGANISM: Homo sapiens

<400> SEQUENCE: 59

Lys Gln Glu Trp Ser Asp Tyr Lys Leu Arg
 1               5                  10

<210> SEQ ID NO 60
<211> LENGTH: 10
```

-continued

```
<212> TYPE: PRT
<213> ORGANISM: Homo sapiens

<400> SEQUENCE: 60

Ala Thr Gly Thr Tyr Asn Ser Lys Lys Tyr
1               5                   10

<210> SEQ ID NO 61
<211> LENGTH: 10
<212> TYPE: PRT
<213> ORGANISM: Homo sapiens

<400> SEQUENCE: 61

Asn Ala Asp Gly Glu Phe Ala Val Thr His
1               5                   10

<210> SEQ ID NO 62
<211> LENGTH: 10
<212> TYPE: PRT
<213> ORGANISM: Homo sapiens

<400> SEQUENCE: 62

Thr Val His Trp Val Pro Pro Ala Ile Tyr
1               5                   10

<210> SEQ ID NO 63
<211> LENGTH: 10
<212> TYPE: PRT
<213> ORGANISM: Homo sapiens

<400> SEQUENCE: 63

Ser Cys Pro Val Phe Leu Ser Phe Thr Lys
1               5                   10

<210> SEQ ID NO 64
<211> LENGTH: 10
<212> TYPE: PRT
<213> ORGANISM: Homo sapiens

<400> SEQUENCE: 64

Glu Leu Leu Leu Ser Pro His Met Gln Lys
1               5                   10

<210> SEQ ID NO 65
<211> LENGTH: 10
<212> TYPE: PRT
<213> ORGANISM: Homo sapiens

<400> SEQUENCE: 65

Val Val Glu Glu Glu Asp Arg Trp Ala Cys
1               5                   10

<210> SEQ ID NO 66
<211> LENGTH: 10
<212> TYPE: PRT
<213> ORGANISM: Homo sapiens

<400> SEQUENCE: 66

Gly Glu Glu Ala Lys Arg Pro Pro Pro Arg
1               5                   10

<210> SEQ ID NO 67
<211> LENGTH: 10
<212> TYPE: PRT
<213> ORGANISM: Homo sapiens
```

```
<400> SEQUENCE: 67

Asp Ser Ser Val Lys Glu Asp Trp Lys Tyr
1               5                   10

<210> SEQ ID NO 68
<211> LENGTH: 10
<212> TYPE: PRT
<213> ORGANISM: Homo sapiens

<400> SEQUENCE: 68

Cys Ser Ile Asp Val Thr Phe Phe Pro Phe
1               5                   10

<210> SEQ ID NO 69
<211> LENGTH: 10
<212> TYPE: PRT
<213> ORGANISM: Homo sapiens

<400> SEQUENCE: 69

Thr Ser Asp Val Val Ile Val Arg Phe Gly
1               5                   10

<210> SEQ ID NO 70
<211> LENGTH: 10
<212> TYPE: PRT
<213> ORGANISM: Homo sapiens

<400> SEQUENCE: 70

Tyr Pro Asp Val Thr Tyr Ala Phe Val Ile
1               5                   10

<210> SEQ ID NO 71
<211> LENGTH: 10
<212> TYPE: PRT
<213> ORGANISM: Homo sapiens

<400> SEQUENCE: 71

Leu Ile Asp Val Asp Glu Lys Asn Gln Met
1               5                   10

<210> SEQ ID NO 72
<211> LENGTH: 10
<212> TYPE: PRT
<213> ORGANISM: Homo sapiens

<400> SEQUENCE: 72

Ile Ala Asp His Leu Arg Ser Glu Asp Ala
1               5                   10

<210> SEQ ID NO 73
<211> LENGTH: 10
<212> TYPE: PRT
<213> ORGANISM: Homo sapiens

<400> SEQUENCE: 73

Leu Ile Ser Cys Leu Thr Val Leu Val Phe
1               5                   10

<210> SEQ ID NO 74
<211> LENGTH: 10
<212> TYPE: PRT
<213> ORGANISM: Homo sapiens

<400> SEQUENCE: 74
```

```
Asp Ala Asp Ser Ser Val Lys Glu Asp Trp
1               5                   10
```

<210> SEQ ID NO 75
<211> LENGTH: 10
<212> TYPE: PRT
<213> ORGANISM: Homo sapiens

<400> SEQUENCE: 75

```
Gly Cys Val Pro Arg Trp Leu Leu Met Asn
1               5                   10
```

<210> SEQ ID NO 76
<211> LENGTH: 10
<212> TYPE: PRT
<213> ORGANISM: Homo sapiens

<400> SEQUENCE: 76

```
Ser Leu Val Ile Pro Leu Ile Gly Glu Tyr
1               5                   10
```

<210> SEQ ID NO 77
<211> LENGTH: 10
<212> TYPE: PRT
<213> ORGANISM: Homo sapiens

<400> SEQUENCE: 77

```
Val Ile Asp Arg Ile Phe Leu Trp Leu Phe
1               5                   10
```

<210> SEQ ID NO 78
<211> LENGTH: 10
<212> TYPE: PRT
<213> ORGANISM: Homo sapiens

<400> SEQUENCE: 78

```
Gly Thr Ile Gly Leu Phe Leu Pro Pro Phe
1               5                   10
```

<210> SEQ ID NO 79
<211> LENGTH: 10
<212> TYPE: PRT
<213> ORGANISM: Homo sapiens

<400> SEQUENCE: 79

```
Asp Val Thr Tyr Ala Phe Val Ile Arg Arg
1               5                   10
```

<210> SEQ ID NO 80
<211> LENGTH: 10
<212> TYPE: PRT
<213> ORGANISM: Homo sapiens

<400> SEQUENCE: 80

```
Asn Val Asp Ala Glu Glu Arg Glu Val Val
1               5                   10
```

<210> SEQ ID NO 81
<211> LENGTH: 10
<212> TYPE: PRT
<213> ORGANISM: Homo sapiens

<400> SEQUENCE: 81

Glu Ile Ile Pro Ser Thr Ser Leu Val Ile

```
1               5                   10

<210> SEQ ID NO 82
<211> LENGTH: 10
<212> TYPE: PRT
<213> ORGANISM: Homo sapiens

<400> SEQUENCE: 82

Lys Ile Asp Leu Glu Gln Met Glu Gln Thr
1               5                   10

<210> SEQ ID NO 83
<211> LENGTH: 10
<212> TYPE: PRT
<213> ORGANISM: Homo sapiens

<400> SEQUENCE: 83

Asn Thr Ser Asp Val Val Ile Val Arg Phe
1               5                   10

<210> SEQ ID NO 84
<211> LENGTH: 10
<212> TYPE: PRT
<213> ORGANISM: Homo sapiens

<400> SEQUENCE: 84

Thr Val Asp Leu Lys Asp Tyr Trp Glu Ser
1               5                   10

<210> SEQ ID NO 85
<211> LENGTH: 10
<212> TYPE: PRT
<213> ORGANISM: Homo sapiens

<400> SEQUENCE: 85

Leu Ile Ile Pro Cys Leu Leu Ile Ser Cys
1               5                   10

<210> SEQ ID NO 86
<211> LENGTH: 10
<212> TYPE: PRT
<213> ORGANISM: Homo sapiens

<400> SEQUENCE: 86

Trp Ala Ile Val Asn Ala Thr Gly Thr Tyr
1               5                   10

<210> SEQ ID NO 87
<211> LENGTH: 10
<212> TYPE: PRT
<213> ORGANISM: Homo sapiens

<400> SEQUENCE: 87

Leu Thr Pro Ala Gly Gly Glu Glu Ala Lys
1               5                   10

<210> SEQ ID NO 88
<211> LENGTH: 10
<212> TYPE: PRT
<213> ORGANISM: Homo sapiens

<400> SEQUENCE: 88

Pro Val Glu Leu Cys His Pro Leu Arg Leu
1               5                   10
```

```
<210> SEQ ID NO 89
<211> LENGTH: 10
<212> TYPE: PRT
<213> ORGANISM: Homo sapiens

<400> SEQUENCE: 89

Glu Gly Glu Leu Leu Leu Ser Pro His Met
1               5                   10

<210> SEQ ID NO 90
<211> LENGTH: 10
<212> TYPE: PRT
<213> ORGANISM: Homo sapiens

<400> SEQUENCE: 90

Ala Leu Glu Gly Val His Tyr Ile Ala Asp
1               5                   10

<210> SEQ ID NO 91
<211> LENGTH: 10
<212> TYPE: PRT
<213> ORGANISM: Homo sapiens

<400> SEQUENCE: 91

Pro Ser Asp Cys Gly Glu Lys Ile Thr Leu
1               5                   10

<210> SEQ ID NO 92
<211> LENGTH: 10
<212> TYPE: PRT
<213> ORGANISM: Homo sapiens

<400> SEQUENCE: 92

Ala Ser Gly Pro Lys Ala Glu Ala Leu Leu
1               5                   10

<210> SEQ ID NO 93
<211> LENGTH: 10
<212> TYPE: PRT
<213> ORGANISM: Homo sapiens

<400> SEQUENCE: 93

Lys Ser Ser Cys Ser Ile Asp Val Thr Phe
1               5                   10

<210> SEQ ID NO 94
<211> LENGTH: 10
<212> TYPE: PRT
<213> ORGANISM: Homo sapiens

<400> SEQUENCE: 94

Pro Ser Glu Met Ile Trp Ile Pro Asp Ile
1               5                   10

<210> SEQ ID NO 95
<211> LENGTH: 10
<212> TYPE: PRT
<213> ORGANISM: Homo sapiens

<400> SEQUENCE: 95

His Thr Met Pro His Trp Val Arg Gly Ala
1               5                   10

<210> SEQ ID NO 96
```

```
<211> LENGTH: 10
<212> TYPE: PRT
<213> ORGANISM: Homo sapiens

<400> SEQUENCE: 96

Ser Thr His Thr Met Pro His Trp Val Arg
1               5                   10

<210> SEQ ID NO 97
<211> LENGTH: 10
<212> TYPE: PRT
<213> ORGANISM: Homo sapiens

<400> SEQUENCE: 97

Val Thr His Met Thr Lys Ala His Leu Phe
1               5                   10

<210> SEQ ID NO 98
<211> LENGTH: 10
<212> TYPE: PRT
<213> ORGANISM: Homo sapiens

<400> SEQUENCE: 98

Val Thr Leu Ser Ile Val Ile Thr Val Phe
1               5                   10

<210> SEQ ID NO 99
<211> LENGTH: 10
<212> TYPE: PRT
<213> ORGANISM: Homo sapiens

<400> SEQUENCE: 99

Phe Val Ile Arg Arg Leu Pro Leu Phe Tyr
1               5                   10

<210> SEQ ID NO 100
<211> LENGTH: 10
<212> TYPE: PRT
<213> ORGANISM: Homo sapiens

<400> SEQUENCE: 100

Ser Gly Glu Trp Ala Ile Val Asn Ala Thr
1               5                   10

<210> SEQ ID NO 101
<211> LENGTH: 9
<212> TYPE: PRT
<213> ORGANISM: Homo sapiens

<400> SEQUENCE: 101

Tyr Leu Leu Phe Thr Met Ile Phe Val
1               5

<210> SEQ ID NO 102
<211> LENGTH: 9
<212> TYPE: PRT
<213> ORGANISM: Homo sapiens

<400> SEQUENCE: 102

Trp Leu Phe Ile Ile Val Cys Phe Leu
1               5

<210> SEQ ID NO 103
<211> LENGTH: 9
<212> TYPE: PRT
```

```
<213> ORGANISM: Homo sapiens

<400> SEQUENCE: 103

Cys Leu Thr Val Leu Val Phe Tyr Leu
 1               5

<210> SEQ ID NO 104
<211> LENGTH: 9
<212> TYPE: PRT
<213> ORGANISM: Homo sapiens

<400> SEQUENCE: 104

Val Leu Leu Ser Leu Thr Val Phe Leu
 1               5

<210> SEQ ID NO 105
<211> LENGTH: 9
<212> TYPE: PRT
<213> ORGANISM: Homo sapiens

<400> SEQUENCE: 105

Phe Leu Trp Leu Phe Ile Ile Val Cys
 1               5

<210> SEQ ID NO 106
<211> LENGTH: 9
<212> TYPE: PRT
<213> ORGANISM: Homo sapiens

<400> SEQUENCE: 106

Lys Leu Ser Pro Ser Tyr His Trp Leu
 1               5

<210> SEQ ID NO 107
<211> LENGTH: 9
<212> TYPE: PRT
<213> ORGANISM: Homo sapiens

<400> SEQUENCE: 107

Phe Leu Gly Thr Ile Gly Leu Phe Leu
 1               5

<210> SEQ ID NO 108
<211> LENGTH: 9
<212> TYPE: PRT
<213> ORGANISM: Homo sapiens

<400> SEQUENCE: 108

Leu Leu Ser Leu Thr Val Phe Leu Leu
 1               5

<210> SEQ ID NO 109
<211> LENGTH: 9
<212> TYPE: PRT
<213> ORGANISM: Homo sapiens

<400> SEQUENCE: 109

Gln Met Met Thr Thr Asn Val Trp Leu
 1               5

<210> SEQ ID NO 110
<211> LENGTH: 9
<212> TYPE: PRT
<213> ORGANISM: Homo sapiens
```

```
<400> SEQUENCE: 110

Cys Leu Leu Ile Ser Cys Leu Thr Val
1               5

<210> SEQ ID NO 111
<211> LENGTH: 9
<212> TYPE: PRT
<213> ORGANISM: Homo sapiens

<400> SEQUENCE: 111

Leu Leu Phe Thr Met Ile Phe Val Thr
1               5

<210> SEQ ID NO 112
<211> LENGTH: 9
<212> TYPE: PRT
<213> ORGANISM: Homo sapiens

<400> SEQUENCE: 112

Phe Leu Pro Pro Phe Leu Ala Gly Met
1               5

<210> SEQ ID NO 113
<211> LENGTH: 9
<212> TYPE: PRT
<213> ORGANISM: Homo sapiens

<400> SEQUENCE: 113

Leu Leu Gln Glu Gly Glu Leu Leu Leu
1               5

<210> SEQ ID NO 114
<211> LENGTH: 9
<212> TYPE: PRT
<213> ORGANISM: Homo sapiens

<400> SEQUENCE: 114

Val Ile Thr Val Phe Val Leu Asn Val
1               5

<210> SEQ ID NO 115
<211> LENGTH: 9
<212> TYPE: PRT
<213> ORGANISM: Homo sapiens

<400> SEQUENCE: 115

Lys Leu Ser Leu Trp Trp Leu Leu Leu
1               5

<210> SEQ ID NO 116
<211> LENGTH: 9
<212> TYPE: PRT
<213> ORGANISM: Homo sapiens

<400> SEQUENCE: 116

Gly Leu Phe Leu Pro Pro Phe Leu Ala
1               5

<210> SEQ ID NO 117
<211> LENGTH: 9
<212> TYPE: PRT
<213> ORGANISM: Homo sapiens

<400> SEQUENCE: 117
```

```
Phe Leu Ser Phe Thr Lys Leu Ser Leu
 1               5

<210> SEQ ID NO 118
<211> LENGTH: 9
<212> TYPE: PRT
<213> ORGANISM: Homo sapiens

<400> SEQUENCE: 118

Lys Ala Leu Glu Gly Val His Tyr Ile
 1               5

<210> SEQ ID NO 119
<211> LENGTH: 9
<212> TYPE: PRT
<213> ORGANISM: Homo sapiens

<400> SEQUENCE: 119

Ser Leu Thr Val Phe Leu Leu Leu Ile
 1               5

<210> SEQ ID NO 120
<211> LENGTH: 9
<212> TYPE: PRT
<213> ORGANISM: Homo sapiens

<400> SEQUENCE: 120

Leu Ile Gly Glu Tyr Leu Leu Phe Thr
 1               5

<210> SEQ ID NO 121
<211> LENGTH: 9
<212> TYPE: PRT
<213> ORGANISM: Homo sapiens

<400> SEQUENCE: 121

Leu Met Asn Arg Pro Pro Pro Val
 1               5

<210> SEQ ID NO 122
<211> LENGTH: 9
<212> TYPE: PRT
<213> ORGANISM: Homo sapiens

<400> SEQUENCE: 122

Ala Met Val Ile Asp Arg Ile Phe Leu
 1               5

<210> SEQ ID NO 123
<211> LENGTH: 9
<212> TYPE: PRT
<213> ORGANISM: Homo sapiens

<400> SEQUENCE: 123

Met Ile Phe Val Thr Leu Ser Ile Val
 1               5

<210> SEQ ID NO 124
<211> LENGTH: 9
<212> TYPE: PRT
<213> ORGANISM: Homo sapiens

<400> SEQUENCE: 124

Leu Leu Gly Cys Val Pro Arg Trp Leu
 1               5
```

<210> SEQ ID NO 125
<211> LENGTH: 9
<212> TYPE: PRT
<213> ORGANISM: Homo sapiens

<400> SEQUENCE: 125

Ala Leu Leu Gln Glu Gly Glu Leu Leu
1               5

<210> SEQ ID NO 126
<211> LENGTH: 9
<212> TYPE: PRT
<213> ORGANISM: Homo sapiens

<400> SEQUENCE: 126

Phe Leu Leu Leu Ile Thr Glu Ile Ile
1               5

<210> SEQ ID NO 127
<211> LENGTH: 9
<212> TYPE: PRT
<213> ORGANISM: Homo sapiens

<400> SEQUENCE: 127

Leu Leu Ile Ser Cys Leu Thr Val Leu
1               5

<210> SEQ ID NO 128
<211> LENGTH: 9
<212> TYPE: PRT
<213> ORGANISM: Homo sapiens

<400> SEQUENCE: 128

Arg Ile Phe Leu Trp Leu Phe Ile Ile
1               5

<210> SEQ ID NO 129
<211> LENGTH: 9
<212> TYPE: PRT
<213> ORGANISM: Homo sapiens

<400> SEQUENCE: 129

Phe Ser Thr Gly Thr Val His Trp Val
1               5

<210> SEQ ID NO 130
<211> LENGTH: 9
<212> TYPE: PRT
<213> ORGANISM: Homo sapiens

<400> SEQUENCE: 130

Val Ile Asp Arg Ile Phe Leu Trp Leu
1               5

<210> SEQ ID NO 131
<211> LENGTH: 9
<212> TYPE: PRT
<213> ORGANISM: Homo sapiens

<400> SEQUENCE: 131

Leu Leu Ser Pro His Met Gln Lys Ala
1               5

-continued

```
<210> SEQ ID NO 132
<211> LENGTH: 9
<212> TYPE: PRT
<213> ORGANISM: Homo sapiens

<400> SEQUENCE: 132

Met Ile Trp Ile Pro Asp Ile Val Leu
 1               5

<210> SEQ ID NO 133
<211> LENGTH: 9
<212> TYPE: PRT
<213> ORGANISM: Homo sapiens

<400> SEQUENCE: 133

Leu Ile Thr Glu Ile Ile Pro Ser Thr
 1               5

<210> SEQ ID NO 134
<211> LENGTH: 9
<212> TYPE: PRT
<213> ORGANISM: Homo sapiens

<400> SEQUENCE: 134

Leu Ile Ser Cys Leu Thr Val Leu Val
 1               5

<210> SEQ ID NO 135
<211> LENGTH: 9
<212> TYPE: PRT
<213> ORGANISM: Homo sapiens

<400> SEQUENCE: 135

Ser Ile Val Ile Thr Val Phe Val Leu
 1               5

<210> SEQ ID NO 136
<211> LENGTH: 9
<212> TYPE: PRT
<213> ORGANISM: Homo sapiens

<400> SEQUENCE: 136

Val Thr Leu Ser Ile Val Ile Thr Val
 1               5

<210> SEQ ID NO 137
<211> LENGTH: 9
<212> TYPE: PRT
<213> ORGANISM: Homo sapiens

<400> SEQUENCE: 137

Val Ile Pro Leu Ile Gly Glu Tyr Leu
 1               5

<210> SEQ ID NO 138
<211> LENGTH: 9
<212> TYPE: PRT
<213> ORGANISM: Homo sapiens

<400> SEQUENCE: 138

Arg Val Pro Ser Glu Met Ile Trp Ile
 1               5

<210> SEQ ID NO 139
<211> LENGTH: 9
```

```
<212> TYPE: PRT
<213> ORGANISM: Homo sapiens

<400> SEQUENCE: 139

Asn Asn Ala Asp Gly Glu Phe Ala Val
1               5

<210> SEQ ID NO 140
<211> LENGTH: 9
<212> TYPE: PRT
<213> ORGANISM: Homo sapiens

<400> SEQUENCE: 140

Asn Leu Ile Ile Pro Cys Leu Leu Ile
1               5

<210> SEQ ID NO 141
<211> LENGTH: 9
<212> TYPE: PRT
<213> ORGANISM: Homo sapiens

<400> SEQUENCE: 141

Lys Ile Thr Leu Cys Ile Ser Val Leu
1               5

<210> SEQ ID NO 142
<211> LENGTH: 9
<212> TYPE: PRT
<213> ORGANISM: Homo sapiens

<400> SEQUENCE: 142

Val Ile Val Arg Phe Gly Leu Ser Ile
1               5

<210> SEQ ID NO 143
<211> LENGTH: 9
<212> TYPE: PRT
<213> ORGANISM: Homo sapiens

<400> SEQUENCE: 143

Phe Ile Ile Val Cys Phe Leu Gly Thr
1               5

<210> SEQ ID NO 144
<211> LENGTH: 9
<212> TYPE: PRT
<213> ORGANISM: Homo sapiens

<400> SEQUENCE: 144

Ser Val Lys Glu Asp Trp Lys Tyr Val
1               5

<210> SEQ ID NO 145
<211> LENGTH: 9
<212> TYPE: PRT
<213> ORGANISM: Homo sapiens

<400> SEQUENCE: 145

Thr Met Ile Phe Val Thr Leu Ser Ile
1               5

<210> SEQ ID NO 146
<211> LENGTH: 9
<212> TYPE: PRT
<213> ORGANISM: Homo sapiens
```

```
<400> SEQUENCE: 146

Ala Leu Pro Gln Gly Gly Ser His Thr
1               5

<210> SEQ ID NO 147
<211> LENGTH: 9
<212> TYPE: PRT
<213> ORGANISM: Homo sapiens

<400> SEQUENCE: 147

Tyr Pro Asp Val Thr Tyr Ala Phe Val
1               5

<210> SEQ ID NO 148
<211> LENGTH: 9
<212> TYPE: PRT
<213> ORGANISM: Homo sapiens

<400> SEQUENCE: 148

Thr Ile Asn Leu Ile Ile Pro Cys Leu
1               5

<210> SEQ ID NO 149
<211> LENGTH: 9
<212> TYPE: PRT
<213> ORGANISM: Homo sapiens

<400> SEQUENCE: 149

Ser Thr His Thr Met Pro His Trp Val
1               5

<210> SEQ ID NO 150
<211> LENGTH: 9
<212> TYPE: PRT
<213> ORGANISM: Homo sapiens

<400> SEQUENCE: 150

Ile Gly Leu Phe Leu Pro Pro Phe Leu
1               5

<210> SEQ ID NO 151
<211> LENGTH: 10
<212> TYPE: PRT
<213> ORGANISM: Homo sapiens

<400> SEQUENCE: 151

Val Leu Leu Ser Leu Thr Val Phe Leu Leu
1               5                   10

<210> SEQ ID NO 152
<211> LENGTH: 10
<212> TYPE: PRT
<213> ORGANISM: Homo sapiens

<400> SEQUENCE: 152

Tyr Leu Leu Phe Thr Met Ile Phe Val Thr
1               5                   10

<210> SEQ ID NO 153
<211> LENGTH: 10
<212> TYPE: PRT
<213> ORGANISM: Homo sapiens

<400> SEQUENCE: 153
```

```
Leu Leu Met Asn Arg Pro Pro Pro Val
 1               5                  10
```

<210> SEQ ID NO 154
<211> LENGTH: 10
<212> TYPE: PRT
<213> ORGANISM: Homo sapiens

<400> SEQUENCE: 154

```
Thr Leu Ser Ile Val Ile Thr Val Phe Val
 1               5                  10
```

<210> SEQ ID NO 155
<211> LENGTH: 10
<212> TYPE: PRT
<213> ORGANISM: Homo sapiens

<400> SEQUENCE: 155

```
Leu Leu Gly Cys Val Pro Arg Trp Leu Leu
 1               5                  10
```

<210> SEQ ID NO 156
<211> LENGTH: 10
<212> TYPE: PRT
<213> ORGANISM: Homo sapiens

<400> SEQUENCE: 156

```
Leu Leu Phe Thr Met Ile Phe Val Thr Leu
 1               5                  10
```

<210> SEQ ID NO 157
<211> LENGTH: 10
<212> TYPE: PRT
<213> ORGANISM: Homo sapiens

<400> SEQUENCE: 157

```
Gly Leu Ser Ile Ala Gln Leu Ile Asp Val
 1               5                  10
```

<210> SEQ ID NO 158
<211> LENGTH: 10
<212> TYPE: PRT
<213> ORGANISM: Homo sapiens

<400> SEQUENCE: 158

```
Met Val Ile Asp Arg Ile Phe Leu Trp Leu
 1               5                  10
```

<210> SEQ ID NO 159
<211> LENGTH: 10
<212> TYPE: PRT
<213> ORGANISM: Homo sapiens

<400> SEQUENCE: 159

```
Leu Leu Ile Ser Cys Leu Thr Val Leu Val
 1               5                  10
```

<210> SEQ ID NO 160
<211> LENGTH: 10
<212> TYPE: PRT
<213> ORGANISM: Homo sapiens

<400> SEQUENCE: 160

```
Ser Leu Trp Trp Leu Leu Leu Thr Pro Ala
```

```
                1               5                  10

<210> SEQ ID NO 161
<211> LENGTH: 10
<212> TYPE: PRT
<213> ORGANISM: Homo sapiens

<400> SEQUENCE: 161

Ile Val Ile Thr Val Phe Val Leu Asn Val
 1               5                  10

<210> SEQ ID NO 162
<211> LENGTH: 10
<212> TYPE: PRT
<213> ORGANISM: Homo sapiens

<400> SEQUENCE: 162

Ala Leu Leu Gly Cys Val Pro Arg Trp Leu
 1               5                  10

<210> SEQ ID NO 163
<211> LENGTH: 10
<212> TYPE: PRT
<213> ORGANISM: Homo sapiens

<400> SEQUENCE: 163

Ala Leu Leu Gln Glu Gly Glu Leu Leu Leu
 1               5                  10

<210> SEQ ID NO 164
<211> LENGTH: 10
<212> TYPE: PRT
<213> ORGANISM: Homo sapiens

<400> SEQUENCE: 164

Cys Leu Leu Ile Ser Cys Leu Thr Val Leu
 1               5                  10

<210> SEQ ID NO 165
<211> LENGTH: 10
<212> TYPE: PRT
<213> ORGANISM: Homo sapiens

<400> SEQUENCE: 165

Leu Leu Leu Ser Pro His Met Gln Lys Ala
 1               5                  10

<210> SEQ ID NO 166
<211> LENGTH: 10
<212> TYPE: PRT
<213> ORGANISM: Homo sapiens

<400> SEQUENCE: 166

Leu Leu Ser Leu Thr Val Phe Leu Leu Leu
 1               5                  10

<210> SEQ ID NO 167
<211> LENGTH: 10
<212> TYPE: PRT
<213> ORGANISM: Homo sapiens

<400> SEQUENCE: 167

Phe Val Thr Leu Ser Ile Val Ile Thr Val
 1               5                  10
```

```
<210> SEQ ID NO 168
<211> LENGTH: 10
<212> TYPE: PRT
<213> ORGANISM: Homo sapiens

<400> SEQUENCE: 168

Leu Ile Gly Glu Tyr Leu Leu Phe Thr Met
1               5                   10

<210> SEQ ID NO 169
<211> LENGTH: 10
<212> TYPE: PRT
<213> ORGANISM: Homo sapiens

<400> SEQUENCE: 169

Lys Leu Ser Leu Trp Trp Leu Leu Leu Thr
1               5                   10

<210> SEQ ID NO 170
<211> LENGTH: 10
<212> TYPE: PRT
<213> ORGANISM: Homo sapiens

<400> SEQUENCE: 170

Thr Leu Cys Ile Ser Val Leu Leu Ser Leu
1               5                   10

<210> SEQ ID NO 171
<211> LENGTH: 10
<212> TYPE: PRT
<213> ORGANISM: Homo sapiens

<400> SEQUENCE: 171

Thr Met Ile Phe Val Thr Leu Ser Ile Val
1               5                   10

<210> SEQ ID NO 172
<211> LENGTH: 10
<212> TYPE: PRT
<213> ORGANISM: Homo sapiens

<400> SEQUENCE: 172

Asn Gln Met Met Thr Thr Asn Val Trp Leu
1               5                   10

<210> SEQ ID NO 173
<211> LENGTH: 10
<212> TYPE: PRT
<213> ORGANISM: Homo sapiens

<400> SEQUENCE: 173

Ser Val Leu Leu Ser Leu Thr Val Phe Leu
1               5                   10

<210> SEQ ID NO 174
<211> LENGTH: 10
<212> TYPE: PRT
<213> ORGANISM: Homo sapiens

<400> SEQUENCE: 174

Ser Cys Leu Thr Val Leu Val Phe Tyr Leu
1               5                   10

<210> SEQ ID NO 175
```

```
<211> LENGTH: 10
<212> TYPE: PRT
<213> ORGANISM: Homo sapiens

<400> SEQUENCE: 175

Leu Leu Ser Pro His Met Gln Lys Ala Leu
1               5                   10

<210> SEQ ID NO 176
<211> LENGTH: 10
<212> TYPE: PRT
<213> ORGANISM: Homo sapiens

<400> SEQUENCE: 176

Leu Leu Ile Thr Glu Ile Ile Pro Ser Thr
1               5                   10

<210> SEQ ID NO 177
<211> LENGTH: 10
<212> TYPE: PRT
<213> ORGANISM: Homo sapiens

<400> SEQUENCE: 177

Arg Ile Phe Leu Trp Leu Phe Ile Ile Val
1               5                   10

<210> SEQ ID NO 178
<211> LENGTH: 10
<212> TYPE: PRT
<213> ORGANISM: Homo sapiens

<400> SEQUENCE: 178

Tyr Leu Pro Ser Asp Cys Gly Glu Lys Ile
1               5                   10

<210> SEQ ID NO 179
<211> LENGTH: 10
<212> TYPE: PRT
<213> ORGANISM: Homo sapiens

<400> SEQUENCE: 179

Arg Leu Pro Leu Phe Tyr Thr Ile Asn Leu
1               5                   10

<210> SEQ ID NO 180
<211> LENGTH: 10
<212> TYPE: PRT
<213> ORGANISM: Homo sapiens

<400> SEQUENCE: 180

Trp Thr Tyr Asp Lys Ala Lys Ile Asp Leu
1               5                   10

<210> SEQ ID NO 181
<211> LENGTH: 10
<212> TYPE: PRT
<213> ORGANISM: Homo sapiens

<400> SEQUENCE: 181

Thr Ile Gly Leu Phe Leu Pro Pro Phe Leu
1               5                   10

<210> SEQ ID NO 182
<211> LENGTH: 10
<212> TYPE: PRT
```

<213> ORGANISM: Homo sapiens

<400> SEQUENCE: 182

Tyr Asn Asn Ala Asp Gly Glu Phe Ala Val
1               5                   10

<210> SEQ ID NO 183
<211> LENGTH: 10
<212> TYPE: PRT
<213> ORGANISM: Homo sapiens

<400> SEQUENCE: 183

Ile Ile Pro Cys Leu Leu Ile Ser Cys Leu
1               5                   10

<210> SEQ ID NO 184
<211> LENGTH: 10
<212> TYPE: PRT
<213> ORGANISM: Homo sapiens

<400> SEQUENCE: 184

Lys Ile Thr Leu Cys Ile Ser Val Leu Leu
1               5                   10

<210> SEQ ID NO 185
<211> LENGTH: 10
<212> TYPE: PRT
<213> ORGANISM: Homo sapiens

<400> SEQUENCE: 185

Val Ala Met Val Ile Asp Arg Ile Phe Leu
1               5                   10

<210> SEQ ID NO 186
<211> LENGTH: 10
<212> TYPE: PRT
<213> ORGANISM: Homo sapiens

<400> SEQUENCE: 186

Val Ile Arg Arg Leu Pro Leu Phe Tyr Thr
1               5                   10

<210> SEQ ID NO 187
<211> LENGTH: 10
<212> TYPE: PRT
<213> ORGANISM: Homo sapiens

<400> SEQUENCE: 187

Cys Ile Ser Val Leu Leu Ser Leu Thr Val
1               5                   10

<210> SEQ ID NO 188
<211> LENGTH: 10
<212> TYPE: PRT
<213> ORGANISM: Homo sapiens

<400> SEQUENCE: 188

Leu Val Ile Pro Leu Ile Gly Glu Tyr Leu
1               5                   10

<210> SEQ ID NO 189
<211> LENGTH: 10
<212> TYPE: PRT
<213> ORGANISM: Homo sapiens

```
<400> SEQUENCE: 189

Val Leu Val Phe Tyr Leu Pro Ser Asp Cys
1               5                   10

<210> SEQ ID NO 190
<211> LENGTH: 10
<212> TYPE: PRT
<213> ORGANISM: Homo sapiens

<400> SEQUENCE: 190

Thr Val Phe Leu Leu Leu Ile Thr Glu Ile
1               5                   10

<210> SEQ ID NO 191
<211> LENGTH: 10
<212> TYPE: PRT
<213> ORGANISM: Homo sapiens

<400> SEQUENCE: 191

Phe Ile Ile Val Cys Phe Leu Gly Thr Ile
1               5                   10

<210> SEQ ID NO 192
<211> LENGTH: 10
<212> TYPE: PRT
<213> ORGANISM: Homo sapiens

<400> SEQUENCE: 192

Trp Leu Phe Ile Ile Val Cys Phe Leu Gly
1               5                   10

<210> SEQ ID NO 193
<211> LENGTH: 10
<212> TYPE: PRT
<213> ORGANISM: Homo sapiens

<400> SEQUENCE: 193

Ser Leu Thr Val Phe Leu Leu Leu Ile Thr
1               5                   10

<210> SEQ ID NO 194
<211> LENGTH: 10
<212> TYPE: PRT
<213> ORGANISM: Homo sapiens

<400> SEQUENCE: 194

Phe Leu Trp Leu Phe Ile Ile Val Cys Phe
1               5                   10

<210> SEQ ID NO 195
<211> LENGTH: 10
<212> TYPE: PRT
<213> ORGANISM: Homo sapiens

<400> SEQUENCE: 195

Phe Leu Pro Pro Phe Leu Ala Gly Met Ile
1               5                   10

<210> SEQ ID NO 196
<211> LENGTH: 10
<212> TYPE: PRT
<213> ORGANISM: Homo sapiens

<400> SEQUENCE: 196
```

```
Val Val Ile Val Arg Phe Gly Leu Ser Ile
1               5                   10
```

<210> SEQ ID NO 197
<211> LENGTH: 10
<212> TYPE: PRT
<213> ORGANISM: Homo sapiens

<400> SEQUENCE: 197

```
Tyr Ala Phe Val Ile Arg Arg Leu Pro Leu
1               5                   10
```

<210> SEQ ID NO 198
<211> LENGTH: 10
<212> TYPE: PRT
<213> ORGANISM: Homo sapiens

<400> SEQUENCE: 198

```
Val Ile Pro Leu Ile Gly Glu Tyr Leu Leu
1               5                   10
```

<210> SEQ ID NO 199
<211> LENGTH: 10
<212> TYPE: PRT
<213> ORGANISM: Homo sapiens

<400> SEQUENCE: 199

```
Lys Glu Asp Trp Lys Tyr Val Ala Met Val
1               5                   10
```

<210> SEQ ID NO 200
<211> LENGTH: 10
<212> TYPE: PRT
<213> ORGANISM: Homo sapiens

<400> SEQUENCE: 200

```
Ser Ser Val Lys Glu Asp Trp Lys Tyr Val
1               5                   10
```

<210> SEQ ID NO 201
<211> LENGTH: 9
<212> TYPE: PRT
<213> ORGANISM: Homo sapiens

<400> SEQUENCE: 201

```
Met Met Thr Thr Asn Val Trp Leu Lys
1               5
```

<210> SEQ ID NO 202
<211> LENGTH: 9
<212> TYPE: PRT
<213> ORGANISM: Homo sapiens

<400> SEQUENCE: 202

```
Leu Leu Leu Ser Pro His Met Gln Lys
1               5
```

<210> SEQ ID NO 203
<211> LENGTH: 9
<212> TYPE: PRT
<213> ORGANISM: Homo sapiens

<400> SEQUENCE: 203

```
Gln Met Glu Gln Thr Val Asp Leu Lys
1               5
```

<210> SEQ ID NO 204
<211> LENGTH: 9
<212> TYPE: PRT
<213> ORGANISM: Homo sapiens

<400> SEQUENCE: 204

Lys Met Lys Phe Gly Ser Trp Thr Tyr
1               5

<210> SEQ ID NO 205
<211> LENGTH: 9
<212> TYPE: PRT
<213> ORGANISM: Homo sapiens

<400> SEQUENCE: 205

Val Thr Tyr Ala Phe Val Ile Arg Arg
1               5

<210> SEQ ID NO 206
<211> LENGTH: 9
<212> TYPE: PRT
<213> ORGANISM: Homo sapiens

<400> SEQUENCE: 206

Trp Leu Phe Ile Ile Val Cys Phe Leu
1               5

<210> SEQ ID NO 207
<211> LENGTH: 9
<212> TYPE: PRT
<213> ORGANISM: Homo sapiens

<400> SEQUENCE: 207

Gly Leu Phe Leu Pro Pro Phe Leu Ala
1               5

<210> SEQ ID NO 208
<211> LENGTH: 9
<212> TYPE: PRT
<213> ORGANISM: Homo sapiens

<400> SEQUENCE: 208

Lys Leu Ser Leu Trp Trp Leu Leu Leu
1               5

<210> SEQ ID NO 209
<211> LENGTH: 9
<212> TYPE: PRT
<213> ORGANISM: Homo sapiens

<400> SEQUENCE: 209

Phe Leu Trp Leu Phe Ile Ile Val Cys
1               5

<210> SEQ ID NO 210
<211> LENGTH: 9
<212> TYPE: PRT
<213> ORGANISM: Homo sapiens

<400> SEQUENCE: 210

Tyr Leu Pro Ser Asp Cys Gly Glu Lys
1               5

```
<210> SEQ ID NO 211
<211> LENGTH: 9
<212> TYPE: PRT
<213> ORGANISM: Homo sapiens

<400> SEQUENCE: 211

Lys Leu Arg Trp Asn Pro Thr Asp Phe
 1               5

<210> SEQ ID NO 212
<211> LENGTH: 9
<212> TYPE: PRT
<213> ORGANISM: Homo sapiens

<400> SEQUENCE: 212

Cys Leu Thr Val Leu Val Phe Tyr Leu
 1               5

<210> SEQ ID NO 213
<211> LENGTH: 9
<212> TYPE: PRT
<213> ORGANISM: Homo sapiens

<400> SEQUENCE: 213

Ser Leu Thr Val Phe Leu Leu Leu Ile
 1               5

<210> SEQ ID NO 214
<211> LENGTH: 9
<212> TYPE: PRT
<213> ORGANISM: Homo sapiens

<400> SEQUENCE: 214

Leu Leu Ser Leu Thr Val Phe Leu Leu
 1               5

<210> SEQ ID NO 215
<211> LENGTH: 9
<212> TYPE: PRT
<213> ORGANISM: Homo sapiens

<400> SEQUENCE: 215

Thr Leu Ser Ile Val Ile Thr Val Phe
 1               5

<210> SEQ ID NO 216
<211> LENGTH: 9
<212> TYPE: PRT
<213> ORGANISM: Homo sapiens

<400> SEQUENCE: 216

Arg Ile Phe Leu Trp Leu Phe Ile Ile
 1               5

<210> SEQ ID NO 217
<211> LENGTH: 9
<212> TYPE: PRT
<213> ORGANISM: Homo sapiens

<400> SEQUENCE: 217

Trp Leu Lys Gln Glu Trp Ser Asp Tyr
 1               5

<210> SEQ ID NO 218
<211> LENGTH: 9
```

```
<212> TYPE: PRT
<213> ORGANISM: Homo sapiens

<400> SEQUENCE: 218

Ala Thr Gly Thr Tyr Asn Ser Lys Lys
1               5

<210> SEQ ID NO 219
<211> LENGTH: 9
<212> TYPE: PRT
<213> ORGANISM: Homo sapiens

<400> SEQUENCE: 219

Lys Leu Ser Pro Ser Tyr His Trp Leu
1               5

<210> SEQ ID NO 220
<211> LENGTH: 9
<212> TYPE: PRT
<213> ORGANISM: Homo sapiens

<400> SEQUENCE: 220

Ala Gln Leu Ile Asp Val Asp Glu Lys
1               5

<210> SEQ ID NO 221
<211> LENGTH: 9
<212> TYPE: PRT
<213> ORGANISM: Homo sapiens

<400> SEQUENCE: 221

Asn Leu Ile Ile Pro Cys Leu Leu Ile
1               5

<210> SEQ ID NO 222
<211> LENGTH: 9
<212> TYPE: PRT
<213> ORGANISM: Homo sapiens

<400> SEQUENCE: 222

Thr Met Ile Phe Val Thr Leu Ser Ile
1               5

<210> SEQ ID NO 223
<211> LENGTH: 9
<212> TYPE: PRT
<213> ORGANISM: Homo sapiens

<400> SEQUENCE: 223

Gly Ser Trp Thr Tyr Asp Lys Ala Lys
1               5

<210> SEQ ID NO 224
<211> LENGTH: 9
<212> TYPE: PRT
<213> ORGANISM: Homo sapiens

<400> SEQUENCE: 224

Leu Leu Phe Thr Met Ile Phe Val Thr
1               5

<210> SEQ ID NO 225
<211> LENGTH: 9
<212> TYPE: PRT
<213> ORGANISM: Homo sapiens
```

```
<400> SEQUENCE: 225

Asn Thr Ser Asp Val Val Ile Val Arg
 1               5

<210> SEQ ID NO 226
<211> LENGTH: 9
<212> TYPE: PRT
<213> ORGANISM: Homo sapiens

<400> SEQUENCE: 226

Ser Ile Asp Val Thr Phe Phe Pro Phe
 1               5

<210> SEQ ID NO 227
<211> LENGTH: 9
<212> TYPE: PRT
<213> ORGANISM: Homo sapiens

<400> SEQUENCE: 227

Leu Leu Gln Glu Gly Glu Leu Leu Leu
 1               5

<210> SEQ ID NO 228
<211> LENGTH: 9
<212> TYPE: PRT
<213> ORGANISM: Homo sapiens

<400> SEQUENCE: 228

Ala Met Val Ile Asp Arg Ile Phe Leu
 1               5

<210> SEQ ID NO 229
<211> LENGTH: 9
<212> TYPE: PRT
<213> ORGANISM: Homo sapiens

<400> SEQUENCE: 229

Phe Leu Gly Thr Ile Gly Leu Phe Leu
 1               5

<210> SEQ ID NO 230
<211> LENGTH: 9
<212> TYPE: PRT
<213> ORGANISM: Homo sapiens

<400> SEQUENCE: 230

Phe Leu Leu Leu Ile Thr Glu Ile Ile
 1               5

<210> SEQ ID NO 231
<211> LENGTH: 9
<212> TYPE: PRT
<213> ORGANISM: Homo sapiens

<400> SEQUENCE: 231

Leu Leu Ile Ser Cys Leu Thr Val Leu
 1               5

<210> SEQ ID NO 232
<211> LENGTH: 9
<212> TYPE: PRT
<213> ORGANISM: Homo sapiens

<400> SEQUENCE: 232
```

Glu Leu Cys His Pro Leu Arg Leu Lys
1               5

<210> SEQ ID NO 233
<211> LENGTH: 9
<212> TYPE: PRT
<213> ORGANISM: Homo sapiens

<400> SEQUENCE: 233

Ala Leu Leu Gly Cys Val Pro Arg Trp
1               5

<210> SEQ ID NO 234
<211> LENGTH: 9
<212> TYPE: PRT
<213> ORGANISM: Homo sapiens

<400> SEQUENCE: 234

Ala Leu Glu Gly Val His Tyr Ile Ala
1               5

<210> SEQ ID NO 235
<211> LENGTH: 9
<212> TYPE: PRT
<213> ORGANISM: Homo sapiens

<400> SEQUENCE: 235

Phe Leu Pro Pro Phe Leu Ala Gly Met
1               5

<210> SEQ ID NO 236
<211> LENGTH: 9
<212> TYPE: PRT
<213> ORGANISM: Homo sapiens

<400> SEQUENCE: 236

Phe Leu Ser Phe Thr Lys Leu Ser Leu
1               5

<210> SEQ ID NO 237
<211> LENGTH: 9
<212> TYPE: PRT
<213> ORGANISM: Homo sapiens

<400> SEQUENCE: 237

His Leu Phe Ser Thr Gly Thr Val His
1               5

<210> SEQ ID NO 238
<211> LENGTH: 9
<212> TYPE: PRT
<213> ORGANISM: Homo sapiens

<400> SEQUENCE: 238

Phe Pro Phe Asp Gln Gln Asn Cys Lys
1               5

<210> SEQ ID NO 239
<211> LENGTH: 9
<212> TYPE: PRT
<213> ORGANISM: Homo sapiens

<400> SEQUENCE: 239

His Leu Phe Arg Gly Tyr Asn Arg Trp

```
<210> SEQ ID NO 240
<211> LENGTH: 9
<212> TYPE: PRT
<213> ORGANISM: Homo sapiens

<400> SEQUENCE: 240

Ala Leu Leu Gln Glu Gly Glu Leu Leu
 1               5

<210> SEQ ID NO 241
<211> LENGTH: 9
<212> TYPE: PRT
<213> ORGANISM: Homo sapiens

<400> SEQUENCE: 241

Thr Ile Gly Leu Phe Leu Pro Pro Phe
 1               5

<210> SEQ ID NO 242
<211> LENGTH: 9
<212> TYPE: PRT
<213> ORGANISM: Homo sapiens

<400> SEQUENCE: 242

Ser Leu Arg Val Pro Ser Glu Met Ile
 1               5

<210> SEQ ID NO 243
<211> LENGTH: 9
<212> TYPE: PRT
<213> ORGANISM: Homo sapiens

<400> SEQUENCE: 243

Cys Pro Val Phe Leu Ser Phe Thr Lys
 1               5

<210> SEQ ID NO 244
<211> LENGTH: 9
<212> TYPE: PRT
<213> ORGANISM: Homo sapiens

<400> SEQUENCE: 244

Met Ile Trp Ile Pro Asp Ile Val Leu
 1               5

<210> SEQ ID NO 245
<211> LENGTH: 9
<212> TYPE: PRT
<213> ORGANISM: Homo sapiens

<400> SEQUENCE: 245

Gln Met Met Thr Thr Asn Val Trp Leu
 1               5

<210> SEQ ID NO 246
<211> LENGTH: 9
<212> TYPE: PRT
<213> ORGANISM: Homo sapiens

<400> SEQUENCE: 246

Tyr Leu Leu Phe Thr Met Ile Phe Val
 1               5
```

```
<210> SEQ ID NO 247
<211> LENGTH: 9
<212> TYPE: PRT
<213> ORGANISM: Homo sapiens

<400> SEQUENCE: 247

Val Leu Leu Ser Leu Thr Val Phe Leu
 1               5

<210> SEQ ID NO 248
<211> LENGTH: 9
<212> TYPE: PRT
<213> ORGANISM: Homo sapiens

<400> SEQUENCE: 248

Pro Leu Ile Gly Glu Tyr Leu Leu Phe
 1               5

<210> SEQ ID NO 249
<211> LENGTH: 9
<212> TYPE: PRT
<213> ORGANISM: Homo sapiens

<400> SEQUENCE: 249

Ser Ile Val Ile Thr Val Phe Val Leu
 1               5

<210> SEQ ID NO 250
<211> LENGTH: 9
<212> TYPE: PRT
<213> ORGANISM: Homo sapiens

<400> SEQUENCE: 250

Val Ile Arg Arg Leu Pro Leu Phe Tyr
 1               5

<210> SEQ ID NO 251
<211> LENGTH: 10
<212> TYPE: PRT
<213> ORGANISM: Homo sapiens

<400> SEQUENCE: 251

Gln Met Met Thr Thr Asn Val Trp Leu Lys
 1               5                  10

<210> SEQ ID NO 252
<211> LENGTH: 10
<212> TYPE: PRT
<213> ORGANISM: Homo sapiens

<400> SEQUENCE: 252

Trp Leu Lys Gln Glu Trp Ser Asp Tyr Lys
 1               5                  10

<210> SEQ ID NO 253
<211> LENGTH: 10
<212> TYPE: PRT
<213> ORGANISM: Homo sapiens

<400> SEQUENCE: 253

Glu Leu Leu Leu Ser Pro His Met Gln Lys
 1               5                  10

<210> SEQ ID NO 254
```

```
<211> LENGTH: 10
<212> TYPE: PRT
<213> ORGANISM: Homo sapiens

<400> SEQUENCE: 254

Phe Leu Trp Leu Phe Ile Ile Val Cys Phe
1               5                   10

<210> SEQ ID NO 255
<211> LENGTH: 10
<212> TYPE: PRT
<213> ORGANISM: Homo sapiens

<400> SEQUENCE: 255

Leu Leu Phe Thr Met Ile Phe Val Thr Leu
1               5                   10

<210> SEQ ID NO 256
<211> LENGTH: 10
<212> TYPE: PRT
<213> ORGANISM: Homo sapiens

<400> SEQUENCE: 256

Val Leu Leu Ser Leu Thr Val Phe Leu Leu
1               5                   10

<210> SEQ ID NO 257
<211> LENGTH: 10
<212> TYPE: PRT
<213> ORGANISM: Homo sapiens

<400> SEQUENCE: 257

Arg Leu Phe Lys His Leu Phe Arg Gly Tyr
1               5                   10

<210> SEQ ID NO 258
<211> LENGTH: 10
<212> TYPE: PRT
<213> ORGANISM: Homo sapiens

<400> SEQUENCE: 258

His Leu His Ser Gly Ala Ser Gly Pro Lys
1               5                   10

<210> SEQ ID NO 259
<211> LENGTH: 10
<212> TYPE: PRT
<213> ORGANISM: Homo sapiens

<400> SEQUENCE: 259

Thr Val Phe Val Leu Asn Val His His Arg
1               5                   10

<210> SEQ ID NO 260
<211> LENGTH: 10
<212> TYPE: PRT
<213> ORGANISM: Homo sapiens

<400> SEQUENCE: 260

Leu Leu Ser Leu Thr Val Phe Leu Leu Leu
1               5                   10

<210> SEQ ID NO 261
<211> LENGTH: 10
<212> TYPE: PRT
```

<213> ORGANISM: Homo sapiens

<400> SEQUENCE: 261

Arg Leu Pro Leu Phe Tyr Thr Ile Asn Leu
1               5                   10

<210> SEQ ID NO 262
<211> LENGTH: 10
<212> TYPE: PRT
<213> ORGANISM: Homo sapiens

<400> SEQUENCE: 262

Gly Thr Ile Gly Leu Phe Leu Pro Pro Phe
1               5                   10

<210> SEQ ID NO 263
<211> LENGTH: 10
<212> TYPE: PRT
<213> ORGANISM: Homo sapiens

<400> SEQUENCE: 263

Val Leu Tyr Asn Asn Ala Asp Gly Glu Phe
1               5                   10

<210> SEQ ID NO 264
<211> LENGTH: 10
<212> TYPE: PRT
<213> ORGANISM: Homo sapiens

<400> SEQUENCE: 264

Met Ile Trp Ile Pro Asp Ile Val Leu Tyr
1               5                   10

<210> SEQ ID NO 265
<211> LENGTH: 10
<212> TYPE: PRT
<213> ORGANISM: Homo sapiens

<400> SEQUENCE: 265

Leu Leu Gly Cys Val Pro Arg Trp Leu Leu
1               5                   10

<210> SEQ ID NO 266
<211> LENGTH: 10
<212> TYPE: PRT
<213> ORGANISM: Homo sapiens

<400> SEQUENCE: 266

Thr Leu Cys Ile Ser Val Leu Leu Ser Leu
1               5                   10

<210> SEQ ID NO 267
<211> LENGTH: 10
<212> TYPE: PRT
<213> ORGANISM: Homo sapiens

<400> SEQUENCE: 267

Val Ile Asp Arg Ile Phe Leu Trp Leu Phe
1               5                   10

<210> SEQ ID NO 268
<211> LENGTH: 10
<212> TYPE: PRT
<213> ORGANISM: Homo sapiens

```
<400> SEQUENCE: 268

Lys Leu Ser Leu Trp Trp Leu Leu Leu Thr
1               5                   10

<210> SEQ ID NO 269
<211> LENGTH: 10
<212> TYPE: PRT
<213> ORGANISM: Homo sapiens

<400> SEQUENCE: 269

Gly Leu Phe Leu Pro Pro Phe Leu Ala Gly
1               5                   10

<210> SEQ ID NO 270
<211> LENGTH: 10
<212> TYPE: PRT
<213> ORGANISM: Homo sapiens

<400> SEQUENCE: 270

Ser Leu Val Ile Pro Leu Ile Gly Glu Tyr
1               5                   10

<210> SEQ ID NO 271
<211> LENGTH: 10
<212> TYPE: PRT
<213> ORGANISM: Homo sapiens

<400> SEQUENCE: 271

Asp Val Thr Tyr Ala Phe Val Ile Arg Arg
1               5                   10

<210> SEQ ID NO 272
<211> LENGTH: 10
<212> TYPE: PRT
<213> ORGANISM: Homo sapiens

<400> SEQUENCE: 272

Glu Ile Tyr Pro Asp Val Thr Tyr Ala Phe
1               5                   10

<210> SEQ ID NO 273
<211> LENGTH: 10
<212> TYPE: PRT
<213> ORGANISM: Homo sapiens

<400> SEQUENCE: 273

His Thr Glu Thr Glu Asp Arg Leu Phe Lys
1               5                   10

<210> SEQ ID NO 274
<211> LENGTH: 10
<212> TYPE: PRT
<213> ORGANISM: Homo sapiens

<400> SEQUENCE: 274

Ala Leu Leu Gln Glu Gly Glu Leu Leu Leu
1               5                   10

<210> SEQ ID NO 275
<211> LENGTH: 10
<212> TYPE: PRT
<213> ORGANISM: Homo sapiens

<400> SEQUENCE: 275
```

Gly Leu Ser Ile Ala Gln Leu Ile Asp Val
1               5                   10

<210> SEQ ID NO 276
<211> LENGTH: 10
<212> TYPE: PRT
<213> ORGANISM: Homo sapiens

<400> SEQUENCE: 276

Gly Glu Phe Ala Val Thr His Met Thr Lys
1               5                   10

<210> SEQ ID NO 277
<211> LENGTH: 10
<212> TYPE: PRT
<213> ORGANISM: Homo sapiens

<400> SEQUENCE: 277

Ser Leu Trp Trp Leu Leu Leu Thr Pro Ala
1               5                   10

<210> SEQ ID NO 278
<211> LENGTH: 10
<212> TYPE: PRT
<213> ORGANISM: Homo sapiens

<400> SEQUENCE: 278

Cys Leu Leu Ile Ser Cys Leu Thr Val Leu
1               5                   10

<210> SEQ ID NO 279
<211> LENGTH: 10
<212> TYPE: PRT
<213> ORGANISM: Homo sapiens

<400> SEQUENCE: 279

Met Lys Phe Gly Ser Trp Thr Tyr Asp Lys
1               5                   10

<210> SEQ ID NO 280
<211> LENGTH: 10
<212> TYPE: PRT
<213> ORGANISM: Homo sapiens

<400> SEQUENCE: 280

Ala Met Val Ile Asp Arg Ile Phe Leu Trp
1               5                   10

<210> SEQ ID NO 281
<211> LENGTH: 10
<212> TYPE: PRT
<213> ORGANISM: Homo sapiens

<400> SEQUENCE: 281

Glu Gln Met Glu Gln Thr Val Asp Leu Lys
1               5                   10

<210> SEQ ID NO 282
<211> LENGTH: 10
<212> TYPE: PRT
<213> ORGANISM: Homo sapiens

<400> SEQUENCE: 282

Gly Val His Tyr Ile Ala Asp His Leu Arg
1               5                   10

<210> SEQ ID NO 283
<211> LENGTH: 10
<212> TYPE: PRT
<213> ORGANISM: Homo sapiens

<400> SEQUENCE: 283

Phe Val Ile Arg Arg Leu Pro Leu Phe Tyr
1               5                   10

<210> SEQ ID NO 284
<211> LENGTH: 10
<212> TYPE: PRT
<213> ORGANISM: Homo sapiens

<400> SEQUENCE: 284

Cys Val Pro Arg Trp Leu Leu Met Asn Arg
1               5                   10

<210> SEQ ID NO 285
<211> LENGTH: 10
<212> TYPE: PRT
<213> ORGANISM: Homo sapiens

<400> SEQUENCE: 285

Leu Ile Ser Cys Leu Thr Val Leu Val Phe
1               5                   10

<210> SEQ ID NO 286
<211> LENGTH: 10
<212> TYPE: PRT
<213> ORGANISM: Homo sapiens

<400> SEQUENCE: 286

Leu Thr Pro Ala Gly Gly Glu Glu Ala Lys
1               5                   10

<210> SEQ ID NO 287
<211> LENGTH: 10
<212> TYPE: PRT
<213> ORGANISM: Homo sapiens

<400> SEQUENCE: 287

His Leu Phe Ser Thr Gly Thr Val His Trp
1               5                   10

<210> SEQ ID NO 288
<211> LENGTH: 10
<212> TYPE: PRT
<213> ORGANISM: Homo sapiens

<400> SEQUENCE: 288

Ser Thr His Thr Met Pro His Trp Val Arg
1               5                   10

<210> SEQ ID NO 289
<211> LENGTH: 10
<212> TYPE: PRT
<213> ORGANISM: Homo sapiens

<400> SEQUENCE: 289

Asn Ala Thr Gly Thr Tyr Asn Ser Lys Lys
1               5                   10

```
<210> SEQ ID NO 290
<211> LENGTH: 10
<212> TYPE: PRT
<213> ORGANISM: Homo sapiens

<400> SEQUENCE: 290

Pro Leu Phe Tyr Thr Ile Asn Leu Ile Ile
1               5                   10

<210> SEQ ID NO 291
<211> LENGTH: 10
<212> TYPE: PRT
<213> ORGANISM: Homo sapiens

<400> SEQUENCE: 291

Arg Leu Lys Leu Ser Pro Ser Tyr His Trp
1               5                   10

<210> SEQ ID NO 292
<211> LENGTH: 10
<212> TYPE: PRT
<213> ORGANISM: Homo sapiens

<400> SEQUENCE: 292

Glu Met Ile Trp Ile Pro Asp Ile Val Leu
1               5                   10

<210> SEQ ID NO 293
<211> LENGTH: 10
<212> TYPE: PRT
<213> ORGANISM: Homo sapiens

<400> SEQUENCE: 293

Lys Leu Ser Pro Ser Tyr His Trp Leu Glu
1               5                   10

<210> SEQ ID NO 294
<211> LENGTH: 10
<212> TYPE: PRT
<213> ORGANISM: Homo sapiens

<400> SEQUENCE: 294

Met Val Ile Asp Arg Ile Phe Leu Trp Leu
1               5                   10

<210> SEQ ID NO 295
<211> LENGTH: 10
<212> TYPE: PRT
<213> ORGANISM: Homo sapiens

<400> SEQUENCE: 295

Tyr Leu Leu Phe Thr Met Ile Phe Val Thr
1               5                   10

<210> SEQ ID NO 296
<211> LENGTH: 10
<212> TYPE: PRT
<213> ORGANISM: Homo sapiens

<400> SEQUENCE: 296

Met Ile Phe Val Thr Leu Ser Ile Val Ile
1               5                   10

<210> SEQ ID NO 297
<211> LENGTH: 10
```

```
<212> TYPE: PRT
<213> ORGANISM: Homo sapiens

<400> SEQUENCE: 297

Arg Ile Phe Leu Trp Leu Phe Ile Ile Val
 1               5                  10

<210> SEQ ID NO 298
<211> LENGTH: 10
<212> TYPE: PRT
<213> ORGANISM: Homo sapiens

<400> SEQUENCE: 298

Tyr Leu Pro Ser Asp Cys Gly Glu Lys Ile
 1               5                  10

<210> SEQ ID NO 299
<211> LENGTH: 10
<212> TYPE: PRT
<213> ORGANISM: Homo sapiens

<400> SEQUENCE: 299

Ile Ala Gln Leu Ile Asp Val Asp Glu Lys
 1               5                  10

<210> SEQ ID NO 300
<211> LENGTH: 10
<212> TYPE: PRT
<213> ORGANISM: Homo sapiens

<400> SEQUENCE: 300

Thr Val His Trp Val Pro Pro Ala Ile Tyr
 1               5                  10

<210> SEQ ID NO 301
<211> LENGTH: 9
<212> TYPE: PRT
<213> ORGANISM: Homo sapiens

<400> SEQUENCE: 301

Leu Leu Leu Ser Pro His Met Gln Lys
 1               5

<210> SEQ ID NO 302
<211> LENGTH: 9
<212> TYPE: PRT
<213> ORGANISM: Homo sapiens

<400> SEQUENCE: 302

Lys Phe Gly Ser Trp Thr Tyr Asp Lys
 1               5

<210> SEQ ID NO 303
<211> LENGTH: 9
<212> TYPE: PRT
<213> ORGANISM: Homo sapiens

<400> SEQUENCE: 303

Ala Thr Gly Thr Tyr Asn Ser Lys Lys
 1               5

<210> SEQ ID NO 304
<211> LENGTH: 9
<212> TYPE: PRT
<213> ORGANISM: Homo sapiens
```

```
<400> SEQUENCE: 304

Cys Pro Val Phe Leu Ser Phe Thr Lys
 1               5

<210> SEQ ID NO 305
<211> LENGTH: 9
<212> TYPE: PRT
<213> ORGANISM: Homo sapiens

<400> SEQUENCE: 305

Ala Gln Leu Ile Asp Val Asp Glu Lys
 1               5

<210> SEQ ID NO 306
<211> LENGTH: 9
<212> TYPE: PRT
<213> ORGANISM: Homo sapiens

<400> SEQUENCE: 306

Val Thr Tyr Ala Phe Val Ile Arg Arg
 1               5

<210> SEQ ID NO 307
<211> LENGTH: 9
<212> TYPE: PRT
<213> ORGANISM: Homo sapiens

<400> SEQUENCE: 307

Met Met Thr Thr Asn Val Trp Leu Lys
 1               5

<210> SEQ ID NO 308
<211> LENGTH: 9
<212> TYPE: PRT
<213> ORGANISM: Homo sapiens

<400> SEQUENCE: 308

Lys Tyr Val Ala Met Val Ile Asp Arg
 1               5

<210> SEQ ID NO 309
<211> LENGTH: 9
<212> TYPE: PRT
<213> ORGANISM: Homo sapiens

<400> SEQUENCE: 309

Phe Pro Phe Asp Gln Gln Asn Cys Lys
 1               5

<210> SEQ ID NO 310
<211> LENGTH: 9
<212> TYPE: PRT
<213> ORGANISM: Homo sapiens

<400> SEQUENCE: 310

Tyr Leu Pro Ser Asp Cys Gly Glu Lys
 1               5

<210> SEQ ID NO 311
<211> LENGTH: 9
<212> TYPE: PRT
<213> ORGANISM: Homo sapiens

<400> SEQUENCE: 311
```

Gln Met Glu Gln Thr Val Asp Leu Lys
1               5

<210> SEQ ID NO 312
<211> LENGTH: 9
<212> TYPE: PRT
<213> ORGANISM: Homo sapiens

<400> SEQUENCE: 312

Asn Thr Ser Asp Val Val Ile Val Arg
1               5

<210> SEQ ID NO 313
<211> LENGTH: 9
<212> TYPE: PRT
<213> ORGANISM: Homo sapiens

<400> SEQUENCE: 313

Thr Pro Ala Gly Gly Glu Glu Ala Lys
1               5

<210> SEQ ID NO 314
<211> LENGTH: 9
<212> TYPE: PRT
<213> ORGANISM: Homo sapiens

<400> SEQUENCE: 314

Asn Ala Thr Gly Thr Tyr Asn Ser Lys
1               5

<210> SEQ ID NO 315
<211> LENGTH: 9
<212> TYPE: PRT
<213> ORGANISM: Homo sapiens

<400> SEQUENCE: 315

Gly Ala Leu Leu Gly Cys Val Pro Arg
1               5

<210> SEQ ID NO 316
<211> LENGTH: 9
<212> TYPE: PRT
<213> ORGANISM: Homo sapiens

<400> SEQUENCE: 316

Glu Val Val Val Glu Glu Glu Asp Arg
1               5

<210> SEQ ID NO 317
<211> LENGTH: 9
<212> TYPE: PRT
<213> ORGANISM: Homo sapiens

<400> SEQUENCE: 317

Glu Phe Ala Val Thr His Met Thr Lys
1               5

<210> SEQ ID NO 318
<211> LENGTH: 9
<212> TYPE: PRT
<213> ORGANISM: Homo sapiens

<400> SEQUENCE: 318

Asp Val Thr Tyr Ala Phe Val Ile Arg

-continued

```
                1               5

<210> SEQ ID NO 319
<211> LENGTH: 9
<212> TYPE: PRT
<213> ORGANISM: Homo sapiens

<400> SEQUENCE: 319

Thr Glu Thr Glu Asp Arg Leu Phe Lys
 1               5

<210> SEQ ID NO 320
<211> LENGTH: 9
<212> TYPE: PRT
<213> ORGANISM: Homo sapiens

<400> SEQUENCE: 320

Arg Val Pro Ser Glu Met Ile Trp Ile
 1               5

<210> SEQ ID NO 321
<211> LENGTH: 9
<212> TYPE: PRT
<213> ORGANISM: Homo sapiens

<400> SEQUENCE: 321

Met Val Ile Asp Arg Ile Phe Leu Trp
 1               5

<210> SEQ ID NO 322
<211> LENGTH: 9
<212> TYPE: PRT
<213> ORGANISM: Homo sapiens

<400> SEQUENCE: 322

Val Pro Arg Trp Leu Leu Met Asn Arg
 1               5

<210> SEQ ID NO 323
<211> LENGTH: 9
<212> TYPE: PRT
<213> ORGANISM: Homo sapiens

<400> SEQUENCE: 323

Gly Leu Phe Leu Pro Pro Phe Leu Ala
 1               5

<210> SEQ ID NO 324
<211> LENGTH: 9
<212> TYPE: PRT
<213> ORGANISM: Homo sapiens

<400> SEQUENCE: 324

Arg Ile Phe Leu Trp Leu Phe Ile Ile
 1               5

<210> SEQ ID NO 325
<211> LENGTH: 9
<212> TYPE: PRT
<213> ORGANISM: Homo sapiens

<400> SEQUENCE: 325

Gly Ser Trp Thr Tyr Asp Lys Ala Lys
 1               5
```

<210> SEQ ID NO 326
<211> LENGTH: 9
<212> TYPE: PRT
<213> ORGANISM: Homo sapiens

<400> SEQUENCE: 326

His Trp Val Pro Pro Ala Ile Tyr Lys
 1               5

<210> SEQ ID NO 327
<211> LENGTH: 9
<212> TYPE: PRT
<213> ORGANISM: Homo sapiens

<400> SEQUENCE: 327

Gly Val His Tyr Ile Ala Asp His Leu
 1               5

<210> SEQ ID NO 328
<211> LENGTH: 9
<212> TYPE: PRT
<213> ORGANISM: Homo sapiens

<400> SEQUENCE: 328

Ser Glu Asp Ala Asp Ser Ser Val Lys
 1               5

<210> SEQ ID NO 329
<211> LENGTH: 9
<212> TYPE: PRT
<213> ORGANISM: Homo sapiens

<400> SEQUENCE: 329

Val Phe Val Leu Asn Val His His Arg
 1               5

<210> SEQ ID NO 330
<211> LENGTH: 9
<212> TYPE: PRT
<213> ORGANISM: Homo sapiens

<400> SEQUENCE: 330

Gly Thr Leu Cys Ser His Gly His Leu
 1               5

<210> SEQ ID NO 331
<211> LENGTH: 9
<212> TYPE: PRT
<213> ORGANISM: Homo sapiens

<400> SEQUENCE: 331

Gly Thr Val His Trp Val Pro Pro Ala
 1               5

<210> SEQ ID NO 332
<211> LENGTH: 9
<212> TYPE: PRT
<213> ORGANISM: Homo sapiens

<400> SEQUENCE: 332

Thr Val Phe Val Leu Asn Val His His
 1               5

<210> SEQ ID NO 333

```
<211> LENGTH: 9
<212> TYPE: PRT
<213> ORGANISM: Homo sapiens

<400> SEQUENCE: 333

Pro Val Glu Leu Cys His Pro Leu Arg
 1               5

<210> SEQ ID NO 334
<211> LENGTH: 9
<212> TYPE: PRT
<213> ORGANISM: Homo sapiens

<400> SEQUENCE: 334

Lys His Leu Phe Arg Gly Tyr Asn Arg
 1               5

<210> SEQ ID NO 335
<211> LENGTH: 9
<212> TYPE: PRT
<213> ORGANISM: Homo sapiens

<400> SEQUENCE: 335

Lys Gln Glu Trp Ser Asp Tyr Lys Leu
 1               5

<210> SEQ ID NO 336
<211> LENGTH: 9
<212> TYPE: PRT
<213> ORGANISM: Homo sapiens

<400> SEQUENCE: 336

Val Val Val Glu Glu Asp Arg Trp
 1               5

<210> SEQ ID NO 337
<211> LENGTH: 9
<212> TYPE: PRT
<213> ORGANISM: Homo sapiens

<400> SEQUENCE: 337

Leu Val Ile Pro Leu Ile Gly Glu Tyr
 1               5

<210> SEQ ID NO 338
<211> LENGTH: 9
<212> TYPE: PRT
<213> ORGANISM: Homo sapiens

<400> SEQUENCE: 338

Val Thr Leu Ser Ile Val Ile Thr Val
 1               5

<210> SEQ ID NO 339
<211> LENGTH: 9
<212> TYPE: PRT
<213> ORGANISM: Homo sapiens

<400> SEQUENCE: 339

Phe Val Ile Arg Arg Leu Pro Leu Phe
 1               5

<210> SEQ ID NO 340
<211> LENGTH: 9
<212> TYPE: PRT
```

```
<213> ORGANISM: Homo sapiens

<400> SEQUENCE: 340

Ser Val Leu Leu Ser Leu Thr Val Phe
1               5

<210> SEQ ID NO 341
<211> LENGTH: 9
<212> TYPE: PRT
<213> ORGANISM: Homo sapiens

<400> SEQUENCE: 341

Asp Val Val Ile Val Arg Phe Gly Leu
1               5

<210> SEQ ID NO 342
<211> LENGTH: 9
<212> TYPE: PRT
<213> ORGANISM: Homo sapiens

<400> SEQUENCE: 342

Lys Met Lys Phe Gly Ser Trp Thr Tyr
1               5

<210> SEQ ID NO 343
<211> LENGTH: 9
<212> TYPE: PRT
<213> ORGANISM: Homo sapiens

<400> SEQUENCE: 343

Lys Leu Ser Leu Trp Trp Leu Leu Leu
1               5

<210> SEQ ID NO 344
<211> LENGTH: 9
<212> TYPE: PRT
<213> ORGANISM: Homo sapiens

<400> SEQUENCE: 344

Phe Thr Lys Leu Ser Leu Trp Trp Leu
1               5

<210> SEQ ID NO 345
<211> LENGTH: 9
<212> TYPE: PRT
<213> ORGANISM: Homo sapiens

<400> SEQUENCE: 345

Tyr Val Ala Met Val Ile Asp Arg Ile
1               5

<210> SEQ ID NO 346
<211> LENGTH: 9
<212> TYPE: PRT
<213> ORGANISM: Homo sapiens

<400> SEQUENCE: 346

Leu His Ser Gly Ala Ser Gly Pro Lys
1               5

<210> SEQ ID NO 347
<211> LENGTH: 9
<212> TYPE: PRT
<213> ORGANISM: Homo sapiens
```

```
<400> SEQUENCE: 347

Thr Val His Trp Val Pro Pro Ala Ile
 1               5

<210> SEQ ID NO 348
<211> LENGTH: 9
<212> TYPE: PRT
<213> ORGANISM: Homo sapiens

<400> SEQUENCE: 348

Leu Lys Gln Glu Trp Ser Asp Tyr Lys
 1               5

<210> SEQ ID NO 349
<211> LENGTH: 9
<212> TYPE: PRT
<213> ORGANISM: Homo sapiens

<400> SEQUENCE: 349

His Val Ala Pro Ser Val Gly Thr Leu
 1               5

<210> SEQ ID NO 350
<211> LENGTH: 9
<212> TYPE: PRT
<213> ORGANISM: Homo sapiens

<400> SEQUENCE: 350

Ile Val Arg Phe Gly Leu Ser Ile Ala
 1               5

<210> SEQ ID NO 351
<211> LENGTH: 10
<212> TYPE: PRT
<213> ORGANISM: Homo sapiens

<400> SEQUENCE: 351

His Thr Glu Thr Glu Asp Arg Leu Phe Lys
 1               5                  10

<210> SEQ ID NO 352
<211> LENGTH: 10
<212> TYPE: PRT
<213> ORGANISM: Homo sapiens

<400> SEQUENCE: 352

Gln Met Met Thr Thr Asn Val Trp Leu Lys
 1               5                  10

<210> SEQ ID NO 353
<211> LENGTH: 10
<212> TYPE: PRT
<213> ORGANISM: Homo sapiens

<400> SEQUENCE: 353

Gly Val His Tyr Ile Ala Asp His Leu Arg
 1               5                  10

<210> SEQ ID NO 354
<211> LENGTH: 10
<212> TYPE: PRT
<213> ORGANISM: Homo sapiens

<400> SEQUENCE: 354
```

-continued

Leu Thr Pro Ala Gly Gly Glu Glu Ala Lys
1               5                   10

<210> SEQ ID NO 355
<211> LENGTH: 10
<212> TYPE: PRT
<213> ORGANISM: Homo sapiens

<400> SEQUENCE: 355

Thr Val Phe Val Leu Asn Val His His Arg
1               5                   10

<210> SEQ ID NO 356
<211> LENGTH: 10
<212> TYPE: PRT
<213> ORGANISM: Homo sapiens

<400> SEQUENCE: 356

Cys Val Pro Arg Trp Leu Leu Met Asn Arg
1               5                   10

<210> SEQ ID NO 357
<211> LENGTH: 10
<212> TYPE: PRT
<213> ORGANISM: Homo sapiens

<400> SEQUENCE: 357

Gly Glu Phe Ala Val Thr His Met Thr Lys
1               5                   10

<210> SEQ ID NO 358
<211> LENGTH: 10
<212> TYPE: PRT
<213> ORGANISM: Homo sapiens

<400> SEQUENCE: 358

Phe Tyr Leu Pro Ser Asp Cys Gly Glu Lys
1               5                   10

<210> SEQ ID NO 359
<211> LENGTH: 10
<212> TYPE: PRT
<213> ORGANISM: Homo sapiens

<400> SEQUENCE: 359

Ser Cys Pro Val Phe Leu Ser Phe Thr Lys
1               5                   10

<210> SEQ ID NO 360
<211> LENGTH: 10
<212> TYPE: PRT
<213> ORGANISM: Homo sapiens

<400> SEQUENCE: 360

Trp Leu Lys Gln Glu Trp Ser Asp Tyr Lys
1               5                   10

<210> SEQ ID NO 361
<211> LENGTH: 10
<212> TYPE: PRT
<213> ORGANISM: Homo sapiens

<400> SEQUENCE: 361

Ser Thr His Thr Met Pro His Trp Val Arg
1               5                   10

```
<210> SEQ ID NO 362
<211> LENGTH: 10
<212> TYPE: PRT
<213> ORGANISM: Homo sapiens

<400> SEQUENCE: 362

His Leu His Ser Gly Ala Ser Gly Pro Lys
 1               5                  10

<210> SEQ ID NO 363
<211> LENGTH: 10
<212> TYPE: PRT
<213> ORGANISM: Homo sapiens

<400> SEQUENCE: 363

Glu Gln Met Glu Gln Thr Val Asp Leu Lys
 1               5                  10

<210> SEQ ID NO 364
<211> LENGTH: 10
<212> TYPE: PRT
<213> ORGANISM: Homo sapiens

<400> SEQUENCE: 364

Glu Leu Leu Leu Ser Pro His Met Gln Lys
 1               5                  10

<210> SEQ ID NO 365
<211> LENGTH: 10
<212> TYPE: PRT
<213> ORGANISM: Homo sapiens

<400> SEQUENCE: 365

Asp Val Thr Tyr Ala Phe Val Ile Arg Arg
 1               5                  10

<210> SEQ ID NO 366
<211> LENGTH: 10
<212> TYPE: PRT
<213> ORGANISM: Homo sapiens

<400> SEQUENCE: 366

Phe Phe Pro Phe Asp Gln Gln Asn Cys Lys
 1               5                  10

<210> SEQ ID NO 367
<211> LENGTH: 10
<212> TYPE: PRT
<213> ORGANISM: Homo sapiens

<400> SEQUENCE: 367

Asn Ala Thr Gly Thr Tyr Asn Ser Lys Lys
 1               5                  10

<210> SEQ ID NO 368
<211> LENGTH: 10
<212> TYPE: PRT
<213> ORGANISM: Homo sapiens

<400> SEQUENCE: 368

Ile Ala Gln Leu Ile Asp Val Asp Glu Lys
 1               5                  10
```

```
<210> SEQ ID NO 369
<211> LENGTH: 10
<212> TYPE: PRT
<213> ORGANISM: Homo sapiens

<400> SEQUENCE: 369

Lys Gln Glu Trp Ser Asp Tyr Lys Leu Arg
1               5                   10

<210> SEQ ID NO 370
<211> LENGTH: 10
<212> TYPE: PRT
<213> ORGANISM: Homo sapiens

<400> SEQUENCE: 370

Met Lys Phe Gly Ser Trp Thr Tyr Asp Lys
1               5                   10

<210> SEQ ID NO 371
<211> LENGTH: 10
<212> TYPE: PRT
<213> ORGANISM: Homo sapiens

<400> SEQUENCE: 371

Val His Trp Val Pro Pro Ala Ile Tyr Lys
1               5                   10

<210> SEQ ID NO 372
<211> LENGTH: 10
<212> TYPE: PRT
<213> ORGANISM: Homo sapiens

<400> SEQUENCE: 372

Leu Phe Arg Gly Tyr Asn Arg Trp Ala Arg
1               5                   10

<210> SEQ ID NO 373
<211> LENGTH: 10
<212> TYPE: PRT
<213> ORGANISM: Homo sapiens

<400> SEQUENCE: 373

Arg Ser Glu Asp Ala Asp Ser Ser Val Lys
1               5                   10

<210> SEQ ID NO 374
<211> LENGTH: 10
<212> TYPE: PRT
<213> ORGANISM: Homo sapiens

<400> SEQUENCE: 374

Ile Val Ile Thr Val Phe Val Leu Asn Val
1               5                   10

<210> SEQ ID NO 375
<211> LENGTH: 10
<212> TYPE: PRT
<213> ORGANISM: Homo sapiens

<400> SEQUENCE: 375

Phe Val Ile Arg Arg Leu Pro Leu Phe Tyr
1               5                   10

<210> SEQ ID NO 376
<211> LENGTH: 10
```

```
<212> TYPE: PRT
<213> ORGANISM: Homo sapiens

<400> SEQUENCE: 376

Met Val Ile Asp Arg Ile Phe Leu Trp Leu
1               5                   10

<210> SEQ ID NO 377
<211> LENGTH: 10
<212> TYPE: PRT
<213> ORGANISM: Homo sapiens

<400> SEQUENCE: 377

Val Val Ile Val Arg Phe Gly Leu Ser Ile
1               5                   10

<210> SEQ ID NO 378
<211> LENGTH: 10
<212> TYPE: PRT
<213> ORGANISM: Homo sapiens

<400> SEQUENCE: 378

Arg Glu Val Val Val Glu Glu Glu Asp Arg
1               5                   10

<210> SEQ ID NO 379
<211> LENGTH: 10
<212> TYPE: PRT
<213> ORGANISM: Homo sapiens

<400> SEQUENCE: 379

Arg Ile Phe Leu Trp Leu Phe Ile Ile Val
1               5                   10

<210> SEQ ID NO 380
<211> LENGTH: 10
<212> TYPE: PRT
<213> ORGANISM: Homo sapiens

<400> SEQUENCE: 380

Gly Thr Ile Gly Leu Phe Leu Pro Pro Phe
1               5                   10

<210> SEQ ID NO 381
<211> LENGTH: 10
<212> TYPE: PRT
<213> ORGANISM: Homo sapiens

<400> SEQUENCE: 381

Gly Thr Val His Trp Val Pro Pro Ala Ile
1               5                   10

<210> SEQ ID NO 382
<211> LENGTH: 10
<212> TYPE: PRT
<213> ORGANISM: Homo sapiens

<400> SEQUENCE: 382

Gly Thr Leu Cys Ser His Gly His Leu His
1               5                   10

<210> SEQ ID NO 383
<211> LENGTH: 10
<212> TYPE: PRT
<213> ORGANISM: Homo sapiens
```

```
<400> SEQUENCE: 383

Trp Thr Tyr Asp Lys Ala Lys Ile Asp Leu
 1               5                  10

<210> SEQ ID NO 384
<211> LENGTH: 10
<212> TYPE: PRT
<213> ORGANISM: Homo sapiens

<400> SEQUENCE: 384

Ile Val Cys Phe Leu Gly Thr Ile Gly Leu
 1               5                  10

<210> SEQ ID NO 385
<211> LENGTH: 10
<212> TYPE: PRT
<213> ORGANISM: Homo sapiens

<400> SEQUENCE: 385

Thr Val Phe Leu Leu Leu Ile Thr Glu Ile
 1               5                  10

<210> SEQ ID NO 386
<211> LENGTH: 10
<212> TYPE: PRT
<213> ORGANISM: Homo sapiens

<400> SEQUENCE: 386

Val Asn Ala Thr Gly Thr Tyr Asn Ser Lys
 1               5                  10

<210> SEQ ID NO 387
<211> LENGTH: 10
<212> TYPE: PRT
<213> ORGANISM: Homo sapiens

<400> SEQUENCE: 387

Phe Val Thr Leu Ser Ile Val Ile Thr Val
 1               5                  10

<210> SEQ ID NO 388
<211> LENGTH: 10
<212> TYPE: PRT
<213> ORGANISM: Homo sapiens

<400> SEQUENCE: 388

Thr Pro Ala Gly Gly Glu Glu Ala Lys Arg
 1               5                  10

<210> SEQ ID NO 389
<211> LENGTH: 10
<212> TYPE: PRT
<213> ORGANISM: Homo sapiens

<400> SEQUENCE: 389

Ser Val Lys Glu Asp Trp Lys Tyr Val Ala
 1               5                  10

<210> SEQ ID NO 390
<211> LENGTH: 10
<212> TYPE: PRT
<213> ORGANISM: Homo sapiens

<400> SEQUENCE: 390
```

```
Phe Thr Met Ile Phe Val Thr Leu Ser Ile
1               5                   10

<210> SEQ ID NO 391
<211> LENGTH: 10
<212> TYPE: PRT
<213> ORGANISM: Homo sapiens

<400> SEQUENCE: 391

Gly Glu Glu Ala Lys Arg Pro Pro Arg
1               5                   10

<210> SEQ ID NO 392
<211> LENGTH: 10
<212> TYPE: PRT
<213> ORGANISM: Homo sapiens

<400> SEQUENCE: 392

Leu Val Ile Pro Leu Ile Gly Glu Tyr Leu
1               5                   10

<210> SEQ ID NO 393
<211> LENGTH: 10
<212> TYPE: PRT
<213> ORGANISM: Homo sapiens

<400> SEQUENCE: 393

Ser Val Leu Leu Ser Leu Thr Val Phe Leu
1               5                   10

<210> SEQ ID NO 394
<211> LENGTH: 10
<212> TYPE: PRT
<213> ORGANISM: Homo sapiens

<400> SEQUENCE: 394

Gly Leu Ser Ile Ala Gln Leu Ile Asp Val
1               5                   10

<210> SEQ ID NO 395
<211> LENGTH: 10
<212> TYPE: PRT
<213> ORGANISM: Homo sapiens

<400> SEQUENCE: 395

Arg Leu Pro Leu Phe Tyr Thr Ile Asn Leu
1               5                   10

<210> SEQ ID NO 396
<211> LENGTH: 10
<212> TYPE: PRT
<213> ORGANISM: Homo sapiens

<400> SEQUENCE: 396

Arg Leu Lys Leu Ser Pro Ser Tyr His Trp
1               5                   10

<210> SEQ ID NO 397
<211> LENGTH: 10
<212> TYPE: PRT
<213> ORGANISM: Homo sapiens

<400> SEQUENCE: 397

Asn Val His His Arg Ser Pro Ser Thr His
```

```
                  1               5              10

<210> SEQ ID NO 398
<211> LENGTH: 10
<212> TYPE: PRT
<213> ORGANISM: Homo sapiens

<400> SEQUENCE: 398

Phe Thr Lys Leu Ser Leu Trp Trp Leu Leu
 1               5              10

<210> SEQ ID NO 399
<211> LENGTH: 10
<212> TYPE: PRT
<213> ORGANISM: Homo sapiens

<400> SEQUENCE: 399

Trp Val Arg Gly Ala Leu Leu Gly Cys Val
 1               5              10

<210> SEQ ID NO 400
<211> LENGTH: 10
<212> TYPE: PRT
<213> ORGANISM: Homo sapiens

<400> SEQUENCE: 400

Asn Val Asp Ala Glu Glu Arg Glu Val Val
 1               5              10

<210> SEQ ID NO 401
<211> LENGTH: 9
<212> TYPE: PRT
<213> ORGANISM: Homo sapiens

<400> SEQUENCE: 401

Thr Tyr Ala Phe Val Ile Arg Arg Leu
 1               5

<210> SEQ ID NO 402
<211> LENGTH: 9
<212> TYPE: PRT
<213> ORGANISM: Homo sapiens

<400> SEQUENCE: 402

Ile Tyr Pro Asp Val Thr Tyr Ala Phe
 1               5

<210> SEQ ID NO 403
<211> LENGTH: 9
<212> TYPE: PRT
<213> ORGANISM: Homo sapiens

<400> SEQUENCE: 403

Thr Tyr Asp Lys Ala Lys Ile Asp Leu
 1               5

<210> SEQ ID NO 404
<211> LENGTH: 9
<212> TYPE: PRT
<213> ORGANISM: Homo sapiens

<400> SEQUENCE: 404

Leu Tyr Asn Asn Ala Asp Gly Glu Phe
 1               5
```

```
<210> SEQ ID NO 405
<211> LENGTH: 9
<212> TYPE: PRT
<213> ORGANISM: Homo sapiens

<400> SEQUENCE: 405

Glu Tyr Leu Leu Phe Thr Met Ile Phe
1               5

<210> SEQ ID NO 406
<211> LENGTH: 9
<212> TYPE: PRT
<213> ORGANISM: Homo sapiens

<400> SEQUENCE: 406

Arg Phe Gly Leu Ser Ile Ala Gln Leu
1               5

<210> SEQ ID NO 407
<211> LENGTH: 9
<212> TYPE: PRT
<213> ORGANISM: Homo sapiens

<400> SEQUENCE: 407

Leu Phe Thr Met Ile Phe Val Thr Leu
1               5

<210> SEQ ID NO 408
<211> LENGTH: 9
<212> TYPE: PRT
<213> ORGANISM: Homo sapiens

<400> SEQUENCE: 408

Ala Phe Val Ile Arg Arg Leu Pro Leu
1               5

<210> SEQ ID NO 409
<211> LENGTH: 9
<212> TYPE: PRT
<213> ORGANISM: Homo sapiens

<400> SEQUENCE: 409

Cys Phe Leu Gly Thr Ile Gly Leu Phe
1               5

<210> SEQ ID NO 410
<211> LENGTH: 9
<212> TYPE: PRT
<213> ORGANISM: Homo sapiens

<400> SEQUENCE: 410

Lys Gln Glu Trp Ser Asp Tyr Lys Leu
1               5

<210> SEQ ID NO 411
<211> LENGTH: 9
<212> TYPE: PRT
<213> ORGANISM: Homo sapiens

<400> SEQUENCE: 411

Leu Ser Leu Thr Val Phe Leu Leu Leu
1               5

<210> SEQ ID NO 412
```

```
<211> LENGTH: 9
<212> TYPE: PRT
<213> ORGANISM: Homo sapiens

<400> SEQUENCE: 412

Lys Tyr Asp Cys Cys Ala Glu Ile Tyr
1               5

<210> SEQ ID NO 413
<211> LENGTH: 9
<212> TYPE: PRT
<213> ORGANISM: Homo sapiens

<400> SEQUENCE: 413

Val Phe Leu Leu Leu Ile Thr Glu Ile
1               5

<210> SEQ ID NO 414
<211> LENGTH: 9
<212> TYPE: PRT
<213> ORGANISM: Homo sapiens

<400> SEQUENCE: 414

Lys Leu Ser Pro Ser Tyr His Trp Leu
1               5

<210> SEQ ID NO 415
<211> LENGTH: 9
<212> TYPE: PRT
<213> ORGANISM: Homo sapiens

<400> SEQUENCE: 415

Ile Phe Val Thr Leu Ser Ile Val Ile
1               5

<210> SEQ ID NO 416
<211> LENGTH: 9
<212> TYPE: PRT
<213> ORGANISM: Homo sapiens

<400> SEQUENCE: 416

Asp Val Val Ile Val Arg Phe Gly Leu
1               5

<210> SEQ ID NO 417
<211> LENGTH: 9
<212> TYPE: PRT
<213> ORGANISM: Homo sapiens

<400> SEQUENCE: 417

Ile Asn Leu Ile Ile Pro Cys Leu Leu
1               5

<210> SEQ ID NO 418
<211> LENGTH: 9
<212> TYPE: PRT
<213> ORGANISM: Homo sapiens

<400> SEQUENCE: 418

Val Ile Pro Leu Ile Gly Glu Tyr Leu
1               5

<210> SEQ ID NO 419
<211> LENGTH: 9
<212> TYPE: PRT
```

<213> ORGANISM: Homo sapiens

<400> SEQUENCE: 419

Thr Ile Asn Leu Ile Ile Pro Cys Leu
1               5

<210> SEQ ID NO 420
<211> LENGTH: 9
<212> TYPE: PRT
<213> ORGANISM: Homo sapiens

<400> SEQUENCE: 420

Ile Thr Leu Cys Ile Ser Val Leu Leu
1               5

<210> SEQ ID NO 421
<211> LENGTH: 9
<212> TYPE: PRT
<213> ORGANISM: Homo sapiens

<400> SEQUENCE: 421

Leu Cys Ile Ser Val Leu Leu Ser Leu
1               5

<210> SEQ ID NO 422
<211> LENGTH: 9
<212> TYPE: PRT
<213> ORGANISM: Homo sapiens

<400> SEQUENCE: 422

Lys Ile Thr Leu Cys Ile Ser Val Leu
1               5

<210> SEQ ID NO 423
<211> LENGTH: 9
<212> TYPE: PRT
<213> ORGANISM: Homo sapiens

<400> SEQUENCE: 423

Lys Leu Ser Leu Trp Trp Leu Leu Leu
1               5

<210> SEQ ID NO 424
<211> LENGTH: 9
<212> TYPE: PRT
<213> ORGANISM: Homo sapiens

<400> SEQUENCE: 424

His Tyr Ile Ala Asp His Leu Arg Ser
1               5

<210> SEQ ID NO 425
<211> LENGTH: 9
<212> TYPE: PRT
<213> ORGANISM: Homo sapiens

<400> SEQUENCE: 425

Gly Tyr Asn Arg Trp Ala Arg Pro Val
1               5

<210> SEQ ID NO 426
<211> LENGTH: 9
<212> TYPE: PRT
<213> ORGANISM: Homo sapiens

```
<400> SEQUENCE: 426

Thr Tyr Asn Ser Lys Lys Tyr Asp Cys
1               5

<210> SEQ ID NO 427
<211> LENGTH: 9
<212> TYPE: PRT
<213> ORGANISM: Homo sapiens

<400> SEQUENCE: 427

Val Leu Leu Ser Leu Thr Val Phe Leu
1               5

<210> SEQ ID NO 428
<211> LENGTH: 9
<212> TYPE: PRT
<213> ORGANISM: Homo sapiens

<400> SEQUENCE: 428

Glu Gln Met Glu Gln Thr Val Asp Leu
1               5

<210> SEQ ID NO 429
<211> LENGTH: 9
<212> TYPE: PRT
<213> ORGANISM: Homo sapiens

<400> SEQUENCE: 429

Ile Gly Leu Phe Leu Pro Pro Phe Leu
1               5

<210> SEQ ID NO 430
<211> LENGTH: 9
<212> TYPE: PRT
<213> ORGANISM: Homo sapiens

<400> SEQUENCE: 430

Leu Leu Gln Glu Gly Glu Leu Leu Leu
1               5

<210> SEQ ID NO 431
<211> LENGTH: 9
<212> TYPE: PRT
<213> ORGANISM: Homo sapiens

<400> SEQUENCE: 431

Leu Phe Tyr Thr Ile Asn Leu Ile Ile
1               5

<210> SEQ ID NO 432
<211> LENGTH: 9
<212> TYPE: PRT
<213> ORGANISM: Homo sapiens

<400> SEQUENCE: 432

Val Ile Asp Arg Ile Phe Leu Trp Leu
1               5

<210> SEQ ID NO 433
<211> LENGTH: 9
<212> TYPE: PRT
<213> ORGANISM: Homo sapiens

<400> SEQUENCE: 433
```

```
Glu Ala Leu Leu Gln Glu Gly Glu Leu
1               5

<210> SEQ ID NO 434
<211> LENGTH: 9
<212> TYPE: PRT
<213> ORGANISM: Homo sapiens

<400> SEQUENCE: 434

Leu Cys His Pro Leu Arg Leu Lys Leu
1               5

<210> SEQ ID NO 435
<211> LENGTH: 9
<212> TYPE: PRT
<213> ORGANISM: Homo sapiens

<400> SEQUENCE: 435

Gly Thr Leu Cys Ser His Gly His Leu
1               5

<210> SEQ ID NO 436
<211> LENGTH: 9
<212> TYPE: PRT
<213> ORGANISM: Homo sapiens

<400> SEQUENCE: 436

Ser Ile Val Ile Thr Val Phe Val Leu
1               5

<210> SEQ ID NO 437
<211> LENGTH: 9
<212> TYPE: PRT
<213> ORGANISM: Homo sapiens

<400> SEQUENCE: 437

Met Gly Pro Ser Cys Pro Val Phe Leu
1               5

<210> SEQ ID NO 438
<211> LENGTH: 9
<212> TYPE: PRT
<213> ORGANISM: Homo sapiens

<400> SEQUENCE: 438

Ser Gly Pro Lys Ala Glu Ala Leu Leu
1               5

<210> SEQ ID NO 439
<211> LENGTH: 9
<212> TYPE: PRT
<213> ORGANISM: Homo sapiens

<400> SEQUENCE: 439

Leu Ser Pro His Met Gln Lys Ala Leu
1               5

<210> SEQ ID NO 440
<211> LENGTH: 9
<212> TYPE: PRT
<213> ORGANISM: Homo sapiens

<400> SEQUENCE: 440

Ala Leu Leu Gln Glu Gly Glu Leu Leu
1               5
```

```
<210> SEQ ID NO 441
<211> LENGTH: 9
<212> TYPE: PRT
<213> ORGANISM: Homo sapiens

<400> SEQUENCE: 441

Ala Met Val Ile Asp Arg Ile Phe Leu
 1               5

<210> SEQ ID NO 442
<211> LENGTH: 9
<212> TYPE: PRT
<213> ORGANISM: Homo sapiens

<400> SEQUENCE: 442

Leu Pro Leu Phe Tyr Thr Ile Asn Leu
 1               5

<210> SEQ ID NO 443
<211> LENGTH: 9
<212> TYPE: PRT
<213> ORGANISM: Homo sapiens

<400> SEQUENCE: 443

Ser Tyr His Trp Leu Glu Ser Asn Val
 1               5

<210> SEQ ID NO 444
<211> LENGTH: 9
<212> TYPE: PRT
<213> ORGANISM: Homo sapiens

<400> SEQUENCE: 444

Asp Tyr Lys Leu Arg Trp Asn Pro Thr
 1               5

<210> SEQ ID NO 445
<211> LENGTH: 9
<212> TYPE: PRT
<213> ORGANISM: Homo sapiens

<400> SEQUENCE: 445

Ile Pro Leu Ile Gly Glu Tyr Leu Leu
 1               5

<210> SEQ ID NO 446
<211> LENGTH: 9
<212> TYPE: PRT
<213> ORGANISM: Homo sapiens

<400> SEQUENCE: 446

Asp Tyr Trp Glu Ser Gly Glu Trp Ala
 1               5

<210> SEQ ID NO 447
<211> LENGTH: 9
<212> TYPE: PRT
<213> ORGANISM: Homo sapiens

<400> SEQUENCE: 447

Leu Leu Ile Ser Cys Leu Thr Val Leu
 1               5
```

```
<210> SEQ ID NO 448
<211> LENGTH: 9
<212> TYPE: PRT
<213> ORGANISM: Homo sapiens

<400> SEQUENCE: 448

Gln Met Met Thr Thr Asn Val Trp Leu
1               5

<210> SEQ ID NO 449
<211> LENGTH: 9
<212> TYPE: PRT
<213> ORGANISM: Homo sapiens

<400> SEQUENCE: 449

Gly Val His Tyr Ile Ala Asp His Leu
1               5

<210> SEQ ID NO 450
<211> LENGTH: 9
<212> TYPE: PRT
<213> ORGANISM: Homo sapiens

<400> SEQUENCE: 450

Phe Leu Gly Thr Ile Gly Leu Phe Leu
1               5

<210> SEQ ID NO 451
<211> LENGTH: 10
<212> TYPE: PRT
<213> ORGANISM: Homo sapiens

<400> SEQUENCE: 451

Lys Tyr Val Ala Met Val Ile Asp Arg Ile
1               5                   10

<210> SEQ ID NO 452
<211> LENGTH: 10
<212> TYPE: PRT
<213> ORGANISM: Homo sapiens

<400> SEQUENCE: 452

Asp Tyr Trp Glu Ser Gly Glu Trp Ala Ile
1               5                   10

<210> SEQ ID NO 453
<211> LENGTH: 10
<212> TYPE: PRT
<213> ORGANISM: Homo sapiens

<400> SEQUENCE: 453

Cys Phe Leu Gly Thr Ile Gly Leu Phe Leu
1               5                   10

<210> SEQ ID NO 454
<211> LENGTH: 10
<212> TYPE: PRT
<213> ORGANISM: Homo sapiens

<400> SEQUENCE: 454

Val Phe Leu Ser Phe Thr Lys Leu Ser Leu
1               5                   10

<210> SEQ ID NO 455
<211> LENGTH: 10
```

```
<212> TYPE: PRT
<213> ORGANISM: Homo sapiens

<400> SEQUENCE: 455

Ser Phe Thr Lys Leu Ser Leu Trp Trp Leu
1               5                   10

<210> SEQ ID NO 456
<211> LENGTH: 10
<212> TYPE: PRT
<213> ORGANISM: Homo sapiens

<400> SEQUENCE: 456

Arg Phe Gly Leu Ser Ile Ala Gln Leu Ile
1               5                   10

<210> SEQ ID NO 457
<211> LENGTH: 10
<212> TYPE: PRT
<213> ORGANISM: Homo sapiens

<400> SEQUENCE: 457

Ala Phe Val Ile Arg Arg Leu Pro Leu Phe
1               5                   10

<210> SEQ ID NO 458
<211> LENGTH: 10
<212> TYPE: PRT
<213> ORGANISM: Homo sapiens

<400> SEQUENCE: 458

Met Val Ile Asp Arg Ile Phe Leu Trp Leu
1               5                   10

<210> SEQ ID NO 459
<211> LENGTH: 10
<212> TYPE: PRT
<213> ORGANISM: Homo sapiens

<400> SEQUENCE: 459

Arg Leu Pro Leu Phe Tyr Thr Ile Asn Leu
1               5                   10

<210> SEQ ID NO 460
<211> LENGTH: 10
<212> TYPE: PRT
<213> ORGANISM: Homo sapiens

<400> SEQUENCE: 460

Lys Ile Thr Leu Cys Ile Ser Val Leu Leu
1               5                   10

<210> SEQ ID NO 461
<211> LENGTH: 10
<212> TYPE: PRT
<213> ORGANISM: Homo sapiens

<400> SEQUENCE: 461

Val Phe Leu Leu Leu Ile Thr Glu Ile Ile
1               5                   10

<210> SEQ ID NO 462
<211> LENGTH: 10
<212> TYPE: PRT
<213> ORGANISM: Homo sapiens
```

```
-continued

<400> SEQUENCE: 462

Glu Thr Glu Asp Arg Leu Phe Lys His Leu
1               5                   10

<210> SEQ ID NO 463
<211> LENGTH: 10
<212> TYPE: PRT
<213> ORGANISM: Homo sapiens

<400> SEQUENCE: 463

Leu Val Ile Pro Leu Ile Gly Glu Tyr Leu
1               5                   10

<210> SEQ ID NO 464
<211> LENGTH: 10
<212> TYPE: PRT
<213> ORGANISM: Homo sapiens

<400> SEQUENCE: 464

Ile Tyr Pro Asp Val Thr Tyr Ala Phe Val
1               5                   10

<210> SEQ ID NO 465
<211> LENGTH: 10
<212> TYPE: PRT
<213> ORGANISM: Homo sapiens

<400> SEQUENCE: 465

Ala Leu Leu Gly Cys Val Pro Arg Trp Leu
1               5                   10

<210> SEQ ID NO 466
<211> LENGTH: 10
<212> TYPE: PRT
<213> ORGANISM: Homo sapiens

<400> SEQUENCE: 466

Thr Met Pro His Trp Val Arg Gly Ala Leu
1               5                   10

<210> SEQ ID NO 467
<211> LENGTH: 10
<212> TYPE: PRT
<213> ORGANISM: Homo sapiens

<400> SEQUENCE: 467

Tyr Thr Ile Asn Leu Ile Ile Pro Cys Leu
1               5                   10

<210> SEQ ID NO 468
<211> LENGTH: 10
<212> TYPE: PRT
<213> ORGANISM: Homo sapiens

<400> SEQUENCE: 468

Glu Gly Val His Tyr Ile Ala Asp His Leu
1               5                   10

<210> SEQ ID NO 469
<211> LENGTH: 10
<212> TYPE: PRT
<213> ORGANISM: Homo sapiens

<400> SEQUENCE: 469
```

```
Thr Ile Asn Leu Ile Ile Pro Cys Leu Leu
1               5                   10

<210> SEQ ID NO 470
<211> LENGTH: 10
<212> TYPE: PRT
<213> ORGANISM: Homo sapiens

<400> SEQUENCE: 470

Leu Trp Leu Phe Ile Ile Val Cys Phe Leu
1               5                   10

<210> SEQ ID NO 471
<211> LENGTH: 10
<212> TYPE: PRT
<213> ORGANISM: Homo sapiens

<400> SEQUENCE: 471

Cys Pro Val Phe Leu Ser Phe Thr Lys Leu
1               5                   10

<210> SEQ ID NO 472
<211> LENGTH: 10
<212> TYPE: PRT
<213> ORGANISM: Homo sapiens

<400> SEQUENCE: 472

Thr Tyr Asn Ser Lys Lys Tyr Asp Cys Cys
1               5                   10

<210> SEQ ID NO 473
<211> LENGTH: 10
<212> TYPE: PRT
<213> ORGANISM: Homo sapiens

<400> SEQUENCE: 473

Leu Tyr Asn Asn Ala Asp Gly Glu Phe Ala
1               5                   10

<210> SEQ ID NO 474
<211> LENGTH: 10
<212> TYPE: PRT
<213> ORGANISM: Homo sapiens

<400> SEQUENCE: 474

Glu Tyr Leu Leu Phe Thr Met Ile Phe Val
1               5                   10

<210> SEQ ID NO 475
<211> LENGTH: 10
<212> TYPE: PRT
<213> ORGANISM: Homo sapiens

<400> SEQUENCE: 475

Ile Ile Pro Cys Leu Leu Ile Ser Cys Leu
1               5                   10

<210> SEQ ID NO 476
<211> LENGTH: 10
<212> TYPE: PRT
<213> ORGANISM: Homo sapiens

<400> SEQUENCE: 476

Ser Val Leu Leu Ser Leu Thr Val Phe Leu
```

```
1               5                  10
```

<210> SEQ ID NO 477
<211> LENGTH: 10
<212> TYPE: PRT
<213> ORGANISM: Homo sapiens

<400> SEQUENCE: 477

```
Ser Cys Leu Thr Val Leu Val Phe Tyr Leu
 1               5                  10
```

<210> SEQ ID NO 478
<211> LENGTH: 10
<212> TYPE: PRT
<213> ORGANISM: Homo sapiens

<400> SEQUENCE: 478

```
Leu Leu Ser Leu Thr Val Phe Leu Leu Leu
 1               5                  10
```

<210> SEQ ID NO 479
<211> LENGTH: 10
<212> TYPE: PRT
<213> ORGANISM: Homo sapiens

<400> SEQUENCE: 479

```
Leu Leu Phe Thr Met Ile Phe Val Thr Leu
 1               5                  10
```

<210> SEQ ID NO 480
<211> LENGTH: 10
<212> TYPE: PRT
<213> ORGANISM: Homo sapiens

<400> SEQUENCE: 480

```
Phe Tyr Thr Ile Asn Leu Ile Ile Pro Cys
 1               5                  10
```

<210> SEQ ID NO 481
<211> LENGTH: 10
<212> TYPE: PRT
<213> ORGANISM: Homo sapiens

<400> SEQUENCE: 481

```
Val Ile Pro Leu Ile Gly Glu Tyr Leu Leu
 1               5                  10
```

<210> SEQ ID NO 482
<211> LENGTH: 10
<212> TYPE: PRT
<213> ORGANISM: Homo sapiens

<400> SEQUENCE: 482

```
Ala Leu Leu Gln Glu Gly Glu Leu Leu Leu
 1               5                  10
```

<210> SEQ ID NO 483
<211> LENGTH: 10
<212> TYPE: PRT
<213> ORGANISM: Homo sapiens

<400> SEQUENCE: 483

```
Glu Ala Leu Leu Gln Glu Gly Glu Leu Leu
 1               5                  10
```

```
<210> SEQ ID NO 484
<211> LENGTH: 10
<212> TYPE: PRT
<213> ORGANISM: Homo sapiens

<400> SEQUENCE: 484

Glu Met Ile Trp Ile Pro Asp Ile Val Leu
1               5                   10

<210> SEQ ID NO 485
<211> LENGTH: 10
<212> TYPE: PRT
<213> ORGANISM: Homo sapiens

<400> SEQUENCE: 485

Asn Gln Met Met Thr Thr Asn Val Trp Leu
1               5                   10

<210> SEQ ID NO 486
<211> LENGTH: 10
<212> TYPE: PRT
<213> ORGANISM: Homo sapiens

<400> SEQUENCE: 486

Leu Ser Ile Val Ile Thr Val Phe Val Leu
1               5                   10

<210> SEQ ID NO 487
<211> LENGTH: 10
<212> TYPE: PRT
<213> ORGANISM: Homo sapiens

<400> SEQUENCE: 487

Val Ala Met Val Ile Asp Arg Ile Phe Leu
1               5                   10

<210> SEQ ID NO 488
<211> LENGTH: 10
<212> TYPE: PRT
<213> ORGANISM: Homo sapiens

<400> SEQUENCE: 488

Cys Leu Leu Ile Ser Cys Leu Thr Val Leu
1               5                   10

<210> SEQ ID NO 489
<211> LENGTH: 10
<212> TYPE: PRT
<213> ORGANISM: Homo sapiens

<400> SEQUENCE: 489

Ile Thr Glu Ile Ile Pro Ser Thr Ser Leu
1               5                   10

<210> SEQ ID NO 490
<211> LENGTH: 10
<212> TYPE: PRT
<213> ORGANISM: Homo sapiens

<400> SEQUENCE: 490

Val Leu Leu Ser Leu Thr Val Phe Leu Leu
1               5                   10

<210> SEQ ID NO 491
```

```
<211> LENGTH: 10
<212> TYPE: PRT
<213> ORGANISM: Homo sapiens

<400> SEQUENCE: 491

Val Thr Tyr Ala Phe Val Ile Arg Arg Leu
1               5                   10

<210> SEQ ID NO 492
<211> LENGTH: 10
<212> TYPE: PRT
<213> ORGANISM: Homo sapiens

<400> SEQUENCE: 492

Lys Ser Ser Cys Ser Ile Asp Val Thr Phe
1               5                   10

<210> SEQ ID NO 493
<211> LENGTH: 10
<212> TYPE: PRT
<213> ORGANISM: Homo sapiens

<400> SEQUENCE: 493

Thr Leu Cys Ile Ser Val Leu Leu Ser Leu
1               5                   10

<210> SEQ ID NO 494
<211> LENGTH: 10
<212> TYPE: PRT
<213> ORGANISM: Homo sapiens

<400> SEQUENCE: 494

Glu Leu Cys His Pro Leu Arg Leu Lys Leu
1               5                   10

<210> SEQ ID NO 495
<211> LENGTH: 10
<212> TYPE: PRT
<213> ORGANISM: Homo sapiens

<400> SEQUENCE: 495

Met Asn Arg Pro Pro Pro Val Glu Leu
1               5                   10

<210> SEQ ID NO 496
<211> LENGTH: 10
<212> TYPE: PRT
<213> ORGANISM: Homo sapiens

<400> SEQUENCE: 496

Ile Tyr Lys Ser Ser Cys Ser Ile Asp Val
1               5                   10

<210> SEQ ID NO 497
<211> LENGTH: 10
<212> TYPE: PRT
<213> ORGANISM: Homo sapiens

<400> SEQUENCE: 497

Ala Ser Gly Pro Lys Ala Glu Ala Leu Leu
1               5                   10

<210> SEQ ID NO 498
<211> LENGTH: 10
<212> TYPE: PRT
```

<213> ORGANISM: Homo sapiens

<400> SEQUENCE: 498

Ile Pro Ser Thr Ser Leu Val Ile Pro Leu
1               5                   10

<210> SEQ ID NO 499
<211> LENGTH: 10
<212> TYPE: PRT
<213> ORGANISM: Homo sapiens

<400> SEQUENCE: 499

Phe Thr Lys Leu Ser Leu Trp Trp Leu Leu
1               5                   10

<210> SEQ ID NO 500
<211> LENGTH: 10
<212> TYPE: PRT
<213> ORGANISM: Homo sapiens

<400> SEQUENCE: 500

Thr Ile Gly Leu Phe Leu Pro Pro Phe Leu
1               5                   10

<210> SEQ ID NO 501
<211> LENGTH: 9
<212> TYPE: PRT
<213> ORGANISM: Homo sapiens

<400> SEQUENCE: 501

Met Pro His Trp Val Arg Gly Ala Leu
1               5

<210> SEQ ID NO 502
<211> LENGTH: 9
<212> TYPE: PRT
<213> ORGANISM: Homo sapiens

<400> SEQUENCE: 502

Pro Pro Arg Ala Pro Gly Asp Pro Leu
1               5

<210> SEQ ID NO 503
<211> LENGTH: 9
<212> TYPE: PRT
<213> ORGANISM: Homo sapiens

<400> SEQUENCE: 503

Ile Pro Leu Ile Gly Glu Tyr Leu Leu
1               5

<210> SEQ ID NO 504
<211> LENGTH: 9
<212> TYPE: PRT
<213> ORGANISM: Homo sapiens

<400> SEQUENCE: 504

Ile Pro Cys Leu Leu Ile Ser Cys Leu
1               5

<210> SEQ ID NO 505
<211> LENGTH: 9
<212> TYPE: PRT
<213> ORGANISM: Homo sapiens

```
<400> SEQUENCE: 505

Leu Pro Leu Phe Tyr Thr Ile Asn Leu
1               5

<210> SEQ ID NO 506
<211> LENGTH: 9
<212> TYPE: PRT
<213> ORGANISM: Homo sapiens

<400> SEQUENCE: 506

Asp Val Val Ile Val Arg Phe Gly Leu
1               5

<210> SEQ ID NO 507
<211> LENGTH: 9
<212> TYPE: PRT
<213> ORGANISM: Homo sapiens

<400> SEQUENCE: 507

Gly Val His Tyr Ile Ala Asp His Leu
1               5

<210> SEQ ID NO 508
<211> LENGTH: 9
<212> TYPE: PRT
<213> ORGANISM: Homo sapiens

<400> SEQUENCE: 508

His Val Ala Pro Ser Val Gly Thr Leu
1               5

<210> SEQ ID NO 509
<211> LENGTH: 9
<212> TYPE: PRT
<213> ORGANISM: Homo sapiens

<400> SEQUENCE: 509

Ala Met Val Ile Asp Arg Ile Phe Leu
1               5

<210> SEQ ID NO 510
<211> LENGTH: 9
<212> TYPE: PRT
<213> ORGANISM: Homo sapiens

<400> SEQUENCE: 510

Ala Leu Leu Gln Glu Gly Glu Leu Leu
1               5

<210> SEQ ID NO 511
<211> LENGTH: 9
<212> TYPE: PRT
<213> ORGANISM: Homo sapiens

<400> SEQUENCE: 511

Gln Met Met Thr Thr Asn Val Trp Leu
1               5

<210> SEQ ID NO 512
<211> LENGTH: 9
<212> TYPE: PRT
<213> ORGANISM: Homo sapiens

<400> SEQUENCE: 512
```

```
Ala Ser Gly Pro Lys Ala Glu Ala Leu
 1               5

<210> SEQ ID NO 513
<211> LENGTH: 9
<212> TYPE: PRT
<213> ORGANISM: Homo sapiens

<400> SEQUENCE: 513

Glu Gln Met Glu Gln Thr Val Asp Leu
 1               5

<210> SEQ ID NO 514
<211> LENGTH: 9
<212> TYPE: PRT
<213> ORGANISM: Homo sapiens

<400> SEQUENCE: 514

Glu Ala Leu Leu Gln Glu Gly Glu Leu
 1               5

<210> SEQ ID NO 515
<211> LENGTH: 9
<212> TYPE: PRT
<213> ORGANISM: Homo sapiens

<400> SEQUENCE: 515

Leu Gly Cys Val Pro Arg Trp Leu Leu
 1               5

<210> SEQ ID NO 516
<211> LENGTH: 9
<212> TYPE: PRT
<213> ORGANISM: Homo sapiens

<400> SEQUENCE: 516

Pro Pro Val Glu Leu Cys His Pro Leu
 1               5

<210> SEQ ID NO 517
<211> LENGTH: 9
<212> TYPE: PRT
<213> ORGANISM: Homo sapiens

<400> SEQUENCE: 517

Leu Pro Ser Asp Cys Gly Glu Lys Ile
 1               5

<210> SEQ ID NO 518
<211> LENGTH: 9
<212> TYPE: PRT
<213> ORGANISM: Homo sapiens

<400> SEQUENCE: 518

Leu Pro Pro Phe Leu Ala Gly Met Ile
 1               5

<210> SEQ ID NO 519
<211> LENGTH: 9
<212> TYPE: PRT
<213> ORGANISM: Homo sapiens

<400> SEQUENCE: 519

Val Pro Asn Thr Ser Asp Val Val Ile
 1               5
```

```
<210> SEQ ID NO 520
<211> LENGTH: 9
<212> TYPE: PRT
<213> ORGANISM: Homo sapiens

<400> SEQUENCE: 520

Met Ile Trp Ile Pro Asp Ile Val Leu
1               5

<210> SEQ ID NO 521
<211> LENGTH: 9
<212> TYPE: PRT
<213> ORGANISM: Homo sapiens

<400> SEQUENCE: 521

Leu Cys His Pro Leu Arg Leu Lys Leu
1               5

<210> SEQ ID NO 522
<211> LENGTH: 9
<212> TYPE: PRT
<213> ORGANISM: Homo sapiens

<400> SEQUENCE: 522

Ser Leu Arg Val Pro Ser Glu Met Ile
1               5

<210> SEQ ID NO 523
<211> LENGTH: 9
<212> TYPE: PRT
<213> ORGANISM: Homo sapiens

<400> SEQUENCE: 523

Trp Val Arg Gly Ala Leu Leu Gly Cys
1               5

<210> SEQ ID NO 524
<211> LENGTH: 9
<212> TYPE: PRT
<213> ORGANISM: Homo sapiens

<400> SEQUENCE: 524

Ile Val Arg Phe Gly Leu Ser Ile Ala
1               5

<210> SEQ ID NO 525
<211> LENGTH: 9
<212> TYPE: PRT
<213> ORGANISM: Homo sapiens

<400> SEQUENCE: 525

Lys Leu Ser Pro Ser Tyr His Trp Leu
1               5

<210> SEQ ID NO 526
<211> LENGTH: 9
<212> TYPE: PRT
<213> ORGANISM: Homo sapiens

<400> SEQUENCE: 526

Ile Thr Leu Cys Ile Ser Val Leu Leu
1               5
```

```
<210> SEQ ID NO 527
<211> LENGTH: 9
<212> TYPE: PRT
<213> ORGANISM: Homo sapiens

<400> SEQUENCE: 527

Val Cys Phe Leu Gly Thr Ile Gly Leu
1               5

<210> SEQ ID NO 528
<211> LENGTH: 9
<212> TYPE: PRT
<213> ORGANISM: Homo sapiens

<400> SEQUENCE: 528

Lys Leu Ser Leu Trp Trp Leu Leu Leu
1               5

<210> SEQ ID NO 529
<211> LENGTH: 9
<212> TYPE: PRT
<213> ORGANISM: Homo sapiens

<400> SEQUENCE: 529

Cys Leu Thr Val Leu Val Phe Tyr Leu
1               5

<210> SEQ ID NO 530
<211> LENGTH: 9
<212> TYPE: PRT
<213> ORGANISM: Homo sapiens

<400> SEQUENCE: 530

Leu Leu Ile Ser Cys Leu Thr Val Leu
1               5

<210> SEQ ID NO 531
<211> LENGTH: 9
<212> TYPE: PRT
<213> ORGANISM: Homo sapiens

<400> SEQUENCE: 531

Val Thr His Met Thr Lys Ala His Leu
1               5

<210> SEQ ID NO 532
<211> LENGTH: 9
<212> TYPE: PRT
<213> ORGANISM: Homo sapiens

<400> SEQUENCE: 532

Val Ile Pro Leu Ile Gly Glu Tyr Leu
1               5

<210> SEQ ID NO 533
<211> LENGTH: 9
<212> TYPE: PRT
<213> ORGANISM: Homo sapiens

<400> SEQUENCE: 533

Leu Leu Gly Cys Val Pro Arg Trp Leu
1               5

<210> SEQ ID NO 534
<211> LENGTH: 9
```

```
<212> TYPE: PRT
<213> ORGANISM: Homo sapiens

<400> SEQUENCE: 534

Phe Thr Lys Leu Ser Leu Trp Trp Leu
 1               5

<210> SEQ ID NO 535
<211> LENGTH: 9
<212> TYPE: PRT
<213> ORGANISM: Homo sapiens

<400> SEQUENCE: 535

Lys Ile Thr Leu Cys Ile Ser Val Leu
 1               5

<210> SEQ ID NO 536
<211> LENGTH: 9
<212> TYPE: PRT
<213> ORGANISM: Homo sapiens

<400> SEQUENCE: 536

Met Gly Pro Ser Cys Pro Val Phe Leu
 1               5

<210> SEQ ID NO 537
<211> LENGTH: 9
<212> TYPE: PRT
<213> ORGANISM: Homo sapiens

<400> SEQUENCE: 537

Leu Cys Ile Ser Val Leu Leu Ser Leu
 1               5

<210> SEQ ID NO 538
<211> LENGTH: 9
<212> TYPE: PRT
<213> ORGANISM: Homo sapiens

<400> SEQUENCE: 538

Ile Gly Leu Phe Leu Pro Pro Phe Leu
 1               5

<210> SEQ ID NO 539
<211> LENGTH: 9
<212> TYPE: PRT
<213> ORGANISM: Homo sapiens

<400> SEQUENCE: 539

Trp Leu Phe Ile Ile Val Cys Phe Leu
 1               5

<210> SEQ ID NO 540
<211> LENGTH: 9
<212> TYPE: PRT
<213> ORGANISM: Homo sapiens

<400> SEQUENCE: 540

Ile Asn Leu Ile Ile Pro Cys Leu Leu
 1               5

<210> SEQ ID NO 541
<211> LENGTH: 9
<212> TYPE: PRT
<213> ORGANISM: Homo sapiens
```

```
<400> SEQUENCE: 541

Phe Leu Ser Phe Thr Lys Leu Ser Leu
1               5

<210> SEQ ID NO 542
<211> LENGTH: 9
<212> TYPE: PRT
<213> ORGANISM: Homo sapiens

<400> SEQUENCE: 542

Leu Leu Ser Leu Thr Val Phe Leu Leu
1               5

<210> SEQ ID NO 543
<211> LENGTH: 9
<212> TYPE: PRT
<213> ORGANISM: Homo sapiens

<400> SEQUENCE: 543

Gly Thr Leu Cys Ser His Gly His Leu
1               5

<210> SEQ ID NO 544
<211> LENGTH: 9
<212> TYPE: PRT
<213> ORGANISM: Homo sapiens

<400> SEQUENCE: 544

Ser Ile Val Ile Thr Val Phe Val Leu
1               5

<210> SEQ ID NO 545
<211> LENGTH: 9
<212> TYPE: PRT
<213> ORGANISM: Homo sapiens

<400> SEQUENCE: 545

Leu Ser Leu Thr Val Phe Leu Leu Leu
1               5

<210> SEQ ID NO 546
<211> LENGTH: 9
<212> TYPE: PRT
<213> ORGANISM: Homo sapiens

<400> SEQUENCE: 546

Ser Gly Pro Lys Ala Glu Ala Leu Leu
1               5

<210> SEQ ID NO 547
<211> LENGTH: 9
<212> TYPE: PRT
<213> ORGANISM: Homo sapiens

<400> SEQUENCE: 547

Arg Pro Val Pro Asn Thr Ser Asp Val
1               5

<210> SEQ ID NO 548
<211> LENGTH: 9
<212> TYPE: PRT
<213> ORGANISM: Homo sapiens

<400> SEQUENCE: 548
```

```
Leu Ser Ser Pro Ser Pro Thr Ala Leu
 1               5
```

<210> SEQ ID NO 549
<211> LENGTH: 9
<212> TYPE: PRT
<213> ORGANISM: Homo sapiens

<400> SEQUENCE: 549

```
Leu Leu Gln Glu Gly Glu Leu Leu Leu
 1               5
```

<210> SEQ ID NO 550
<211> LENGTH: 9
<212> TYPE: PRT
<213> ORGANISM: Homo sapiens

<400> SEQUENCE: 550

```
Leu Ser Pro His Met Gln Lys Ala Leu
 1               5
```

<210> SEQ ID NO 551
<211> LENGTH: 10
<212> TYPE: PRT
<213> ORGANISM: Homo sapiens

<400> SEQUENCE: 551

```
Met Pro His Trp Val Arg Gly Ala Leu Leu
 1               5                  10
```

<210> SEQ ID NO 552
<211> LENGTH: 10
<212> TYPE: PRT
<213> ORGANISM: Homo sapiens

<400> SEQUENCE: 552

```
Ile Pro Ser Thr Ser Leu Val Ile Pro Leu
 1               5                  10
```

<210> SEQ ID NO 553
<211> LENGTH: 10
<212> TYPE: PRT
<213> ORGANISM: Homo sapiens

<400> SEQUENCE: 553

```
Cys Pro Val Phe Leu Ser Phe Thr Lys Leu
 1               5                  10
```

<210> SEQ ID NO 554
<211> LENGTH: 10
<212> TYPE: PRT
<213> ORGANISM: Homo sapiens

<400> SEQUENCE: 554

```
Met Asn Arg Pro Pro Pro Pro Val Glu Leu
 1               5                  10
```

<210> SEQ ID NO 555
<211> LENGTH: 10
<212> TYPE: PRT
<213> ORGANISM: Homo sapiens

<400> SEQUENCE: 555

```
Ala Val Thr His Met Thr Lys Ala His Leu
```

```
                1               5                   10
```

\<210\> SEQ ID NO 556
\<211\> LENGTH: 10
\<212\> TYPE: PRT
\<213\> ORGANISM: Homo sapiens

\<400\> SEQUENCE: 556

```
Val Ala Met Val Ile Asp Arg Ile Phe Leu
 1               5                   10
```

\<210\> SEQ ID NO 557
\<211\> LENGTH: 10
\<212\> TYPE: PRT
\<213\> ORGANISM: Homo sapiens

\<400\> SEQUENCE: 557

```
Phe Pro Phe Asp Gln Gln Asn Cys Lys Met
 1               5                   10
```

\<210\> SEQ ID NO 558
\<211\> LENGTH: 10
\<212\> TYPE: PRT
\<213\> ORGANISM: Homo sapiens

\<400\> SEQUENCE: 558

```
Met Val Ile Asp Arg Ile Phe Leu Trp Leu
 1               5                   10
```

\<210\> SEQ ID NO 559
\<211\> LENGTH: 10
\<212\> TYPE: PRT
\<213\> ORGANISM: Homo sapiens

\<400\> SEQUENCE: 559

```
Ser Val Leu Leu Ser Leu Thr Val Phe Leu
 1               5                   10
```

\<210\> SEQ ID NO 560
\<211\> LENGTH: 10
\<212\> TYPE: PRT
\<213\> ORGANISM: Homo sapiens

\<400\> SEQUENCE: 560

```
Ile Val Cys Phe Leu Gly Thr Ile Gly Leu
 1               5                   10
```

\<210\> SEQ ID NO 561
\<211\> LENGTH: 10
\<212\> TYPE: PRT
\<213\> ORGANISM: Homo sapiens

\<400\> SEQUENCE: 561

```
Leu Val Ile Pro Leu Ile Gly Glu Tyr Leu
 1               5                   10
```

\<210\> SEQ ID NO 562
\<211\> LENGTH: 10
\<212\> TYPE: PRT
\<213\> ORGANISM: Homo sapiens

\<400\> SEQUENCE: 562

```
Tyr Ala Phe Val Ile Arg Arg Leu Pro Leu
 1               5                   10
```

```
<210> SEQ ID NO 563
<211> LENGTH: 10
<212> TYPE: PRT
<213> ORGANISM: Homo sapiens

<400> SEQUENCE: 563

Ala Leu Leu Gln Glu Gly Glu Leu Leu Leu
1               5                   10

<210> SEQ ID NO 564
<211> LENGTH: 10
<212> TYPE: PRT
<213> ORGANISM: Homo sapiens

<400> SEQUENCE: 564

Gly Ala Ser Gly Pro Lys Ala Glu Ala Leu
1               5                   10

<210> SEQ ID NO 565
<211> LENGTH: 10
<212> TYPE: PRT
<213> ORGANISM: Homo sapiens

<400> SEQUENCE: 565

Pro Pro Pro Arg Ala Pro Gly Asp Pro Leu
1               5                   10

<210> SEQ ID NO 566
<211> LENGTH: 10
<212> TYPE: PRT
<213> ORGANISM: Homo sapiens

<400> SEQUENCE: 566

Ala Leu Leu Gly Cys Val Pro Arg Trp Leu
1               5                   10

<210> SEQ ID NO 567
<211> LENGTH: 10
<212> TYPE: PRT
<213> ORGANISM: Homo sapiens

<400> SEQUENCE: 567

Glu Ala Leu Leu Gln Glu Gly Glu Leu Leu
1               5                   10

<210> SEQ ID NO 568
<211> LENGTH: 10
<212> TYPE: PRT
<213> ORGANISM: Homo sapiens

<400> SEQUENCE: 568

Ala Ser Gly Pro Lys Ala Glu Ala Leu Leu
1               5                   10

<210> SEQ ID NO 569
<211> LENGTH: 10
<212> TYPE: PRT
<213> ORGANISM: Homo sapiens

<400> SEQUENCE: 569

Asn Gln Met Met Thr Thr Asn Val Trp Leu
1               5                   10

<210> SEQ ID NO 570
```

```
<211> LENGTH: 10
<212> TYPE: PRT
<213> ORGANISM: Homo sapiens

<400> SEQUENCE: 570

Trp Val Arg Gly Ala Leu Leu Gly Cys Val
1               5                   10

<210> SEQ ID NO 571
<211> LENGTH: 10
<212> TYPE: PRT
<213> ORGANISM: Homo sapiens

<400> SEQUENCE: 571

Leu Leu Gly Cys Val Pro Arg Trp Leu Leu
1               5                   10

<210> SEQ ID NO 572
<211> LENGTH: 10
<212> TYPE: PRT
<213> ORGANISM: Homo sapiens

<400> SEQUENCE: 572

Pro Pro Pro Val Glu Leu Cys His Pro Leu
1               5                   10

<210> SEQ ID NO 573
<211> LENGTH: 10
<212> TYPE: PRT
<213> ORGANISM: Homo sapiens

<400> SEQUENCE: 573

Leu Pro Leu Phe Tyr Thr Ile Asn Leu Ile
1               5                   10

<210> SEQ ID NO 574
<211> LENGTH: 10
<212> TYPE: PRT
<213> ORGANISM: Homo sapiens

<400> SEQUENCE: 574

Glu Met Ile Trp Ile Pro Asp Ile Val Leu
1               5                   10

<210> SEQ ID NO 575
<211> LENGTH: 10
<212> TYPE: PRT
<213> ORGANISM: Homo sapiens

<400> SEQUENCE: 575

Glu Leu Cys His Pro Leu Arg Leu Lys Leu
1               5                   10

<210> SEQ ID NO 576
<211> LENGTH: 10
<212> TYPE: PRT
<213> ORGANISM: Homo sapiens

<400> SEQUENCE: 576

Thr Met Pro His Trp Val Arg Gly Ala Leu
1               5                   10

<210> SEQ ID NO 577
<211> LENGTH: 10
<212> TYPE: PRT
```

```
<213> ORGANISM: Homo sapiens

<400> SEQUENCE: 577

Ser Cys Leu Thr Val Leu Val Phe Tyr Leu
1               5                   10

<210> SEQ ID NO 578
<211> LENGTH: 10
<212> TYPE: PRT
<213> ORGANISM: Homo sapiens

<400> SEQUENCE: 578

Ile Ile Pro Cys Leu Leu Ile Ser Cys Leu
1               5                   10

<210> SEQ ID NO 579
<211> LENGTH: 10
<212> TYPE: PRT
<213> ORGANISM: Homo sapiens

<400> SEQUENCE: 579

Val Ile Pro Leu Ile Gly Glu Tyr Leu Leu
1               5                   10

<210> SEQ ID NO 580
<211> LENGTH: 10
<212> TYPE: PRT
<213> ORGANISM: Homo sapiens

<400> SEQUENCE: 580

Cys Leu Leu Ile Ser Cys Leu Thr Val Leu
1               5                   10

<210> SEQ ID NO 581
<211> LENGTH: 10
<212> TYPE: PRT
<213> ORGANISM: Homo sapiens

<400> SEQUENCE: 581

Val Pro Asn Thr Ser Asp Val Val Ile Val
1               5                   10

<210> SEQ ID NO 582
<211> LENGTH: 10
<212> TYPE: PRT
<213> ORGANISM: Homo sapiens

<400> SEQUENCE: 582

Glu Gly Val His Tyr Ile Ala Asp His Leu
1               5                   10

<210> SEQ ID NO 583
<211> LENGTH: 10
<212> TYPE: PRT
<213> ORGANISM: Homo sapiens

<400> SEQUENCE: 583

Thr Leu Cys Ile Ser Val Leu Leu Ser Leu
1               5                   10

<210> SEQ ID NO 584
<211> LENGTH: 10
<212> TYPE: PRT
<213> ORGANISM: Homo sapiens
```

```
<400> SEQUENCE: 584

Leu Leu Ser Pro His Met Gln Lys Ala Leu
 1               5                  10

<210> SEQ ID NO 585
<211> LENGTH: 10
<212> TYPE: PRT
<213> ORGANISM: Homo sapiens

<400> SEQUENCE: 585

Trp Thr Tyr Asp Lys Ala Lys Ile Asp Leu
 1               5                  10

<210> SEQ ID NO 586
<211> LENGTH: 10
<212> TYPE: PRT
<213> ORGANISM: Homo sapiens

<400> SEQUENCE: 586

Thr Ile Gly Leu Phe Leu Pro Pro Phe Leu
 1               5                  10

<210> SEQ ID NO 587
<211> LENGTH: 10
<212> TYPE: PRT
<213> ORGANISM: Homo sapiens

<400> SEQUENCE: 587

Lys Ile Thr Leu Cys Ile Ser Val Leu Leu
 1               5                  10

<210> SEQ ID NO 588
<211> LENGTH: 10
<212> TYPE: PRT
<213> ORGANISM: Homo sapiens

<400> SEQUENCE: 588

Leu Leu Ser Leu Thr Val Phe Leu Leu Leu
 1               5                  10

<210> SEQ ID NO 589
<211> LENGTH: 10
<212> TYPE: PRT
<213> ORGANISM: Homo sapiens

<400> SEQUENCE: 589

Leu Leu Phe Thr Met Ile Phe Val Thr Leu
 1               5                  10

<210> SEQ ID NO 590
<211> LENGTH: 10
<212> TYPE: PRT
<213> ORGANISM: Homo sapiens

<400> SEQUENCE: 590

Val Leu Leu Ser Leu Thr Val Phe Leu Leu
 1               5                  10

<210> SEQ ID NO 591
<211> LENGTH: 10
<212> TYPE: PRT
<213> ORGANISM: Homo sapiens

<400> SEQUENCE: 591
```

```
Thr Ile Asn Leu Ile Ile Pro Cys Leu Leu
1               5                   10
```

<210> SEQ ID NO 592
<211> LENGTH: 10
<212> TYPE: PRT
<213> ORGANISM: Homo sapiens

<400> SEQUENCE: 592

```
Tyr Thr Ile Asn Leu Ile Ile Pro Cys Leu
1               5                   10
```

<210> SEQ ID NO 593
<211> LENGTH: 10
<212> TYPE: PRT
<213> ORGANISM: Homo sapiens

<400> SEQUENCE: 593

```
Arg Leu Pro Leu Phe Tyr Thr Ile Asn Leu
1               5                   10
```

<210> SEQ ID NO 594
<211> LENGTH: 10
<212> TYPE: PRT
<213> ORGANISM: Homo sapiens

<400> SEQUENCE: 594

```
Val Gly Thr Leu Cys Ser His Gly His Leu
1               5                   10
```

<210> SEQ ID NO 595
<211> LENGTH: 10
<212> TYPE: PRT
<213> ORGANISM: Homo sapiens

<400> SEQUENCE: 595

```
Arg Pro Val Pro Asn Thr Ser Asp Val Val
1               5                   10
```

<210> SEQ ID NO 596
<211> LENGTH: 10
<212> TYPE: PRT
<213> ORGANISM: Homo sapiens

<400> SEQUENCE: 596

```
Phe Thr Lys Leu Ser Leu Trp Trp Leu Leu
1               5                   10
```

<210> SEQ ID NO 597
<211> LENGTH: 10
<212> TYPE: PRT
<213> ORGANISM: Homo sapiens

<400> SEQUENCE: 597

```
Val Thr Tyr Ala Phe Val Ile Arg Arg Leu
1               5                   10
```

<210> SEQ ID NO 598
<211> LENGTH: 10
<212> TYPE: PRT
<213> ORGANISM: Homo sapiens

<400> SEQUENCE: 598

```
Gly Ser His Thr Glu Thr Glu Asp Arg Leu
1               5                   10
```

```
<210> SEQ ID NO 599
<211> LENGTH: 10
<212> TYPE: PRT
<213> ORGANISM: Homo sapiens

<400> SEQUENCE: 599

Leu Ser Ile Val Ile Thr Val Phe Val Leu
 1               5                  10

<210> SEQ ID NO 600
<211> LENGTH: 10
<212> TYPE: PRT
<213> ORGANISM: Homo sapiens

<400> SEQUENCE: 600

Asp Pro Leu Ser Ser Pro Ser Pro Thr Ala
 1               5                  10

<210> SEQ ID NO 601
<211> LENGTH: 9
<212> TYPE: PRT
<213> ORGANISM: Homo sapiens

<400> SEQUENCE: 601

Lys Ala Lys Ile Asp Leu Glu Gln Met
 1               5

<210> SEQ ID NO 602
<211> LENGTH: 9
<212> TYPE: PRT
<213> ORGANISM: Homo sapiens

<400> SEQUENCE: 602

Met Pro His Trp Val Arg Gly Ala Leu
 1               5

<210> SEQ ID NO 603
<211> LENGTH: 9
<212> TYPE: PRT
<213> ORGANISM: Homo sapiens

<400> SEQUENCE: 603

Ile Pro Leu Ile Gly Glu Tyr Leu Leu
 1               5

<210> SEQ ID NO 604
<211> LENGTH: 9
<212> TYPE: PRT
<213> ORGANISM: Homo sapiens

<400> SEQUENCE: 604

Ile Pro Cys Leu Leu Ile Ser Cys Leu
 1               5

<210> SEQ ID NO 605
<211> LENGTH: 9
<212> TYPE: PRT
<213> ORGANISM: Homo sapiens

<400> SEQUENCE: 605

Leu Pro Leu Phe Tyr Thr Ile Asn Leu
 1               5
```

```
<210> SEQ ID NO 606
<211> LENGTH: 9
<212> TYPE: PRT
<213> ORGANISM: Homo sapiens

<400> SEQUENCE: 606

Leu Pro Ser Asp Cys Gly Glu Lys Ile
1               5

<210> SEQ ID NO 607
<211> LENGTH: 9
<212> TYPE: PRT
<213> ORGANISM: Homo sapiens

<400> SEQUENCE: 607

Ser Ser Val Lys Glu Asp Trp Lys Tyr
1               5

<210> SEQ ID NO 608
<211> LENGTH: 9
<212> TYPE: PRT
<213> ORGANISM: Homo sapiens

<400> SEQUENCE: 608

Lys Met Lys Phe Gly Ser Trp Thr Tyr
1               5

<210> SEQ ID NO 609
<211> LENGTH: 9
<212> TYPE: PRT
<213> ORGANISM: Homo sapiens

<400> SEQUENCE: 609

Thr Ser Leu Arg Val Pro Ser Glu Met
1               5

<210> SEQ ID NO 610
<211> LENGTH: 9
<212> TYPE: PRT
<213> ORGANISM: Homo sapiens

<400> SEQUENCE: 610

Trp Leu Lys Gln Glu Trp Ser Asp Tyr
1               5

<210> SEQ ID NO 611
<211> LENGTH: 9
<212> TYPE: PRT
<213> ORGANISM: Homo sapiens

<400> SEQUENCE: 611

Arg Pro Val Pro Asn Thr Ser Asp Val
1               5

<210> SEQ ID NO 612
<211> LENGTH: 9
<212> TYPE: PRT
<213> ORGANISM: Homo sapiens

<400> SEQUENCE: 612

Val Pro Asn Thr Ser Asp Val Val Ile
1               5

<210> SEQ ID NO 613
<211> LENGTH: 9
```

```
<212> TYPE: PRT
<213> ORGANISM: Homo sapiens

<400> SEQUENCE: 613

Leu Pro Pro Phe Leu Ala Gly Met Ile
1               5

<210> SEQ ID NO 614
<211> LENGTH: 9
<212> TYPE: PRT
<213> ORGANISM: Homo sapiens

<400> SEQUENCE: 614

Pro Pro Arg Ala Pro Gly Asp Pro Leu
1               5

<210> SEQ ID NO 615
<211> LENGTH: 9
<212> TYPE: PRT
<213> ORGANISM: Homo sapiens

<400> SEQUENCE: 615

Val Ile Arg Arg Leu Pro Leu Phe Tyr
1               5

<210> SEQ ID NO 616
<211> LENGTH: 9
<212> TYPE: PRT
<213> ORGANISM: Homo sapiens

<400> SEQUENCE: 616

Lys Leu Arg Trp Asn Pro Thr Asp Phe
1               5

<210> SEQ ID NO 617
<211> LENGTH: 9
<212> TYPE: PRT
<213> ORGANISM: Homo sapiens

<400> SEQUENCE: 617

Leu Ser Leu Thr Val Phe Leu Leu Leu
1               5

<210> SEQ ID NO 618
<211> LENGTH: 9
<212> TYPE: PRT
<213> ORGANISM: Homo sapiens

<400> SEQUENCE: 618

Ser Ser Cys Ser Ile Asp Val Thr Phe
1               5

<210> SEQ ID NO 619
<211> LENGTH: 9
<212> TYPE: PRT
<213> ORGANISM: Homo sapiens

<400> SEQUENCE: 619

Leu Ser Ser Pro Ser Pro Thr Ala Leu
1               5

<210> SEQ ID NO 620
<211> LENGTH: 9
<212> TYPE: PRT
<213> ORGANISM: Homo sapiens
```

```
<400> SEQUENCE: 620

Ile Ser Cys Leu Thr Val Leu Val Phe
1               5

<210> SEQ ID NO 621
<211> LENGTH: 9
<212> TYPE: PRT
<213> ORGANISM: Homo sapiens

<400> SEQUENCE: 621

Leu Ser Pro His Met Gln Lys Ala Leu
1               5

<210> SEQ ID NO 622
<211> LENGTH: 9
<212> TYPE: PRT
<213> ORGANISM: Homo sapiens

<400> SEQUENCE: 622

Ala Ser Gly Pro Lys Ala Glu Ala Leu
1               5

<210> SEQ ID NO 623
<211> LENGTH: 9
<212> TYPE: PRT
<213> ORGANISM: Homo sapiens

<400> SEQUENCE: 623

Lys Ala Leu Glu Gly Val His Tyr Ile
1               5

<210> SEQ ID NO 624
<211> LENGTH: 9
<212> TYPE: PRT
<213> ORGANISM: Homo sapiens

<400> SEQUENCE: 624

Pro Pro Val Glu Leu Cys His Pro Leu
1               5

<210> SEQ ID NO 625
<211> LENGTH: 9
<212> TYPE: PRT
<213> ORGANISM: Homo sapiens

<400> SEQUENCE: 625

Asn Pro Thr Asp Phe Gly Asn Ile Thr
1               5

<210> SEQ ID NO 626
<211> LENGTH: 9
<212> TYPE: PRT
<213> ORGANISM: Homo sapiens

<400> SEQUENCE: 626

Arg Pro Pro Pro Pro Val Glu Leu Cys
1               5

<210> SEQ ID NO 627
<211> LENGTH: 9
<212> TYPE: PRT
<213> ORGANISM: Homo sapiens

<400> SEQUENCE: 627
```

```
Glu Ala Leu Leu Gln Glu Gly Glu Leu
 1               5
```

<210> SEQ ID NO 628
<211> LENGTH: 9
<212> TYPE: PRT
<213> ORGANISM: Homo sapiens

<400> SEQUENCE: 628

```
Phe Thr Lys Leu Ser Leu Trp Trp Leu
 1               5
```

<210> SEQ ID NO 629
<211> LENGTH: 9
<212> TYPE: PRT
<213> ORGANISM: Homo sapiens

<400> SEQUENCE: 629

```
Glu Gln Thr Val Asp Leu Lys Asp Tyr
 1               5
```

<210> SEQ ID NO 630
<211> LENGTH: 9
<212> TYPE: PRT
<213> ORGANISM: Homo sapiens

<400> SEQUENCE: 630

```
Val Ala Met Val Ile Asp Arg Ile Phe
 1               5
```

<210> SEQ ID NO 631
<211> LENGTH: 9
<212> TYPE: PRT
<213> ORGANISM: Homo sapiens

<400> SEQUENCE: 631

```
Leu Ser Phe Thr Lys Leu Ser Leu Trp
 1               5
```

<210> SEQ ID NO 632
<211> LENGTH: 9
<212> TYPE: PRT
<213> ORGANISM: Homo sapiens

<400> SEQUENCE: 632

```
Lys Leu Ser Pro Ser Tyr His Trp Leu
 1               5
```

<210> SEQ ID NO 633
<211> LENGTH: 9
<212> TYPE: PRT
<213> ORGANISM: Homo sapiens

<400> SEQUENCE: 633

```
Ala Pro Ser Val Gly Thr Leu Cys Ser
 1               5
```

<210> SEQ ID NO 634
<211> LENGTH: 9
<212> TYPE: PRT
<213> ORGANISM: Homo sapiens

<400> SEQUENCE: 634

```
Gly Cys Val Pro Arg Trp Leu Leu Met
```

```
                              1               5

<210> SEQ ID NO 635
<211> LENGTH: 9
<212> TYPE: PRT
<213> ORGANISM: Homo sapiens

<400> SEQUENCE: 635

Phe Leu Pro Pro Phe Leu Ala Gly Met
 1               5

<210> SEQ ID NO 636
<211> LENGTH: 9
<212> TYPE: PRT
<213> ORGANISM: Homo sapiens

<400> SEQUENCE: 636

Ser Cys Leu Thr Val Leu Val Phe Tyr
 1               5

<210> SEQ ID NO 637
<211> LENGTH: 9
<212> TYPE: PRT
<213> ORGANISM: Homo sapiens

<400> SEQUENCE: 637

Leu Val Ile Pro Leu Ile Gly Glu Tyr
 1               5

<210> SEQ ID NO 638
<211> LENGTH: 9
<212> TYPE: PRT
<213> ORGANISM: Homo sapiens

<400> SEQUENCE: 638

Ser Pro Ser Tyr His Trp Leu Glu Ser
 1               5

<210> SEQ ID NO 639
<211> LENGTH: 9
<212> TYPE: PRT
<213> ORGANISM: Homo sapiens

<400> SEQUENCE: 639

Glu Gln Met Glu Gln Thr Val Asp Leu
 1               5

<210> SEQ ID NO 640
<211> LENGTH: 9
<212> TYPE: PRT
<213> ORGANISM: Homo sapiens

<400> SEQUENCE: 640

Thr Gly Thr Tyr Asn Ser Lys Lys Tyr
 1               5

<210> SEQ ID NO 641
<211> LENGTH: 9
<212> TYPE: PRT
<213> ORGANISM: Homo sapiens

<400> SEQUENCE: 641

Lys Ile Thr Leu Cys Ile Ser Val Leu
 1               5
```

<210> SEQ ID NO 642
<211> LENGTH: 9
<212> TYPE: PRT
<213> ORGANISM: Homo sapiens

<400> SEQUENCE: 642

Gly Pro Ser Cys Pro Val Phe Leu Ser
1               5

<210> SEQ ID NO 643
<211> LENGTH: 9
<212> TYPE: PRT
<213> ORGANISM: Homo sapiens

<400> SEQUENCE: 643

Val Pro Pro Ala Ile Tyr Lys Ser Ser
1               5

<210> SEQ ID NO 644
<211> LENGTH: 9
<212> TYPE: PRT
<213> ORGANISM: Homo sapiens

<400> SEQUENCE: 644

Leu Leu Gln Glu Gly Glu Leu Leu Leu
1               5

<210> SEQ ID NO 645
<211> LENGTH: 9
<212> TYPE: PRT
<213> ORGANISM: Homo sapiens

<400> SEQUENCE: 645

Lys Leu Ser Leu Trp Trp Leu Leu Leu
1               5

<210> SEQ ID NO 646
<211> LENGTH: 9
<212> TYPE: PRT
<213> ORGANISM: Homo sapiens

<400> SEQUENCE: 646

Asp Pro Leu Ser Ser Pro Ser Pro Thr
1               5

<210> SEQ ID NO 647
<211> LENGTH: 9
<212> TYPE: PRT
<213> ORGANISM: Homo sapiens

<400> SEQUENCE: 647

Ala Ile Val Asn Ala Thr Gly Thr Tyr
1               5

<210> SEQ ID NO 648
<211> LENGTH: 9
<212> TYPE: PRT
<213> ORGANISM: Homo sapiens

<400> SEQUENCE: 648

Ser Val Lys Glu Asp Trp Lys Tyr Val
1               5

<210> SEQ ID NO 649

```
<211> LENGTH: 9
<212> TYPE: PRT
<213> ORGANISM: Homo sapiens

<400> SEQUENCE: 649

Val Val Val Glu Glu Asp Arg Trp
1               5

<210> SEQ ID NO 650
<211> LENGTH: 9
<212> TYPE: PRT
<213> ORGANISM: Homo sapiens

<400> SEQUENCE: 650

Thr Ser Asp Val Val Ile Val Arg Phe
1               5

<210> SEQ ID NO 651
<211> LENGTH: 10
<212> TYPE: PRT
<213> ORGANISM: Homo sapiens

<400> SEQUENCE: 651

Phe Pro Phe Asp Gln Gln Asn Cys Lys Met
1               5                   10

<210> SEQ ID NO 652
<211> LENGTH: 10
<212> TYPE: PRT
<213> ORGANISM: Homo sapiens

<400> SEQUENCE: 652

Ile Pro Leu Ile Gly Glu Tyr Leu Leu Phe
1               5                   10

<210> SEQ ID NO 653
<211> LENGTH: 10
<212> TYPE: PRT
<213> ORGANISM: Homo sapiens

<400> SEQUENCE: 653

Met Pro His Trp Val Arg Gly Ala Leu Leu
1               5                   10

<210> SEQ ID NO 654
<211> LENGTH: 10
<212> TYPE: PRT
<213> ORGANISM: Homo sapiens

<400> SEQUENCE: 654

Ile Pro Ser Thr Ser Leu Val Ile Pro Leu
1               5                   10

<210> SEQ ID NO 655
<211> LENGTH: 10
<212> TYPE: PRT
<213> ORGANISM: Homo sapiens

<400> SEQUENCE: 655

Gly Pro Ser Cys Pro Val Phe Leu Ser Phe
1               5                   10

<210> SEQ ID NO 656
<211> LENGTH: 10
<212> TYPE: PRT
```

<213> ORGANISM: Homo sapiens

<400> SEQUENCE: 656

Cys Pro Val Phe Leu Ser Phe Thr Lys Leu
1               5                   10

<210> SEQ ID NO 657
<211> LENGTH: 10
<212> TYPE: PRT
<213> ORGANISM: Homo sapiens

<400> SEQUENCE: 657

Asp Ser Ser Val Lys Glu Asp Trp Lys Tyr
1               5                   10

<210> SEQ ID NO 658
<211> LENGTH: 10
<212> TYPE: PRT
<213> ORGANISM: Homo sapiens

<400> SEQUENCE: 658

Lys Ser Ser Cys Ser Ile Asp Val Thr Phe
1               5                   10

<210> SEQ ID NO 659
<211> LENGTH: 10
<212> TYPE: PRT
<213> ORGANISM: Homo sapiens

<400> SEQUENCE: 659

Ser Pro Ser Thr His Thr Met Pro His Trp
1               5                   10

<210> SEQ ID NO 660
<211> LENGTH: 10
<212> TYPE: PRT
<213> ORGANISM: Homo sapiens

<400> SEQUENCE: 660

Cys Ser Ile Asp Val Thr Phe Phe Pro Phe
1               5                   10

<210> SEQ ID NO 661
<211> LENGTH: 10
<212> TYPE: PRT
<213> ORGANISM: Homo sapiens

<400> SEQUENCE: 661

Ile Ser Cys Leu Thr Val Leu Val Phe Tyr
1               5                   10

<210> SEQ ID NO 662
<211> LENGTH: 10
<212> TYPE: PRT
<213> ORGANISM: Homo sapiens

<400> SEQUENCE: 662

Met Gln Lys Ala Leu Glu Gly Val His Tyr
1               5                   10

<210> SEQ ID NO 663
<211> LENGTH: 10
<212> TYPE: PRT
<213> ORGANISM: Homo sapiens

```
<400> SEQUENCE: 663

Arg Pro Val Pro Asn Thr Ser Asp Val Val
1               5                   10

<210> SEQ ID NO 664
<211> LENGTH: 10
<212> TYPE: PRT
<213> ORGANISM: Homo sapiens

<400> SEQUENCE: 664

Leu Pro Leu Phe Tyr Thr Ile Asn Leu Ile
1               5                   10

<210> SEQ ID NO 665
<211> LENGTH: 10
<212> TYPE: PRT
<213> ORGANISM: Homo sapiens

<400> SEQUENCE: 665

Ser Ser Cys Ser Ile Asp Val Thr Phe Phe
1               5                   10

<210> SEQ ID NO 666
<211> LENGTH: 10
<212> TYPE: PRT
<213> ORGANISM: Homo sapiens

<400> SEQUENCE: 666

Val Pro Asn Thr Ser Asp Val Val Ile Val
1               5                   10

<210> SEQ ID NO 667
<211> LENGTH: 10
<212> TYPE: PRT
<213> ORGANISM: Homo sapiens

<400> SEQUENCE: 667

Trp Ala Ile Val Asn Ala Thr Gly Thr Tyr
1               5                   10

<210> SEQ ID NO 668
<211> LENGTH: 10
<212> TYPE: PRT
<213> ORGANISM: Homo sapiens

<400> SEQUENCE: 668

Leu Ser Ile Val Ile Thr Val Phe Val Leu
1               5                   10

<210> SEQ ID NO 669
<211> LENGTH: 10
<212> TYPE: PRT
<213> ORGANISM: Homo sapiens

<400> SEQUENCE: 669

Ile Ser Val Leu Leu Ser Leu Thr Val Phe
1               5                   10

<210> SEQ ID NO 670
<211> LENGTH: 10
<212> TYPE: PRT
<213> ORGANISM: Homo sapiens

<400> SEQUENCE: 670
```

Gly Ser His Thr Glu Thr Glu Asp Arg Leu
1               5                   10

<210> SEQ ID NO 671
<211> LENGTH: 10
<212> TYPE: PRT
<213> ORGANISM: Homo sapiens

<400> SEQUENCE: 671

Ala Ser Gly Pro Lys Ala Glu Ala Leu Leu
1               5                   10

<210> SEQ ID NO 672
<211> LENGTH: 10
<212> TYPE: PRT
<213> ORGANISM: Homo sapiens

<400> SEQUENCE: 672

Glu Ala Leu Leu Gln Glu Gly Glu Leu Leu
1               5                   10

<210> SEQ ID NO 673
<211> LENGTH: 10
<212> TYPE: PRT
<213> ORGANISM: Homo sapiens

<400> SEQUENCE: 673

Val Ala Met Val Ile Asp Arg Ile Phe Leu
1               5                   10

<210> SEQ ID NO 674
<211> LENGTH: 10
<212> TYPE: PRT
<213> ORGANISM: Homo sapiens

<400> SEQUENCE: 674

Arg Leu Phe Lys His Leu Phe Arg Gly Tyr
1               5                   10

<210> SEQ ID NO 675
<211> LENGTH: 10
<212> TYPE: PRT
<213> ORGANISM: Homo sapiens

<400> SEQUENCE: 675

Leu Ile Gly Glu Tyr Leu Leu Phe Thr Met
1               5                   10

<210> SEQ ID NO 676
<211> LENGTH: 10
<212> TYPE: PRT
<213> ORGANISM: Homo sapiens

<400> SEQUENCE: 676

Ala Pro Gly Asp Pro Leu Ser Ser Pro Ser
1               5                   10

<210> SEQ ID NO 677
<211> LENGTH: 10
<212> TYPE: PRT
<213> ORGANISM: Homo sapiens

<400> SEQUENCE: 677

Asn Pro Thr Asp Phe Gly Asn Ile Thr Ser
1               5                   10

<210> SEQ ID NO 678
<211> LENGTH: 10
<212> TYPE: PRT
<213> ORGANISM: Homo sapiens

<400> SEQUENCE: 678

Leu Pro Ser Asp Cys Gly Glu Lys Ile Thr
1               5                   10

<210> SEQ ID NO 679
<211> LENGTH: 10
<212> TYPE: PRT
<213> ORGANISM: Homo sapiens

<400> SEQUENCE: 679

Gly Ala Ser Gly Pro Lys Ala Glu Ala Leu
1               5                   10

<210> SEQ ID NO 680
<211> LENGTH: 10
<212> TYPE: PRT
<213> ORGANISM: Homo sapiens

<400> SEQUENCE: 680

Arg Leu Lys Leu Ser Pro Ser Tyr His Trp
1               5                   10

<210> SEQ ID NO 681
<211> LENGTH: 10
<212> TYPE: PRT
<213> ORGANISM: Homo sapiens

<400> SEQUENCE: 681

Met Asn Arg Pro Pro Pro Pro Val Glu Leu
1               5                   10

<210> SEQ ID NO 682
<211> LENGTH: 10
<212> TYPE: PRT
<213> ORGANISM: Homo sapiens

<400> SEQUENCE: 682

Gly Ser Trp Thr Tyr Asp Lys Ala Lys Ile
1               5                   10

<210> SEQ ID NO 683
<211> LENGTH: 10
<212> TYPE: PRT
<213> ORGANISM: Homo sapiens

<400> SEQUENCE: 683

Tyr Ala Phe Val Ile Arg Arg Leu Pro Leu
1               5                   10

<210> SEQ ID NO 684
<211> LENGTH: 10
<212> TYPE: PRT
<213> ORGANISM: Homo sapiens

<400> SEQUENCE: 684

Met Ile Trp Ile Pro Asp Ile Val Leu Tyr
1               5                   10

```
<210> SEQ ID NO 685
<211> LENGTH: 10
<212> TYPE: PRT
<213> ORGANISM: Homo sapiens

<400> SEQUENCE: 685

Phe Thr Lys Leu Ser Leu Trp Trp Leu Leu
 1               5                  10

<210> SEQ ID NO 686
<211> LENGTH: 10
<212> TYPE: PRT
<213> ORGANISM: Homo sapiens

<400> SEQUENCE: 686

Leu Ser Phe Thr Lys Leu Ser Leu Trp Trp
 1               5                  10

<210> SEQ ID NO 687
<211> LENGTH: 10
<212> TYPE: PRT
<213> ORGANISM: Homo sapiens

<400> SEQUENCE: 687

Tyr Pro Asp Val Thr Tyr Ala Phe Val Ile
 1               5                  10

<210> SEQ ID NO 688
<211> LENGTH: 10
<212> TYPE: PRT
<213> ORGANISM: Homo sapiens

<400> SEQUENCE: 688

His Pro Leu Arg Leu Lys Leu Ser Pro Ser
 1               5                  10

<210> SEQ ID NO 689
<211> LENGTH: 10
<212> TYPE: PRT
<213> ORGANISM: Homo sapiens

<400> SEQUENCE: 689

Arg Leu Pro Leu Phe Tyr Thr Ile Asn Leu
 1               5                  10

<210> SEQ ID NO 690
<211> LENGTH: 10
<212> TYPE: PRT
<213> ORGANISM: Homo sapiens

<400> SEQUENCE: 690

Met Val Ile Asp Arg Ile Phe Leu Trp Leu
 1               5                  10

<210> SEQ ID NO 691
<211> LENGTH: 10
<212> TYPE: PRT
<213> ORGANISM: Homo sapiens

<400> SEQUENCE: 691

Asn Thr Ser Asp Val Val Ile Val Arg Phe
 1               5                  10

<210> SEQ ID NO 692
<211> LENGTH: 10
```

```
<212> TYPE: PRT
<213> ORGANISM: Homo sapiens

<400> SEQUENCE: 692

Val Pro Pro Ala Ile Tyr Lys Ser Ser Cys
1               5                   10

<210> SEQ ID NO 693
<211> LENGTH: 10
<212> TYPE: PRT
<213> ORGANISM: Homo sapiens

<400> SEQUENCE: 693

Ser Pro Ser Tyr His Trp Leu Glu Ser Asn
1               5                   10

<210> SEQ ID NO 694
<211> LENGTH: 10
<212> TYPE: PRT
<213> ORGANISM: Homo sapiens

<400> SEQUENCE: 694

Trp Thr Tyr Asp Lys Ala Lys Ile Asp Leu
1               5                   10

<210> SEQ ID NO 695
<211> LENGTH: 10
<212> TYPE: PRT
<213> ORGANISM: Homo sapiens

<400> SEQUENCE: 695

Ala Thr Gly Thr Tyr Asn Ser Lys Lys Tyr
1               5                   10

<210> SEQ ID NO 696
<211> LENGTH: 10
<212> TYPE: PRT
<213> ORGANISM: Homo sapiens

<400> SEQUENCE: 696

Ile Thr Ser Leu Arg Val Pro Ser Glu Met
1               5                   10

<210> SEQ ID NO 697
<211> LENGTH: 10
<212> TYPE: PRT
<213> ORGANISM: Homo sapiens

<400> SEQUENCE: 697

Leu Gly Cys Val Pro Arg Trp Leu Leu Met
1               5                   10

<210> SEQ ID NO 698
<211> LENGTH: 10
<212> TYPE: PRT
<213> ORGANISM: Homo sapiens

<400> SEQUENCE: 698

Pro Pro Pro Arg Ala Pro Gly Asp Pro Leu
1               5                   10

<210> SEQ ID NO 699
<211> LENGTH: 10
<212> TYPE: PRT
<213> ORGANISM: Homo sapiens
```

```
<400> SEQUENCE: 699

Ser Pro Thr Ala Leu Pro Gln Gly Gly Ser
1               5                   10

<210> SEQ ID NO 700
<211> LENGTH: 10
<212> TYPE: PRT
<213> ORGANISM: Homo sapiens

<400> SEQUENCE: 700

Phe Val Ile Arg Arg Leu Pro Leu Phe Tyr
1               5                   10

<210> SEQ ID NO 701
<211> LENGTH: 2666
<212> TYPE: DNA
<213> ORGANISM: Homo sapiens
<220> FEATURE:
<221> NAME/KEY: CDS
<222> LOCATION: (555)...(2144)

<400> SEQUENCE: 701
```

| | | |
|---|---|---|
| gagagaacag cgtgagcctg tgtgcttgtg tgctgagccc tcatcccctc ctggggccag | | 60 |
| gcttgggttt cacctgcaga atcgcttgtg ctgggctgcc tgggctgtcc tcagtggcac | | 120 |
| ctgcatgaag ccgttctggc tgccagagct ggacagcccc aggaaaaccc acctctctgc | | 180 |
| agagcttgcc cagctgtccc cgggaagcca aatgcctctc atgtaagtct tctgctcgac | | 240 |
| ggggtgtctc ctaaaccctc actcttcagc ctctgtttga ccatgaaatg aagtgactga | | 300 |
| gctctattct gtacctgcca ctctatttct ggggtgactt tgtcagctg cccagaatct | | 360 |
| ccaagccagg ctggttctct gcatcctttc aatgaccttgt tttcttctgt aaccacaggt | | 420 |
| tcggtggtga gaggaagcct cgcagaatcc agcagaatcc tcacagaatc cagcagcagc | | 480 |
| tctgctgggg acatggtcca tggtgcaacc cacagcaaag ccctgacctg acctcctgat | | 540 |

```
gctcaggaga agcc atg ggc ccc tcc tgt cct gtg ttc ctg tcc ttc aca         590
             Met Gly Pro Ser Cys Pro Val Phe Leu Ser Phe Thr
               1               5                   10 aag ctc agc ctg tgg tgg ctc ctt ctg acc cca gca ggt gga gag gaa         638
Lys Leu Ser Leu Trp Trp Leu Leu Leu Thr Pro Ala Gly Gly Glu Glu
         15                  20                  25 gct aag cgc cca cct ccc agg gct cct gga gac cca ctc tcc tct ccc         686
Ala Lys Arg Pro Pro Pro Arg Ala Pro Gly Asp Pro Leu Ser Ser Pro
     30                  35                  40 agt ccc acg gca ttg ccg cag gga ggc tcg cat acc gag act gag gac         734
Ser Pro Thr Ala Leu Pro Gln Gly Gly Ser His Thr Glu Thr Glu Asp
 45                  50                  55                  60 cgg ctc ttc aaa cac ctc ttc cgg ggc tac aac cgc tgg gcg cgc ccg         782
Arg Leu Phe Lys His Leu Phe Arg Gly Tyr Asn Arg Trp Ala Arg Pro
                 65                  70                  75 gtg ccc aac act tca gac gtg gtg att gtg cgc ttt gga ctg tcc atc         830
Val Pro Asn Thr Ser Asp Val Val Ile Val Arg Phe Gly Leu Ser Ile
             80                  85                  90 gct cag ctc atc gat gtg gat gag aag aac caa atg atg acc acc aac         878
Ala Gln Leu Ile Asp Val Asp Glu Lys Asn Gln Met Met Thr Thr Asn
         95                 100                 105 gtc tgg cta aaa cag gag tgg agc gac tac aaa ctg cgc tgg aac ccc         926
Val Trp Leu Lys Gln Glu Trp Ser Asp Tyr Lys Leu Arg Trp Asn Pro
    110                 115                 120 act gat ttt ggc aac atc aca tct ctc agg gtc cct tct gag atg atc         974
```

```
                                                        -continued

Thr Asp Phe Gly Asn Ile Thr Ser Leu Arg Val Pro Ser Glu Met Ile
125                 130                 135                 140 tgg atc ccc gac att gtt ctc tac aac aat gca gat ggg gag ttt gca    1022
Trp Ile Pro Asp Ile Val Leu Tyr Asn Asn Ala Asp Gly Glu Phe Ala
                145                 150                 155 gtg acc cac atg acc aag gcc cac ctc ttc tcc acg ggc act gtg cac    1070
Val Thr His Met Thr Lys Ala His Leu Phe Ser Thr Gly Thr Val His
            160                 165                 170 tgg gtg ccc ccg gcc atc tac aag agc tcc tgc agc atc gac gtc acc    1118
Trp Val Pro Pro Ala Ile Tyr Lys Ser Ser Cys Ser Ile Asp Val Thr
        175                 180                 185 ttc ttc ccc ttc gac cag cag aac tgc aag atg aag ttt ggc tcc tgg    1166
Phe Phe Pro Phe Asp Gln Gln Asn Cys Lys Met Lys Phe Gly Ser Trp
    190                 195                 200 act tat gac aag gcc aag atc gac ctg gag cag atg gag cag act gtg    1214
Thr Tyr Asp Lys Ala Lys Ile Asp Leu Glu Gln Met Glu Gln Thr Val
205                 210                 215                 220 gac ctg aag gac tac tgg gag agc ggc gag tgg gcc atc gtc aat gcc    1262
Asp Leu Lys Asp Tyr Trp Glu Ser Gly Glu Trp Ala Ile Val Asn Ala
                225                 230                 235 acg ggc acc tac aac agc aag aag tac gac tgc tgc gcc gag atc tac    1310
Thr Gly Thr Tyr Asn Ser Lys Lys Tyr Asp Cys Cys Ala Glu Ile Tyr
            240                 245                 250 ccc gac gtc acc tac gcc ttc gtc atc cgg cgg ctg ccg ctc ttc tac    1358
Pro Asp Val Thr Tyr Ala Phe Val Ile Arg Arg Leu Pro Leu Phe Tyr
        255                 260                 265 acc atc aac ctc atc atc ccc tgc ctc ctc atc tcc tgc ctc act gtg    1406
Thr Ile Asn Leu Ile Ile Pro Cys Leu Leu Ile Ser Cys Leu Thr Val
    270                 275                 280 ctg gtc ttc tac ctg ccc tcc gac tgc ggc gag aag atc acg ctg tgc    1454
Leu Val Phe Tyr Leu Pro Ser Asp Cys Gly Glu Lys Ile Thr Leu Cys
285                 290                 295                 300 att tcg gtg ctg ctg tca ctc acc gtc ttc ctg ctc atc act gag        1502
Ile Ser Val Leu Leu Ser Leu Thr Val Phe Leu Leu Leu Ile Thr Glu
                305                 310                 315 atc atc ccg tcc acc tcg ctg gtc atc ccg ctc atc ggc gag tac ctg    1550
Ile Ile Pro Ser Thr Ser Leu Val Ile Pro Leu Ile Gly Glu Tyr Leu
            320                 325                 330 ctg ttc acc atg atc ttc gtc acc ctg tcc atc gtc atc acc gtc ttc    1598
Leu Phe Thr Met Ile Phe Val Thr Leu Ser Ile Val Ile Thr Val Phe
        335                 340                 345 gtg ctc aat gtg cac cac cgc tcc ccc agc acc cac acc atg ccc cac    1646
Val Leu Asn Val His His Arg Ser Pro Ser Thr His Thr Met Pro His
    350                 355                 360 tgg gtg cgg ggg gcc ctt ctg ggc tgt gtg ccc cgg tgg ctt ctg atg    1694
Trp Val Arg Gly Ala Leu Leu Gly Cys Val Pro Arg Trp Leu Leu Met
365                 370                 375                 380 aac cgg ccc cca cca ccc gtg gag ctc tgc cac ccc cta cgc ctg aag    1742
Asn Arg Pro Pro Pro Pro Val Glu Leu Cys His Pro Leu Arg Leu Lys
                385                 390                 395 ctc agc ccc tct tat cac tgg ctg gag agc aac gtg gat gcc gag gag    1790
Leu Ser Pro Ser Tyr His Trp Leu Glu Ser Asn Val Asp Ala Glu Glu
            400                 405                 410 agg gag gtg gtg gtg gag gag gag gac aga tgg gca tgt gca ggt cat    1838
Arg Glu Val Val Val Glu Glu Glu Asp Arg Trp Ala Cys Ala Gly His
        415                 420                 425 gtg gcc ccc tct gtg ggc acc ctc tgc agc cac ggc cac ctg cac tct    1886
Val Ala Pro Ser Val Gly Thr Leu Cys Ser His Gly His Leu His Ser
    430                 435                 440
```

-continued

```
ggg gcc tca ggt ccc aag gct gag gct ctg ctg cag gag ggt gag ctg      1934
Gly Ala Ser Gly Pro Lys Ala Glu Ala Leu Leu Gln Glu Gly Glu Leu
445                 450                 455                 460 ctg cta tca ccc cac atg cag aag gca ctg gaa ggt gtg cac tac att      1982
Leu Leu Ser Pro His Met Gln Lys Ala Leu Glu Gly Val His Tyr Ile
                465                 470                 475 gcc gac cac ctg cgg tct gag gat gct gac tct tcg gtg aag gag gac      2030
Ala Asp His Leu Arg Ser Glu Asp Ala Asp Ser Ser Val Lys Glu Asp
            480                 485                 490 tgg aag tat gtt gcc atg gtc atc gac agg atc ttc ctc tgg ctg ttt      2078
Trp Lys Tyr Val Ala Met Val Ile Asp Arg Ile Phe Leu Trp Leu Phe
        495                 500                 505 atc atc gtc tgc ttc ctg ggg acc atc ggc ctc ttt ctg cct ccg ttc      2126
Ile Ile Val Cys Phe Leu Gly Thr Ile Gly Leu Phe Leu Pro Pro Phe
    510                 515                 520 cta gct gga atg atc tga ctgcacctcc ctcgagctgg ctcccagggc             2174
Leu Ala Gly Met Ile *
525 aaagggagg gttcttggat gtggaagggc tttgaacaat gtttagattt ggagatgagc     2234
ccaaagtgcc aggagaaca gccaggtgag gtgggaggtt ggagagccag gtgaggtctc     2294
tgtaagtcag gctggggttg aagtttggag tctgtccgag tttgcagggt gctgagctgt    2354
atggtccagc aggggagtaa taagggctct tctggaaggg gaggaagcgg gaggcagggc    2414
ctgcacctga tgtggaggta cagggcagat cttccctacc ggggagggat ggatggttgg    2474
atacaggtgg ctgggctatt ccatccatct ggaagcacat ttgagcctcc aggcttctcc    2534
ttgacgtcat tcctctcctt ccttgctgca aaatggctct gcaccagccg gcccccagga    2594
ggtctggcag agctgagagc catggcctgc aggggctcca tatgtcccta cgcgtgcagc    2654
aggcaaacaa ga                                                        2666
```

<210> SEQ ID NO 702
<211> LENGTH: 529
<212> TYPE: PRT
<213> ORGANISM: Homo sapiens

<400> SEQUENCE: 702

```
Met Gly Pro Ser Cys Pro Val Phe Leu Ser Phe Thr Lys Leu Ser Leu
1               5                   10                  15

Trp Trp Leu Leu Leu Thr Pro Ala Gly Gly Glu Ala Lys Arg Pro
            20                  25                  30

Pro Pro Arg Ala Pro Gly Asp Pro Leu Ser Ser Pro Ser Pro Thr Ala
            35                  40                  45

Leu Pro Gln Gly Gly Ser His Thr Glu Thr Glu Asp Arg Leu Phe Lys
        50                  55                  60

His Leu Phe Arg Gly Tyr Asn Arg Trp Ala Arg Pro Val Pro Asn Thr
65                  70                  75                  80

Ser Asp Val Val Ile Val Arg Phe Gly Leu Ser Ile Ala Gln Leu Ile
                85                  90                  95

Asp Val Asp Glu Lys Asn Gln Met Met Thr Thr Asn Val Trp Leu Lys
            100                 105                 110

Gln Glu Trp Ser Asp Tyr Lys Leu Arg Trp Asn Pro Thr Asp Phe Gly
        115                 120                 125

Asn Ile Thr Ser Leu Arg Val Pro Ser Glu Met Ile Trp Ile Pro Asp
    130                 135                 140

Ile Val Leu Tyr Asn Asn Ala Asp Gly Glu Phe Ala Val Thr His Met
145                 150                 155                 160
```

-continued

```
Thr Lys Ala His Leu Phe Ser Thr Gly Thr Val His Trp Val Pro Pro
            165                 170                 175
Ala Ile Tyr Lys Ser Ser Cys Ser Ile Asp Val Thr Phe Phe Pro Phe
            180                 185                 190
Asp Gln Gln Asn Cys Lys Met Lys Phe Gly Ser Trp Thr Tyr Asp Lys
            195                 200                 205
Ala Lys Ile Asp Leu Glu Gln Met Glu Gln Thr Val Asp Leu Lys Asp
        210                 215                 220
Tyr Trp Glu Ser Gly Glu Trp Ala Ile Val Asn Ala Thr Gly Thr Tyr
225                 230                 235                 240
Asn Ser Lys Lys Tyr Asp Cys Cys Ala Glu Ile Tyr Pro Asp Val Thr
                245                 250                 255
Tyr Ala Phe Val Ile Arg Arg Leu Pro Leu Phe Tyr Thr Ile Asn Leu
                260                 265                 270
Ile Ile Pro Cys Leu Leu Ile Ser Cys Leu Thr Val Leu Val Phe Tyr
            275                 280                 285
Leu Pro Ser Asp Cys Gly Glu Lys Ile Thr Leu Cys Ile Ser Val Leu
        290                 295                 300
Leu Ser Leu Thr Val Phe Leu Leu Leu Ile Thr Glu Ile Ile Pro Ser
305                 310                 315                 320
Thr Ser Leu Val Ile Pro Leu Ile Gly Glu Tyr Leu Leu Phe Thr Met
                325                 330                 335
Ile Phe Val Thr Leu Ser Ile Val Ile Thr Val Phe Val Leu Asn Val
                340                 345                 350
His His Arg Ser Pro Ser Thr His Thr Met Pro His Trp Val Arg Gly
            355                 360                 365
Ala Leu Leu Gly Cys Val Pro Arg Trp Leu Leu Met Asn Arg Pro Pro
        370                 375                 380
Pro Pro Val Glu Leu Cys His Pro Leu Arg Leu Lys Leu Ser Pro Ser
385                 390                 395                 400
Tyr His Trp Leu Glu Ser Asn Val Asp Ala Glu Glu Arg Glu Val Val
                405                 410                 415
Val Glu Glu Glu Asp Arg Trp Ala Cys Ala Gly His Val Ala Pro Ser
                420                 425                 430
Val Gly Thr Leu Cys Ser His Gly His Leu His Ser Gly Ala Ser Gly
            435                 440                 445
Pro Lys Ala Glu Ala Leu Leu Gln Glu Gly Glu Leu Leu Leu Ser Pro
        450                 455                 460
His Met Gln Lys Ala Leu Glu Gly Val His Tyr Ile Ala Asp His Leu
465                 470                 475                 480
Arg Ser Glu Asp Ala Asp Ser Ser Val Lys Glu Asp Trp Lys Tyr Val
                485                 490                 495
Ala Met Val Ile Asp Arg Ile Phe Leu Trp Leu Phe Ile Ile Val Cys
                500                 505                 510
Phe Leu Gly Thr Ile Gly Leu Phe Leu Pro Pro Phe Leu Ala Gly Met
            515                 520                 525
Ile
```

<210> SEQ ID NO 703
<211> LENGTH: 2664
<212> TYPE: DNA
<213> ORGANISM: Homo sapiens
<220> FEATURE:
<221> NAME/KEY: CDS -continued

<222> LOCATION: (555)...(2144)

<400> SEQUENCE: 703

```
gagagaacag cgtgagcctg tgtgcttgtg tgctgagccc tcatccctc ctggggccag      60
gcttgggttt cacctgcaga atcgcttgtg ctgggctgcc tgggctgtcc tcagtggcac    120
ctgcatgaag ccgttctggc tgccagagct ggacagcccc aggaaaaccc acctctctgc    180
agagcttgcc cagctgtccc cgggaagcca aatgcctctc atgtaagtct tctgctcgac    240
ggggtgtctc ctaaaccctc actcttcagc ctctgtttga ccatgaaatg aagtgactga    300
gctctattct gtacctgcca ctctatttct ggggtgactt ttgtcagctg cccagaatct    360
ccaagccagg ctggttctct gcatcctttc aatgacctgt tttcttctgt aaccacaggt    420
tcggtggtga gaggaagcct cgcagaatcc agcagaatcc tcacagaatc cagcagcagc    480
tctgctgggg acatggtcca tggtgcaacc cacagcaaag ccctgacctg acctcctgat    540
```

| | | | | | | | | | | | | |
|---|---|---|---|---|---|---|---|---|---|---|---|---|
| gctcaggaga agcc | atg | ggc | ccc | tcc | tgt | cct | gtg | ttc | ctg | tcc | ttc | aca | 590 |
| | Met | Gly | Pro | Ser | Cys | Pro | Val | Phe | Leu | Ser | Phe | Thr | |
| | 1 | | | 5 | | | | | 10 | | | | |

```
aag ctc agc ctg tgg tgg ctc ctt ctg acc cca gca ggt gga gag gaa     638
Lys Leu Ser Leu Trp Trp Leu Leu Leu Thr Pro Ala Gly Gly Glu Glu
    15                  20                  25 gct aag cgc cca cct ccc agg gct cct gga gac cca ctc tcc tct ccc     686
Ala Lys Arg Pro Pro Pro Arg Ala Pro Gly Asp Pro Leu Ser Ser Pro
30                  35                  40 agt ccc acg gca ttg ccg cag gga ggc tcg cat acc gag act gag gac     734
Ser Pro Thr Ala Leu Pro Gln Gly Gly Ser His Thr Glu Thr Glu Asp
45                  50                  55                  60 cgg ctc ttc aaa cac ctc ttc cgg ggc tac aac cgc tgg gcg cgc ccg     782
Arg Leu Phe Lys His Leu Phe Arg Gly Tyr Asn Arg Trp Ala Arg Pro
            65                  70                  75 gtg ccc aac act tca gac gtg gtg att gtg cgc ttt gga ctg tcc atc     830
Val Pro Asn Thr Ser Asp Val Val Ile Val Arg Phe Gly Leu Ser Ile
                80                  85                  90 gct cag ctc atc gat gtg gat gag aag aac caa atg atg acc acc aac     878
Ala Gln Leu Ile Asp Val Asp Glu Lys Asn Gln Met Met Thr Thr Asn
            95                 100                 105 gtc tgg cta aaa cag gag tgg agc gac tac aaa ctg cgc tgg aac ccc     926
Val Trp Leu Lys Gln Glu Trp Ser Asp Tyr Lys Leu Arg Trp Asn Pro
110                 115                 120 gct gat ttt ggc aac atc aca tct ctc agg gtc cct tct gag atg atc     974
Ala Asp Phe Gly Asn Ile Thr Ser Leu Arg Val Pro Ser Glu Met Ile
125                 130                 135                 140 tgg atc ccc gac att gtt ctc tac aac aat gca gat ggg gag ttt gca    1022
Trp Ile Pro Asp Ile Val Leu Tyr Asn Asn Ala Asp Gly Glu Phe Ala
                145                 150                 155 gtg acc cac atg acc aag gcc cac ctc ttc tcc acg ggc act gtg cac    1070
Val Thr His Met Thr Lys Ala His Leu Phe Ser Thr Gly Thr Val His
            160                 165                 170 tgg gtg ccc ccg gcc atc tac aag agc tcc tgc agc atc gac gtc acc    1118
Trp Val Pro Pro Ala Ile Tyr Lys Ser Ser Cys Ser Ile Asp Val Thr
175                 180                 185 ttc ttc ccc ttc gac cag cag aac tgc aag atg aag ttt ggc tcc tgg    1166
Phe Phe Pro Phe Asp Gln Gln Asn Cys Lys Met Lys Phe Gly Ser Trp
            190                 195                 200 act tat gac aag gcc aag atc gac ctg gag cag atg gag cag act gtg    1214
Thr Tyr Asp Lys Ala Lys Ile Asp Leu Glu Gln Met Glu Gln Thr Val
205                 210                 215                 220 gac ctg aag gac tac tgg gag agc ggc gag tgg gcc atc gtc aat gcc    1262
```

-continued

```
                Asp Leu Lys Asp Tyr Trp Glu Ser Gly Glu Trp Ala Ile Val Asn Ala
                            225                 230                 235 acg ggc acc tac aac agc aag aag tac gac tgc tgc gcc gag atc tac      1310
Thr Gly Thr Tyr Asn Ser Lys Lys Tyr Asp Cys Cys Ala Glu Ile Tyr
            240                 245                 250 ccc gac gtc acc tac gcc ttc gtc atc cgg cgg ctg ccg ctc ttc tac      1358
Pro Asp Val Thr Tyr Ala Phe Val Ile Arg Arg Leu Pro Leu Phe Tyr
            255                 260                 265 acc atc aac ctc atc atc ccc tgc ctg ctc atc tcc tgc ctc act gtg      1406
Thr Ile Asn Leu Ile Ile Pro Cys Leu Leu Ile Ser Cys Leu Thr Val
            270                 275                 280 ctg gtc ttc tac ctg ccc tcc gac tgc ggc gag aag atc acg ctg tgc      1454
Leu Val Phe Tyr Leu Pro Ser Asp Cys Gly Glu Lys Ile Thr Leu Cys
285                 290                 295                 300 att tcg gtg ctg ctg tca ctc acc gtc ttc ctg ctc atc act gag          1502
Ile Ser Val Leu Leu Ser Leu Thr Val Phe Leu Leu Ile Thr Glu
                305                 310                 315 atc atc ccg tcc acc tcg ctg gtc atc ccg ctc atc ggc gag tac ctg      1550
Ile Ile Pro Ser Thr Ser Leu Val Ile Pro Leu Ile Gly Glu Tyr Leu
            320                 325                 330 ctg ttc acc atg atc ttc gtc acc ctg tcc atc gtc atc acc gtc ttc      1598
Leu Phe Thr Met Ile Phe Val Thr Leu Ser Ile Val Ile Thr Val Phe
            335                 340                 345 gtg ctc aat gtg cac cac cgc tcc ccc agc acc cac acc atg ccc cac      1646
Val Leu Asn Val His His Arg Ser Pro Ser Thr His Thr Met Pro His
            350                 355                 360 tgg gtg cgg ggg gcc ctt ctg ggc tgt gtg ccc cgg tgg ctt ctg atg      1694
Trp Val Arg Gly Ala Leu Leu Gly Cys Val Pro Arg Trp Leu Leu Met
365                 370                 375                 380 aac cgg ccc cca cca ccc gtg gag ctc tgc cac ccc cta cgc ctg aag      1742
Asn Arg Pro Pro Pro Pro Val Glu Leu Cys His Pro Leu Arg Leu Lys
                385                 390                 395 ctc agc ccc tct tat cac tgg ctg gag agc aac gtg gat gcc gag gag      1790
Leu Ser Pro Ser Tyr His Trp Leu Glu Ser Asn Val Asp Ala Glu Glu
            400                 405                 410 agg gag gtg gtg gtg gag gag gag gac aga tgg gca tgt gca ggt cat      1838
Arg Glu Val Val Val Glu Glu Glu Asp Arg Trp Ala Cys Ala Gly His
            415                 420                 425 gtg gcc ccc tct gtg ggc acc ctc tgc agc cac ggc cac ctg cac tct      1886
Val Ala Pro Ser Val Gly Thr Leu Cys Ser His Gly His Leu His Ser
            430                 435                 440 ggg gcc tca ggt ccc aag gct gag gct ctg ctg cag gag ggt gag ctg      1934
Gly Ala Ser Gly Pro Lys Ala Glu Ala Leu Leu Gln Glu Gly Glu Leu
445                 450                 455                 460 ctg cta tca ccc cac atg cag aag gca ctg gaa ggt gtg cac tac att      1982
Leu Leu Ser Pro His Met Gln Lys Ala Leu Glu Gly Val His Tyr Ile
            465                 470                 475 gcc gac cac ctg cgg tct gag gat gct gac tct tcg gtg aag gag gac      2030
Ala Asp His Leu Arg Ser Glu Asp Ala Asp Ser Ser Val Lys Glu Asp
            480                 485                 490 tgg aag tat gtt gcc atg gtc atc gac agg atc ttc ctc tgg ctg ttt      2078
Trp Lys Tyr Val Ala Met Val Ile Asp Arg Ile Phe Leu Trp Leu Phe
            495                 500                 505 atc atc gtc tgc ttc ctg ggg acc atc ggc ctc ttt ctg cct ccg ttc      2126
Ile Ile Val Cys Phe Leu Gly Thr Ile Gly Leu Phe Leu Pro Pro Phe
            510                 515                 520 cta gct gga atg atc tga ctgcacctcc ctcgagctgg ctcccagggc             2174
Leu Ala Gly Met Ile *
525
```

-continued

```
aaaggggagg gttcttggat gtggaagggc ttttgaacaat gtttagatttt ggagatgagc     2234 ccaaagtgcc agggagaaca gccaggtgag gtgggaggtt ggagagccag gtgaggtctc      2294
tctaagtcag gctggggttg aagtttggag tctgtccgag tttgcagggt gctgagctgt      2354
atggtccagc agggagtaa taagggctct tccggaaggg gaggaagcgg gaggcaggcc       2414
tgcacctgat gtggaggtac aggcagatct tccctaccgg ggagggatgg atggttggat      2474
acaggtggct gggctattcc atccatctgg aagcacattt gagcctccag gcttctcctt      2534
gacgtcattc ctctccttcc ttgctgcaaa atggctctgc accagccggc ccccaggagg      2594
tctggcagag ctgagagcca tggcctgcag gggctccata tgtccctacg cgtgcagcag      2654
gcaaacaaga                                                              2664
```

<210> SEQ ID NO 704
<211> LENGTH: 529
<212> TYPE: PRT
<213> ORGANISM: Homo sapiens

<400> SEQUENCE: 704

```
Met Gly Pro Ser Cys Pro Val Phe Leu Ser Phe Thr Lys Leu Ser Leu
 1               5                  10                  15

Trp Trp Leu Leu Leu Thr Pro Ala Gly Gly Glu Glu Ala Lys Arg Pro
            20                  25                  30

Pro Pro Arg Ala Pro Gly Asp Pro Leu Ser Ser Pro Ser Pro Thr Ala
        35                  40                  45

Leu Pro Gln Gly Gly Ser His Thr Glu Thr Glu Asp Arg Leu Phe Lys
    50                  55                  60

His Leu Phe Arg Gly Tyr Asn Arg Trp Ala Arg Pro Val Pro Asn Thr
65                  70                  75                  80

Ser Asp Val Val Ile Val Arg Phe Gly Leu Ser Ile Ala Gln Leu Ile
                85                  90                  95

Asp Val Asp Glu Lys Asn Gln Met Met Thr Thr Asn Val Trp Leu Lys
            100                 105                 110

Gln Glu Trp Ser Asp Tyr Lys Leu Arg Trp Asn Pro Ala Asp Phe Gly
        115                 120                 125

Asn Ile Thr Ser Leu Arg Val Pro Ser Glu Met Ile Trp Ile Pro Asp
    130                 135                 140

Ile Val Leu Tyr Asn Asn Ala Asp Gly Glu Phe Ala Val Thr His Met
145                 150                 155                 160

Thr Lys Ala His Leu Phe Ser Thr Gly Thr Val His Trp Val Pro Pro
                165                 170                 175

Ala Ile Tyr Lys Ser Ser Cys Ser Ile Asp Val Thr Phe Phe Pro Phe
            180                 185                 190

Asp Gln Gln Asn Cys Lys Met Lys Phe Gly Ser Trp Thr Tyr Asp Lys
        195                 200                 205

Ala Lys Ile Asp Leu Glu Gln Met Glu Gln Thr Val Asp Leu Lys Asp
    210                 215                 220

Tyr Trp Glu Ser Gly Glu Trp Ala Ile Val Asn Ala Thr Gly Thr Tyr
225                 230                 235                 240

Asn Ser Lys Lys Tyr Asp Cys Cys Ala Glu Ile Tyr Pro Asp Val Thr
                245                 250                 255

Tyr Ala Phe Val Ile Arg Arg Leu Pro Leu Phe Tyr Thr Ile Asn Leu
            260                 265                 270

Ile Ile Pro Cys Leu Leu Ile Ser Cys Leu Thr Val Leu Val Phe Tyr
        275                 280                 285
```

-continued

```
Leu Pro Ser Asp Cys Gly Glu Lys Ile Thr Leu Cys Ile Ser Val Leu
    290                 295                 300
Leu Ser Leu Thr Val Phe Leu Leu Ile Thr Glu Ile Ile Pro Ser
305                 310                 315                 320
Thr Ser Leu Val Ile Pro Leu Ile Gly Glu Tyr Leu Phe Thr Met
                325                 330                 335
Ile Phe Val Thr Leu Ser Ile Val Ile Thr Val Phe Val Leu Asn Val
            340                 345                 350
His His Arg Ser Pro Ser Thr His Thr Met Pro His Trp Val Arg Gly
                355                 360                 365
Ala Leu Leu Gly Cys Val Pro Arg Trp Leu Leu Met Asn Arg Pro Pro
    370                 375                 380
Pro Pro Val Glu Leu Cys His Pro Leu Arg Leu Lys Leu Ser Pro Ser
385                 390                 395                 400
Tyr His Trp Leu Glu Ser Asn Val Asp Ala Glu Glu Arg Glu Val Val
                405                 410                 415
Val Glu Glu Asp Arg Trp Ala Cys Ala Gly His Val Ala Pro Ser
            420                 425                 430
Val Gly Thr Leu Cys Ser His Gly His Leu His Ser Gly Ala Ser Gly
            435                 440                 445
Pro Lys Ala Glu Ala Leu Leu Gln Glu Gly Leu Leu Leu Ser Pro
    450                 455                 460
His Met Gln Lys Ala Leu Glu Gly Val His Tyr Ile Ala Asp His Leu
465                 470                 475                 480
Arg Ser Glu Asp Ala Asp Ser Ser Val Lys Glu Asp Trp Lys Tyr Val
                485                 490                 495
Ala Met Val Ile Asp Arg Ile Phe Leu Trp Leu Phe Ile Ile Val Cys
            500                 505                 510
Phe Leu Gly Thr Ile Gly Leu Phe Leu Pro Pro Phe Leu Ala Gly Met
            515                 520                 525
Ile

<210> SEQ ID NO 705
<211> LENGTH: 529
<212> TYPE: PRT
<213> ORGANISM: Homo sapiens

<400> SEQUENCE: 705

Met Gly Pro Ser Cys Pro Val Phe Leu Ser Phe Thr Lys Leu Ser Leu
1               5                   10                  15
Trp Trp Leu Leu Leu Thr Pro Ala Gly Gly Glu Glu Ala Lys Arg Pro
            20                  25                  30
Pro Pro Arg Ala Pro Gly Asp Pro Leu Ser Ser Pro Ser Pro Thr Ala
        35                  40                  45
Leu Pro Gln Gly Gly Ser His Thr Glu Thr Glu Asp Arg Leu Phe Lys
    50                  55                  60
His Leu Phe Arg Gly Tyr Asn Arg Trp Ala Arg Pro Val Pro Asn Thr
65                  70                  75                  80
Ser Asp Val Val Ile Val Arg Phe Gly Leu Ser Ile Ala Gln Leu Ile
                85                  90                  95
Asp Val Asp Glu Lys Asn Gln Met Met Thr Thr Asn Val Trp Leu Lys
            100                 105                 110
Gln Glu Trp Ser Asp Tyr Lys Leu Arg Trp Asn Pro Thr Asp Phe Gly
        115                 120                 125
```

```
Asn Ile Thr Ser Leu Arg Val Pro Ser Glu Met Ile Trp Ile Pro Asp
    130                 135                 140

Ile Val Leu Tyr Asn Asn Ala Asp Gly Glu Phe Ala Val Thr His Met
145                 150                 155                 160

Thr Lys Ala His Leu Phe Ser Thr Gly Thr Val His Trp Val Pro Pro
                165                 170                 175

Ala Ile Tyr Lys Ser Ser Cys Ser Ile Asp Val Thr Phe Phe Pro Phe
            180                 185                 190

Asp Gln Gln Asn Cys Lys Met Lys Phe Gly Ser Trp Thr Tyr Asp Lys
        195                 200                 205

Ala Lys Ile Asp Leu Glu Gln Met Glu Gln Thr Val Asp Leu Lys Asp
    210                 215                 220

Tyr Trp Glu Ser Gly Glu Trp Ala Ile Val Asn Ala Thr Gly Thr Tyr
225                 230                 235                 240

Asn Ser Lys Lys Tyr Asp Cys Cys Ala Glu Ile Tyr Pro Asp Val Thr
                245                 250                 255

Tyr Ala Phe Val Ile Arg Arg Leu Pro Leu Phe Tyr Thr Ile Asn Leu
            260                 265                 270

Ile Ile Pro Cys Leu Leu Ile Ser Cys Leu Thr Val Leu Val Phe Tyr
        275                 280                 285

Leu Pro Ser Asp Cys Gly Glu Lys Ile Thr Leu Cys Ile Ser Val Leu
    290                 295                 300

Leu Ser Leu Thr Val Phe Leu Leu Leu Ile Thr Glu Ile Ile Pro Ser
305                 310                 315                 320

Thr Ser Leu Val Ile Pro Leu Ile Gly Glu Tyr Leu Leu Phe Thr Met
                325                 330                 335

Ile Phe Val Thr Leu Ser Ile Val Ile Thr Val Phe Val Leu Asn Val
            340                 345                 350

His His Arg Ser Pro Ser Thr His Thr Met Pro His Trp Val Arg Gly
        355                 360                 365

Ala Leu Leu Gly Cys Val Pro Arg Trp Leu Leu Met Asn Arg Pro Pro
    370                 375                 380

Pro Pro Val Glu Leu Cys His Pro Leu Arg Leu Lys Leu Ser Pro Ser
385                 390                 395                 400

Tyr His Trp Leu Glu Ser Asn Val Asp Ala Glu Glu Arg Glu Val Val
                405                 410                 415

Val Glu Glu Glu Asp Arg Trp Ala Cys Ala Gly His Val Ala Pro Ser
            420                 425                 430

Val Gly Thr Leu Cys Ser His Gly His Leu His Ser Gly Ala Ser Gly
        435                 440                 445

Pro Lys Ala Glu Ala Leu Leu Gln Glu Gly Glu Leu Leu Leu Ser Pro
    450                 455                 460

His Met Gln Lys Ala Leu Glu Gly Val His Tyr Ile Ala Asp His Leu
465                 470                 475                 480

Arg Ser Glu Asp Ala Asp Ser Ser Val Lys Glu Asp Trp Lys Tyr Val
                485                 490                 495

Ala Met Val Ile Asp Arg Ile Phe Leu Trp Leu Phe Ile Ile Val Cys
            500                 505                 510

Phe Leu Gly Thr Ile Gly Leu Phe Leu Pro Pro Phe Leu Ala Gly Met
        515                 520                 525

Ile
```

<210> SEQ ID NO 706
<211> LENGTH: 25
<212> TYPE: DNA
<213> ORGANISM: Homo sapiens

<400> SEQUENCE: 706
atatcgccgc gctcgtcgtc gacaa                                    25

<210> SEQ ID NO 707
<211> LENGTH: 26
<212> TYPE: DNA
<213> ORGANISM: Homo sapiens

<400> SEQUENCE: 707
agccacacgc agctcattgt agaagg                                   26

<210> SEQ ID NO 708
<211> LENGTH: 10
<212> TYPE: DNA
<213> ORGANISM: Homo sapiens

<400> SEQUENCE: 708
gatcctcggc                                                     10

<210> SEQ ID NO 709
<211> LENGTH: 22
<212> TYPE: DNA
<213> ORGANISM: Homo sapiens

<400> SEQUENCE: 709
ctaatacgac tcactatagg gc                                       22

<210> SEQ ID NO 710
<211> LENGTH: 14
<212> TYPE: PRT
<213> ORGANISM: Clostridium tetani

<400> SEQUENCE: 710

Gln Tyr Ile Lys Ala Asn Ser Lys Phe Ile Gly Ile Thr Glu
 1 5 10

<210> SEQ ID NO 711
<211> LENGTH: 21
<212> TYPE: PRT
<213> ORGANISM: Plasmodium faciparum

<400> SEQUENCE: 711

Asp Ile Glu Lys Lys Ile Ala Lys Met Glu Lys Ala Ser Ser Val Phe
1 5 10 15

Asn Val Val Asn Ser
20

<210> SEQ ID NO 712
<211> LENGTH: 16
<212> TYPE: PRT
<213> ORGANISM: Streptococcus mutans

<400> SEQUENCE: 712

Gly Ala Val Asp Ser Ile Leu Gly Gly Val Ala Thr Tyr Gly Ala Ala
1 5 10 15

<210> SEQ ID NO 713
<211> LENGTH: 13
<212> TYPE: PRT

```
<213> ORGANISM: Artificial Sequence
<220> FEATURE:
<221> NAME/KEY: VARIANT
<222> LOCATION: 1, 13
<223> OTHER INFORMATION: A = D-Alanine or L-Alanine
<221> NAME/KEY: VARIANT
<222> LOCATION: 3
<223> OTHER INFORMATION: Xaa = cyclohexylalanine, phenylalanine, or
      tyrosine
<220> FEATURE:
<223> OTHER INFORMATION: Synthetic construct

<400> SEQUENCE: 713

Ala Lys Xaa Val Ala Ala Trp Thr Leu Lys Ala Ala Ala
 1               5                  10

<210> SEQ ID NO 714
<211> LENGTH: 14
<212> TYPE: DNA
<213> ORGANISM: Homo sapiens

<400> SEQUENCE: 714
ttttgatcaa gctt                                                         14

<210> SEQ ID NO 715
<211> LENGTH: 42
<212> TYPE: DNA
<213> ORGANISM: Homo sapiens

<400> SEQUENCE: 715
ctaatacgac tcactatagg gctcgagcgg ccgcccgggc ag                           42

<210> SEQ ID NO 716
<211> LENGTH: 12
<212> TYPE: DNA
<213> ORGANISM: Homo sapiens

<400> SEQUENCE: 716
gatcctgccc gg                                                           12

<210> SEQ ID NO 717
<211> LENGTH: 40
<212> TYPE: DNA
<213> ORGANISM: Homo sapiens

<400> SEQUENCE: 717
gtaatacgac tcactatagg gcagcgtggt cgcggccgag                              40

<210> SEQ ID NO 718
<211> LENGTH: 22
<212> TYPE: DNA
<213> ORGANISM: Homo sapiens

<400> SEQUENCE: 718
tcgagcggcc gcccgggcag ga                                                22

<210> SEQ ID NO 719
<211> LENGTH: 20
<212> TYPE: DNA
<213> ORGANISM: Homo sapiens

<400> SEQUENCE: 719
agcgtggtcg cggccgagga                                                   20

<210> SEQ ID NO 720
```

```
<211> LENGTH: 4
<212> TYPE: PRT
<213> ORGANISM: Homo sapiens

<400> SEQUENCE: 720

Asn Thr Ser Asp
  1

<210> SEQ ID NO 721
<211> LENGTH: 4
<212> TYPE: PRT
<213> ORGANISM: Homo sapiens

<400> SEQUENCE: 721

Asn Ile Thr Ser
  1

<210> SEQ ID NO 722
<211> LENGTH: 4
<212> TYPE: PRT
<213> ORGANISM: Homo sapiens

<400> SEQUENCE: 722

Asn Ala Thr Gly
  1

<210> SEQ ID NO 723
<211> LENGTH: 4
<212> TYPE: PRT
<213> ORGANISM: Homo sapiens

<400> SEQUENCE: 723

Ser His Thr Glu
  1

<210> SEQ ID NO 724
<211> LENGTH: 4
<212> TYPE: PRT
<213> ORGANISM: Homo sapiens

<400> SEQUENCE: 724

Thr Glu Thr Glu
  1

<210> SEQ ID NO 725
<211> LENGTH: 4
<212> TYPE: PRT
<213> ORGANISM: Homo sapiens

<400> SEQUENCE: 725

Ser Asn Val Asp
  1

<210> SEQ ID NO 726
<211> LENGTH: 4
<212> TYPE: PRT
<213> ORGANISM: Homo sapiens

<400> SEQUENCE: 726

Ser Val Lys Glu
  1

<210> SEQ ID NO 727
<211> LENGTH: 8
<212> TYPE: PRT
```

<213> ORGANISM: Homo sapiens

<400> SEQUENCE: 727

Lys Ala Leu Glu Gly Val His Tyr
1               5

<210> SEQ ID NO 728
<211> LENGTH: 6
<212> TYPE: PRT
<213> ORGANISM: Homo sapiens

<400> SEQUENCE: 728

Gly Gly Glu Glu Ala Lys
1               5

<210> SEQ ID NO 729
<211> LENGTH: 6
<212> TYPE: PRT
<213> ORGANISM: Homo sapiens

<400> SEQUENCE: 729

Gly Gly Ser His Thr Glu
1               5

<210> SEQ ID NO 730
<211> LENGTH: 6
<212> TYPE: PRT
<213> ORGANISM: Homo sapiens

<400> SEQUENCE: 730

Gly Leu Ser Ile Ala Gln
1               5

<210> SEQ ID NO 731
<211> LENGTH: 6
<212> TYPE: PRT
<213> ORGANISM: Homo sapiens

<400> SEQUENCE: 731

Gly Asn Ile Thr Ser Leu
1               5

<210> SEQ ID NO 732
<211> LENGTH: 6
<212> TYPE: PRT
<213> ORGANISM: Homo sapiens

<400> SEQUENCE: 732

Gly Thr Tyr Asn Ser Lys
1               5

<210> SEQ ID NO 733
<211> LENGTH: 6
<212> TYPE: PRT
<213> ORGANISM: Homo sapiens

<400> SEQUENCE: 733

Gly Ala Leu Leu Gly Cys
1               5

<210> SEQ ID NO 734
<211> LENGTH: 6
<212> TYPE: PRT
<213> ORGANISM: Homo sapiens -continued

```
<400> SEQUENCE: 734

Gly Thr Leu Cys Ser His
 1               5

<210> SEQ ID NO 735
<211> LENGTH: 15
<212> TYPE: PRT
<213> ORGANISM: Homo sapiens

<400> SEQUENCE: 735

Cys Ser Ile Asp Val Thr Phe Phe Pro Phe Asp Gln Gln Asn Cys
 1               5                  10                  15

<210> SEQ ID NO 736
<211> LENGTH: 289
<212> TYPE: DNA
<213> ORGANISM: Homo sapiens
<220> FEATURE:
<221> NAME/KEY: misc_feature
<222> LOCATION: (1)...(289)
<223> OTHER INFORMATION: n = A,T,C or G

<400> SEQUENCE: 736
gatcttncct accggggagg gatggatggt tggatacagg tggctgggct attccatcca      60
tntggaagca catttgagcc tccaggcttc tccttgacgt cattcctctc cttccttgct    120
gcaaaatggc tctgcaccag ccggccccca ggaggtctgg cagagctgag agccatggcc    180
tgnaggggct ccatatgtcc ctacgcgtgc agnaggcaaa caagaaagac catcctgagc    240
tgctnctgac ccacctcaaa ctcatttcat ttggcctgtc ctccctccc                289
```

NUCLEIC ACID AND CORRESPONDING PROTEIN ENTITLED 205P1B5 USEFUL IN TREATMENT AND DETECTION OF CANCER

CROSS REFERENCE TO RELATED APPLICATIONS

This application is a national stage application under 35 USC §371 of International Patent Application No. PCT/US02/27760, having an International Filing Date of Aug. 30, 2002 and published in the English language on Mar. 13, 2003, which claims the priority benefit of U.S. Provisional Patent Application No. 60/316,664 filed Aug. 31, 2001, now abandoned. The contents of those applications are hereby incorporated by reference herein in their entirety.

FIELD OF THE INVENTION

The invention described herein relates to a novel gene and its encoded protein, termed 205P1B5, and to diagnostic and therapeutic, methods and compositions useful in the management of various cancers that express 205P1B5.

BACKGROUND OF THE INVENTION

Cancer is the second leading cause of human death next to coronary disease. Worldwide, millions of people die from cancer every year. In the United States alone, as reported by the American Cancer Society, cancer causes the death of well over a half-million people annually, with over 1.2 million new cases diagnosed per year. While deaths from heart disease have been declining significantly, those resulting from cancer generally are on the rise. In the early part of the next century, cancer is predicted to become the leading cause of death.

Worldwide, several cancers stand out as the leading killers. In particular, carcinomas of the lung, prostate, breast, colon, pancreas, and ovary represent the primary causes of cancer death. These and virtually all other carcinomas share a common lethal feature. With very few exceptions, metastatic disease from a carcinoma is fatal. Moreover, even for those cancer patients who initially survive their primary cancers, common experience has shown that their lives are dramatically altered. Many cancer patients experience strong anxieties driven by the awareness of the potential for recurrence or treatment failure. Many cancer patients experience physical debilitations following treatment. Furthermore, many cancer patients experience a recurrence.

Worldwide, prostate cancer is the fourth most prevalent cancer in men. In North America and Northern Europe, it is by far the most common cancer in males and is the second leading cause of cancer death in men. In the United States alone, well over 30,000 men die annually of this disease-second only to lung cancer. Despite the magnitude of these figures, there is still no effective treatment for metastatic prostate cancer. Surgical prostatectomy, radiation therapy, hormone ablation therapy, surgical castration and chemotherapy continue to be the main treatment modalities. Unfortunately, these treatments are ineffective for many and are often associated with undesirable consequences.

On the diagnostic front, the lack of a prostate tumor marker that can accurately detect early-stage, localized tumors remains a significant limitation in the diagnosis and management of this disease. Although the serum prostate specific antigen (PSA) assay has been a very useful tool, however its specificity and general utility is widely regarded as lacking in several important respects.

Progress in identifying additional specific markers for prostate cancer has been improved by the generation of prostate cancer xenografts that can recapitulate different stages of the disease in mice. The LAPC (Los Angeles Prostate Cancer) xenografts are prostate cancer xenografts that have survived passage in severe combined immune deficient (SCBD) mice and have exhibited the capacity to mimic the transition from androgen dependence to androgen independence (Klein et al., 1997, Nat. Med. 3:402). More recently identified prostate cancer markers include PCTA-1 (Su et al., 1996, Proc. Natl. Acad. Sci. USA 93: 7252), prostate-specific membrane (PSM) antigen (Pinto et al., Clin Cancer Res 1996 Sep. 2 (9): 1445-51), STEAP (Hubert, et al., Proc Natl Acad Sci USA. 1999 Dec. 7; 96(25): 14523-8) and prostate stem cell antigen (PSCA) (Reiter et al., 1998, Proc. Natl. Acad. Sci. USA 95: 1735).

While previously identified markers such as PSA, PSM, PCTA and PSCA have facilitated efforts to diagnose and treat prostate cancer, there is need for the identification of additional markers and therapeutic targets for prostate and related cancers in order to further improve diagnosis and therapy.

Renal cell carcinoma (RCC) accounts for approximately 3 percent of adult malignancies. Once adenomas reach a diameter of 2 to 3 cm, malignant potential exists. In the adult, the two principal malignant renal tumors are renal cell adenocarcinoma and transitional cell carcinoma of the renal pelvis or ureter. The incidence of renal cell adenocarcinoma is estimated at more than 29,000 cases in the United States, and more than 11,600 patients died of this disease in 1998. Transitional cell carcinoma is less frequent, with an incidence of approximately 500 cases per year in the United States.

Surgery has been the primary therapy for renal cell adenocarcinoma for many decades. Until recently, metastatic disease has been refractory to any systemic therapy. With recent developments in systemic therapies, particularly immunotherapies, metastatic renal cell carcinoma may be approached aggressively in appropriate patients with a possibility of durable responses. Nevertheless, there is a remaining need for effective therapies for these patients.

Of all new cases of cancer in the United States, bladder cancer represents approximately 5 percent in men (fifth most common neoplasm) and 3 percent in women (eighth most common neoplasm). The incidence is increasing slowly, concurrent with an increasing older population. In 1998, there was an estimated 54,500 cases, including 39,500 in men and 15,000 in women. The age-adjusted incidence in the United States is 32 per 100,000 for men and 8 per 100,000 in women. The historic male/female ratio of 3:1 may be decreasing related to smoking patterns in women. There were an estimated 11,000 deaths from bladder cancer in 1998 (7,800 in men and 3,900 in women). Bladder cancer incidence and mortality strongly increase with age and will be an increasing problem as the population becomes more elderly.

Most bladder cancers recur in the bladder. Bladder cancer is managed with a combination of transurethral resection of the bladder (TUR) and in transvesical chemotherapy or immunotherapy. The multifocal and recurrent nature of bladder cancer points out the limitations of TUR Most muscle-invasive cancers are not cured by TUR alone. Radical cystectomy and urinary diversion is the most effective means to eliminate the cancer but carry an undeniable impact on urinary and sexual function. There continues to be a significant need for treatment modalities that are beneficial for bladder cancer patients.

An estimated 130,200 cases of colorectal cancer occurred in 2000 in the United States, including 93,800 cases of colon cancer and 36,400 of rectal cancer. Colorectal cancers are the third most common cancers in men and women. Incidence rates declined significantly during 1992-1996 (-2.1% per year). Research suggests that these declines have been due to increased screening and polyp removal, preventing progression of polyps to invasive cancers. There were an estimated 56,300 deaths (47,700 from colon cancer, 8,600 from rectal cancer) in 2000, accounting for about 11% of all U.S. cancer deaths.

At present, surgery is the most common form of therapy for colorectal cancer, and for cancers that have not spread, it is frequently curative. Chemotherapy, or chemotherapy plus radiation is given before or after surgery to most patients whose cancer has deeply perforated the bowel wall or has spread to the lymph nodes. A permanent colostomy (creation of an abdominal opening for elimination of body wastes) is occasionally needed for colon cancer and is infrequently required for rectal cancer. There continues to be a need for effective diagnostic and treatment modalities for colorectal cancer.

There were an estimated 164,100 new cases of lung and bronchial cancer in 2000, accounting for 14% of all U.S. cancer diagnoses. The incidence rate of lung and bronchial cancer is declining significantly in men, from a high of 86.5 per 100,000 in 1984 to 70.0 in 1996. In the 1990s, the rate of increase among women began to slow. In 1996, the incidence rate in women was 42.3 per 100,000.

Lung and bronchial cancer caused an estimated 156,900 deaths in 2000, accounting for 28% of all cancer deaths. During 1992-1996, mortality from lung cancer declined significantly among men (−1.7% per year) while rates for women were still significantly increasing (0.9% per year). Since 1987, more women have died each year of lung cancer than breast cancer, which, for over 40 years, was the major cause of cancer death in women. Decreasing lung cancer incidence and mortality rates most likely resulted from decreased smoking rates over the previous 30 years; however, decreasing smoking patterns among women lag behind those of men. Of concern, although the declines in adult tobacco use have slowed, tobacco use in youth is increasing again.

Treatment options for lung and bronchial cancer are determined by the type and stage of the cancer and include surgery, radiation therapy, and chemotherapy. For many localized cancers, surgery is usually the treatment of choice. Because the disease has usually spread by the time it is discovered, radiation therapy and chemotherapy are often needed in combination with surgery. Chemotherapy alone or combined with radiation is the treatment of choice for small cell lung cancer; on this regimen, a large percentage of patients experience remission, which in some cases is long lasting. There is however, an ongoing need for effective treatment and diagnostic approaches for lung and bronchial cancers.

An estimated 182,800 new invasive cases of breast cancer were expected to occur among women in the United States during 2000. Additionally, about 1,400 new cases of breast cancer were expected to be diagnosed in men in 2000. After increasing about 4% per year in the 1980s, breast cancer incidence rates in women have leveled off in the 1990s to about 110.6 cases per 100,000.

In the U.S. alone, there were an estimated 41,200 deaths (40,800 women, 400 men) in 2000 due to breast cancer. Breast cancer ranks second among cancer deaths in women. According to the most recent data, mortality rates declined significantly during 1992-1996 with the largest decreases in younger women, both white and black. These decreases were probably the result of earlier detection and improved treatment.

Taking into account the medical circumstances and the patient's preferences, treatment of breast cancer may involve lumpectomy (local removal of the tumor) and removal of the lymph nodes under the arm; mastectomy (surgical removal of the breast) and removal of the lymph nodes under the arm; radiation therapy, chemotherapy; or hormone therapy. Often, two or more methods are used in combination. Numerous studies have shown that, for early stage disease, long-term survival rates after lumpectomy plus radiotherapy are similar to survival rates after modified radical mastectomy. Significant advances in reconstruction techniques provide several options for breast reconstruction after mastectomy. Recently, such reconstruction has been done at the same time as the mastectomy.

Local excision of ductal carcinoma in situ (DCIS) with adequate amounts of surrounding normal breast tissue may prevent the local recurrence of the DCIS. Radiation to the breast and/or taroxifen may reduce the chance of DCIS occurring in the remaining breast tissue. This is important because DCIS, if left untreated, may develop into invasive breast cancer. Nevertheless, there are serious side effects or sequelae to these treatments. There is, therefore, a need for efficacious breast cancer treatments.

There were an estimated 23,100 new cases of ovarian cancer in the United States in 2000. It accounts for 4% of all cancers among women and ranks second among gynecologic cancers. During 1992-1996, ovarian cancer incidence rates were significantly declining. Consequent to ovarian cancer, there were an estimated 14,000 deaths in 2000. Ovarian cancer causes more deaths than any other cancer of the female reproductive system.

Surgery, radiation therapy, and chemotherapy are treatment options for ovarian cancer. Surgery usually includes the removal of one or both ovaries, the fallopian tubes (salpingo-oophorectomy), and the uterus (hysterectomy). In some very early tumors, only the involved ovary will be removed, especially in young women who wish to have children. In advanced disease, an attempt is made to remove all intra-abdominal disease to enhance the effect of chemotherapy. There continues to be an important need for effective treatment options for ovarian cancer.

There were an estimated 28,300 new cases of pancreatic cancer in the United States in 2000. Over the past 20 years, rates of pancreatic cancer have declined in men. Rates among women have remained approximately constant but may be beginning to decline. Pancreatic cancer caused an estimated 28,200 deaths in 2000 in the United States. Over the past 20 years, there has been a slight but significant decrease in mortality rates among men (about −0.9% per year) while rates have increased slightly among women.

Surgery, radiation therapy, and chemotherapy are treatment options for pancreatic cancer. These treatment options can extend survival and/or relieve symptoms in many patients but are not likely to produce a cure for most. There is a significant need for additional therapeutic and diagnostic options for pancreatic cancer.

SUMMARY OF TIE INVENTION

The present invention relates to a gene, designated 205P1B5, that is over-expressed in the cancer(s) listed in Table I. There are two variants of 205P1B5 (see, e.g. FIG. 2); unless the context clearly indicates otherwise. Reference herein to 205P1B5 refers to either of these variants. Northern blot expression analysis of 205P1B5 gene expression in normal tissues shows a restricted expression pattern in adult tissues. The nucleotide (FIG. 2) and amino acid (FIG. 2, and FIG. 3) sequences of 205P1B5 are provided. The tissue-related profile of 205P1B5 in normal adult tissues, combined with the over-expression observed in prostate tumors, shows that 205P1B5 is aberrantly over-expressed in at least some cancers, and thus serves as a useful diagnostic, prophylactic, prognostic, and/or therapeutic target for cancers of the tissue(s) such as those listed in Table I.

The invention provides polynucleotides corresponding or complementary to all or part of the 205P1B5 genes, mRNAs, and/or coding sequences, preferably in isolated form, including polynucleotides encoding 205P1B5-related proteins and fragments of 4, 5, 6, 7, 8, 9, 10, 11, 12, 13, 14, 15, 16, 17, 18, 19, 20, 21, 22, 23, 24, 25, or more tan 25 contiguous amino acids; at least 30, 35, 40, 45, 50, 55, 60, 65, 70, 80, 85, 90, 95, 100or more than 100 contiguous amino acids of a 205P1B5-related protein, as well as the peptides/proteins themselves; DNA, RNA, DNA/RNA hybrids, and related molecules, polynucleotides or oligonucleotides complementary or having at least a 90% homology to the 205P1B5 genes or mRNA sequences or parts thereof, and polynucleotides or oligonucleotides that hybridize to the 205P1B5 genes, mRNAs, or to 205P1B5-encoding polynucleotides. Also provided are means for isolating cDNAs and the genes encoding 205P1B5. Recombinant DNA molecules containing 205P1B5 polynucleotides, cells transformed or transduced with such molecules, and host-vector systems for the expression of 205P1B5 gene products are also provided. The invention further provides antibodies that bind to 205P1B5 proteins and polypeptide fragments thereof, including polyclonal and monoclonal antibodies, murine and other mammalian antibodies, chimeric antibodies, humanized and fully human antibodies, and antibodies labeled with a detectable marker. In certain embodiments there is a proviso that the entire nucleic acid sequence of FIG. 2 is not encoded and/or the entire amino acid sequence of FIG. 2 is not prepared. In certain embodiments, the entire nucleic acid sequence of FIG. 2 is encoded and/or the entire amino acid sequence of FIG. 2 is prepared, either of which are in respective human unit dose forms.

The invention further provides methods for detecting the presence and status of 205P1B5 polynucleotides and proteins in various biological samples, as well as methods for identifying cells that express 205P1B5. A typical embodiment of this invention provides methods for monitoring 205P1B5 gene products in a tissue or hematology sample having or suspected of having some form of growth dysregulation such as cancer.

The invention further provides various immunogenic or therapeutic compositions and strategies for treating cancers that express 205P1B5 such as prostate cancers, including therapies aimed at inhibiting the transcription, translation, processing or function of 205P1B5 as well as cancer vaccines.

BRIEF DESCRIPTION OF THE FIGURES

FIG. 1. 205P1B5 SSH sequence. The 205P1B5 SSH sequence (SEQ ID NO.:736).

FIG. 2. The cDNA (SEQ ID. NO.:701) and amino acid sequence (SEQ ID. NO.:702) of 205P1B5 v.1 and the cDNA (SEQ ID. NO.:703) and amino acid sequence (SEQ ID. NO.:704) of 205P1B5 v.2. The start methionine is underlined. The open reading frame extends from nucleic acid 555 to 2144 including the stop codon.

FIG. 3. Amino acid sequence of 205P1B5 v.1 (SEQ ID. NO.:702) and amino acid sequence of 205P1B5 v.2 (SEQ ID. NO.:704). Each 205P1B5 protein has 529 amino acids.

FIG. 4. Sequence alignment of 205P1B5v.1 (SEQ ID NO.: 702) with GenBank accession number (SEQ ID. NO.:705).

FIG. 5. Hydrophilicity amino acid profile of 205P1B5 determined by computer algorithm sequence analysis using the method of Hopp and Woods (Hopp T. P., Woods K. R., 1981. Proc. Natl. Acad. Sci. U.S.A. 78:3824-3828) accessed on the Protscale website (world wide web URL ch/cgi-bin/protscale.pl) through the ExPasy molecular biology server.

FIG. 6. Hydropathicity amino acid profile of 205P1B5 determined by computer algorithm sequence analysis using the method of Kyte and Doolittle (Kyte J., Doolittle R. F., 1982. J. Mol. Biol. 157:105-132) accessed on the ProtScale website (world wide web URL expasy.ch/cgi-bin/protscale.pl) through the ExPasy molecular biology server.

FIG. 7. Percent accessible residues amino acid profile of 205P1B5 determined by computer algorithm sequence analysis using the method of Janin (Janin J., 1979 Nature 277:491-492) accessed on the ProtScale website (world wide web URL expasy.ch/cgi-bin/protscale.pl) through the ExPasy molecular biology server.

FIG. 8. Average flexibility amino acid profile of 205P1B5 determined by computer algorithm sequence analysis using the method of Bhaskaran and Ponnuswamy (Bhaskaran R, and Ponnuswamy P. K., 1988. Int. J. Pept. Protein Res. 32:242-255) accessed on the ProtScale website (world wide web URL expasy.ch/cgi-bin/protscale.pl) through the ExPasy molecular biology server.

FIG. 9. Beta-turn amino acid profile of 205P1B5 determined by computer algorithm sequence analysis using the method of Deleage and Roux (Deleage, G., Roux B. 1987 Protein Engineering 1:289-294) accessed on the ProtScale website (world wide web URL expasy.ch/cgi-bin/protscale.pl) through the ExPasy molecular biology server.

FIG. 10. RT-PCR analysis of 205P1B5 expression. First strand cDNA was prepared from vital pool 1 (VP: live lung and kidney), vital pool 2 (VP2: pancreas, colon and stomach), prostate xenograft pool (LAPC-4AD, LAPC-4AI, LAPC-9AD, LAPC-9AI), prostate cancer pool, and cancer metastasis pool. Normalization was performed by PCR using primers to actin and GAPDH. Semi-quantitative PCR, using primers to 205P1B5, was performed at 26 and 30 cycles of amplification. Results show expression of 205P1B5 in prostate cancer pool, prostate xenograft pool, cancer metastasis pool, but not in VP1 and VP2.

FIG. 11. Expression of 205P1B5 in normal human tissues. Two multiple tissue northern blots (Clontech) with 2 mg of mRNA/lane, were probed with 205P1B5 sequences. Size standards in kilobases (kb) are indicated on the side. The results show restricted expression of an approximately 5 kb 205P1B5 transcript (indicated with an arrow) in prostate and to lower level in brain tissues. A larger transcript of approximately 7.5 kb in size is detected in liver.

FIG. 12. Expression of 205P1B5 in human patient cancer specimens. RNA was extracted from a pool of 3 prostate cancer tumors, as well as from normal prostate (NP), normal bladder (NB), normal kidney (NK) and normal colon (NC). Northern blots with 10 mg of total RNA/lane were probed with 205P1B5 sequences. Size standards in kilobases (kb) are indicated on the side. The results show expression of 205P1B5 in prostate cancer pool and normal prostate, but not in the other normal tissues.

FIG. 13. Expression of 205P1B5 in Prostate Cancer Xenografts and Prostate Cancer Patient Specimens. RNA was extracted from prostate cancer xenografts (LAPC-4AD, LAPC-4AI, LAPC-9AD, LAPC-9AI), prostate cancer cell line PC3, normal prostate (N), prostate tumors (T) and normal adjacent tissue (Nat) derived from prostate cancer patients.

Northern blot with 10 mg of total RNA/lane was probed with the 205P1B5 SSH sequence. Size standards in kilobases (kb) are indicated on the side. Results show expression of 205P1B5 in all prostate tumor specimens tested. Expression is also seen in 3 of the 4 xenografts, but not in the PC3 cell line.

FIG. 14. Secondary structure and transmembrane prediction for 205P1B5. Panel A. The secondary structure of 205P1B5v.1 protein (SEQ ID NO.:702) was depicted using the HNN—Hierarchical Neural Network method (Guermeur, 1997, world wide web URL pbil.ibcp.fr/cgi-bin/npsa_automat.pl?page=npsa_nn.html), accessed from the ExPasy molecular biology server (world wide web URL expasy.ch/tools/). This method indicates the presence and location of alpha helices, extended strands, and random coils from the primary protein sequence. The percent of the protein in a given secondary structure is also given. Panel B. Schematic representation of transmembrane regions and orientation of 205P1B5 based on the TMpred algorithm of Hofmann and Stoffel which utilizes TMBASE (K. Hofmann, W. Stoffel. TMBASE—A database of membrane spanning protein segments Biol. Chem. Hoppe-Seyler 374:166, 1993). Panel C. Schematic representation of transmembrane regions and the extracellular and intracellular orientation of 205P1B5 based on the algorithm of Sonnhammer, von Heijne, and Krogh (Erik L. L., et al., A hidden Markov model for predicting transmembrane helices in protein sequences. In Proc. of Sixth Int. Conf. on Intelligent Systems for Molecular Biology, p 175-182 Ed J. Glasgow, et al., Menlo Park, Calif.: AAAI Press, 1998). Both transmembrane programs presented in Panel B and Panel C indicate that 205P1B5 contains 5 transmembrane domains consistent with it being a G-protein coupled receptor.

Figure 15:
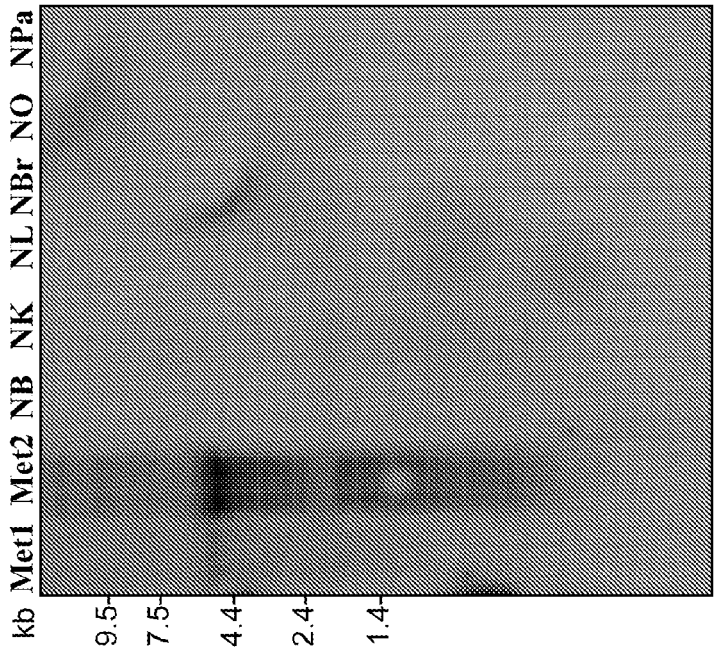

FIG. 15. Expression of 205P1B5 in cancer metastasis patient specimens. RNA was extracted from prostate cancer metastasis to lymph node obtained from two different patients, as well as from normal bladder (NB), normal kidney (NK), normal lung (NL), normal breast (NBr), normal ovary (NO), and normal pancreas (NPa). Northern blots with 10 μg of total RNA/lane were probed with 205P1B5 sequence. Size standards in kilobases (kb) are indicated on the side. The results show expression of 205P1B5 in both cancer metastasis samples but not in the normal tissues tested.

Figure 16:
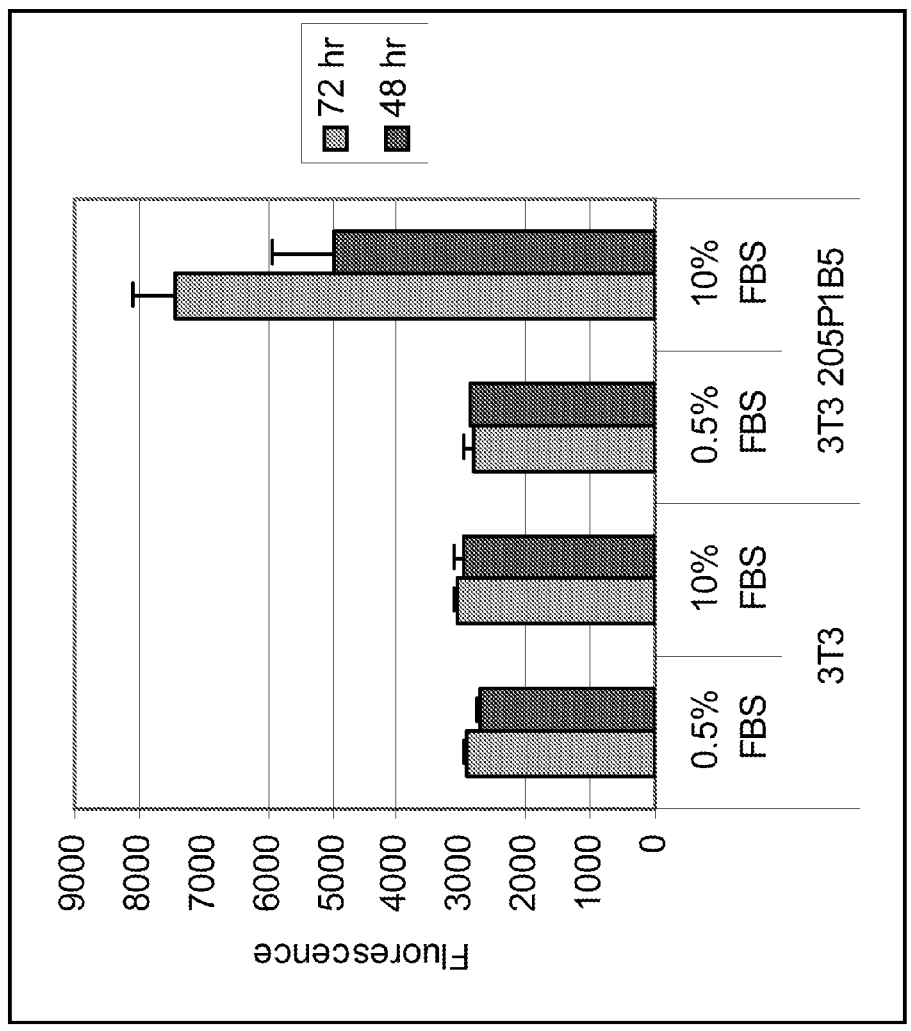

FIG. 16. Enhanced Proliferation of Recombinant 3T3-205P1B5 Cells. For this data, control 3T3 and 3T3-205P1B5 cells were grown in 96 well plate in 0.5 or 10% FBS. Proliferation was measured by Alamar blue after 48 and 72 hours. Enhanced proliferation of 3T3-205P1B5 relative to control cells is observed as early as 48 hours.

DETAILED DESCRIPTION OF THE INVENTION

Outline of Sections
I.) Definitions
II.) 205P1B5 Polynucleotides
II.A.) Uses of 205P1B5 Polynucleotides
   II.A.1.) Monitoring of Genetic Abnormalities
   II.A.2.) Antisense Embodiments
   II.A.3.) Primers and Primer Pairs
   II.A.4.) Isolation of 205P1B5-Encoding Nucleic Acid Molecules
   II.A.5.) Recombinant Nucleic Acid Molecules and Host-Vector Systems
III.) 205P1B5-related Proteins
III.A.) Motif-bearing Protein Embodiments
III.B.) Expression of 205P1B5-related Proteins
III.C.) Modifications of 205P1B5-related Proteins
III.D.) Uses of 205P1B5-related Proteins
IV.) 205P1B5 Antibodies
V.) 205P1B5 Cellular Immune Responses
VI.) 205P1B5 Transgenic Animals
VII.) Methods for the Detection of 205P1B5
VIII.) Methods for Monitoring the Status of 205P1B5-related Genes and Their Products
IX.) Identification of Molecules That Interact With 205P1B5
X.) Therapeutic Methods and Compositions
X.A.) Anti-Cancer Vaccines
X.B.) 205P1B5 as a Target for Antibody-Based Therapy
X.C.) 205P1B5 as a Target for Cellular Immune Responses
   X.C.1. Minigene Vaccines
   X.C.2. Combinations of CTL Peptides with Helper Peptides
   X.C.3. Combinations of CTL Peptides with T Cell Priming Agents
   X.C.4. Vaccine Compositions Comprising DC Pulsed with CTL and/or HTL Peptides
X.D.) Adoptive Immunotherapy
X.E.) Administration of Vaccines for Therapeutic or Prophylactic Purposes
XI.) Diagnostic and Prognostic Embodiments of 205P1B5.
XII.) Inhibition of 205P1B5 Protein Function
XII.A.) Inhibition of 205P1B5 With Intracellular Antibodies
XII.B.) Inhibition of 205P1B5 with Recombinant Proteins
XII.C.) Inhibition of 205P1B5 Transcription or Translation
XII.D.) General Considerations for Therapeutic Strategies
XIII.) KITS
I.) Definitions:

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art, such as, for example, the widely utilized molecular cloning methodologies described in Sambrook et al., Molecular Cloning: A Laboratory Manual 2nd. edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

The terms "advanced prostate cancer", "locally advanced prostate cancer", "advanced disease" and "locally advanced disease" mean prostate cancers that have extended through the prostate capsule, and are meant to include stage C disease under the American Urological Association (AUA) system, stage C1-C2 disease under the Whitmore-Jewett system, and stage T3-T4 and N+ disease under the TNM (tumor, node, metastasis) system. In general, surgery is not recommended for patients with locally advanced disease, and these patients have substantially less favorable outcomes compared to patients having clinically localized (organ-confined) prostate cancer. Locally advanced disease is clinically identified by palpable evidence of induration beyond the lateral border of the prostate, or asymmetry or induration above the prostate base. Locally advanced prostate cancer is presently diagnosed pathologically following radical prostatectomy if the tumor invades or penetrates the prostatic capsule, extends into the surgical margin, or invades the seminal vesicles.

"Altering the native glycosylation pattern" is intended for purposes herein to mean deleting one or more carbohydrate moieties found in native sequence 205P1B5 (either by removing the underlying glycosylation site or by deleting the glycosylation by chemical and/or enzymatic means), and/or adding one or more glycosylation sites that are not present in the native sequence 205P1B5. In addition, the phrase includes qualitative changes in the glycosylation of the native proteins, involving a change in the nature and proportions of the various carbohydrate moieties present.

The term "analog" refers to a molecule which is structurally similar or shares similar or corresponding attributes with another molecule (e.g. a 205P1B5-related protein). For example an analog of the 205P1B5 protein can be specifically bound by an antibody or T cell that specifically binds to 205P1B5.

The term "antibody" is used in the broadest sense. Therefore an "antibody" can be naturally occurring or man-made such as monoclonal antibodies produced by conventional hybridoma technology. Anti-205P1B5 antibodies comprise monoclonal and polyclonal antibodies as well as fragments containing the antigen-binding domain and/or one or more complementarity determining regions of these antibodies.

An "antibody fragment" is defined as at least a portion of the variable region of the immunoglobulin molecule that binds to its target, i.e., the antigen-binding region. In one embodiment it specifically covers single anti-205P1B5 antibodies and clones thereof (including agonist, antagonist and neutralizing antibodies) and anti-205P1B5 antibody compositions with polyepitopic specificity.

The term "codon optimized sequences" refers to nucleotide sequences that have been optimized for a particular host species by replacing any codons having a usage frequency of less than about 20%. Nucleotide sequences that have been optimized for expression in a given host species by elimination of spurious polyadenylation sequences, elimination of exon/intron splicing signals, elimination of transposon-like repeats and/or optimization of GC content in addition to codon optimization are referred to herein as an "expression enhanced sequences."

The term "cytotoxic agent" refers to a substance that inhibits or prevents the function of cells and/or causes destruction of cells. The term is intended to include radioactive isotopes chemotherapeutic agents, and toxins such as small molecule toxins or enzymatically active toxins of bacterial, fungal, plant or animal origin, including fragments and/or variants thereof. Examples of cytotoxic agents include, but are not limited to maytansinoids, yttrium, bismuth, ricin, ricin A-chain, doxorubicin, daunorubicin, taxol, ethidium bromide, mitomycin, etoposide, tenoposide, vincristine, vinblastine, colchicine, dihydroxy anthracin dione, actinomycin, diphtheria toxin, Pseudomonas exotoxin (PE) A, PE40, abrin, abrin A chain, modeccin A chain, alpha-sarcin, gelonin, mitogellin, retstrictocin, phenomycin, enomycin, curicin, crotin, calicheamicin, sapaonaria officinalis inhibitor, and glucocorticoid and other chemotherapeutic agents, as well as radioisotopes such as $At^{211}$, $I^{131}$, $I^{125}$, $Y^{90}$, $Re^{186}$, $Re^{188}$, $SM^{153}$, $Bi^{212}$, $P^{32}$ and radioactive isotopes of Lu. Antibodies may also be conjugated to an anti-cancer pro-drug activating enzyme capable of converting the pro-drug to its active form.

The term "homolog" refers to a molecule which exhibits homology to another molecule, by for example, having sequences of chemical residues that are the same or similar at corresponding positions.

"Human Leukocyte Antigen" or "HLA" is a human class I or class II Major Histocompatibility Complex (MHC) protein (see, e.g., Stites, et al., IMMUNOLOGY, $8^{Th}$ ED., Lange Publishing, Los Altos, Calif. (1994).

The terms "hybridize", "hybridizing", "hybridizes" and the like, used in the context of polynucleotides, are meant to refer to conventional hybridization conditions, preferably such as hybridization in 50% formamide/6×SSC/0.1% SDS/100 μg/ml mDNA, in which temperatures for hybridization are above 37 degrees C. and temperatures for washing in 0.1×SSC/0.1% SDS are above 55 degrees C.

The phrases "isolated" or "biologically pure" refer to material which is substantially or essentially free from components which normally accompany the material as it is found in its native state. Thus, isolated peptides in accordance with the invention preferably do not contain materials normally associated with the peptides in their in situ environment. For example, a polynucleotide is said to be "isolated" when it is substantially separated from contaminant polynucleotides that correspond or are complementary to genes other than the 205P1B5 gene or that encode polypeptides other than 205P1B5 gene product or fragments thereof. A skilled artisan can readily employ nucleic acid isolation procedures to obtain an isolated 205P1B5 polynucleotide. A protein is said to be "isolated," for example, when physical, mechanical or chemical methods are employed to remove the 205P1B5 protein from cellular constituents that are normally associated with the protein. A skilled artisan can readily employ standard purification methods to obtain an isolated 205P1B5 protein. Alternatively, an isolated protein can be prepared by chemical means.

The term "mammal" refers to any organism classified as a mammal, including mice, rats, rabbits, dogs, cats, cows, horses and humans. In one embodiment of the invention, the mammal is a mouse. In another embodiment of the invention, the mammal is a human.

The terms "metastatic prostate cancer" and "metastatic disease" mean prostate cancers that have spread to regional lymph nodes or to distant sites, and are meant to include stage D disease under the AUA system and stage TxNxM+ under the TNM system. As is the case with locally advanced prostate cancer, surgery is generally not indicated for patients with metastatic disease, and hormonal (androgen ablation) therapy is a preferred treatment modality. Patients with metastatic prostate cancer eventually develop an androgen-refractory state within 12 to 18 months of treatment initiation. Approximately half of these androgen-refractory patients die within 6 months after developing that status. The most common site for prostate cancer metastasis is bone. Prostate cancer bone metastases are often osteoblastic rather than osteolytic (i.e., resulting in net bone formation). Bone metastases are found most frequently in the spine, followed by the femur, pelvis, rib cage, skull and humerus. Other common sites for metastasis include lymph nodes, lung, liver and brain. Metastatic prostate cancer is typically diagnosed by open or laparoscopic pelvic lymphadenectomy, whole body radionuclide scans, skeletal radiography, and/or bone lesion biopsy.

The term "monoclonal antibody" refers to an antibody obtained from a population of substantially homogeneous antibodies, i.e., the antibodies comprising the population are identical except for possible naturally occurring mutations that are present in minor amounts.

A "motif", as in biological motif of an 205P1B5-related protein, refers to any pattern of amino acids forming part of the primary sequence of a protein, that is associated with a particular function (e.g. protein-protein interaction, protein-DNA interaction, etc.) or modification (e.g. that is phosphorylated, glycosylated or amidated), or localization (e.g. secretory sequence, nuclear localization sequence, etc.) or a sequence that is correlated with being immunogenic, either humoraly or cellularly. A motif can be either contiguous or capable of being aligned to certain positions that are generally correlated with a certain function or property. In the context of HIA motifs, "motif" refers to the pattern of residues in a peptide of defined length, usually a peptide of from about 8 to about 13 amino acids for a class I HLA motif and from about 6 to about 25 amino acids for a class II HLA motif, which is recognized by a particular HLA molecule. Peptide motifs for HLA binding are typically different for each protein encoded by each human HLA allele and differ in the pattern of the primary and secondary anchor residues.

A "pharmaceutical excipient" comprises a material such as an adjuvant, a carrier, pH-adjusting and buffering agents, tonicity adjusting agents, wetting agents, preservative, and the like.

"Pharmaceutically acceptable" refers to a non-toxic, inert, and/or composition that is physiologically compatible with humans or other mammals.

The term "polynucleotide" means a polymeric form of nucleotides of at least 10 bases or base pairs in length, either ribonucleotides or deoxynucleotides or a modified form of either type of nucleotide, and is meant to include single and double stranded forms of DNA and/or RNA. In the art, this term if often used interchangeably with "oligonucleotide". A polynucleotide can comprise a nucleotide sequence disclosed herein wherein thymidine (T) (as shown for example in SEQ ID NO: 702) can also be uracil (U); this definition pertains to the differences between the chemical structures of DNA and RNA, in particular the observation that one of the four major bases in RNA is uracil (U) instead of thymidine (T).

The term "polypeptide" means a polymer of at least about 4, 5, 6, 7, or 8 amino acids. Throughout the specification, standard three letter or single letter designations for amino acids are used. In the art, this term is often used interchangeably with "peptide" or "protein".

An HLA "primary anchor residue" is an amino acid at a specific position along a peptide sequence which is understood to provide a contact point between the immunogenic peptide and the HLA molecule. One to three, usually two, primary anchor residues within a peptide of defined length generally defines a "motif" for an immunogenic peptide. These residues are understood to fit in close contact with peptide binding groove of an HLA molecule, with their side chains buried in specific pockets of the binding groove. In one embodiment, for example, the primary anchor residues for an HLA class I molecule are located at position 2 (from the amino terminal position) and at the carboxyl terminal position of a 8, 9, 10, 11, or 12 residue peptide epitope in accordance with the invention. In another embodiment for example, the primary anchor residues of a peptide that will bind an HLA class II molecule are spaced relative to each other, rather than to the termini of a peptide, where the peptide is generally of at least 9 amino acids in length. The primary anchor positions for each motif and supermotif are set forth in Table IV. For example, analog peptides can be created by altering the presence or absence of particular residues in the primary and/or secondary anchor positions shown in Table IV. Such analogs are used to modulate the binding affinity and/or population coverage of a peptide comprising a particular HLA motif or supermotif.

A "recombinant" DNA or RNA molecule is a DNA or RNA molecule that has been subjected to molecular manipulation in vitro.

"Stringency" of hybridization reactions is readily determinable by one of ordinary skill in the art and generally is an empirical calculation dependent upon probe length, washing temperature, and salt concentration. In general longer probes require higher temperatures for proper annealing, while shorter probes need lower temperatures. Hybridization generally depends on the ability of denatured nucleic acid sequences to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions" or "high stringency conditions", as defined herein, are identified by, but not limited to, those that (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. "Moderately stringent conditions" are described by, but not limited to, those in Sambrook et al., Molecular Cloning: A Laboratory Manual, New York: Cold Spring Harbor Press, 1989, and include the use of washing solution and hybridization conditions (e.g., temperature, ionic strength and % SDS) less stringent than those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

An HLA "supermotif" is a peptide binding specificity shared by HLA molecules encoded by two or more HLA alleles.

As used herein "to treat" or "therapeutic" and grammatically related terms, refer to any improvement of any consequence of disease, such as prolonged survival, less morbidity, and/or a lessening of side effects which are the byproducts of an alternative therapeutic modality; full eradication of disease is not required.

A "transgenic animal" (e.g., a mouse or rat) is an animal having cells that contain a transgene, which transgene was introduced into the animal or an ancestor of the animal at a prenatal, e.g., an embryonic stage. A "transgene" is a DNA that is integrated into the genome of a cell from which a transgenic animal develops.

As used herein, an HLA or cellular immune response "vaccine" is a composition that contains or encodes one or more peptides of the invention. There are numerous embodiments of such vaccines, such as a cocktail of one or more individual peptides; one or more peptides of the invention comprised by a polyepitopic peptide; or nucleic acids that encode such individual peptides or polypeptides, e.g., a minigene that encodes a polyepitopic peptide. The "one or more peptides" can include any whole unit integer from 1-150 or more, e.g., at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 105, 110, 115, 120, 125, 130, 135, 140, 145, or 150 or more peptides of the invention. The peptides or polypeptides can optionally be modified, such as by lipidation, addition of targeting or other sequences. HLA class I peptides of the invention can be admixed with, or linked to, HLA class II peptides, to facilitate activation of both cytotoxic T lymphocytes and helper T lymphocytes. HLA vaccines can also comprise peptide-pulsed antigen presenting cells, e.g., dendritic cells.

The term "variant" refers to a molecule that exhibits a variation from a described type or norm, such as a protein that has one or more different amino acid residues in the corresponding position(s) of a specifically described protein (e.g. the 205P1B5 protein shown in FIG. 2 or FIG. 3). An analog is an example of a variant protein. Splice isoforms and single nucleotides polymorphisms (SNPs) are further examples of variants.

The 205P1B5-related proteins of the invention include those specifically identified herein, as well as allelic variants, conservative substitution variants, analogs and homologs that can be isolated/generated and characterized without undue experimentation following the methods outlined herein or readily available in the art. Fusion proteins that combine parts of different 205P1B5 proteins or fragments thereof, as well as fusion proteins of a 205P1B5 protein and a heterologous polypeptide are also included. Such 205P1B5 proteins are collectively referred to as the 205P1B5-related proteins, the proteins of the invention, or 205P1B5. The term "205P1B5-related protein" refers to a polypeptide fragment or an 205P1B5 protein sequence of 4, 5, 6, 7, 8, 9, 10, 11, 12, 13, 14, 15, 16, 17, 18, 19, 20, 21, 22, 23, 24, 25, or more than 25 amino acids; or, at least 30, 35, 40, 45, 50, 55, 60, 65, 70, 80, 85, 90, 95, 100, 105, 110, 115, 120, 125, 130, 135, 140, 145, 150, 155, 160, 165, 170, 175, 180, 185, 190, 195, 200, 225, 250, 275, 300, 325, 350, 375, 400, 425, 450, 475, 500, 525, or 529 or more amino acids.

II.) 205P1B5 Polynucleotides

One aspect of the invention provides polynucleotides corresponding or complementary to all or part of an 205P1B5 gene, mRNA, and/or coding sequence, preferably in isolated form, including polynucleotides encoding an 205P1B5-related protein and fragments thereof DNA, RNA, DNA/RNA hybrid, and related molecules, polynucleotides or oligonucleotides complementary to an 205P1B5 gene or mRNA sequence or a part thereof, and polynucleotides or oligonucleotides that hybridize to an 205P1B5 gene, mRNA, or to an 205P1B5 encoding polynucleotide (collectively, "205P1B5 polynucleotides"). In all instances when referred to in this section, T can also be U in FIG. 2.

Embodiments of a 205P1B5 polynucleotide include: a 205P1B5 polynucleotide having the sequence shown in FIG. 2, the nucleotide sequence of 205P1B5 as shown in FIG. 2, wherein T is U; at least 10 contiguous nucleotides of a polynucleotide having the sequence as shown in FIG. 2; or, at least 10 contiguous nucleotides of a polynucleotide having the sequence as shown in FIG. 2 where T is U. For example, embodiments of 205P1B5 nucleotides comprise, without limitation:

(a) a polynucleotide comprising or consisting of the sequence as shown in FIG. 2 (SEQ ID NO.:701), wherein T can also be U;
(b) a polynucleotide comprising or consisting of the sequence as shown in FIG. 2 (SEQ ID NO.:701), from nucleotide residue member 555 through nucleotide residue number 2144, wherein T can also be U;
(c) a polynucleotide that encodes a 205P1B5-related protein whose sequence is encoded by the cDNAs contained in the plasmid designated _____ deposited with American Type Culture Collection as Accession No. _____;
(d) a polynucleotide that encodes an 205P1B5-related protein that is at least 90% homologous to the entire amino acid sequence shown in FIG. 2 (SEQ ID NO.:702);
(e) a polynucleotide that encodes an 205P1B5-related protein that is at least 90% identical to the entire amino acid sequence shown in FIG. 2 (SEQ ID NO:702).
(f) a polynucleotide that encodes at least one peptide set forth in Tables V-XVIII;
(g) a polynucleotide that encodes a peptide region of at least 5 amino acids of FIG. 3 in any whole number increment up to 529 that includes an amino acid position having a value greater than 0.5 in the Hydrophilicity profile of FIG. 5;
(h) a polynucleotide that encodes a peptide region of at least 5 amino acids of FIG. 3 in any whole number increment up to 529 that includes an amino acid position having a value less than 0.5 in the Hydropathicity profile of FIG. 6;
(i) a polynucleotide that encodes a peptide region of at least 5 amino acids of FIG. 3 in any whole number increment up to 529 that includes an amino acid position having a value greater than 0.5 in the Percent Accessible Residues profile of FIG. 7;
(j) a polynucleotide that encodes a peptide region of at least 5 amino acids of FIG. 3 in any whole number increment up to 529 that includes an amino acid position having a value greater than 0.5 in the Average Flexibility profile on FIG. 8;
(k) a polynucleotide that encodes a peptide region of at least 5 amino acids of FIG. 3 in any whole number increment up to 529 that includes an amino acid position having a value greater than 0.5 in the Beta-turn profile of FIG. 9;
(l) a polynucleotide that is fully complementary to a polynucleotide of any one of (a)-(k);
(m) a polynucleotide that selectively hybridizes under stringent conditions to a polynucleotide of (a)-(l);
(n) a peptide that is encoded by any of (a)-(k); and,
(o) a polynucleotide of any of (a)-(m) or peptide of (n) together with a pharmaceutical excipient and/or in a human unit dose form.

As used herein, a range is understood to specifically disclose all whole unit positions thereof.

Typical embodiments of the invention disclosed herein include 205P1B5 polynucleotides that encode specific portions of the 205P1B5 mRNA sequence (and those which are complementary to such sequences) such as those that encode the protein and fragments thereof, for example of 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 250, 275, 300, 325, 350, 375, 400, 425, 450, 475, 500, 525 or 529 contiguous amino acids.

For example, representative embodiments of the invention disclosed herein include: polynucleotides and their encoded peptides themselves encoding about amino acid 1 to about amino acid 10 of the 205P1B5 protein shown in FIG. 2 or FIG. 3, polynucleotides encoding about amino acid 10 to about amino acid 20 of the 205P1B5 protein shown in FIG. 2, or FIG. 3, polynucleotides encoding about amino acid 20 to about amino acid 30 of the 205P1B5 protein shown in FIG. 2 or FIG. 3, polynucleotides encoding about amino acid 30 to about amino acid 40 of the 205P1B5 protein shown in FIG. 2 or FIG. 3, polynucleotides encoding about amino acid 40 to about amino acid 50 of the 205P1B5 protein shown in FIG. 2 or FIG. 3, polynucleotides encoding about amino acid 50 to about amino acid 60 of the 205P1B5 protein shown in FIG. 2 or FIG. 3, polynucleotides encoding about amino acid 60 to about amino acid 70 of the 205P1B5 protein shown in FIG. 2 or FIG. 3, polynucleotides encoding about amino acid 70 to about amino acid 80 of the 205P1B5 protein shown in FIG. 2 or FIG. 3, polynucleotides encoding about amino acid 80 to about amino acid 90 of the 205P1B5 protein shown in FIG. 2 or FIG. 3, polynucleotides encoding about amino acid 90 to about amino acid 100 of the 205P1B5 protein shown in FIG. 2 or FIG. 3, in increments of about 10 amino acids, ending at the carboxyl terminal amino acid set forth in FIG. 2 or FIG. 3. Accordingly polynucleotides encoding portions of the amino acid sequence (of about 10 amino acids), of amino acids 100 through the carboxyl terminal amino acid of the 205P1B5 protein are embodiments of the invention. Wherein it is understood that each particular amino acid position discloses that position plus or minus five amino acid residues.

Polynucleotides encoding relatively long portions of the 205P1B5 protein are also within the scope of the invention. For example, polynucleotides encoding from about amino acid 1 (or 20 or 30 or 40 etc.) to about amino acid 20, (or 30, or 40 or 50 etc.) of the 205P1B500 protein shown in FIG. 2 or FIG. 3 can be generated by a variety of techniques well known in the art. These polynucleotide fragments can include any portion of the 205P1B5 sequence as shown in FIG. 2 or FIG. 3.

Additional illustrative embodiments of the invention disclosed herein include 205P1B5 polynucleotide fragments encoding one or more of the biological motifs contained within the 205P1B5 protein sequence, including one or more of the motif-bearing subsequences of the 205P1B5 protein set forth in Tables V-XVIII. In another embodiment, typical polynucleotide fragments of the invention encode one or more of the regions of 205P1B5 that exhibit homology to a known molecule. In another embodiment of the invention, typical polynucleotide fragments can encode one or more of the 205P1B5 N-glycosylation sites, cAMP and cGMP-dependent protein kinase phosphorylation sites, casein kinase II phosphorylation sites or N-myristoylation site and amidation sites.

II.A.) Uses of 205P1B5 Polynucleotides

II.A.1.) Monitoring of Genetic Abnormalities

The polynucleotides of the preceding paragraphs have a number of different specific uses. The human 205P1B5 gene maps to the chromosomal location set forth in Example 3. For example, because the 205P1B5 gene maps to this chromosome, polynucleotides that encode different regions of the 205P1B5 protein are used to characterize cytogenetic abnormalities of this chromosomal locale, such as abnormalities that are identified as being associated with various cancers. In certain genes, a variety of chromosomal abnormalities including rearrangements have been identified as frequent cytogenetic abnormalities in a number of different cancers (see e.g. Krajinovic et al., Mutat. Res. 382(3-4): 81-83 (1998); Johansson et al., Blood 86(10): 3905-3914 (1995) and Finger et al., P.N.A.S. 85(23): 9158-9162 (1988)). Thus, polynucleotides encoding specific regions of the 205P1B5 protein provide new tools that can be used to delineate, with greater precision than previously possible, cytogenetic abnormalities in the chromosomal region that encodes 205P1B5 that may contribute to the malignant phenotype. In this context, these polynucleotides satisfy a need in the art for expanding the sensitivity of chromosomal screening in order to identify more subtle and less common chromosomal abnormalities (see e.g. Evans et al., Am. J. Obstet. Gynecol. 171(4): 1055-1057 (1994)).

Furthermore, as 205P1B5 was shown to be highly expressed in prostate and other cancers, 205P1B5 polynucleotides are used in methods assessing the status of 205P1B5 gene products in normal versus cancerous tissues. Typically, polynucleotides that encode specific regions of the 205P1B5 protein are used to assess the presence of perturbations (such as deletions, insertions, point mutations, or alterations resulting in a loss of an antigen etc.) in specific regions of the 205P1B5 gene, such as such regions containing one or more motifs. Exemplary assays include both RT-PCR assays as well as single-strand conformation polymorphism (SSCP) analysis (see, e.g., Marrogi et al., J. Cutan. Pathol. 26(8): 369-378 (1999), both of which utilize polynucleotides encoding specific regions of a protein to examine these regions within the protein.

II.A.2.) Antisense Embodiments

Other specifically contemplated nucleic acid related embodiments of the invention disclosed herein are genomic DNA, cDNAs, ribozymes, and antisense molecules, as well as nucleic acid molecules based on an alternative backbone, or including alternative bases, whether derived from natural sources or synthesized, and include molecules capable of inhibiting the RNA or protein expression of 205P1B5. For example, antisense molecules can be RNAs or other molecules, including peptide nucleic acids (PNAs) or non-nucleic acid molecules such as phosphorothioate derivatives, that specifically bind DNA or RNA in a base pair-dependent manner. A skilled artisan can readily obtain these classes of nucleic acid molecules using the 205P1B5 polynucleotides and polynucleotide sequences disclosed herein.

Antisense technology entails the administration of exogenous oligonucleotides that bind to a target polynucleotide located within the cells. The term "antisense" refers to the fact that such oligonucleotides are complementary to their intracellular targets, e.g., 205P1B5. See for example, Jack Cohen, Oligodeoxynucleotides, Antisense Inhibitors of Gene Expression, CRC Press, 1989; and Synthesis 1:1-5 (1988). The 205P1B5 antisense oligonucleotides of the present invention include derivatives such as S-oligonucleotides (phosphorothioate derivatives or S-oligos, see, Jack Cohen, supra), which exhibit enhanced cancer cell growth inhibitory action. S-oligos (nucleoside phosphorothioates) are isoelectronic analogs of an oligonucleotide (O-oligo) in which a nonbridging oxygen atom of the phosphate group is replaced by a sulfur atom The S-oligos of the present invention can be prepared by treatment of the corresponding O-oligos with 3H-1,2-benzodithiol-3-one-1,1-dioxide, which is a sulfur transfer reagent See Iyer, R. P. et al., J. Org. Chem. 55:4693-4698 (1990); and Iyer, R. P. et al., J. Am. Chem. Soc. 112: 1253-1254 (1990). Additional 205P1B5 antisense oligonucleotides of the present invention include morpholino antisense oligonucleotides known in the art (see, e.g., Partridge et al., 1996, Antisense & Nucleic Acid Drug Development 6: 169-175).

The 205P1B5 antisense oligonucleotides of the present invention typically can be RNA or DNA that is complementary to and stably hybridizes with the first 100 5' codons or last 100 3' codons of the 205P1B5 genomic sequence or the corresponding mRNA. Absolute complementarity is not required, although high degrees of complementarity are preferred. Use of an oligonucleotide complementary to this region allows for the selective hybridization to 205P1B5 mRNA and not to mRNA specifying other regulatory subunits of protein kinase. In one embodiment, 205P1B5 antisense oligonucleotides of the present invention are 15 to 30-mer fragments of the antisense DNA molecule that have a sequence that hybridizes to 205P1B5 mRNA. Optionally, 205P1B5 antisense oligonucleotide is a 30-mer oligonucleotide that is complementary to a region in the first 10 5' codons or last 10 3' codons of 205P1B5. Alternatively, the antisense molecules are modified to employ ribozymes in the inhibition of 205P1B5 expression, see, e.g., L. A. Couture & D. T. Stinchcomb; Trends Genet. 12: 510-515 (1996).

II.A3.) Primers and Primer Pairs

Further specific embodiments of this nucleotides of the invention include primers and primer pairs, which allow the specific amplification of polynucleotides of the invention or of any specific parts thereof, and probes that selectively or specifically hybridize to nucleic acid molecules of the invention or to any part thereof. Probes can be labeled with a detectable marker, such as, for example, a radioisotope, fluorescent compound, bioluminescent compound, a chemiluminescent compound, metal chelator or enzyme. Such probes and primers are used to detect the presence of a 205P1B5 polynucleotide in a sample and as a means for detecting a cell expressing a 205P1B5 protein.

Examples of such probes include polypeptides comprising all or part of the human 205P1B5 cDNA sequence shown in FIG. 2. Examples of primer pairs capable of specifically amplifying 205P1B5 mRNAs are also described in the Examples. As will be understood by the skilled artisan, a great many different primers and probes can be prepared based on the sequences provided herein and used effectively to amplify and/or detect a 205P1B5 mRNA.

The 205P1B5 polynucleotides of the invention are useful for a variety of purposes, including but not limited to their use as probes and primers for the amplification and/or detection of the 205P1B5 gene(s), mRNA(s), or fragments thereof; as reagents for the diagnosis and/or prognosis of prostate cancer and other cancers; as coding sequences capable of directing the expression of 205P1B5 polypeptides; as tools for modulating or inhibiting the expression of the 205P1B5 gene(s) and/or translation of the 205P1B5 transcript(s); and as therapeutic agents.

The present invention includes the use of any probe as described herein to identify and isolate a 205P1B5 or 205P1B5 related nucleic acid sequence from a naturally occurring source, such as humans or other mammals, as well as the isolated nucleic acid sequence per se, which would comprise all or most of the sequences found in the probe used.

II.A.4.) Isolation of 205P1B5 Encoding Nucleic Acid Molecules

The 205P1B5 cDNA sequences described herein enable the isolation of other polynucleotides encoding 205P1B5 gene product(s), as well as the isolation of polynucleotides encoding 205P1B5 gene product homologs, alternatively spliced isoforms, allelic variants, and mutant forms of the 205P1B5 gene product as well as polynucleotides that encode analogs of 205P1B5-related proteins. Various molecular cloning methods that can be employed to isolate full length cDNAs encoding an 205P1B5 gene are well known (see, for example, Sambrook J. et al., Molecular Cloning: A Laboratory Manual, 2d edition, Cold Spring Harbor Press, New York, 1989; Current Protocols in Molecular Biology. Ausubel et al., Eds., Wiley and Sons, 1995). For example, lambda phage cloning methodologies can be conveniently employed, using commercially available cloning systems (e.g., Lambda ZAP Express, Stratagene). Phage clones containing 205P1B5 gene cDNAs can be identified by probing with a labeled 205P1B5 cDNA or a fragment thereof. For example, in one embodiment, the 205P1B5 cDNA (FIG. 2) or a portion thereof can be synthesized and used as a probe to retrieve overlapping and full-length cDNAs corresponding to a 205P1B5 gene. The 205P1B5 gene itself can be isolated by screening genomic DNA libraries, bacterial artificial chromosome libraries (BACs), yeast artificial chromosome libraries (YACs), and the like, with 205P1B5 DNA probes or primers.

II.A.5.) Recombinant Nucleic Acid Molecules and Host-Vector Systems

The invention also provides recombinant DNA or RNA molecules containing an 205P1B5 polynucleotide, a fragment, analog or homologue thereof, including but not limited to phages, plasmids, phagemids, cosmids, YACs, BACs, as well as various viral and non-viral vectors well known in the art, and cells transformed or transfected with such recombinant DNA or RNA molecules. Methods for generating such molecules are well known (see, for example, Sambrook et al., 1989, supra).

The invention further provides a host-vector system comprising a recombinant DNA molecule containing a 205P1B5 polynucleotide, fragment, analog or homologue thereof within a suitable prokaryotic or eukaryotic host cell. Examples of suitable eukaryotic host cells include a yeast cell, a plant cell, or an animal cell, such as a mammalian cell or an insect cell (e.g., a baculovirus-infectible cell such as an Sf9 or HighFive cell). Examples of suitable mammalian cells include various prostate cancer cell lines such as DU145 and TsuPr1, other transfectable or transducible prostate cancer cell lines, primary cells (PrEC), as well as a number of mammalian cells routinely used for the expression of recombinant proteins (e.g., COS, CHO, 293, 293T cells). More particularly, a polynucleotide comprising the coding sequence of 205P1B5 or a fragment, analog or homolog thereof can be used to generate 205P1B5 proteins or fragments thereof using any number of host-vector systems routinely used and widely known in the art.

A wide range of host-vector systems suitable for the expression of 205P1B5 proteins or fragments thereof are available, see for example, Sambrook et al., 1989, supra; Current Protocols in Molecular Biology, 1995, supra). Preferred vectors for mammalian expression include but are not limited to pcDNA 3.1 myc-His-tag (Invitrogen) and the retroviral vector pSRαtkneo (Muller et al., 1991, MCB 11:1785). Using these expression vectors, 205P1B5 can be expressed in several prostate cancer and non-prostate cell lines, including for example 293, 293T, rat-1, NIH 3T3 and TsuPr1. The host-vector systems of the invention are useful for the production of a 205P1B5 protein or fragment thereof. Such host-vector systems can be employed to study the functional properties of 205P1B5 and 205P1B5 mutations or analogs.

Recombinant human 205P1B5 protein or an analog or homolog or fragment thereof can be produced by mammalian cells transfected with a construct encoding a 205P1B5-related nucleotide. For example, 293T cells can be transfected with an expression plasmid encoding 205P1B5 or fragment, analog or homolog thereof, the 205P1B5 or related protein is expressed in the 293T cells, and the recombinant 205P1B5 protein is isolated using standard purification methods (e.g., affinity purification using anti-205P1B5 antibodies). In another embodiment, a 205P1B5 coding sequence is subcloned into the retroviral vector pSRαMSVtkneo and used to infect various mammalian cell lines, such as NIH 3T3, TsuPr1, 293 and rat-1 in order to establish 205P1B5 expressing cell lines. Various other expression systems well known in the art can also be employed. Expression constructs encoding a leader peptide joined in frame to the 205P1B5 coding sequence can be used for the generation of a secreted form of recombinant 205P1B5 protein.

As discussed herein, redundancy in the genetic code permits variation in 205P1B5 gene sequences. In particular, it is known in the art that specific host species often have specific codon preferences, and thus one can adapt the disclosed sequence as preferred for a desired host. For example, preferred analog codon sequences typically have rare codons (i.e., codons having a usage frequency of less than about 20% in known sequences of the desired host) replaced with higher frequency codons. Codon preferences for a specific species are calculated, for example, by utilizing codon usage tables available on the INTERNET such as at world wide web URL dna.affrc.go.jp/-nakamura/codon.html.

Additional sequence modifications are known to enhance protein expression in a cellular host. These include elimination of sequences encoding spurious polyadenylation signals, exon/intron splice site signals, transposon-like repeats, and/or other such well-characterized sequences that are deleterious to gene expression. The GC content of the sequence is adjusted to levels average for a given cellular host, as calculated by reference to known genes expressed in the host cell. Where possible, the sequence is modified to avoid predicted hairpin secondary mRNA structures. Other useful modifications include the addition of a translational initiation consensus sequence at the start of the open reading frame, as described in Kozak, Mol. Cell Biol., 9:5073-5080 (1989). Skilled artisans understand that the general rule that eukaryotic ribosomes initiate translation exclusively at the 5' proximal AUG codon is abrogated only under rare conditions (see, e.g., Kozak PNAS 92(7): 2662-2666, (1995) and Kozak NAR 15(20): 8125-8148 (1987)).

III.) 205P1B5-Related Proteins

Another aspect of the present invention provides 205P1B5-related proteins. Specific embodiments of 205P1B5 proteins comprise a polypeptide having all or part of the amino acid sequence of human 205P1B5 as shown in FIG. 2 or FIG. 3. Alternatively, embodiments of 265P1B5 proteins comprise variant, homolog or analog polypeptides that have alterations in the amino acid sequence of 205P1B5 shown in FIG. 2 or FIG. 3.

In general, naturally occurring allelic variants of human 205P1B5 share a high degree of structural identity and homology (e.g., 90% or more homology). Typically, allelic variants of the 205P1B5 protein contain conservative amino acid substitutions within the 205P1B5 sequences described herein or contain a substitution of an amino acid from a corresponding position in a homologue of 205P1B5. One class of 205P1B5 allelic variants are proteins that share a high degree of homology with at least a small region of a particular 205P1B5 amino acid sequence, but further contain a radical departure from the sequence, such as a non-conservative substitution, truncation, insertion or frame shift In comparisons of protein sequences, the terms, similarity, identity, and homology each have a distinct meaning as appreciated in the field of genetics. Moreover, orthology and paralogy can be important concepts describing the relationship of members of a given protein family in one organism to the members of the same family in other organisms.

Amino acid abbreviations are provided in Table II. Conservative amino acid substitutions can frequently be made in a protein without altering either the conformation or the function of the protein. Proteins of the invention can comprise 1, 2, 3, 4, 5, 6, 7, 8, 9, 10, 11, 12, 13, 14, 15 conservative substitutions. Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant Still other changes can be considered "conservative" in particular environments (see, e.g. Table III herein; pages 13-15 "Biochemistry" $2^{nd}$ ED. Lubert Stryer ed. (Stanford University); Henikoff et al., PNAS 1992 Vol. 89 10915-10919; Lei et al., J. Biol. Chem. 1995 May 19; 270(20):11882-6).

Embodiments of the invention disclosed herein include a wide variety of art-accepted variants or analogs of 205P1B5 proteins such as polypeptides having amino acid insertions, deletions and substitutions. 205P1B5 variants can be made using methods known in the art such as site-directed mutagenesis, alanine scanning, and PCR mutagenesis. Site-directed mutagenesis (Carter et al., Nucl. Acids Res., 13:4331 (1986); Zoller et al., Nucl. Acids Res., 10:6487 (1987)), cassette mutagenesis (Wells et al., Gene, 34:315 (1985)), restriction selection mutagenesis (Wells et al., Philos. Trans. R. Soc. London SerA, 317:415 (1986)) or other known techniques can be performed on the cloned DNA to produce the 205P1B5 variant DNA.

Scanning amino acid analysis can also be employed to identify one or more amino acids along a contiguous sequence that is involved in a specific biological activity such as a protein-protein interaction. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Alanine is also typically preferred because it is the most common amino acid. Further, it is frequently found in both buried and exposed positions (Creighton, The Proteins, (W. H. Freeman & Co., N.Y.); Chothia, J. Mol. Biol., 150:1 (1976)). If alanine substitution does not yield adequate amounts of variant, an isosteric amino acid can be used.

As defined herein, 205P1B5 variants, analogs or homologs, have the distinguishing attribute of having at least one epitope that is "cross reactive" with a 205P1B5 protein having the amino acid sequence of SEQ ID NO: 703. As used in this sentence, "cross reactive" means that an antibody or T cell that specifically binds to an 205P1B5 variant also specifically binds to the 205P1B5 protein having the amino acid sequence of SEQ ID NO: 703. A polypeptide ceases to be a variant of the protein shown in SEQ ID NO: 703 when it no longer contains any epitope capable of being recognized by an antibody or T cell that specifically binds to the 205P1B5 protein. Those skilled in the art understand that antibodies that recognize proteins bind to epitopes of varying size, and a grouping of the order of about four or five amino acids, contiguous or not, is regarded as a typical number of amino acids in a minimal epitope. See, e.g., Nair et al., J. Immunol. 2000 165(12): 6949-6955; Hebbes et al., Mol. Immunol. (1989) 26(9):865-73; Schwartz et al., J. Immunol. (1985) 135(4):2598-608.

Another class of 205P1B5-related protein variants share 70%, 75%, 80%, 85% or 90% or more similarity with the amino acid sequence of SEQ ID NO: 703 or a fragment thereof. Another specific class of 205P1B5 protein variants or analogs comprise one or more of the 205P1B5 biological motifs described herein or presently known in the art. Thus, encompassed by the present invention are analogs of 205P1B5 fragments (nucleic or amino acid) that have altered functional (e.g. immunogenic) properties relative to the starting fragment. It is to be appreciated that motifs now or which become part of the art are to be applied to the nucleic or amino acid sequences of FIG. 2 or FIG. 3.

As discussed herein, embodiments of the claimed invention include polypeptides containing less than the full amino acid sequence of the 205P1B5 protein shown in FIG. 2 or FIG. 3. For example, representative embodiments of the invention comprise peptides/proteins having any 4, 5, 6, 7, 8, 9, 10, 11, 12, 13, 14, 15 or more contiguous amino acids of the 205P1B5 protein shown in FIG. 2 or FIG. 3.

Moreover, representative embodiments of the invention disclosed herein include polypeptides consisting of about amino acid 1 to about amino acid 10 of the 205P1B5 protein shown in FIG. 2 or FIG. 3, polypeptides consisting of about amino acid 10 to about amino acid 20 of the 205P1B5 protein shown in FIG. 2 or FIG. 3, polypeptides consisting of about amino acid 20 to about amino acid 30 of the 205P1B5 protein shown in FIG. 2 or FIG. 3, polypeptides consisting of about amino acid 30 to about amino acid 40 of the 205P1B5 protein shown in FIG. 2 or FIG. 3, polypeptides consisting of about amino acid 40 to about amino acid 50 of the 205P1B5 protein shown in FIG. 2 or FIG. 3, polypeptides consisting of about amino acid 50 to about amino acid 60 of the 205P1B5 protein shown in FIG. 2 or FIG. 3, polypeptides consisting of about amino acid 60 to about amino acid 70 of the 205P1B5 protein shown in FIG. 2 or FIG. 3, polypeptides consisting of about amino acid 70 to about amino acid 80 of the 205P1B5 protein shown in FIG. 2 or FIG. 3, polypeptides consisting of about amino acid 80 to about amino acid 90 of the 205P1B5 protein shown in FIG. 2 or FIG. 3, polypeptides consisting of about amino acid 90 to about amino acid 100 of the 205P1B5 protein shown in FIG. 2 or FIG. 3, etc. throughout the entirety of the 205P1B5 amino acid sequence. Moreover, polypeptides consisting of about amino acid 1 (or 20 or 30 or 40 etc.) to about amino acid 20, (or 130, or 140 or 150 etc.) of the 205P1B5 protein shown in FIG. 2 or FIG. 3 are embodiments of the invention. It is to be appreciated that the starting and stopping positions in this paragraph refer to the specified position as well as that position plus or minus 5 residues.

205P1B5-related proteins are generated using standard peptide synthesis technology or using chemical cleavage methods well known in the art. Alternatively, recombinant methods can be used to generate nucleic acid molecules that encode a 205P1B5-related protein. In one embodiment, nucleic acid molecules provide a means to generate defined fragments of the 205P1B5 protein (or variants, homologs or analogs thereof).

III.A.) Motif-Bearing Protein Embodiments

Additional illustrative embodiments of the invention disclosed herein include 205P1B5 polypeptides comprising the amino acid residues of one or more of the biological motifs contained within the 205P1B5 polypeptide sequence set forth in FIG. 2 or FIG. 3. Various motifs are known in the art, and a protein can be evaluated for the presence of such motifs by a number of publicly available Internet sites (see, e.g., URL addresses: pfam.wustl.edu/; searchlauncher.bcm.tmc.edu/seq-search/struc-predict.html psort.ims.u-tokvo.ac.jp/; world wide web URL cbs.dtu.dk/; world wide web URL ebi.ac.uk/interpro/scan.html; world wide web URL expasy.c/tools/scnpsitl.html; Epimatrix™ and Epimer™, Brown University, world wide web URL brown.edu/Research/TB-HIV_Lab/epimatri/epimatrix.html; and BIMAS, bimas.dcrt.nih.gov/.).

Motif bearing subsequences of the 205P1B5 protein are set forth and identified in Table XIX. Table XX sets forth several frequently occurring motifs based on pfam searches (see URL address pfamwustl.edu/). The columns of Table XX list (1) motif name abbreviation, (2) percent identity found amongst the different member of the motif family, (3) motif name or description and (4) most common function; location information is included if the motif is relevant for location.

Polypeptides comprising one or more of the 205P1B5 motifs discussed above are useful in elucidating the specific characteristics of a malignant phenotype in view of the observation that the 205P1B5 motifs discussed above are associated with growth dysregulation and because 205P1B5 is overexpressed in certain cancers (See, e.g., Table I). Casein kinase II, cAMP and camp-dependent protein kinase, and Protein Kinase C, for example, are enzymes known to be associated with the development of the malignant phenotype (see e.g. Chen et al., Lab Invest., 78(2): 165-174 (1998); Gaiddon et al., Endocrinology 136(10): 4331-4338 (1995); Hall et al., Nucleic Acids Research 24(6): 1119-1126 (1996); Peterziel et al., Oncogene 18(46): 6322-6329 (1999) and O'Brian, Oncol. Rep. 5(2): 305-309 (1998)). Moreover, both glycosylation and myristoylation are protein modifications also associated with cancer and cancer progression (see e.g. Dennis et al., Biochem. Biophys. Acta 1473(1):21-34 (1999); Raju et al., Exp. Cell. Res. 235(1): 145-154 (1997)). Amidation is another protein modification also associated with cancer and cancer progression (see e.g. Treston et al., J. Natl. Cancer Inst. Monogr. (13): 169-175 (1992)).

In another embodiment, proteins of the invention comprise one or more of the immunoreactive epitopes identified in accordance with art-accepted methods, such as the peptides set forth in Tables V-XVIII. CTL epitopes can be determined using specific algorithms to identify peptides within an 205P1B5 protein that are capable of optimally binding to specified HLA alleles (e.g., Table IV; EphnaTrix™ and Epimer™, Brown University, URL world wide web URL brown.edu/Research/TB-HIV_Lab/epimatrix/epimatrix.html; and BIMAS, URL bimas.dcrt.nih.gov/.) Moreover, processes for identifying peptides that have sufficient binding affinity for HLA molecules and which are correlated with being immunogenic epitopes, are well known in the art, and are carried out without undue experimentation. In addition, processes for identifying peptides that are inmunogenic epitopes, are well known in the art, and are carried out without undue experimentation either in vitro or in vivo.

Also known in the art are principles for creating analogs of such epitopes in order to modulate immunogenicity. For example, one begins with an epitope that bears a CTL or HTL motif (see, e.g., the HLA Class I and HLA Class II motifs/supermotifs of Table IV). The epitope is analogued by substituting out an amino acid at one of the specified positions, and replacing it with another amino acid specified for that position. For example, one can substitute out a deleterious residue in favor of any other residue, such as a preferred residue as defined in Table IV; substitute a less-preferred residue with a preferred residue as defined in Table IV; or substitute an originally-occurring preferred residue with another preferred residue as defined in Table IV. Substitutions can occur at primary anchor positions or at other positions in a peptide; see, e.g., Table IV.

A variety of references reflect the art regarding the identification and generation of epitopes in a protein of interest as well as analogs thereof. See, for example, WO 9733602 to Chesnut et al.; Sette, Immunogenetics 1999 50(3-4): 201-212; Sette et al., J. Immunol. 2001 166(2): 1389-1397; Sidney et al., Hum. Immunol. 1997 58(1): 12-20; Kondo et al., Immunogenetics 1997 45(4): 249-258; Sidney et al., J. Immunol. 1996 157(8): 3480-90; and Falk et al., Nature 351: 290-6 (1991); Hunt et al., Science 255:1261-3 (1992); Parker et al., J. Immunol. 149:3580-7 (1992); Parker et al., J. Immunol. 152:163-75 (1994)); Kast et al., 1994 152(8): 3904-12; Borras-Cuesta et al., Hum. Immunol. 2000 61(3): 266-278; Alexander et al., J. Immunol. 2000 164(3); 164(3): 1625-1633; Alexander et al., PMID: 7895164, U: 95202582; O'Sullivan et al., J. Immunol. 1991 147(8): 2663-2669; Alexander et al., Immunol. 1994 1(9): 751-761 and Alexander et al., Immunol. Res. 1998 18(2): 79-92.

Related embodiments of the inventions include polypeptides comprising combinations of the different motifs set forth in Table XIX, and/or, one or more of the predicted CTL epitopes of Table V through Table XVIII, and/or, one or more of the T cell binding motifs known in the art. Preferred embodiments contain no insertions, deletions or substitutions either within the motifs or the intervening sequences of the polypeptides. In addition, embodiments which include a number of either N-terminal and/or C-terminal amino acid residues on either side of these motifs may be desirable (to, for example, include a greater portion of the polypeptide architecture in which the motif is located). Typically the number of N-terminal and/or C-terminal amino acid residues on either side of a motif is between about 1 to about 100 amino acid residues, preferably 5 to about 50 amino acid residues.

205P1B5-related proteins are embodied in many forms, preferably in isolated form A purified 205P1B5 protein molecule will be substantially free of other proteins or molecules that impair the binding of 205P1B5 to antibody, T cell or other ligand. The nature and degree of isolation and purification will depend on the intended use. Embodiments of a 205P1B5-related proteins include purified 205P1B5-related proteins and functional, soluble 205P1B5-related proteins. In one embodiment, a functional soluble 205P1B5 protein or fragment thereof retains the ability to be bound by antibody, T cell or other ligand.

The invention also provides 205P1B5 proteins comprising biologically active fragments of the 205P1B5 amino acid sequence shown in FIG. 2 or FIG. 3. Such proteins exhibit properties of the 205P1B5 protein, such as the ability to elicit the generation of antibodies that specifically bind an epitope associated with the 205P1B5 protein; to be bound by such antibodies; to elicit the activation of HTL or CTL; and/or, to be recognized by HTL or CTL. 205P1B5-related polypeptides that contain particularly interesting structures can be predicted and/or identified using various analytical techniques well known in the art, including, for example, the methods of Chou-Fasman, Garnier-Robson, Kyte-Doolittle, Eisenberg, Karplus-Schultz or Jameson-Wolf analysis, or on the basis of immunogenicity. Fragments that contain such structures are particularly useful in generating subunit-specific anti-205P1B5 antibodies, or T cells or in identifying cellular factors that bind to 205P1B5.

CTL epitopes can be determined using specific algorithms to identify peptides within an 205P1B5 protein that are capable of optimally binding to specified HLA alleles (e.g., by using the SYFPEITHI site at World Wide Web URL syfpeithi.bmi-heidelberg.com/; the listings in Table IV(A)-(E); Epimatrix™ and Epimer™, Brown University, URL (world wide web URL brown.edu/Research/TB-IIIV_Lab/epimatrix/epimatrix.html); and BIMAS, URL bimas.dcrt.nih.gov/). Illustrating this, peptide epitopes from 205P1B5 that are presented in the context of human MHC class I molecules HLA-A1, A2, A3, A11, A24, B7 and B35 were predicted (Tables V-XVIII). Specifically, the complete amino acid sequence of the 205P1B5 protein was entered into the HLA Peptide Motif Search algorithm found in the Bioinformatics and Molecular Analysis Section (BIMAS) web site listed above. The HLA peptide motif search algorithm was developed by Dr. Ken Parker based on binding of specific peptide sequences in the groove of HLA Class I molecules, in particular HLA-A2 (see, e.g., Falk et al., Nature 351: 290-6 (1991); Hunt et al., Science 255:1261-3 (1992); Parker et al., J. Immunol. 149:3580-7 (1992); Parker et al., J. Immunol. 152:163-75 (1994)). This algorithm allows location and ranking of 8-mer, 9-mer, and 10-mer peptides from a complete protein sequence for predicted binding to HLA-A2 as well as numerous other HLA Class I molecules. Many HLA class I binding peptides are 8-, 9-, 10 or 11-mers. For example, for class I HLA-A2, the epitopes preferably contain a leucine (L) or methionine (M) at position 2 and a valine (V) or leucine (L) at the C-terminus (see, e.g., Parker et al., J. Immunol. 149:3580-7 (1992)). Selected results of 205P1B5 predicted binding peptides are shown in Tables V-XVII herein. In Tables V-XVIII, the top 50 ranking candidates, 9-mers and 10-mers, for each family member are shown along with their location, the amino acid sequence of each specific peptide, and an estimated binding score. The binding score corresponds to the estimated half time of dissociation of complexes containing the peptide at 37° C. at pH 6.5. Peptides with the highest binding score are predicted to be the most tightly bound to HLA Class I on the cell surface for the greatest period of time and thus represent the best immunogenic targets for T-cell recognition.

Actual binding of peptides to an HLA allele can be evaluated by stabilization of HLA expression on the antigen-processing defective cell line T2 (see, e.g., Xue et al., Prostate 30:73-8 (1997) and Peshwa et al., Prostate 36:129-38 (1998)). Immunogenicity of specific peptides can be evaluated an vitro by stimulation of CD8+ cytotoxic T lymphocytes (CTL) in the presence of antigen presenting cells such as dendritic cells.

It is to be appreciated that every epitope predicted by the BIMAS site, Epimer™ and Epimatrix™ sites, or specified by the HLA class I or class II motifs available in the art or which become part of the art such as set forth in Table IV (or determined using World Wide Web site URL syfpeithi.bmi-heidelberg.com/) are to be "applied" to the 205P1B5 protein. As used in this context "applied" means that the 205P1B5 protein is evaluated, e.g., visually or by computer-based patterns finding methods, as appreciated by those of skill in the relevant art. Every subsequence of the 205P1B5 of 8, 9, 10, or 11 amino acid residues that bears an HLA Class I motif, or a subsequence of 9 or more amino acid residues that bear an HLA Class II motif are within the scope of the invention.

III.B.) Expression of 205P1B5-Related Proteins

In an embodiment described in the examples that follow, 205P1B5 can be conveniently expressed in cells (such as 293T cells) transfected with a commercially available expression vector such as a CMV-driven expression vector encoding 205P1B5 with a C-terminal 6×His and MYC tag (pcDNA3.1/mycHIS, Invitrogen or Tag5, GenHunter Corporation, Nashville Tenn.). The Tag5 vector provides an IgGK secretion signal that can be used to facilitate the production of a secreted 205P1B5 protein in transfected cells. The secreted HIS-tagged 205P1B5 in the culture media can be purified, e.g., using a nickel column using standard techniques.

III.C.) Modifications of 205P1B5-Related Proteins

Modifications of 205P1B5-related proteins such as covalent modifications are included within the scope of this invention. One type of covalent modification includes reacting targeted amino acid residues of a 205P1B5 polypeptide with an organic derivatizing agent that is capable of reacting with selected side chains or the N- or C-terminal residues of the 205P1B5. Another type of covalent modification of the 205P1B5 polypeptide included within the scope of this invention comprises altering the native glycosylation pattern of a protein of the invention. Another type of covalent modification of 205P1B5 comprises linking the 205P1B5 polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337.

The 205P1B5-related proteins of the present invention can also be modified to form a chimeric molecule comprising 205P1B5 fused to another, heterologous polypeptide or amino acid sequence. Such a chimeric molecule can be synthesized chemically or recombinantly. A chimeric molecule can have a protein of the invention fused to another tumor-associated antigen or fragment thereof. Alternatively, a protein in accordance with the invention can comprise a fusion of fragments of the 205P1B5 sequence (amino or nucleic acid) such that a molecule is created that is not, through its length, directly homologous to the amino or nucleic acid sequences shown in FIG. 2 or FIG. 3. Such a chimeric molecule can comprise multiples of the same subsequence of 205P1B5. A chimeric molecule can comprise a fusion of a 205P1B5-related protein with a polyhistidine epitope tag, which provides an epitope to which immobilized nickel can selectively bind, with cytolines or with growth factors. The epitope tag is generally placed at the amino- or carboxyl-terminus of the 205P1B5. In an alternative embodiment, the chimeric molecule can comprise a fusion of a 205P1B5-related protein with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of a 205P1B5 polypeptide in place of at least one variable region within an Ig molecule. In a preferred embodiment, the immunoglobulin fusion includes the hinge, CH2 and CH3, or the hinge, CH1, CH2 and CH3 regions of an IgGl molecule. For the production of immunoglobulin fusions see, e.g., U.S. Pat. No. 5,428,130 issued Jun. 27, 1995.

III.D.) Uses of 205P1B5-Related Proteins

The proteins of the invention have a number of different specific uses. As 205P1B5 is highly expressed in prostate and other cancers, 205P1B5-related proteins are used in methods that assess the status of 205P1B5 gene products in normal versus cancerous tissues, thereby elucidating the malignant phenotype. Typically, polypeptides from specific regions of the 205P1B5 protein are used to assess the presence of perturbations (such as deletions, insertions, point mutations etc.) in those regions (such as regions containing one or more motifs). Exemplary assays utilize antibodies or T cells targeting 205P1B5-related proteins comprising the amino acid residues of one or more of the biological motifs contained within the 205P1B5 polypeptide sequence in order to evaluate the characteristics of this region in normal versus cancerous tissues or to elicit an immune response to the epitope. Alternatively, 205P1B5-related proteins that contain the amino acid residues of one or more of the biological motifs in the 205P1B5 protein are used to screen for factors that interact with that region of 205P1B5.

205P1B5 protein fragments/subsequences are particularly useful in generating and characterizing domain specific antibodies (e.g., antibodies recognizing an extracellular or intracellular epitope of an 205P1B5 protein), for identifying agents or cellular factors that bind to 205P1B5 or a particular structural domain thereof, and in various therapeutic and diagnostic contexts, including but not limited to diagnostic assays, cancer vaccines and methods of preparing such vaccines.

Proteins encoded by the 205P1B5 genes, or by analogs, homologs or fragments thereof, have a variety of uses, including but not limited to generating antibodies and in methods for identifying ligands and other agents and cellular constituents that bind to an 205P1B5 gene product Antibodies raised against an 205P1B5 protein or fragment thereof are useful in diagnostic and prognostic assays, and imaging methodologies in the management of human cancers characterized by expression of 205P1B5 protein, such as those listed in Table I. Such antibodies can be expressed intracellularly and used in methods of treating patients with such cancers. 205P1B5-related nucleic acids or proteins are also used in generating HTL or CTL responses.

Various immunological assays useful for the detection of 205P1B5 proteins are used, including but not limited to various types of radioimmunoassays, enzyme-linked immunosorbent assays (ELISA), enzyme-linked immunofluorescent assays (ELIFA), immunocytochemical methods, and the like. Antibodies can be labeled and used as immunological imaging reagents capable of detecting 205P1B5expressing cells (e.g., in radioscintigraphic imaging methods). 205P1B5 proteins are also particularly useful in generating cancer vaccines, as further described herein.

IV.) 205P1B5 Antibodies

Another aspect of the invention provides antibodies that bind to 205P1B5-related proteins. Preferred antibodies specifically bind to a 205P1B5-related protein and do not bind (or bind weakly) to peptides or proteins that are not 205P1B5-related proteins. For example, antibodies bind 205P1B5 can bind 205P1B5-related proteins such as the homologs or analogs thereof.

205P1B5 antibodies of the invention are particularly useful in prostate cancer diagnostic and prognostic assays, and imaging methodologies. Similarly, such antibodies are useful in the treatment, diagnosis, and/or prognosis of other cancers, to the extent 205P1B5 is also expressed or overexpressed in these other cancers. Moreover, intracellularly expressed antibodies (e.g., single chain antibodies) are therapeutically useful in treating cancers in which the expression of 205P1B5 is involved, such as advanced or metastatic prostate cancers.

The invention also provides various immunological assays useful for the detection and quantification of 205P1B5 and mutant 205P1B5-related proteins. Such assays can comprise one or more 205P1B5 antibodies capable of recognizing and binding a 205P1B5-related protein, as appropriate. These assays are performed within various immunological assay formats well known in the art, including but not limited to various types of radioimmunoassays, enzyme-linked immunosorbent assays (ELISA), enzyme linked immunofluorescent assays (ELIFA), and the like.

Immunological non-antibody assays of the invention also comprise T cell immunogenicity assays (inhibitory or stimulatory) as well as major histocompatibility complex (MHC) binding assays.

In addition, immunological imaging methods capable of detecting prostate cancer and other cancers expressing 205P1B5 are also provided by the invention, including but not limited to radioscintigraphic imaging methods using labeled 205P1B5 antibodies. Such assays are clinically useful in the detection, monitoring, and prognosis of 205P1B5 expressing cancers such as prostate cancer. 205P1B5 antibodies are also used in methods r purifying a 205P1B5-related protein and for isolating 205P1B5 homologues and related molecules. For example, a method of purifying a 205P1B5-related protein comprises incubating an 205P1B5 antibody, which has been coupled to a solid matrix, with a lysate or other solution containing a 205P1B5-related protein under conditions that permit the 205P1B5 antibody to bind to the 205P1B5-related protein; washing the solid matrix to eliminate impurities; and eluting the 205P1B5-related protein from the coupled antibody. Other uses of the 205P1B5 antibodies of the invention include generating anti-idiotypic antibodies that mimic the 205P1B5 protein.

Various methods for the preparation of antibodies are well known in the art. For example, antibodies can be prepared by immunizing a suitable mammalian host using a 205P1B5-related protein, peptide, or fragment, in isolated or immunoconjugated form (Antibodies: A Laboratory Manual, CSH Press, Eds., Harlow, and Lane (1988); Harlow, Antibodies, Cold Spring Harbor Press, N.Y. (1989)). In addition, fusion proteins of 205P1B5 can also be used, such as a 205P1B5 GST-fusion protein. In a particular embodiment, a GST fusion protein comprising all or most of the amino acid sequence of FIG. 2 or FIG. 3 is produced, then used as an immunogen to generate appropriate antibodies. In another embodiment, a 205P1B5-related protein is synthesized and used as an immunogen.

In addition, naked DNA immunization techniques known in the art are used (with or without purified 205P1B5-related protein or 205P1B5 expressing cells) to generate an immune response to the encoded immunogen (for review, see Donnelly et al., 1997, Ann. Rev. Immunol. 15: 61768).

The amino acid sequence of 205P1B5 as shown in FIG. 2 or FIG. 3 can be analyzed to select specific regions of the 205P1B5 protein for generating antibodies. For example, hydrophobicity and hydrophilicity analyses of the 205P1B5 amino acid sequence are used to identify hydrophilic regions in the 205P1B5 structure. Regions of the 205P1B5 protein that show immunogenic structure, as well as other regions and domains, can readily be identified using various other methods known in the ark such as Chou-Fasman, Garnier-Robson, Kyte-Doolittle, Eisenberg, Karplus-Schultz or Jameson-Wolf analysis. Thus, each region identified by any of these programs or methods is within the scope of the present invention. Methods for the generation of 205P1B5 antibodies are further illustrated by way of the examples provided herein. Methods for preparing a protein or polypeptide for use as an immunogen are well known in the art. Also well known in the art are methods for preparing immunogenic conjugates of a protein with a carrier, such as BSA, KLH or other carrier protein. In some circumstances, direct conjugation using, for example, carbodiimide reagents are used; in other instances linking reagents such as those supplied by Pierce Chemical Co., Rockford, Ill., are effective. Administration of a 205P1B5 immunogen is often conducted by injection over a suitable time period and with use of a suitable adjuvant, as is understood in the art. During the immunization schedule, titers of antibodies can be taken to determine adequacy of antibody formation.

205P1B5 monoclonal antibodies can be produced by various means well known in the art. For example, immortalized cell lines that secrete a desired monoclonal antibody are prepared using the standard hybridoma technology of Kohler and Milstein or modifications that immortalize antibody-producing B cells, as is generally known Immortalized cell lines that secrete the desired antibodies are screened by immunoassay in which the antigen is a 205P1B5-related protein. When the appropriate immortalized cell culture is identified, the cells can be expanded and antibodies produced either from in vitro cultures or from ascites fluid.

The antibodies or fragments of the invention can also be produced, by recombinant means. Regions that bind specifically to the desired regions of the 205P1B5 protein can also be produced in the context of chimeric or complementarity determining region (CDR) gifted antibodies of multiple species origin. Humanized or human 205P1B5 antibodies can also be produced, and are preferred for use in therapeutic contexts. Methods for humming mine and other non-human antibodies, by substituting one or more of the non-human antibody CDRs for corresponding human antibody sequences, are well known (see for example, Jones et al., 1986, Nature 321: 522-525; Riechmann et al., 1988, Nature 332: 323-327; Verhoeyen et al., 1988, Science 239: 1534-1536). See also, Carter et al., 1993, Proc. Natl. Acad. Sci. USA 89: 4285 and Sims et al., 1993, J. Immunol. 151: 2296.

Methods for producing fully human monoclonal antibodies include phage display and transgenic methods (for review, see Vaughan et al., 1998, Nature Biotechnology 16: 535-539). Fully human 205P1B5 monoclonal antibodies can be generated using cloning technologies employing large human Ig gene combinatorial libraries (i.e., phage display) (Griffiths and Hoogenboom, Building an in vitro immune system human antibodies from phage display libraries. In: Protein Engineering of Antibody Molecules for Prophylactic and Therapeutic Applications in Man, Clark, M. (Ed.), Nottingham Academic, pp 45-64 (1993); Burton and Barbas, Human Antibodies from combinatorial libraries. Id, pp 65-82). Fully human 205P1B5 monoclonal antibodies can also be produced using transgenic mice engineered to contain human immunoglobulin gene loci as described in PCT Patent Application WO98/24893, Kucherlapati and Jakobovits et al., published Dec. 3, 1997 (see also, Jakobovits, 1998, Exp. Opin. Invest. Drugs 7(4): 607-614; U.S. Pat. No. 6,162,963 issued 19 Dec. 2000; U.S. Pat. No. 6,150,584 issued 12 Nov. 2000; and, U.S. Pat. No. 6,114,598 issued 5 Sep. 2000). This method avoids the in vitro manipulation required with phage display technology and efficiently produces high affinity authentic human antibodies.

Reactivity of 205P1B5 antibodies with an 205P1B5-related protein can be established by a number of well known means, including Western blot, immunoprecipitation, ELISA, and FACS analyses using, as appropriate, 205P1B5-related proteins, 205P1B5-expressing cells or extracts thereof. A 205P1B5 antibody or fragment thereof can be labeled with a detectable marker or conjugated to a second molecule. Suitable detectable markers include, but are not limited to, a radioisotope, a fluorescent compound, a bioluminescent compound, chemiluminescent compound, a metal chelator or an enzyme. Further, bi-specific antibodies specific for two or more 205P1B5 epitopes are generated using methods generally known in the art Homodimeric antibodies can also be generated by cross-linking techniques known in the art (e.g., Wolff et al., Cancer Res. 53: 2560-2565).

V.) 205P1B5 Cellular Immune Responses

The mechanism by which T cells recognize antigens has been delineated. Efficacious peptide epitope vaccine compositions of the invention induce a therapeutic or prophylactic immune responses in very broad segments of the world-wide population. For an understanding of the value and efficacy of compositions of the invention that induce cellular immune responses, a brief review of immunology-related technology is provided A complex of an HLA molecule and a peptidic antigen acts as the ligand recognized by HLA-restricted T cells (Buus, S. et al., *Cell* 47:1071, 1986; Babbitt, B. P. et al., *Nature* 317: 359, 1985; Townsend, A. and Bodmer, H., *Annu. Rev. Immunol.* 7:601, 1989; Germain, R. N., *Annu. Rev. Immunol.* 11:403, 1993). Through the study of single amino acid substituted antigen analogs and the sequencing of endogenously bound, naturally processed peptides, critical residues that correspond to motifs required for specific binding to HLA antigen molecules have been identified and are set forth in Table IV (see also, e.g., Southwood, et al., *J. Immunol.* 160: 3363, 1998; Rammensee, et al., *Immunogenetics* 41:178, 1995; Rammensee et al., SYFPEITHI, access via World Wide Web at URL syfpeithi.bmi-heidelberg.com/; Sette, A. and Sidney, *J. Curr. Opin. Immunol.* 10:478, 1998; Engelhard, V. H., *Curr. Opin. Immunol.* 6:13, 1994; Sette, A. and Grey, H. M., *Curr. Opin. Immunol.* 4:79, 1992; Sinigaglia, F. and Hammer, J. *Curr. Biol.* 6:52, 1994; Ruppert et al., *Cell* 74:929-937, 1993; Kondo et al., *J. Immunol.* 155:4307-4312, 1995; Sidney et al., *J. Immunol.* 157:3480-3490, 1996; Sidney et al., *Human Immunol.* 45:79-93, 1996; Sette, A. and Sidney, J. *Immunogenetics* 1999 November; 50(34):201-12, Review).

Furthermore, x-ray crystallographic analyses of HLA-peptide complexes have revealed pockets within the peptide binding cleft/groove of HLA molecules which accommodate, in an allele-specific mode, residues borne by peptide ligands; these residues in turn determine the HLA binding capacity of the peptides in which they are present (See, e.g., Madden, D. R. *Annu. Rev. Immunol.* 13:587, 1995; Smith, et al., *Immunity* 4:203, 1996; Fremont et al., *Immunity* 8:305, 1998; Stern et al., *Structure* 2:245, 1994; Jones, E. Y. *Curr. Opin. Immunol.* 9:75, 1997; Brown, J. H. et al., *Nature* 364:33, 1993; Guo, H. C. et al., *Proc. Natl. Acad. Sci. USA* 90:8053, 1993; Guo, H. C. et al., *Nature* 360:364, 1992; Silver, M. L. et al., *Nature* 360:367, 1992; Matsumura, M. et al., *Science* 257:927, 1992; Madden et al., *Cell* 70:1035, 1992; Fremont, D. H. et al., *Science* 257:919, 1992; Saper, M. A., Bjorkman, P. J. and Wiley, D. C., *J. Mol. Biol.* 219:277, 1991.)

Accordingly, the definition of class I and class II allele-specific HLA binding motifs, or class I or class II supermotifs allows identification of regions within a protein that are correlated with binding to particular HLA antigen(s).

Thus, by a process of HLA motif identification, candidates for epitope-based vaccines have been identified; such candidates can be further evaluated by HLA-peptide binding assays to determine binding affinity and/or the time period of association of the epitope and its corresponding HLA molecule. Additional confirmatory work can be performed to select, amongst these vaccine candidates, epitopes with preferred characteristics in terms of population coverage, and/or immunogenicity.

Various strategies can be utilized to evaluate cellular immunogenicity, including:

1) Evaluation of primary T cell cultures from normal individuals (see, e.g., Wentworth, P. A. et al., *Mol. Immunol.* 32:603, 1995; Celis, E. et al., *Proc. Natl. Acad. Sci. USA* 91:2105, 1994; Tsai, V. et al., *J. Immunol.* 158:1796, 1997; Kawashima, I. et al., *Human Immunol.* 59:1, 1998). This procedure involves the stimulation of peripheral blood lymphocytes (PBL) from normal subjects with a test peptide in the presence of antigen presenting cells in vitro over a period of several weeks. T cells specific for the peptide become activated during this time and are detected using, e.g., a lymphokine- or $^{51}$Cr-release assay involving peptide sensitized target cells.

2) Immunization of HLA transgenic mice (see, e.g., Wentworth, P. A. et al., *J. Immunol.* 26:97, 1996; Wentworth, P. A. et al., *Int. Immunol.* 8:651, 1996; Alexander, J. et al., *J. Immunol.* 159:4753, 1997). For example, in such methods peptides in incomplete Freund's adjuvant are administered subcutaneously to HLA transgenic mice. Several weeks following immunization, splenocytes are removed and cultured in vitro in the presence of test peptide for approximately one week. Peptide-specific T cells are detected using, e.g., a $^{51}$Cr-release assay involving peptide sensitized target cells and target cells expressing endogenously generated antigen.

3) Demonstration of recall T cell responses from immune individuals who have been either effectively vaccinated and/or from chronically ill patients (see, e.g., Rehermann, B. et al., *J. Exp. Med.* 181:1047, 1995; Doolan, D. L. et al., *Immunity* 7:97, 1997; Bertoni, R et al., *J. Clin. Invest.* 100:503, 1997; Threlkeld, S. C. et al., *J. Immunol.* 159:1648, 1997; Diepolder, H. M. et al., *J. Virol.* 71:6011, 1997). Accordingly, recall responses are detected by culturing PBL from subjects that have been exposed to the antigen due to disease and thus have generated an immune response "naturally", or from patients who were vaccinated against the antigen. PBL from subjects are cultured in vitro for 1-2 weeks in the presence of test peptide plus antigen presenting cells (APC) to allow activation of "memory" T cells, as compared to "naive" T cells. At the end of the culture period, T cell activity is detected using assays including $^{51}$Cr release involving peptide-sensitized targets, T cell proliferation, or lymphokine release.

VI.) 205P1B5 Transgenic Animals

Nucleic acids that encode a 205P1B5-related protein can also be used to generate either transgenic animals or "knock out" animals which, in turn, are useful in the development and screening of therapeutically useful reagents. In accordance with established techniques, cDNA encoding 205P1B5 can be used to clone genomic DNA that encodes 205P1B5. The cloned genomic sequences can then be used to generate transgenic animals containing cells that express DNA that encode 205P1B5. Methods for generating transgenic animals, particularly animals such as mice or rats, have become conventional in the art and are described, for example, in U.S. Pat. No. 4,736,866 issued 12 Apr. 1988, and U.S. Pat. No. 4,870,009 issued 26 Sep. 1989. Typically, particular cells would be targeted for 205P1B5 transgene incorporation with tissue-specific enhancers.

Transgenic animals that include a copy of a transgene encoding 205P1B5 can be used to examine the effect of increased expression of DNA that encodes 205P1B5. Such animals can be used as tester animals for reagents thought to confer protection from, for example, pathological conditions associated with its overexpression. In accordance with this aspect of the invention, an animal is treated with a reagent and a reduced incidence of a pathological condition, compared to untreated animals that bear the transgene, would indicate a potential therapeutic intervention for the pathological condition.

Alternatively, non-human homologues of 205P1B5 can be used to construct a 205P1B5 "knock out" animal that has a defective or altered gene encoding 205P1B5 as a result of homologous recombination between the endogenous gene encoding 205P1B5 and altered genomic DNA encoding 205P1B5 introduced into an embryonic cell of the animal. For example, cDNA that encodes 205P1B5 can be used to clone genomic DNA encoding 205P1B5 in accordance with established techniques. A portion of the genomic DNA encoding 205P1B5 can be deleted or replaced with another gene, such as a gene encoding a selectable marker that can be used to monitor integration. Typically, several kilobases of unaltered flanking DNA (both at the 5' and 3' ends) are included in the vector (see, e.g., Thomas and Capecchi, *Cell*, 51:503 (1987) for a description of homologous recombination vectors). The vector is introduced into an embryonic stem cell line (e.g., by electroporation) and cells in which the introduced DNA has homologously recombined with the endogenous DNA are selected (see, e.g., Li et al., *Cell* 69:915 (1992)). The selected cells are then injected into a blastocyst of an animal (e.g., a mouse or rat) to form aggregation chimeras (see, e.g., Bradley, in *Teratocarcinomas and Embryonic Stem Cells: A Practical Approach*, E. J. Robertson, ed. (IRL, Oxford, 1987), pp. 113-152). A chimeric embryo can then be implanted into a suitable pseudopregnant female foster animal, and the embryo brought to term to create a "knock out" animal. Progeny harboring the homologously recombined DNA in their germ cells can be identified by standard techniques and used to breed animals in which all cells of the animal contain the homologously recombined DNA. Knock out animals can be characterized, for example, for their ability to defend against certain pathological conditions or for their development of pathological conditions due to absence of the 205P1B5 polypeptide.

VII.) Methods for the Detection of 205P1B5

Another aspect of the present invention relates to methods for detecting 205P1B5 polynucleotides and 205P1B5-related proteins, as well as methods for identifying a cell that expresses 205P1B5. The expression profile of 205P1B5 makes it a diagnostic marker for metastasized disease. Accordingly, the status of 205P1B5 gene products provides information useful for predicting a variety of factors including susceptibility to advanced stage disease, rate of progression, and/or tumor aggressiveness. As discussed in detail herein, the status of 205P1B5 gene products in patient samples can be analyzed by a variety protocols that are well known in the art including immunohistochemical analysis, the variety of Northern blotting techniques including in situ hybridization, RT-PCR analysis (for example on laser capture microdissected samples), Western blot analysis and tissue array analysis.

More particularly, the invention provides assays for the detection of 205P1B5 polynucleotides in a biological sample, such as serum, bone, prostate, and other tissues, urine, semen, cell preparations, and the like. Detectable 205P1B5 polynucleotides include, for example, a 205P1B5 gene or fragment thereof, 205P1B5 mRNA, alternative splice variant 205P1B5 mRNAs, and recombinant DNA or RNA molecules that contain a 205P1B5 polynucleotide. A number of methods for amplifying and/or detecting the presence of 205P1B5 polynucleotides are well known in the art and can be employed in the practice of this aspect of the invention.

In one embodiment, a method for detecting an 205P1B5 mRNA in a biological sample comprises producing cDNA from the sample by reverse transcription using at least one primer; amplifying the cDNA so produced using an 205P1B5 polynucleotides as sense and antisense primers to amplify 205P1B5 cDNAs therein; and detecting the presence of the amplified 205P1B5 cDNA. Optionally, the sequence of the amplified 205P1B5 cDNA can be determined.

In another embodiment, a method of detecting a 205P1B5 gene in a biological sample comprises first isolating genomic DNA from the sample; amplifying the isolated genomic DNA using 205P1B5 polynucleotides as sense and antisense primers; and detecting the presence of the amplified 205P1B5 gene. Any number of appropriate sense and antisense probe combinations can be designed from the nucleotide sequence provided for the 205P1B5 (FIG. 2) and used for this purpose.

The invention also provides assays for detecting the presence of an 205P1B5 protein in a tissue or other biological sample such as serum, semen, bone, prostate, urine, cell preparations, and the like. Methods for detecting a 205P1B5-related protein are also well known and include, for example, immunoprecipitation, immunohistochemical analysis, Western blot analysis, molecular binding assays, ELISA, ELIFA and the like. For example, a method of detecting the presence of a 205P1B5-related protein in a biological sample comprises first contacting the sample with a 205P1B5 antibody, a 205P1B5-reactive fragment thereof, or a recombinant protein containing an antigen binding region of a 205P1B5 antibody; and then detecting the binding of 205P1B5-related protein in the sample.

Methods for identifying a cell that expresses 205P1B5 are also within the scope of the invention In one embodiment, an assay for identifying a cell that expresses a 205P1B5 gene comprises detecting the presence of 205P1B5 mRNA in the cell. Methods for the detection of particular mRNAs in cells are well known and include, for example, hybridization assays using complementary DNA probes (such as in situ hybridization using labeled 205P1B5 riboprobes, Northern blot and related techniques) and various nucleic acid amplification assays (such as RT-PCR using complementary primers specific for 205P1B5, and other amplification type detection methods, such as, for example, branched DNA, SISBA, TMA and the like). Alternatively, an assay for identifying a cell that expresses a 205P1B5 gene comprises detecting the presence of 205P1B5-related protein in the cell or secreted by the cell. Various methods for the detection of proteins are well known in the art and are employed for the detection of 205P1B5-related proteins and cells that express 205P1B5-related proteins. 205P1B5 expression analysis is also useful as a tool for identifying and evaluating agents that modulate 205P1B5 gene expression. For example, 205P1B5 expression is significantly upregulated in prostate cancer, and is expressed in cancers of the tissues listed in Table I. Identification of a molecule or biological agent that inhibits 205P1B5 expression or over-expression in cancer cells is of therapeutic value. For example, such an agent can be identified by using a screen that quantifies 205P1B5 expression by RT-PCR, nucleic acid hybridization or antibody binding.

VIII.) Methods for Monitoring the Status of 205P1B5-Related Genes and Their Products Oncogenesis is known to be a multistep process where cellular growth becomes progressively dysregulated and cells progress from a normal physiological state to precancerous and then cancerous states (see, e.g., Alers, et al., Lab Invest. 77(5): 437-438 (1997) and Isaacs et al., Cancer Surv. 23: 19-32 (1995)). In this context, examining a biological sample for evidence of dysregulated cell growth (such as aberrant 205P1B5 expression in cancers) allows for early detection of such aberrant physiology, before a pathologic state such as cancer has progressed to a stage that therapeutic options are more limited and or the prognosis is worse. In such examinations, the status of 205P1B5 in a biological sample of interest can be compared, for example, to the status of 205P1B5 in a corresponding normal sample (e.g. a sample from that individual or alternatively another individual that is not affected by a pathology). An alteration in the status of 205P1B5 in the biological sample (as compared to the normal sample) provides evidence of dysregulated cellular growth. In addition to using a biological sample that is not affected by a pathology as a normal sample, one can also use a predetermined normative value such as a predetermined normal level of mRNA expression (see, e.g., Grever et al., J. Comp. Neurol. 1996 Dec. 9;376(2):306-14 and U.S. Pat. No. 5,837,501) to compare 205P1B5 status in a sample.

The term "status" in this context is used according to its art accepted meaning and refers to the condition or state of a gene and its products. Typically, skilled artisans use a number of parameters to evaluate the condition or state of a gene and its products. These include, but are not limited to the location of expressed gene products (including the location of 205P1B5 expressing cells) as well as the level, and biological activity of expressed gene products (such as 205P1B5 mRNA, polynucleotides and polypeptides). Typically, an alteration in the status of 205P1B5 comprises a change in the location of 205P1B5 and/or 205P1B5 expressing cells and/or an increase in 205P1B5 mRNA and/or protein expression.

205P1B5 status in a sample can be analyzed by a number of means well known in the art, including without limitation, immunohistochemical analysis, in situ hybridization, RT-PCR analysis on laser capture micro-dissected samples, Western blot analysis, and tissue array analysis. Typical protocols for evaluating the status of the 205P1B5 gene and gene products are found, for example in Ausubel et al. eds., 1995, Current Protocols In Molecular Biology, Units 2 (Northern Blotting), 4 (Southern Blotting), 15 (Immunoblotting) and 18 (PCR Analysis). Thus, the status of 205P1B5 in a biological sample is evaluated by various methods utilized by skilled artisans including, but not limited to genomic Southern analysis (to examine, for example perturbations in the 205P1B5 gene), Northern analysis and/or PCR analysis of 205P1B5 mRNA (to examine, for example alterations in the polynucleotide sequences or expression levels of 205P1B5 mRNAs), and, Western and/or immunohistochemical analysis (to examine, for example alterations in polypeptide sequences, alterations in polypeptide localization within a sample, alterations in expression levels of 205P1B5 proteins and/or associations of 205P1B5 proteins with polypeptide binding partners). Detectable 205P1B5 polynucleotides include, for example, a 205P1B5 gene or fragment thereof, 205P1B5 mRNA, alternative splice variants, 205P1B5 mRNAs, and recombinant DNA or RNA molecules containing a 205P1B5 polynucleotide.

The expression profile of 205P1B5 makes it a diagnostic marker for local and/or metastasized disease, and provides information on the growth or oncogenic potential of a biological sample. In particular, the status of 205P1B5 provides information useful for predicting susceptibility to particular disease stages, progression, and/or tumor aggressiveness. The invention provides methods and assays for determining 205P1B5 status and diagnosing cancers that express 205P1B5, such as cancers of the tissues listed in Table I. For example, because 205P1B5 mRNA is so highly expressed in prostate and other cancers relative to normal prostate tissue, assays that evaluate the levels of 205P1B5 mRNA transcripts or proteins in a biological sample can be used to diagnose a disease associated with 205P1B5 dysregulation, and can provide prognostic information useful in defining appropriate therapeutic options.

The expression status of 205P1B5 provides information including the presence, stage and location of dysplastic, precancerous and cancerous cells, predicting susceptibility to various stages of disease, and/or for gauging tumor aggressiveness. Moreover, the expression profile makes it useful as an imaging reagent for metastasized disease. Consequently, an aspect of the invention is directed to the various molecular prognostic and diagnostic methods for examining the status of 205P1B5 in biological samples such as those from individuals suffering from, or suspected of suffering from a pathology characterized by dysregulated cellular growth, such as cancer.

As described above, the status of 205P1B5 in a biological sample can be examined by a number of well-known procedures in the art. For example, the status of 205P1B5 in a biological sample taken from a specific location in the body can be examined by evaluating the sample for the presence or absence of 205P1B5expressing cells (e.g. those that express 205P1B5 mRNAs or proteins). This examination can provide evidence of dysregulated cellular growth, for example, when 205P1B5-expressing cells are found in a biological sample that does not normally contain such cells (such as a lymph node), because such alterations in the status of 205P1B5 in a biological sample are often associated with dysregulated cellular growth. Specifically, one indicator of dysregulated cellular growth is the metastases of cancer cells from an organ of origin (such as the prostate) to a different area of the body (such as a lymph node). In this context, evidence of dysregulated cellular growth is important for example because occult lymph node metastases can be detected in a substantial proportion of patients with prostate cancer, and such metastases are associated with known predictors of disease progression (see, e.g., Murphy et al., Prostate 42(4): 315-317 (2000);Su et al., Semin. Surg. Oncol. 18(1): 17-28 (2000) and Freeman et al., J. Urol 1995 August 154(2 Pt 1):474-8).

In one aspect, the invention provides methods for monitoring 205P1B5 gene products by determining the status of 205P1B5 gene products expressed by cells from an individual suspected of having a disease associated with dysregulated cell growth (such as hyperplasia or cancer) and then comparing the status so determined to the status of 205P1B5 gene products in a corresponding normal sample. The presence of aberrant 205P1B5 gene products in the test sample relative to the normal sample provides an indication of the presence of dysregulated cell growth within the cells of the individual.

In another aspect, the invention provides assays useful in determining the presence of cancer in an individual, comprising detecting a significant increase in 205P1B5 mRNA or protein expression in a test cell or tissue sample relative to expression levels in the corresponding normal cell or tissue. The presence of 205P1B5 mRNA can, for example, be evaluated in tissue samples including but not limited to those listed in Table I. The presence of significant 205P1B5 expression in any of these tissues is useful to indicate the emergence, presence and/or severity of a cancer, since the corresponding normal tissues do not express 205P1B5 mRNA or express it at lower levels.

In a related embodiment, 205P1B5 status is determined at the protein level rather than at the nucleic acid level. For example, such a method comprises determining the level of 205P1B5 protein expressed by cells in a test tissue sample and comparing the level so determined to the level of 205P1B5 expressed in a corresponding normal sample. In one embodiment, the presence of 205P1B5 protein is evaluated, for example, using immunohistochemical methods. 205P1B5 antibodies or binding partners capable of detecting 205P1B5 protein expression are used in a variety of assay formats well known in the art for this purpose.

In a further embodiment, one can evaluate the status of 205P1B5 nucleotide and amino acid sequences in a biological sample in order to identify perturbations in the structure of these molecules. These perturbations can include insertions, deletions, substitutions and the like. Such evaluations are useful because perturbations in the nucleotide and amino acid sequences are observed in a large number of proteins associated with a growth dysregulated phenotype (see, e.g., Marrogi et al., 1999, J. Cutan. Pathol. 26(8):369-378). For example, a mutation in the sequence of 205P1B5 may be indicative of the presence or promotion of a tumor. Such assays therefore have diagnostic and predictive value where a mutation in 205P1B5 indicates a potential loss of function or increase in tumor growth.

A wide variety of assays for observing perturbations m nucleotide and amino acid sequences are well known in the art. For example, the size and structure of nucleic acid or amino acid sequences of 205P1B5 gene products are observed by the Northern, Southern, Western, PCR and DNA sequencing protocols discussed herein. In addition, other methods for observing perturbations in nucleotide and amino acid sequences such as single strand conformation polymorphism analysis are well known in the art (see, e.g., U.S. Pat. No. 5,382,510 issued 7 Sep. 1999, and U.S. Pat. No. 5,952, 170 issued 17 Jan. 1995).

Additionally, one can examine the methylation status of the 205P1B5 gene in a biological sample. Aberrant demethylation and/or hypermethylation of CpG islands in gene 5' regulatory regions frequently occurs in immortalized and transformed cells, and can result in altered expression of various genes. For example, promoter hypermethylation of the pi-class glutathione S-transferase (a protein expressed in normal prostate but not expressed in>90% of prostate carcinomas) appears to permanently silence transcription of this gene and is the most frequently detected genomic alteration in prostate carcinomas (De Marzo et al., Am. J. Pathol. 155(6): 1985-1992 (1999)). In addition, this alteration is present in at least 70% of cases of high-grade prostatic intraepithelial neoplasia (PIN) (Brooks et al., Cancer Epidemiol. Biomarkers Prev., 1998, 7:531-536). In another example, expression of the LAGE-I tumor specific gene (which is not expressed in normal prostate but is expressed in 25-50% of prostate cancers) is induced by deoxy-azacytidine in lymphoblastoid cells, suggesting that tumoral expression is due to demethylation (Lethe et al., Int. J. Cancer 76(6): 903-908 (1998)). A variety of assays for examining methylation status of a gene are well known in the art For example, one can utilize, in Southern hybridization approaches, methylation-sensitive restriction enzymes which cannot cleave sequences that contain methylated CpG sites to assess the methylation status of CpG islands. In addition, MSP (methylation specific PCR) can rapidly profile the methylation status of all the CpG sites present in a CpG island of a given gene. This procedure involves initial modification of DNA by sodium bisulfite (which will convert all unmethylated cytosines to uracil) followed by amplification using priers specific for methylated versus unmethylated DNA. Protocols involving methylation interference can also be found for example in Current Protocols In Molecular Biology, Unit 12, Frederick M. Ausubel et al. eds., 1995.

Gene amplification is an additional method for assessing the status of 205P1B5. Gene amplification is measured in a sample directly, for example, by conventional Southern blotting or Northern blotting to quantitate the transcription of mRNA (Thomas, 1980, Proc. Natl. Acad. Sci. USA, 77:5201-5205), dot blotting (DNA analysis), or in situ hybridization, using an appropriately labeled probe, based on the sequences provided herein. Alternatively, antibodies are employed that recognize specific duplexes, including DNA duplexes, RNA duplexes, and DNA-RNA hybrid duplexes or DNA-protein duplexes. The antibodies in turn are labeled and the assay carried out where the duplex is bound to a surface, so that upon the formation of duplex on the surface, the presence of antibody bound to the duplex can be detected.

Biopsied tissue or peripheral blood can be conveniently assayed for the presence of cancer cells using for example, Northern, dot blot or RT-PCR analysis to detect 205P1B5 expression. The presence of RT-PCR amplifiable 205P1B5 mRNA provides an indication of the presence of cancer. RT-PCR assays are well known in the art RT-PCR detection assays for tumor cells in peripheral blood are currently being evaluated for use in the diagnosis and management of a number of human solid tumors. In the prostate cancer field, these include RT-PCR assays for the detection of cells expressing PSA and PSM (Verkaik et al., 1997, Urol. Res. 25:373-384; Ghossein et al., 1995, J. Clin. Oncol. 13:1195-2000; Heston et al., 1995, Clin. Chem. 41:1687-1688).

A further aspect of the invention is an assessment of the susceptibility that an individual has for developing cancer. In one embodiment, a method for predicting susceptibility to cancer comprises detecting 205P1B5 mRNA or 205P1B5 protein in a tissue sample, its presence indicating susceptibility to cancer, wherein the degree of 205P1B5 mRNA expression correlates to the degree of susceptibility. In a specific embodiment, the presence of 205P1B5 in prostate or other tissue is examined, with the presence of 205P1B5 in the sample providing an indication of prostate cancer susceptibility (or the emergence or existence of a prostate tumor). Similarly, one can evaluate the integrity 205P1B5 nucleotide and amino acid sequences in a biological sample, in order to identify perturbations in the structure of these molecules such as insertions, deletions, substitutions and the like. The presence of one or more perturbations in 205P1B5 gene products in the sample is an indication of cancer susceptibility (or the emergence or existence of a tumor).

The invention also comprises methods for gauging tumor aggressiveness. In one embodiment, a method for gauging aggressiveness of a tumor comprises determining the level of 205P1B5 mRNA or 205P1B5 protein expressed by tumor cells, comparing the level so determined to the level of 205P1B5 mRNA or 205P1B5 protein expressed in a corresponding normal issue taken from the same individual or a normal tissue reference sample, wherein the degree of 205P1B5 mRNA or 205P1B5 protein expression in the tumor sample relative to the normal sample indicates the degree of aggressiveness. In a specific embodiment, aggressiveness of a tumor is evaluated by determining the extent to which 205P1B5 is expressed in the tumor cells, with higher expression levels indicating more aggressive tumors. Another embodiment is the evaluation of the integrity of 205P1B5 nucleotide and amino acid sequences in a biological sample, in order to identify perturbations in the structure of these molecules such as insertions, deletions, substitutions and the like. The presence of one or more perturbations indicates more aggressive tumors.

Another embodiment of the invention is directed to methods for observing the progression of a malignancy in an individual over time. In one embodiment, methods for observing the progression of a malignancy in an individual over time comprise determining the level of 205P1B5 mRNA or 205P1B5 protein expressed by cells in a sample of the tumor, comparing the level so determined to the level of 205P1B5 mRNA or 205P1B5 protein expressed in an equivalent tissue sample taken from the same individual at a different time, wherein the degree of 205P1B5 mRNA or 205P1B5 protein expression in the tumor sample overtime provides information on the progression of the cancer. In a specific embodiment, the progression of a cancer is evaluated by determining 205P1B5 expression in the tumor cells over time, where increased expression over time indicates a progression of the cancer. Also, one can evaluate the integrity 205P1B5 nucleotide and amino acid sequences in a biological sample in order to identify perturbations in the structure of these molecules such as insertions, deletions, substitutions and the like, where the presence of one or more perturbations indicates a progression of the cancer.

The above diagnostic approaches can be combined with any one of a wide variety of prognostic and diagnostic protocols known in the art. For example, another embodiment of the invention is directed to methods for observing a coincidence between the expression of 205P1B5 gene and 205P1B5 gene products (or perturbations in 205P1B5 gene and 205P1B5 gene products) and a factor that is associated with malignancy, as a means for diagnosing and prognosticating the status of a tissue sample. A wide variety of factors associated with malignancy can be utilized, such as the expression of genes associated with malignancy (e.g. PSA, PSCA and PSM expression for prostate cancer etc.) as well as gross cytological observations (see, e.g., Bocking et al., 1984, Anal. Quant. Cytol. 6(2):74-88; Epstein, 1995, Hum. Pathol. 26(2): 223-9; Thorson et al., 1998, Mod. Pathol. 11(6):543-51; Baisden et al., 1999, Am. J. Surg. Pathol. 23(8):918-24). Methods for observing a coincidence between the expression of 205P1B5 gene and 205P1B5 gene products (or perturbations in 205P1B5 gene and 205P1B5 gene products) and another factor that is associated with malignancy are useful, for example, because the presence of a set of specific factors that coincide with disease provides information crucial for diagnosing and prognosticating the status of a tissue sample.

In one embodiment, methods for observing a coincidence between the expression of 205P1B5 gene and 205P1B5 gene products (or perturbations in 205P1B5 gene and 205P1B5 gene products) and another factor associated with malignancy entails detecting the overexpression of 205P1B5 mRNA or protein in a tissue sample, detecting the overexpression of PSA mRNA or protein in a tissue sample (or PSCA or PSM expression), and observing a coincidence of 205P1B5 mRNA or protein and PSA mRNA or protein overexpression (or PSCA or PSM expression). In a specific embodiment, the expression of 205P1B5 and PSA mRNA in prostate tissue is examined, where the coincidence of 205P1B5 and PSA mRNA overexpression in the sample indicates the existence of prostate cancer, prostate cancer susceptibility or the emergence or status of a prostate tumor.

Methods for detecting and quantifying the expression of 205P1B5 mRNA or protein are described herein, and standard nucleic acid and protein detection and quantification technologies are well known in the art. Standard methods for the detection and quantification of 205P1B5 mRNA include in situ hybridization using labeled 205P1B5 riboprobes, Northern blot and related techniques using 205P1B5 polynucleotide probes, RT-PCR analysis using primers specific for 205P1B5, and other amplification type detection methods, such as, for example, branched DNA, SISBA, TMA and the like. In a specific embodiment, semi-quantitative RT-PCR is used to detect and quantify 205P1B5 mRNA expression. Any number of primers capable of amplifying 205P1B5 can be used for this purpose, including but not limited to the various primer sets specifically described herein. In a specific embodiment, polyclonal or monoclonal antibodies specifically reactive with the wild-type 205P1B5 protein can be used in an immumohistochemical assay of biopsied issue.

IX) Identification of Molecules that Interact with 205P1B5

The 205P1B5 protein and nucleic acid sequences disclosed herein allow a skilled artisan to identify proteins, small molecules and other agents that interact with 205P1B5, as well as pathways activated by 205P1B5 via any one of a variety of art accepted protocols. For example, one can utilize one of the so-called interaction trap systems (also referred to as the "two-hybrid assay"). In such systems, molecules interact and reconstitute a transcription factor which directs expression of a reporter gene, whereupon the expression of the reporter gene is assayed. Other systems identify protein-protein interactions in vivo through reconstitution of a eukaryotic transcriptional activator, see, e.g., U.S. Pat. No. 5,955,280 issued 21 Sep. 1999, U.S. Pat. No. 5,925,523 issued 20 Jul. 1999, U.S. Pat. No. 5,846,722 issued 8 Dec. 1998 and U.S. Pat. No. 6,004,746 issued 21 Dec. 1999. Algorithms are also available in the art for genome-based predictions of protein function (see, e.g., Marcotte, et al., Nature 402: 4 Nov. 1999, 83-86).

Alternatively one can screen peptide libraries to identify molecules that interact with 205P1B5 protein sequences. In such methods, peptides that bind to 205P1B5 are identified by screening libraries that encode a random or controlled collection of amino acids. Peptides encoded by the libraries are expressed as fusion proteins of bacteriophage coat proteins, the bacteriophage particles are then screened against the 205P1B5 protein.

Accordingly, peptides having a wide variety of uses, such as therapeutic, prognostic or diagnostic reagents, are thus identified without any prior information on the structure of the expected ligand or receptor molecule. Typical peptide libraries and screening methods that can be used to identify molecules that interact with 205P1B5 protein sequences are disclosed for example in U.S. Pat. No. 5,723,286 issued 3 Mar. 1998 and U.S. Pat. No. 5,733,731 issued 31 Mar. 1998.

Alternatively, cell lines that express 205P1B5 are used to identify protein-protein interactions mediated by 205P1B5. Such interactions can be examined using immunoprecipitation techniques (see, e.g., Hamilton B J, et al. Biochem. Biophys. Res. Commun. 1999, 261 :646-51). 205P1B5 protein can be immunoprecipitated from 205P1B5-expressing cell lines using anti-205P1B5 antibodies. Alternatively, antibodies against His-tag can be used in a cell line engineered to express fusions of 205P1B5 and a His-tag (vectors mentioned above). The immunoprecipitated complex can be examined for protein association by procedures such as Western blotting, $^{35}$S-methionine labeling of proteins, protein microsequencing, silver staining and two-dimensional gel electrophoresis.

Small molecules and ligands that interact with 205P1B5 can be identified through related embodiments of such screening assays. For example, small molecules can be identified that interfere with protein function, including molecules that interfere with 205P1B5's ability to mediate phosphorylation and de-phosphorylation, interaction with DNA or RNA molecules as an indication of regulation of cell cycles, second messenger signaling or tumorigenesis. Similarly, small molecules that modulate 205P1B5-related ion channel, protein pump, or cell communication functions are identified and used to treat patients that have a cancer that expresses 205P1B5 (see, e.g., Hille, B., Ionic Channels of Excitable Membranes $2^{nd}$ Ed., Sinauer Assoc., Sunderland, Mass., 1992). Moreover, ligands that regulate 205P1B5 function can be identified based on their ability to bind 205P1B5 and activate a reporter construct Typical methods are discussed for example in U.S. Pat. No. 5,928,868 issued 27 Jul. 1999, and include methods for forming hybrid ligands in which at least one ligand is a small molecule. In an illustrative embodiment, cells engineered to express a fusion protein of 205P1B5 and a DNA-binding protein are used to co-express a fusion protein of a hybrid ligand/small molecule and a cDNA library transcriptional activator protein. The cells further contain a reporter gene, the expression of which is conditioned on the proximity of the first and second fusion proteins to each other, an event that occurs only if the hybrid ligand binds to target sites on both hybrid proteins. Those cells that express the reporter gene are selected and the unknown small molecule or the unknown ligand is identified. This method provides a means of identifying modulators which activate or inhibit 205P1B5.

An embodiment of this invention comprises a method of screening for a molecule that interacts with an 205P1B5 amino acid sequence shown in FIG. 2 or FIG. 3, comprising the steps of contacting a population of molecules with the 205P1B5 amino acid sequence, allowing the population of molecules and the 205P1B5 amino acid sequence to interact under conditions that facilitate an interaction, determining the presence of a molecule that interacts with the 205P1B5 amino acid sequence, and then separating molecules that do not interact with the 205P1B5 amino acid sequence from molecules that do. In a specific embodiment, the method further comprises purifying, characterizing and identifying a molecule that interacts with the 205P1B5 amino acid sequence. The identified molecule can be used to modulate a function performed by 205P1B5. In a preferred embodiment, the 205P1B5 amino acid sequence is contacted with a library of peptides.

X.) Therapeutic Methods and Compositions

The identification of 205P1B5 as a protein that is normally expressed in a restricted set of tissues, but which is also expressed in prostate and other cancers, opens a number of therapeutic approaches to the treatment of such cancers. As contemplated herein, 205P1B5 functions as a transcription factor involved in activating tumor-promoting genes or repressing genes that block tumorigenesis.

Accordingly, therapeutic approaches that inhibit the activity of the 205P1B5 protein are useful for patients suffering from a cancer that expresses 205P1B5. These therapeutic approaches generally fall into two classes. One class comprises various methods for inhibiting the binding or association of the 205P1B5 protein with its binding partner or with other proteins. Another class comprises a variety of methods for inhibiting the transcription of the 205P1B5 gene or translation of 205P1B5 mRNA.

X.A.) Anti-Cancer Vaccines

The invention provides cancer vaccines comprising a 205P1B5-related protein or 205P1B5-related nucleic acid. In view of the expression of 205P1B5, cancer vaccines prevent and/or treat 205P1B5-expressing cancers with minimal or no effects on non-target tissues. The use of a tumor antigen in a vaccine that generates humoral and/or cell-mediated immune responses as anti-cancer therapy is well known in the art and has been employed in prostate cancer using human PSMA and rodent PAP immunogens (Hodge et al., 1995, Int. J. Cancer 63:231-237; Fong et al., 1997, J. Immunol. 159:3113-3117).

Such methods can be readily practiced by employing a 205P1B5-related protein, or an 205P1B5-encoding nucleic acid molecule and recombinant vectors capable of expressing and presenting the 205P1B5 immunogen (which typically comprises a number of antibody or T cell epitopes). Skilled artisans understand that a wide variety of vaccine systems for delivery of immunoreactive epitopes are known in the art (see, e.g., Heryln et al., Ann Med 1999 Feb. 31(1):66-78; Maruyama et al., Cancer Immunol Immunother 2000 June 49(3):123-32) Briefly, such methods of generating an immune response (e.g. humoral and/or cell-mediated) in a mammal, comprise the steps of: exposing the mammal's immune system to an immunoreactive epitope (e.g. an epitope present in the 205P1B5 protein shown in SEQ ID NO: 703 or analog or homolog thereof) so that the mammal generates an immune response that is specific for that epitope (e.g. generates antibodies that specifically recognize that epitope). In a preferred method, the 205P1B5 immunogen contains a biological motif, see e.g., Tables V-XVIII, or a peptide of a size range from 205P1B5 indicated in FIG. 5, FIG. 6, FIG. 7, FIG. 8, and FIG. 9.

The entire 205P1B5 protein, immunogenic regions or epitopes thereof can be combined and delivered by various means. Such vaccine compositions can include, for example, lipopeptides (e.g., Vitiello, A. et al., *J. Clin. Invest.* 95:341, 1995), peptide compositions encapsulated in poly(DL-lactide-co-glycolide) ("PLG") microspheres (see, e.g., Eldridge, et al., *Molec. Immunol.* 28:287-294, 1991: Alonso et al., *Vaccine* 12:299-306, 1994; Jones et al., *Vaccine* 13:675-681, 1995), peptide compositions contained in immune stimulating complexes (ISCOMS) (see, e.g., Takahashi et al., *Nature* 344:873-875, 1990; Hu et al., *Clin Exp Immunol.* 113:235-243, 1998), multiple antigen peptide systems (MAPs) (see e.g., Tam, J. P., *Proc. Natl. Acad. Sci. U.S.A.* 85:5409-5413, 1988; Tam, J. P., *J. Immunol. Methods* 196:17-32, 1996), peptides formulated as multivalent peptides; peptides for use in ballistic delivery systems, typically crystallized peptides, viral delivery vectors (Perkus, M. E. et al., In: *Concepts in vaccine development*, Kaufmann, S. H. E., ed., p. 379, 1996; Chakrabarti, S. et al., *Nature* 320:535, 1986; Hu, S. L. et al., *Nature* 320:537, 1986; Kieny, M.-P. et al., *AIDS Bio/Technology* 4:790, 1986; Top, F. H. et al., *J. Infect. Dis.* 124:148, 1971; Chanda, P. K. et al., *Virology* 175:535, 1990), particles of viral or synthetic origin (e.g., Kofler, N. et al., *J. Immunol. Methods.* 192:25, 1996; Eldridge, J. H. et al., *Sem. Hematol.* 30:16, 1993; Falo, L. D., Jr. et al., *Nature Med.* 7:649, 1995), adjuvants (Warren, H. S., Vogel, F. R., and Chedid, L. A. *Annu. Rev. Immunol.* 4:369, 1986; Gupta, R. K. et al., *Vaccine* 11:293, 1993), liposomes (Reddy, R. et al., *J. Immunol.* 148: 1585, 1992; Rock, K. L., *Immunol. Today* 17:131, 1996), or, naked or particle absorbed cDNA (Ulmer, J. B. et al., *Science* 259:1745, 1993; Robinson, H. L., Hunt, L. A., and Webster, R. G., *Vaccine* 11:957, 1993; Shiver, J. W. et al., In: *Concepts in vaccine development*, Kaufmann, S. H. E., ed., p. 423, 1996; Cease, K. B., and Berzofsky, J. A., *Annu. Rev. Immunol.* 12:923, 1994 and Eldridge, J. H. et al., *Sem. Hematol.* 30:16, 1993). Toxin-targeted delivery technologies, also known as receptor mediated targeting, such as those of Avant Immunotherapeutics, Inc. (Needham, Mass.) may also be used.

In patients with 205P1B5-associated cancer, the vaccine compositions of the invention can also be used in conjunction with other treatments used for cancer, e.g., surgery, chemotherapy, drug therapies, radiation therapies, etc. including use in combination with immune adjuvants such as IL-2, IL-12, GM-CSF, and the like.

Cellular Vaccines:

CTL epitopes can be determined using specific algorithms to identify peptides within 205P1B5 protein that bind corresponding HLA alleles (see e.g., Table IV; Epimer™ and Epimatrix™, Brown University (URL world wide web URL brown.edu/Research/TB-HIV_Lab/epimatrix/epimatrix.html); and, BIMAS, (URL bimas.dcrt.nih.gov/; SYFPEITHI at URL syfpeithi.bmi-heidelberg.com/). In a preferred embodiment, the 205P1B5 immunogen contains one or more amino acid sequences identified using techniques well known in the art, such as the sequences shown in Tables V-XVIII or a peptide of 8, 9, 10 or 11 amino acids specified by an HLA Class I motif/supermotif (e.g., Table IV (A), Table IV (D), or Table IV (E)) and/or a peptide of at least 9 amino acids that comprises an HLA Class II motif/supermotif (e.g., Table IV (B) or Table IV (C)). As is appreciated in the art, the HLA Class I binding groove is essentially closed ended so that peptides of only a particular size range can fit into the groove and be bound, generally HLA Class I epitopes are 8, 9, 10, or 11 amino acids long. In contrast, the HLA Class II binding groove is essentially open ended; therefore a peptide of about 9 or more amino acids can be bound by an HLA Class II molecule. Due to the binding groove differences between HLA Class I and II, HLA Class I motifs are length specific, i.e., position two of a Class I motif is the second amino acid in an amino to carboxyl direction of the peptide. The amino acid positions in a Class II motif are relative only to each other, not the overall peptide, i.e., additional amino acids can be attached to the amino and/or carboxyl termini of a motif-bearing sequence. HLA Class II epitopes are often 9, 10, 11, 12, 13, 14, 15, 16, 17, 18, 19, 20, 21, 22, 23, 24, or 25 amino acids long, or longer than 25 amino acids.

Antibody-Based Vaccines

A wide variety of methods for generating an immune response in a mammal are known in the art (for example as the first step in the generation of hybridomas). Methods of generating an immune response in a mammal comprise exposing the mammal's immune system to an immunogenic epitope on a protein (e.g. the 205P1B5 protein) so that an immune response is generated. A typical embodiment consists of a method for generating an immune response to 205P1B5 in a host, by contacting the host with a sufficient amount of at least one 205P1B5 B cell or cytotoxic T-cell epitope or analog thereof; and at least one periodic interval thereafter re-contacting the host with the 205P1B5 B cell or cytotoxic T-cell epitope or analog thereof. A specific embodiment consists of a method of generating an immune response against a 205P1B5-related protein or a man-made multiepitopic peptide comprising: administering 205P1B5 immunogen (e.g. the 205P1B5 protein or a peptide fragment thereof, an 205P1B5 fusion protein or analog etc.) in a vaccine preparation to a human or another mammal. Typically, such vaccine preparations further contain a suitable adjuvant (see, e.g., U.S. Pat. No. 6,146,635) or a universal helper epitope such as a PADRE™ peptide (Epimmune Inc., San Diego, Calif.; see, e.g., Alexander et al., J. Immunol. 2000 164(3); 164(3): 1625-1633; Alexander et al., Immunity 1994 1(9): 751-761 and Alexander et al., Immunol. Res. 1998 18(2): 79-92). An alternative method comprises generating an immune response in an individual against a 205P1B5 immunogen by: administering in vivo to muscle or skin of the individual's body a DNA molecule that comprises a DNA sequence that encodes an 205P1B5 immunogen, the DNA sequence operatively linked to regulatory sequences which control the expression of the DNA sequence; wherein the DNA molecule is taken up by cells, the DNA sequence is expressed in the cells and an immune response is generated against the immunogen (see, e.g., U.S. Pat. No. 5,962,428). Optionally a genetic vaccine facilitator such as anionic lipids; saponins; lectins; estrogenic compounds; hydroxylated lower alkyls; dimethyl sulfoxide; and urea is also administered.

Nucleic Acid Vaccines:

Vaccine compositions of the invention include nucleic acid-mediated modalities. DNA or RNA that encode protein(s) of the invention can be administered to a patient Genetic immunization methods can be employed to generate prophylactic or therapeutic humoral and cellular immune responses directed against cancer cells expressing 205P1B5. Constructs comprising DNA encoding a 205P1B5-related protein/immunogen and appropriate regulatory sequences can be injected directly into muscle or skin of an individual, such that the cells of the muscle or skin take-up the construct and express the encoded 205P1B5 protein/immunogen. Alternatively, a vaccine comprises a 205P1B5-related protein. Expression of the 205P1B5-related protein immunogen results in the generation of prophylactic or therapeutic humoral and cellular immunity against cells that bear 205P1B5 protein. Various prophylactic and therapeutic genetic immunization techniques known in the art can be used (for review, see information and references published at Internet address world wide web URL genweb.com). Nucleic acid-based delivery is described, for instance, in Wolff et. al., Science 247:1465 (1990) as well as U.S. Pat. Nos. 5,580,859; 5,589,466; 5,804,566; 5,739,118; 5,736,524; 5,679,647; WO 98/04720. Examples of DNA-based delivery technologies include "naked DNA", facilitated (bupivicaine, polymers, peptide-mediated) delivery, cationic lipid complexes, and particle-mediated ("gene gun") or pressure-mediated delivery (see, e.g., U.S. Pat. No. 5,922,687).

For therapeutic or prophylactic immunization purposes, proteins of the invention can be expressed via viral or bacterial vectors. Various viral gene delivery systems that can be used in the practice of the invention include, but are not limited to, vaccinia, fowlpox, canarypox, adenovirus, influenza, poliovirus, adeno-associated virus, lentivirus, and sindbis virus (see, e.g., Restifo, 1996, Curr. Opin. Immunol. 8:658-663; Tsang et al. J. Natl. Cancer Inst. 87:982-990 (1995)). Non-viral delivery systems can also be employed by introducing naked DNA encoding a 205P1B5-related protein into the patient (e.g., intramuscularly or intradermally) to induce an anti-tumor response.

Vaccinia virus is used, for example, as a vector to express nucleotide sequences that encode the peptides of the invention. Upon introduction into a host, the recombinant vaccinia virus expresses the protein immunogenic peptide, and thereby elicits a host immune response. Vaccinia vectors and methods useful in immunization protocols are described in, e.g., U.S. Pat. No. 4,722,848. Another vector is BCG (Bacille Calmette Guerin). BCG vectors are described in Stover et al., Nature 351:456-460(1991). A wide variety of other vectors useful for therapeutic administration or immunization of the peptides of the invention, e.g. adeno and adeno-associated virus vectors, retroviral vectors, *Salmonella typhi* vectors, detoxified anthrax toxin vectors, and the like, will be apparent to those skilled in the art from the description herein.

Thus, gene delivery systems are used to deliver a 205P1B5-related nucleic acid molecule. In one embodiment, the full-length human 205P1B5 cDNA is employed. In another embodiment 205P1B5 nucleic acid molecules encoding specific cytotoxic T lymphocyte (CTL) and/or antibody epitopes are employed.

Ex Vivo Vaccines

Various ex vivo strategies can also be employed to generate an immune response. One approach involves the use of antigen presenting cells (APCs) such as dendritic cells (DC) to present 205P1B5 antigen to a patient's immune system. Dendritic cells express MHC class I and II molecules, B7 co-stimulator, and IL-12, and are thus highly specialized antigen presenting cells. In prostate cancer, autologous dendritic cells pulsed with peptides of the prostate-specific membrane antigen (PSMA) are being used in a Phase I clinical trial to stimulate prostate cancer patients' immune systems (Tjoa et al., 1996, Prostate 28:65-69; Murphy et al., 1996, Prostate 29:371-380). Thus, dendritic cells can be used to present 205P1B5 peptides to T cells in the context of MHC class I or II molecules. In one embodiment, autologous dendritic cells are pulsed with 205P1B5 peptides capable of binding to MHC class I and/or class II molecules. In another embodiment, dendritic cells are pulsed with the complete 205P1B5 protein. Yet another embodiment involves engineering the overexpression of the 205P1B5 gene in dendritic cells using various implementing vectors known in the art, such as adenovirus (Arthur et al., 1997, Cancer Gene Ther. 4:17-25), retrovirus (Henderson et al., 1996, Cancer Res. 56:3763-3770), lentivirus, adeno-associated virus, DNA transfection (Ribas et al., 1997, Cancer Res. 57:2865-2869), or tumor-derived RNA transfection (Ashley et al., 1997, J. Exp. Med. 186:1177-1182). Cells that express 205P1B5 can also be engineered to express immune modulators, such as GM-CSF, and used as immunizing agents.

X.)B.) 205P1B5 as a Target for Antibody-Based Therapy

205P1B5 is an attractive target for antibody-based therapeutic strategies. A number of antibody strategies are known in the art for targeting both extracellular and intracellular molecules (see, e.g., complement and ADCC mediated killing as well as the use of intrabodies). Because 205P1B5 is expressed by cancer cells of various lineages relative to corresponding normal cells, systemic administration of 205P1B5 -immunoreactive compositions are prepared that exhibit excellent sensitivity without toxic, non-specific and/or non-target effects caused by binding of the immunoreactive composition to non-target organs and tissues. Antibodies specifically reactive with domains of 205P1B5 are useful to treat 205P1B5 -expressing cancers systemically, either as conjugates with a toxin or therapeutic agent, or as naked antibodies capable of inhibiting cell proliferation or function.

205P1B5 antibodies can be introduced into a patient such that the antibody binds to 205P1B5 and modulates a function, such as an interaction with a binding partner, and consequently mediates destruction of the tumor cells and/or inhibits the growth of the tumor cells. Mechanisms by which such antibodies exert a therapeutic effect can include complement-mediated cytolysis, antibody-dependent cellular cytotoxicity, modulation of the physiological function of 205P1B5, inhibition of ligand binding or signal transduction pathways, modulation of tumor cell differentiation, alteration of tumor angiogenesis factor profiles, and/or apoptosis.

Those skilled in the art understand that antibodies can be used to specifically target and bind immunogenic molecules such as an immunogenic region of the 205P1B5 sequence shown in FIG. 2 or FIG. 3. In addition, skilled artisans understand that it is routine to conjugate antibodies to cytotoxic agents (see, e.g., Slevers et al. *Blood* 93:11 3678-3684 (Jun. 1, 1999)). When cytotoxic and/or therapeutic agents are delivered directly to cells, such as by conjugating them to antibodies specific for a molecule expressed by that cell (e.g. 205P1B5), the cytotoxic agent will exert its known biological effect (i.e. cytotoxicity) on those cells.

A wide variety of compositions and methods for using antibody-cytotoxic agent conjugates to kill cells are known in the art. In the context of cancers, typical methods entail administering to an animal having a tumor a biologically effective amount of a conjugate comprising a selected cytotoxic and/or therapeutic agent linked to a targeting agent (e.g. an anti-205P1B5 antibody) that binds to a marker (e.g. 205P1B5) expressed, accessible to binding or localized on the cell surfaces. A typical embodiment is a method of delivering a cytotoxic and/or therapeutic agent to a cell expressing 205P1B5, comprising conjugating the cytotoxic agent to an antibody that immunospecifically binds to a 205P1B5 epitope, and, exposing the cell to the antibody-agent conjugate. Another illustrative embodiment is a method of treating an individual suspected of suffering from metastasized cancer, comprising a step of administering parenterally to said individual a pharmaceutical composition comprising a therapeutically effective amount of an antibody conjugated to a cytotoxic and/or therapeutic agent.

Cancer immunotherapy using anti-205P1B5 antibodies can be done in accordance with various approaches that have been successfully employed in the treatment of other types of cancer, including but not limited to colon cancer (Arlen et al., 1998, Crit. Rev. Immunol. 18:133-138), multiple myeloma (Ozaki et al., 1997, Blood 90:3179-3186, Tsunenari et al., 1997, Blood 90:2437-2444), gastric cancer (Kasprzyk et al., 1992, Cancer Res. 52:2771-2776), B-cell lymphoma (Funakoshi et al., 1996, J. Immunother. Emphasis Tumor Immunol. 19:93-101), leukemia (Zhong et al., 1996, Leuk. Res. 20:581-589), colorectal cancer (Moun et al., 1994, Cancer Res. 54:6160-6166; Velders et al., 1995, Cancer Res. 55:4398-4403), and breast cancer (Shepard et al., 1991, J. Clin. Immunol. 11:117-127). Some therapeutic approaches involve conjugation of naked antibody to a toxin, such as the conjugation of $Y^{91}$ or $I^{131}$ to anti-CD20 antibodies (e.g., Zevalin™, IDEC Pharmaceuticals Corp. or Bexxar™, Coulter Pharmaceuticals), while others involve co-administration of antibodies and other therapeutic agents, such as Herceptin™ (trastuzumab) with paclitaxel (Genentech, Inc.). To treat prostate cancer, for example, 205P1B5 antibodies can be administered in conjunction with radiation, chemotherapy or hormone ablation.

Although 205P1B5 antibody therapy is useful for all stages of cancer, antibody therapy can be particularly appropriate in advanced or metastatic cancers. Treatment with the antibody therapy of the invention is indicated for patients who have received one or more rounds of chemotherapy. Alternatively, antibody therapy of the invention is combined with a chemotherapeutic or radiation regimen for patients who have not received chemotherapeutic treatment. Additionally, antibody therapy can enable the use of reduced dosages of concomitant chemotherapy, particularly for patients who do not tolerate the toxicity of the chemotherapeutic agent very well.

Cancer patients can be evaluated for the presence and level of 205P1B5 expression, preferably using immunohistochemical assessments of tumor tissue, quantitative 205P1B5 imaging, or other techniques that reliably indicate the presence and degree of 205P1B5 expression. Immunohistochemical analysis of tumor biopsies or surgical specimens is preferred for this purpose. Methods for immunohistochemical analysis of tumor tissues are well known in the art.

Anti-205P1B5 monoclonal antibodies that treat prostate and other cancers include those that initiate a potent immune response against the tumor or those that are directly cytotoxic. In this regard, anti-205P1B5 monoclonal antibodies (mAbs) can elicit tumor cell lysis by either complement-mediated or antibody-dependent cell cytotoxicity (ADCC) mechanisms, both of which require an intact Fc portion of the immunoglobulin molecule for interaction with effector cell Fc receptor sites on complement proteins. In addition, anti-205P1B5 mAbs that exert a direct biological effect on tumor growth are useful to treat cancers that express 205P1B5. Mechanisms by which directly cytotoxic mAbs act include: inhibition of cell growth, modulation of cellular differentiation, modulation of tumor angiogenesis factor profiles, and the induction of apoptosis. The mechanism(s) by which a particular anti-205P1B5 mAb exerts an anti-tumor effect is evaluated using any number of in vitro assays that evaluate cell death such as ADCC, ADMMC, complement-mediated cell lysis, and so forth, as is generally known in the art.

In some patients, the use of murine or other non-human monoclonal antibodies, or human/mouse chimeric mAbs can induce moderate to strong immune responses against the non-human antibody. This can result in clearance of the antibody from circulation and reduced efficacy. In the most severe cases, such an immune response can lead to the extensive formation of immune complexes which, potentially, can cause renal failure. Accordingly, preferred monoclonal antibodies used in the therapeutic methods of the invention are those that are either fully human or humanized and that bind specifically to the target 205P1B5 antigen with high affinity but exhibit low or no antigenicity in the patient.

Therapeutic methods of the invention contemplate the administration of single anti-205P1B5 mAbs as well as combinations, or cocktails, of different mAbs. Such mAb cocktails can have certain advantages inasmuch as they contain mAbs that target different epitopes, exploit different effector mechanisms or combine directly cytotoxic mAbs with mAbs that rely on immune effector functionality. Such mAbs in combination can exhibit synergistic therapeutic effects. In addition, anti-205P1B5 mAbs can be administered concomitantly with other therapeutic modalities, including but not limited to various chemotherapeutic agents, androgen-blockers, immune modulators (e.g., IL-2, GM-CSF), surgery or radiation. The anti-205P1B5 mAbs are administered in their "naked" or unconjugated form, or can have a therapeutic agent(s) conjugated to them.

Anti-205P1B5 antibody formulations are administered via any route capable of delivering the antibodies to a tumor cell. Routes of administration include, but are not limited to, intravenous, intraperitoneal, intramuscular, intratumor, intradermal, and the like. Treatment generally involves repeated administration of the anti-205P1B5 antibody preparation, via an acceptable route of administration such as intravenous injection (IV), typically at a dose in the range of about 0.1 to about 10 mg/kg body weight In general, doses in the range of 10-500 mg mAb per week are effective and well tolerated.

Based on clinical experience with the Herceptin mAb in the treatment of metastatic breast cancer, an initial loading dose of approximately 4 mg/kg patient body weight IV, followed by weekly doses of about 2 mg/kg IV of the anti-205P1B5 mAb preparation represents an acceptable dosing regimen. Preferably, the initial loading dose is administered as a 90 minute or longer infusion. The periodic maintenance dose is administered as a 30 minute or longer infusion, provided the initial dose was well tolerated. As appreciated by those of skill in the art, various factors can influence the ideal dose regimen in a particular case. Such factors include, for example, the binding affinity and half life of the Ab or mAbs used, the degree of 205P1B5 expression in the patient, the extent of circulating shed 205P1B5 antigen, the desired steady-state antibody concentration level, frequency of treatment, and the influence of chemotherapeutic or other agents used in combination with the treatment method of the invention, as well as the health status of a particular patient.

Optionally, patients should be evaluated for the levels of 205P1B5 in a given sample (e.g. the levels of circulating 205P1B5 antigen and/or 205P1B5 expressing cells) in order to assist in the determination of the most effective dosing regimen, etc. Such evaluations are also used for monitoring purposes throughout therapy, and are useful to gauge therapeutic success in combination with the evaluation of other parameters (for example, urine cytology and/or ImmunoCyt levels in bladder cancer therapy, or by analogy, serum PSA levels in prostate cancer therapy).

Anti-idiotypic anti-205P1B5 antibodies can also be used in anti-cancer therapy as a vaccine for inducing an immune response to cells expressing a 205P1B5-related protein. In particular, the generation of anti-idiotypic antibodies is well known in the art; this methodology can readily be adapted to generate anti-idiotypic anti-205P1B5 antibodies that mimic an epitope on a 205P1B5 -related protein (see, for example, Wagner et al., 1997, Hybridoma 16:33-40; Foon et al., 1995, J. Clin. Invest. 96:334-342; Herlyn et al., 1996, Cancer Immunol. Immunother. 43:65-76). Such an anti-idiotypic antibody can be used in cancer vaccine strategies.

X.C.) 205P1B5 as a Target for Cellular Immune Responses

Vaccines and methods of preparing vaccines that contain an immunogenically effective amount of one or more HLA-binding peptides as described herein are further embodiments of the invention. Furthermore, vaccines in accordance with the invention encompass compositions of one or more of the claimed peptides. A peptide can be present in a vaccine individually. Alternatively, the peptide can exist as a homopolymer comprising multiple copies of the same peptide, or as a heteropolymer of various peptides. Polymers have the advantage of increased immunological reaction and, where different peptide epitopes are used to make up the polymer, the additional ability to induce antibodies and/or CTLs that react with different antigenic determinants of the pathogenic organism or tumor-related peptide targeted for an immune response. The composition can be a naturally occurring region of an antigen or can be prepared, e.g., recombinantly or by chemical synthesis.

Carriers that can be used with vaccines of the invention are well known in the art, and include, e.g., thyroglobulin, albumins such as human serum albumin, tetanus toxoid, polyamino acids such as poly L-lysine, poly L-glutamic acid, influenza, hepatitis B virus core protein, and the like. The vaccines can contain a physiologically tolerable (i.e., acceptable) diluent such as water, or saline, preferably phosphate buffered saline. The vaccines also typically include an adjuvant. Adjuvants such as incomplete Freund's adjuvant, aluminum phosphate, aluminum hydroxide, or alum are examples of materials well known in the art. Additionally, as disclosed herein, CTL responses can be primed by conjugating peptides of the invention to lipids, such as tripalmitoyl-S-glycerylcysteinlyseryl-serine ($P_3CSS$). Moreover, an adjuvant such as a synthetic cytosine-phosphorothiolated-guanine-containing (CpG) oligonucleotides has been found to increase CTL responses 10- to 100-fold. (see, e.g. Davila and Celis *J. Immunol.* 165:539-547 (2000))

Upon immunization with a peptide composition in accordance with the invention, via injection, aerosol oral, transdermal, transmucosal, intrapleural, intrathecal, or other suitable routes, the immune system of the host responds to the vaccine by producing large amounts of CTLs and/or HTLs specific for the desired antigen. Consequently, the host becomes at least partially immune to later development of cells that express or overexpress 205P1B5 antigen, or derives at least some therapeutic benefit when the antigen was tumor-associated.

In some embodiments, it may be desirable to combine the class I peptide components with components that induce or facilitate neutralizing antibody and or helper T cell responses directed to the target antigen. A preferred embodiment of such a composition comprises class I and class II epitopes in accordance with the invention. An alternative embodiment of such a composition comprises a class I and/or class II epitope in accordance with the invention, along with a cross reactive HTL epitope such as PADRE™ (Epimmune, San Diego, Calif.) molecule (described e.g., in U.S. Pat. No. 5,736,142).

A vaccine of the invention can also include antigen-presenting cells (APC), such as dendritic cells (DC), as a vehicle to present peptides of the invention. Vaccine compositions can be created in vitro, following dendritic cell mobilization and harvesting, whereby loading of dendritic cells occurs in vitro. For example, dendritic cells are transfected, e.g., with a minigene in accordance with the invention, or are pulsed with peptides. The dendritic cell can then be administered to a patient to elicit immune responses in vivo. Vaccine compositions, either DNA- or peptide-based, can also be administered in vivo in combination with dendritic cell mobilization whereby loading of dendritic cells occurs in vivo.

Preferably, the following principles are utilized when selecting an array of epitopes for inclusion in a polyepitopic composition for use in a vaccine, or for selecting discrete epitopes to be included in a vaccine and/or to be encoded by nucleic acids such as a minigene. It is preferred that each of the following principles be balanced in order to make the selection. The multiple epitopes to be incorporated in a given vaccine composition may be, but need not be, contiguous in sequence in the native antigen from which the epitopes are derived.

1.) Epitopes are selected which, upon administration, mimic immune responses that have been observed to be correlated with tumor clearance. For HLA Class I this includes 3-4 epitopes that come from at least one tumor associated antigen (TAA). For HLA Class II a similar rationale is employed; again 34 epitopes are selected from at least one TAA (see, e.g., Rosenberg et al., *Science* 278:1447-1450). Epitopes from one TAA may be used in combination with epitopes from one or more additional TAAs to produce a vaccine that targets tumors with varying expression patterns of frequently-expressed TAAs.

2.) Epitopes are selected that have the requisite binding affinity established to be correlated with immunogenicity: for HLA Class I an $IC_{50}$ of 500 nM or less, often 200 nM or less; and for Class II an $IC_{50}$ of 1000 nM or less.

3.) Sufficient supermotif bearing-peptides, or a sufficient array of allele-specific motif-bearing peptides, are selected to give broad population coverage. For example, it is preferable to have at least 80% population coverage. A Monte Carlo analysis, a statistical evaluation known in the art, can be employed to assess the breadth, or redundancy of population coverage.

4.) When selecting epitopes from cancer-related antigens it is often useful to select analogs because the patient may have developed tolerance to the native epitope.

5.) Of particular relevance are epitopes referred to as "nested epitopes." Nested epitopes occur where at least two epitopes overlap in a given peptide sequence. A nested peptide sequence can comprise B cell, HLA class I and/or HLA class II epitopes. When providing nested epitopes, a general objective is to provide the greatest number of epitopes per sequence. Thus, an aspect is to avoid providing a peptide that is any longer than the amino terminus of the amino terminal epitope and the carboxyl terminus of the carboxyl terminal epitope in the peptide. When providing a multi-epitopic sequence, such as a sequence comprising nested epitopes, it is generally important to screen the sequence in order to insure that it does not have pathological or other deleterious biological properties.

6.) If a polyepitopic protein is created, or when creating a minigene, an objective is to generate the smallest peptide that encompasses the epitopes of interest. This principle is similar, if not the same as that employed when selecting a peptide comprising nested epitopes. However, with an artificial polyepitopic peptide, the size minimization objective is balanced against the need to integrate any spacer sequences between epitopes in the polyepitopic protein. Spacer amino acid residues can, for example, be introduced to avoid junctional epitopes (an epitope recognized by the immune system, not present in the target antigen, and only created by the man-made juxtaposition of epitopes), or to facilitate cleavage between epitopes and thereby enhance epitope presentation. Junctional epitopes are generally to be avoided because the recipient may generate an immune response to that non-native epitope. Of particular concern is a junctional epitope that is a "dominant epitope." A dominant epitope may lead to such a zealous response that immune responses to other epitopes are diminished or suppressed.

7.) Where the sequences of multiple variants of the same target protein are present, potential peptide epitopes can also be selected on the basis of their conservancy. For example, a criterion for conservancy may define that the entire sequence of an HLA class I binding peptide or the entire 9-mer core of a class II binding peptide be conserved in a designated percentage of the sequences evaluated for a specific protein antigen.

X.C.1. Minigene Vaccines

A number of different approaches are available which allow simultaneous delivery of multiple epitopes. Nucleic acids encoding the peptides of the invention are a particularly useful embodiment of the invention. Epitopes for inclusion in a minigene are preferably selected according to the guidelines set forth in the previous section. A preferred means of administering nucleic acids encoding the peptides of the invention uses minigene constructs encoding a peptide comprising one or multiple epitopes of the invention.

The use of multi-epitope minigenes is described below and in, Ishioka et al., *J. Immunol.* 162:3915-3925, 1999; An, L. and Whitton, J. L., *J. Virol.* 71:2292, 1997; Thomson, S. A. et al., *J. Immunol.* 157:822, 1996; Whitton, J. L. et al., *J. Virol.* 67:348, 1993; Hanke, R. et al., *Vaccine* 16:426, 1998. For example, a multi-epitope DNA plasmid encoding supermotif- and/or motif-bearing epitopes derived 205P1B5, the PADRE® universal helper T cell epitope (or multiple HTL epitopes from 205P1B5), and an endoplasmic reticulum-translocating signal sequence can be engineered. A vaccine may also comprise epitopes that are derived from other TAAs.

The immunogenicity of a multi-epitopic minigene can be confirmed in transgenic mice to evaluate the magnitude of CTL induction responses against the epitopes tested. Further, the immunogenicity of DNA-encoded epitopes in vivo can be correlated with the in vitro responses of specific CTL lines against target cells transfected with the DNA plasmid. Thus, these experiments can show that the minigene serves to both: 1.) generate a CTL response and 2.) that the induced CTLs recognized cells expressing the encoded epitopes.

For example, to create a DNA sequence encoding the selected epitopes (minigene) for expression in human cells, the amino acid sequences of the epitopes may be reverse translated. A human codon usage table can be used to guide the codon choice for each amino acid. These epitope-encoding DNA sequences may be directly adjoined, so that when translated, a continuous polypeptide sequence is created. To optimize expression and/or immunogenicity, additional elements can be incorporated into the minigene design. Examples of amino acid sequences that can be reverse translated and included in the minigene sequence include: HLA class I epitopes, HLA class II epitopes, antibody epitopes, a ubiquitination signal sequence, and/or an endoplasmic reticulum targeting signal. In addition, HLA presentation of CTL and HTL epitopes may be improved by including synthetic (e.g. poly alanine) or naturally-occurring flanking sequences adjacent to the CTL or HTL epitopes; these larger peptides comprising the epitope(s) are within the scope of the invention.

The minigene sequence may be converted to DNA by assembling oligonucleotides that encode the plus and minus strands of the minigene. Overlapping oligonucleotides (30-100 bases long) may be synthesized, phosphorylated, purified and annealed under appropriate conditions using well known techniques. The ends of the oligonucleotides can be joined, for example, using T4 DNA ligase. This synthetic minigene, encoding the epitope polypeptide, can then be cloned into a desired expression vector.

Standard regulatory sequences well known to those of skill in the art are preferably included in the vector to ensure expression in the target cells. Several vector elements are desirable: a promoter with a down-stream cloning site for minigene insertion; a polyadenylation signal for efficient transcription termination; an *E. coli* origin of replication; and an *E. coli* selectable marker (e.g. ampicillin or kanamycin resistance). Numerous promoters can be used for this purpose, e.g., the human cytomegalovirus (hCMV) promoter. See, e.g., U.S. Pat. Nos. 5,580,859 and 5,589,466 for other suitable promoter sequences.

Additional vector modifications may be desired to optimize minigene expression and immunogenicity. In some cases, introns are required for efficient gene expression, and one or more synthetic or naturally-occurring introns could be incorporated into the transcribed region of the minigene. The inclusion of mRNA stabilization sequences and sequences for replication in mammalian cells may also be considered for increasing minigene expression.

Once an expression vector is selected, the minigene is cloned into the polylinker region downstream of the promoter. This plasmid is transformed into an appropriate *E. coli* strain, and DNA is prepared using standard techniques. The orientation and DNA sequence of the minigene, as well as all other elements included in the vector, are confirmed using restriction mapping and DNA sequence analysis. Bacterial cells harboring the correct plasmid can be stored as a master cell bank and a working cell bank.

In addition, immunostimulatory sequences (ISSs or CpGs) appear to play a role in the immunogenicity of DNA vaccines. These sequences may be included in the vector, outside the minigene coding sequence, if desired to enhance immunogenicity.

In some embodiments, a bi-cistronic expression vector which allows production of both the minigene-encoded epitopes and a second protein (included to enhance or decrease immunogenicity) can be used. Examples of proteins or polypeptides that could beneficially enhance the immune response if co-expressed include cytokines (e.g., IL-2, IL-12, GM-CSF), cytokine-inducing molecules (e.g., LeIF), costimulatory molecules, or for HTL responses, pan-DR binding proteins (PADRE™, Epimmune, San Diego, Calif.). Helper (HTL) epitopes can be joined to intracellular targeting signals and expressed separately from expressed CTL epitopes; this allows direction of the HTL epitopes to a cell compartment different than that of the CTL epitopes. If required, this could facilitate more efficient entry of HTL epitopes into the HLA class II pathway, thereby improving HTL induction. In contrast to HTL or CTL induction, specifically decreasing the immune response by co-expression of immunosuppressive molecules (e.g. TGF-β) may be beneficial in certain diseases.

Therapeutic quantities of plasmid DNA can be produced for example, by fermentation in *E. coli*, followed by purification. Aliquots from the working cell bank are used to inoculate growth medium and grown to saturation in shaker flasks or a bioreactor according to well-known techniques. Plasmid DNA can be purified using standard bioseparation technologies such as solid phase anion-exchange resins supplied by QIAGEN, Inc. (Valencia, Calif.). If required, supercoiled DNA can be isolated from the open circular and linear forms using gel electrophoresis or other methods.

Purified plasmid DNA can be prepared for injection using a variety of formulations. The simplest of these is reconstitution of lyophilized DNA in sterile phosphate-buffer saline (PBS). This approach, known as "naked DNA," is currently being used for intramuscular (IM) administration in clinical trials. To maximize the immunotherapeutic effects of minigene DNA vaccines, an alternative method for formulating purified plasmid DNA may be desirable. A variety of methods have been described, and new techniques may become available. Cationic lipids, glycolipids, and fusogenic liposomes can also be used in the formulation (see, e.g., as described. by WO 93/24640; Mannino & Gould-Fogerite, *BioTechniques* 6(7): 682(1988); U.S. Pat. No. 5,279,833; WO 91/06309; and Felgner, et al., *Proc. Nat'l Acad. Sci. USA* 84:7413 (1987). In addition, peptides and compounds referred to collectively as protective, interactive, non-condensing compounds (PINC) could also be complexed to purified plasmid DNA to influence variables such as stability, intramuscular dispersion, or trafficking to specific organs or cell types.

Target cell sensitization can be used as a functional assay for expression and HLA class I presentation of minigene-encoded CTL epitopes. For example, the plasmid DNA is introduced into a mammalian cell line that is suitable as a target for standard CTL chromium release assays. The transfection method used will be dependent on the final formulation. Electroporation can be used for "naked" DNA, whereas cationic lipids allow direct in vitro transfection. A plasmid expressing green fluorescent protein (GFP) can be co-transfected to allow enrichment of transfected cells using fluorescence activated cell sorting (FACS). These cells are then chromium-51 ($^{51}$Cr) labeled and used as target cells for epitope-specific CTL lines; cytolysis, detected by $^{51}$Cr release, indicates both production of, and HLA presentation of, minigene-encoded CTL epitopes. Expression of HTL epitopes may be evaluated in an analogous manner using assays to assess HTL activity.

In vivo immunogenicity is a second approach for functional testing of minigene DNA formulations. Transgenic mice expressing appropriate human HLA proteins are immunized with the DNA product. The dose and route of administration are formulation dependent (e.g., IM for DNA in PBS, intraperitoneal (i.p.) for lipid-complexed DNA). Twenty-one days after immunization, splenocytes are harvested and restimulated for one week in the presence of peptides encoding each epitope being tested. Thereafter, for CTL effector cells, assays are conducted for cytolysis of peptide-loaded, $^{51}$Cr-labeled target cells using standard techniques. Lysis of target cells that were sensitized by HLA loaded with peptide epitopes, corresponding to minigene-encoded epitopes, demonstrates DNA vaccine function for in vivo induction of CTLs. Immunogenicity of HTL epitopes is confirmed in transgenic mice in an analogous manner.

Alternatively, the nucleic acids can be administered using ballistic delivery as described, for instance, in U.S. Pat. No. 5,204,253. Using this technique, particles comprised solely of DNA are administered. In a further alternative embodiment, DNA can be adhered to particles, such as gold particles.

Minigenes can also be delivered using other bacterial or viral delivery systems well known in the art, e.g., an expression construct encoding epitopes of the invention can be incorporated into a viral vector such as vaccinia.

X.C.2. Combinations of CTL Peptides with Helper Peptides

Vaccine compositions comprising CTL peptides of the invention can be modified, e.g., analoged, to provide desired attributes, such as improved serum half life, broadened population coverage or enhanced immunogenicity.

For instance, the ability of a peptide to induce CTL activity can be enhanced by linking the peptide to a sequence which contains at least one epitope that is capable of inducing a T helper cell response. Although a CTL peptide can be directly linked to a T helper peptide, often CTL epitope/HTL epitope conjugates are linked by a spacer molecule. The spacer is typically comprised of relatively small, neutral molecules, such as amino acids or amino acid mimetics, which are substantially uncharged under physiological conditions. The spacers are typically selected from, e.g., Ala, Gly, or other neutral spacers of nonpolar amino acids or neutral polar amino acids. It will be understood that the optionally present spacer need not be comprised of the same residues and thus may be a hetero- or homo-oligomer. When present, the spacer will usually be at least one or two residues, more usually three to six residues and sometimes 10 or more residues. The CTL peptide epitope can be linked to the T helper peptide epitope either directly or via a spacer either at the amino or carboxy terminus of the CTL peptide. The amino terminus of either the immunogenic peptide or the T helper peptide may be acylated.

In certain embodiments, the T helper peptide is one that is recognized by T helper cells present in a majority of a genetically diverse population. This can be accomplished by selecting peptides that bind to many, most, or all of the HLA class II molecules. Examples of such amino acid bind many HLA Class II molecules include sequences from antigens such as tetanus toxoid at positions 830-843 (QYIKANSKFIGITE; SEQ ID NO: 710), *Plasmodium falciparum* circumsporozoite (CS) protein at positions 378-398 (DIEKKIAKMEKASSVFNVVNS; SEQ ID NO: 711), and Streptococcus 18 kD protein at positions 116-131 (GAVDSILGGVATYGAA; SEQ ID NO: 712). Other examples include peptides bearing a DR 1-4-7 supermotif, or either of the DR3 motifs.

Alternatively, it is possible to prepare synthetic peptides capable of stimulating T helper lymphocytes, in a loosely HLA-restricted fashion, using amino acid sequences not found in nature (see, e.g., PCT publication WO 95/07707). These synthetic compounds called Pan-DR-binding epitopes (e.g., PADRE™, Epimmune, Inc., San Diego, Calif.) are designed to most preferably bind most HLA-DR (human HLA class II) molecules. For instance, a pan-DR-binding epitope peptide having the formula: aKXVAAWTLKAAa (SEQ ID NO: 713), where "X" is either cyclohexylalanine, phenylalanine, or tyrosine, and a is either D-alanine or L-alanine, has been found to bind to most HLA-DR alleles, and to stimulate the response of T helper lymphocytes from most individuals, regardless of their HLA type. An alternative of a pan-DR binding epitope comprises all "L" natural amino acids and can be provided in the form of nucleic acids that encode the epitope.

HTL peptide epitopes can also be modified to alter their biological properties. For example, they can be modified to include D-amino acids to increase their resistance to proteases and thus extend their serum half life, or they can be conjugated to other molecules such as lipids, proteins, carbohydrates, and the like to increase their biological activity. For example, a T helper peptide can be conjugated to one or more palmitic acid chains at either the amino or carboxyl termini.

X.C.3. Combinations of CTL Peptides with T Cell Priming Agents

In some embodiments it may be desirable to include in the pharmaceutical compositions of the invention at least one component which primes B lymphocytes or T lymphocytes. Lipids have been identified as agents capable of priming CTL in vivo. For example, palmitic acid residues can be attached to the ε-and α-amino groups of a lysine residue and then linked, e.g., via one or more linking residues such as Gly, Gly-Gly-, Ser, Ser-Ser, or the like, to an immunogenic peptide. The lipidated peptide can then be administered either directly in a micelle or particle, incorporated into a liposome, or emulsified in an adjuvant, e.g., incomplete Freund's adjuvant. In a preferred embodiment, a particularly effective immunogenic composition comprises palmitic acid attached to ε- and α-amino groups of Lys, which is attached via linkage, e.g., Ser-Ser, to the amino terminus of the immunogenic peptide.

As another example of lipid priming of CTL responses, *E. coli* lipoproteins, such as tripalmitoyl-S-glycerylcysteinlyseryl-serine ($P_3CSS$) can be used to prime virus specific CTL when covalently attached to an appropriate peptide (see, e.g., Deres, et al., *Nature* 342:561, 1989). Peptides of the invention can be coupled to $P_3CSS$, for example, and the lipopeptide administered to an individual to specifically prime an immune response to the target antigen. Moreover, because the induction of neutralizing antibodies can also be primed with $P_3CSS$-conjugated epitopes, two such compositions can be combined to more effectively elicit both humoral and cell-mediated responses.

X.C.4. Vaccine Compositions Comprising DC Pulsed with CTL and/or HTL Peptides

An embodiment of a vaccine composition in accordance with the invention comprises ex vivo administration of a cocktail of epitope-bearing peptides to PBMC, or isolated DC therefrom, from the patient's blood. A pharmaceutical to facilitate harvesting of DC can be used, such as Progenipoietin™ (Pharmacia-Monsanto, St. Louis, Mo.) or GM-CSF/IL-4. After pulsing the DC with peptides and prior to reinfusion into patients, the DC are washed to remove unbound peptides. In this embodiment, a vaccine comprises peptide-pulsed DCs which present the pulsed peptide epitopes complexed with HLA molecules on their surfaces.

The DC can be pulsed ex vivo with a cocktail of peptides, some of which stimulate CTL responses to 205P1B5. Optionally, a helper T cell (HTL) peptide, such as a natural or artificial loosely restricted HLA Class II peptide, can be included to facilitate the CTL response. Thus, a vaccine in accordance with the invention is used to treat a cancer which expresses or overexpresses 205P1B5.

X.D. Adoptive Immunotherapy

Antigenic 205P1B5 -related peptides are used to elicit a CTL and/or HTL response ex vivo, as well. The resulting CTL or HTL cells, can be used to treat tumors in patients that do not respond to other conventional forms of therapy, or will not respond to a therapeutic vaccine peptide or nucleic acid in accordance with the invention. Ex vivo CTL or HTL responses to a particular antigen are induced by incubating in tissue culture the patient's, or genetically compatible, CTL or HTL precursor cells together with a source of antigen-presenting cells (APC), such as dendritic cells, and the appropriate immunogenic peptide. After an appropriate incubation time (typically about 7-28 days), in which the precursor cells are activated and expanded into effector cells, the cells are infused back into the patient, where they will destroy (CTL) or facilitate destruction (HTL) of their specific target cell (e.g., a tumor cell). Transfected dendritic cells may also be used as antigen presenting cells.

X.E. Administration of Vaccines for Therapeutic or Prophylactic Purposes

Pharmaceutical and vaccine compositions of the invention are typically used to treat and/or prevent a cancer that expresses or overexpresses 205P1B5. In therapeutic applications, peptide and/or nucleic acid compositions are administered to a patient in an amount sufficient to elicit an effective B cell, CTL and/or HTL response to the antigen and to cure or at least partially arrest or slow symptoms and/or complications. An amount adequate to accomplish this is defined as "therapeutically effective dose." Amounts effective for this use will depend on, e.g., the particular composition administered, the manner of administration, the stage and severity of the disease being treated, the weight and general state of health of the patient, and the judgment of the prescribing physician.

For pharmaceutical compositions, the immunogenic peptides of the invention, or DNA encoding them, are generally administered to an individual already bearing a tumor that expresses 205P1B5. The peptides or DNA encoding them can be administered individually or as fusions of one or more peptide sequences. Patients can be treated with the immunogenic peptides separately or in conjunction with other treatments, such as surgery, as appropriate.

For therapeutic use, administration should generally begin at the first diagnosis of 205P1B5 -associated cancer. This is followed by boosting doses until at least symptoms are substantially abated and for a period thereafter. The embodiment of the vaccine composition (i.e., including, but not limited to embodiments such as peptide cocktails, polyepitopic polypeptides, minigenes, or TAA-specific CTLs or pulsed dendritic cells) delivered to the patient may vary according to the stage of the disease or the patient's health status. For example, in a patient with a tumor that expresses 205P1B5, a vaccine comprising 205P1B5-specific CTL may be more efficacious in killing tumor cells in patient with advanced disease than alternative embodiments.

It is generally important to provide an amount of the peptide epitope delivered by a mode of administration sufficient to effectively stimulate a cytotoxic T cell response; compositions which stimulate helper T cell responses can also be given in accordance with this embodiment of the invention.

The dosage for an initial therapeutic immunization generally occurs in a unit dosage range where the lower value is about 1, 5, 50, 500, or 1,000 µg and the higher value is about 10,000; 20,000; 30,000; or 50,000 µg. Dosage values for a human typically range from about 500 µg to about 50,000 µg per 70 kilogram patient. Boosting dosages of between about 1.0 µg to about 50,000 µg of peptide pursuant to a boosting regimen over weeks to months may be administered depending upon the patients response and condition as determined by measuring the specific activity of CTL and HTL obtained from the patient's blood. Administration should continue until at least clinical symptoms or laboratory tests indicate that the neoplasia, has been eliminated or reduced and for a period thereafter. The dosages, routes of administration, and dose schedules are adjusted in accordance with methodologies known in the art.

In certain embodiments, the peptides and compositions of the present invention are employed in serious disease states, that is, life-threatening or potentially life threatening situations. In such cases, as a result of the minimal amounts of extraneous substances and the relative nontoxic nature of the peptides in preferred compositions of the invention, it is possible and may be felt desirable by the treating physician to administer substantial excesses of these peptide compositions relative to these stated dosage amounts.

The vaccine compositions of the invention can also be used purely as prophylactic agents. Generally the dosage for an initial prophylactic immunization generally occurs in a unit dosage range where the lower value is about 1, 5, 50, 500, or 1000 µg and the higher value is about 10,000; 20,000; 30,000; or 50,000 µg. Dosage values for a human typically range from about 500 µg to about 50,000 µg per 70 kilogram patient. This is followed by boosting dosages of between about 1.0 µg to about 50,000 µg of peptide administered at defined intervals from about four weeks to six months after the initial administration of vaccine. The immunogenicity of the vaccine can be assessed by measuring the specific activity of CTL and HTL obtained from a sample of the patient's blood.

The pharmaceutical compositions for therapeutic treatment are intended for parenteral, topical, oral, nasal, intrathecal, or local (e.g. as a cream or topical ointment) administration. Preferably, the pharmaceutical compositions are administered parentally, e.g., intravenously, subcutaneously, intradermally, or intramuscularly. Thus, the invention provides compositions for parenteral administration which comprise a solution of the immunogenic peptides dissolved or suspended in an acceptable carrier, preferably an aqueous carrier.

A variety of aqueous carriers may be used, e.g., water, buffered water, 0.8% saline, 0.3% glycine, hyaluronic acid and the like. These compositions may be sterilized by conventional, well-known sterilization techniques, or may be sterile filtered. The resulting aqueous solutions may be packaged for use as is, or lyophilized, the lyophilized preparation being combined with a sterile solution prior to administration.

The compositions may contain pharmaceutically acceptable auxiliary substances as required to approximate physiological conditions, such as pH-adjusting and buffering agents, tonicity adjusting agents, wetting agents, preservatives, and the like, for example, sodium acetate, sodium lactate, sodium chloride, potassium chloride, calcium chloride, sorbitan monolaurate, triethanolamine oleate, etc.

The concentration of peptides of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

A human unit dose form of a composition is typically included in a pharmaceutical composition that comprises a human unit dose of an acceptable carrier, in one embodiment an aqueous carrier, and is administered in a volume/quantity that is known by those of skill in the art to be used for administration of such compositions to humans (see, e.g., *Remington's Pharmaceutical Sciences*, $17^{th}$ Edition, A. Gennaro, Editor, Mack Publishing Co., Easton, Pa., 1985). For example a peptide dose for initial immunization can be from about 1 to about 50,000 µg, generally 100-5,000 µg, for a 70 kg patient. For example, for nucleic acids an initial immunization may be performed using an expression vector in the form of naked nucleic acid administered IM (or SC or ID) in the amounts of 0.5-5 mg at multiple sites. The nucleic acid (0.1 to 1000 µg) can also be administered using a gene gun. Following an incubation period of 3-4 weeks, a booster dose is then administered. The booster can be recombinant fowlpox virus administered at a dose of $5-10^7$ to $5\times10^9$ pfu. For antibodies, a treatment generally involves repeated administration of the anti-205P1B5 antibody preparation, via an acceptable route of administration such as intravenous injection (IV), typically at a dose in the range of about 0.1 to about 10 mg/kg body weight In general, doses in the range of 10-500 mg mAb per week are effective and well tolerated. Moreover, an initial loading dose of approximately 4 mg/kg patient body weight IV, followed by weekly doses of about 2 mg/kg IV of the anti-205P1B5 mAb preparation represents an acceptable dosing regimen. As appreciated by those of skill in the art, various factors can influence the ideal dose in a particular case. Such factors include, for example, half life of a composition, the binding affinity of an Ab, the immunogenicity of a substance, the degree of 205P1B5 expression in the patient, the extent of circulating shed 205P1B5 antigen, the desired steady-state concentration level, frequency of treatment, and the influence of chemotherapeutic or other agents used in combination with the treatment method of the invention, as well as the health status of a particular patient.

In one embodiment, human unit dose forms of polynucleotides comprise a suitable dosage range or effective amount that provides any therapeutic effect. As appreciated by one of ordinary skill in the art a therapeutic effect depends on a number of factors, including the sequence of the polynucleotide, molecular weight of the polynucleotide and route of administration. Dosages are generally selected by the physician or other health care professional in accordance with a variety of parameters known in the art, such as severity of symptoms, history of the patient and the like. Generally, for a polynucleotide of about 20 bases, a dosage range may be selected from, for example, an independently selected lower limit such as about 0.1, 0.25, 0.5, 1, 2, 5, 10, 20, 30, 40, 50, 60, 80, 100, 200, 300, 400 or 500 mg/kg up to an independently selected upper limit greater than the lower limit, of about 60, 80, 100, 200, 300, 400, 500, 750, 1000, 1500, 2000, 3000, 4000, 5000, 6000, 7000, 8000, 9000 or 10,000 mg/kg. For example, a dose may be about any of the following: 0.1 to 100 mg/kg, 0.1 to 50 mg/kg, 0.1 to 25 mg/kg, 0.1 to 10 mg/kg, 1 to 500 mg/kg, 100 to 400 mg/kg, 200 to 300 mg/kg, 1 to 100 mg/kg, 100 to 200 mg/kg, 300 to 400 mg/kg, 400 to 500 mg/kg, 500 to 1000 mg/kg, 500 to 5000 mg/kg, or 500 to 10,000 mg/kg. Generally, parenteral routes of administration may require higher doses of polynucleotide compared to more direct application to the nucleotide to diseased tissue, as do polynucleotides of increasing length.

In one embodiment, human unit dose forms of T-cells comprise a suitable dosage range or effective amount that provides any therapeutic effect. As appreciated by one of ordinary skill in the art, a therapeutic effect depends on a number of factors. Dosages are generally selected by the physician or other health care professional in accordance with a variety of parameters known in the art, such as severity of symptoms, history of the patient and the like. A dose may be about $10^4$ cells to about $10^6$ cells, about $10^6$ cells to about $10^8$ cells, about $10^8$ to about $10^{11}$ cells, or about $10^8$ to about $5 \times 10^{10}$ cells. A dose may also about $10^6$ cells/m$^2$ to about $10^{10}$ cells/m$^2$, or about $10^6$ cells/m$^2$ to about $10^8$ cells/m$^2$.

Proteins(s) of the invention, and/or nucleic acids encoding the protein(s), can also be administered via liposomes, which may also serve to: 1) target the proteins(s) to a particular tissue, such as lymphoid tissue; 2) to target selectively to diseases cells; or, 3) to increase the half-life of the peptide composition. Liposomes include emulsions, foams, micelles, insoluble monolayers, liquid crystals, phospholipid dispersions, lamellar layers and the like. In these preparations, the peptide to be delivered is incorporated as part of a liposome, alone or in conjunction with a molecule which binds to a receptor prevalent among lymphoid cells, such as monoclonal antibodies which bind to the CD45 antigen, or with other therapeutic or immunogenic compositions. Thus, liposomes either filled or decorated with a desired peptide of the invention can be directed to the site of lymphoid cells, where the liposomes then deliver the peptide compositions. Liposomes for use in accordance with the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka, et al., *Ann. Rev. Biophys. Bioeng.* 9:467 (1980), and U.S. Pat. Nos. 4,235,871, 4,501,728, 4,837,028, and 5,019,369.

For targeting cells of the immune system, a ligand to be incorporated into the liposome can include, e.g., antibodies or fragments thereof specific for cell surface determinants of the desired immune system cells. A liposome suspension containing a peptide may be administered intravenously, locally, topically, etc. in a dose which varies according to, inter alia, the manner of administration, the peptide being delivered, and the stage of the disease being treated.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient, that is, one or more peptides of the invention, and more preferably at a concentration of 25%-75%.

For aerosol administration, immunogenic peptides are preferably supplied in finely divided form along with a surfactant and propellant. Typical percentages of peptides are about 0.01%-20% by weight, preferably about 1%o-10%. The surfactant must, of course, be nontoxic, and preferably soluble in the propellant. Representative of such agents are the esters or partial esters of fatty acids containing from about 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute about 0.1%-20% by weight of the composition, preferably about 0.25-5%. The balance of the composition is ordinarily propellant. A carrier can also be included, as desired, as with, e.g., lecithin for intranasal delivery.

XI.) Diagnostic and Prognostic Embodiments of 205P1B5.

As disclosed herein, 205P1B5 polynucleotides, polypeptides, reactive cytotoxic T cells (CTL), reactive helper T cells (HTL) and anti-polypeptide antibodies are used in well known diagnostic, prognostic and therapeutic assays that examine conditions associated with dysregulated cell growth such as cancer, in particular the cancers listed in Table I (see, e.g., both its specific pattern of tissue expression as well as its overexpression in certain cancers as described for example in Example 4).

205P1B5 can be analogized to a prostate associated antigen PSA, the archetypal marker that has been used by medical practitioners for years to identify and monitor the presence of prostate cancer (see, e.g., Merrill et al., J. Urol. 163(2): 503-5120 (2000); Polascik et al., J. Urol. August; 162(2):293-306 (1999) and Fortier et al., J. Nat. Cancer Inst. 91(19): 1635-1640(1999)). A variety of other diagnostic markers are also used in similar contexts including p53 and K-ras (see, e.g., Tulchinsky et al., Int J Mol Med 1999 Jul. 4(1):99-102 and Minimoto et al., Cancer Detect Prev 2000;24(1):1-12). Therefore, this disclosure of the 205P1B5 polynucleotides and polypeptides (as well as the 205P1B5 polynucleotide probes and anti-205P1B5 antibodies used to identify the presence of these molecules) and their properties allows skilled artisans to utilize these molecules in methods that are analogous to those used, for example, in a variety of diagnostic assays directed to examining conditions associated with cancer.

Typical embodiments of diagnostic methods which utilize the 205P1B5 polynucleotides, polypeptides, reactive T cells and antibodies are analogous to those methods from well-established diagnostic assays which employ, e.g., PSA polynucleotides, polypeptides, reactive T cells and antibodies. For example, just as PSA polynucleotides are used as probes (for example in Northern analysis, see, e.g., Sharief et al., Biochem. Mol. Biol. Int. 33(3):567-74(1994)) and primers (for example in PCR analysis, see, e.g., Okegawa et al., J. Urol. 163(4): 1189-1190 (2000)) to observe the presence and/or the level of PSA mRNAs in methods of monitoring PSA overexpression or the metastasis of prostate cancers, the 205P1B5 polynucleotides described herein can be utilized in the same way to detect 205P1B5 overexpression or the metastasis of prostate and other cancers expressing this gene. Alternatively, just as PSA polypeptides are used to generate antibodies specific for PSA which can then be used to observe the presence and/or the level of PSA proteins in methods to monitor PSA protein overexpression (see, e.g., Stephan et al., Urology 55(4):560-3 (2000)) or the metastasis of prostate cells (see, e.g., Alanen et al., Pathol. Res. Pract. 192(3):233-7 (1996)), the 205P1B5 polypeptides described herein can be utilized to generate antibodies for use in detecting 205P1B5 overexpression or the metastasis of prostate cells and cells of other cancers expressing this gene.

Specifically, because metastases involves the movement of cancer cells from an organ of origin (such as the lung or prostate gland etc.) to a different area of the body (such as a lymph node), assays which examine a biological sample for the presence of cells expressing 205P1B5 polynucleotides and/or polypeptides can be used to provide evidence of metastasis. For example, when a biological sample from tissue that does not normally contain 205P1B5 -expressing cells (lymph node) is found to contain 205P1B5 -expressing cells such as the 205P1B5 expression seen in LAPC4 and LAPC9, xenografts isolated from lymph node and bone metastasis, respectively, this finding is indicative of metastasis.

Alternatively 205P1B5 polynucleotides and/or polypeptides can be used to provide evidence of cancer, for example, when cells in a biological sample that do not normally express 205P1B5 or express 205P1B5 at a different level are found to express 205P1B5 or have an increased expression of 205P1B5 (see, e.g., the 205P1B5 expression in the cancers listed in Table I and in patient samples etc. shown in the accompanying Figures). In such assays, artisans may further wish to generate supplementary evidence of metastasis by testing the biological sample for the presence of a second tissue restricted marker (in addition to 205P1B5) such as PSA, PSCA etc. (see, e.g., Alanen et al., Pathol. Res. Pract. 192(3): 233-237 (1996)).

Just as PSA polynucleotide fragments and polynucleotide variants are employed by skilled artisans for use in methods of monitoring PSA, 205P1B5 polynucleotide fragments and polynucleotide variants are used in an analogous manner. In particular, typical PSA polynucleotides used in methods of monitoring PSA are probes or primers which consist of fragments of the PSA cDNA sequence. Illustrating this, primers used to PCR amplify a PSA polynucleotide must include less than the whole PSA sequence to function in the polymerase chain reaction. In the context of such PCR reactions, skilled artisans generally create a variety of different polynucleotide fragments that can be used as primers in order to amplify different portions of a polynucleotide of interest or to optimize amplification reactions (see, e.g., Caetano-Anolles, G. Biotechniques 25(3): 472-476,478-480 (1998); Robertson et al., Methods Mol. Biol. 98:121-154 (1998)). An additional illustration of the use of such fragments is provided in Example 4, where a 205P1B5 polynucleotide fragment is used as a probe to show the expression of 205P1B5 RNAs in cancer cells. In addition, variant polynucleotide sequences are typically used as primers and probes for the corresponding mRNAs in PCR and Northern analyses (see, e.g., Sawai et al., Fetal Diagn. Ther. 1996 November-December 11(6):407-13 and Current Protocols In Molecular Biology, Volume 2, Unit 2, Frederick M. Ausubel et al. eds., 1995)). Polynucleotide fragments and variants are useful in this context where they are capable of binding to a target polynucleotide sequence (e.g. the 205P1B5 polynucleotide shown in SEQ ID NO: 701) under conditions of high stringency.

Furthermore, PSA polypeptides which contain an epitope that can be recognized by an antibody or T cell that specifically binds to that epitope are used in methods of monitoring PSA. 205P1B5 polypeptide fragments and polypeptide analogs or variants can also be used in an analogous manner. This practice of using polypeptide fragments or polypeptide variants to generate antibodies (such as anti-PSA antibodies or T cells) is typical in the art with a wide variety of systems such as fusion proteins being used by practitioners (see, e.g., Current Protocols In Molecular Biology, Volume 2, Unit 16, Frederick M. Ausubel et al. eds., 1995). In this context, each epitope(s) functions to provide the architecture with which an antibody or T cell is reactive. Typically, skilled artisans create a variety of different polypeptide fragments that can be used in order to generate immune responses specific for different portions of a polypeptide of interest (see, e.g., U.S. Pat. No. 5,840,501 and U.S. Pat. No. 5,939,533). For example it may be preferable to utilize a polypeptide comprising one of the 205P1B5 biological motifs discussed herein or a motif-bearing subsequence which is readily identified by one of skill in the art based on motifs available in the art. Polypeptide fragments, variants or analogs are typically useful in this context as long as they comprise an epitope capable of generating an antibody or T cell specific for a target polypeptide sequence (e.g. the 205P1B5 polypeptide shown in SEQ ID NO: 703).

As shown herein, the 205P1B5 polynucleotides and polypeptides (as well as the 205P1B5 polynucleotide probes and anti-205P1B5 antibodies or T cells used to identify the presence of these molecules) exhibit specific properties that make them useful in diagnosing cancers such as those listed in Table I. Diagnostic assays that measure the presence of 205P1B5 gene products, in order to evaluate the presence or onset of a disease condition described herein, such as prostate cancer, are used to identify patients for preventive measures or further monitoring, as has been done so successfully with PSA Moreover, these materials satisfy a need in the art for molecules having similar or complementary characteristics to PSA in situations where, for example, a definite diagnosis of metastasis of prostatic origin cannot be made on the basis of a test for PSA alone (see, e.g., Alanen et al., Pathol. Res. Pract. 192(3): 233-237 (1996)), and consequently, materials such as 205P1B5 polynucleotides and polypeptides (as well as the 205P1B5 polynucleotide probes and anti-205P1B5 antibodies used to identify the presence of these molecules) must be employed to confirm metastases of prostatic origin.

Finally, in addition to their use in diagnostic assays, the 205P1B5 polynucleotides disclosed herein have a number of other utilities such as their use in the identification of oncogenetic associated chromosomal abnormalities in the chromosomal region to which the 205P1B5 gene maps (see Example 3 below). Moreover, in addition to their use in diagnostic assays, the 205P1B5 -related proteins and polynucleotides disclosed herein have other utilities such as their use in the forensic analysis of tissues of unknown origin (see, e.g., Takahama K Forensic Sci Int 1996 Jun. 28;80(1-2): 63-9).

Additionally, 205P1B5-related proteins or polynucleotides of the invention can be used to treat a pathologic condition characterized by the over-expression of 205P1B5. For example, the amino acid or nucleic acid sequence of FIG. 2 or FIG. 3, or fragments of either, can be used to generate an immune response to the 205P1B5 antigen. Antibodies or other molecules that react with 205P1B5 can be used to modulate the function of this molecule, and thereby provide a therapeutic benefit.

XII.) Inhibition of 205P1B5 Protein Function

The invention includes various methods and compositions for inhibiting the binding of 205P1B5 to its binding partner or its association with other protein(s) as well as methods for inhibiting 205P1B5 function.

XII.A.) Inhibition of 205P1B5 With Intracellular Antibodies

In one approach, a recombinant vector that encodes single chain antibodies that specifically bind to 205P1B5 are introduced into 205P1B5 expressing cells via gene transfer technologies. Accordingly, the encoded single chain anti-205P1B5 antibody is expressed intracellularly, binds to 205P1B5 protein, and thereby inhibits its function. Methods for engineering such intracellular single chain antibodies are well known. Such intracellular antibodies, also known as "intrabodies", are specifically targeted to a particular compartment within the cell, providing control over where the inhibitory activity of the treatment is focused. This technology has been successfully applied in the art (for review, see Richardson and Marasco, 1995, TIBTECH vol. 13). Intrabodies have been shown to virtually eliminate the expression of otherwise abundant cell surface receptors (see, e.g., Richardson et al., 1995, Proc. Natl. Acad. Sci. USA 92: 3137-3141; Beerli et al., 1994, J. Biol. Chem. 289:23931-23936; Deshane et al., 1994, Gene Ther. 1: 332-337).

Single chain antibodies comprise the variable domains of the heavy and light chain joined by a flexible linker polypeptide, and are expressed as a single polypeptide. Optionally, single chain antibodies are expressed as a single chain variable region fragment joined to the light chain constant region. Well-known intracellular trafficking signals are engineered into recombinant polynucleotide vectors encoding such single chain antibodies in order to precisely target the intrabody to the desired intracellular compartment. For example, intrabodies targeted to the endoplasmic reticulum (ER) are engineered to incorporate a leader peptide and, optionally, a C-terminal ER retention signal, such as the KDEL amino acid motif Intrabodies intended to exert activity in the nucleus are engineered to include a nuclear localization signal. Lipid moieties are joined to intrabodies in order to tether the intrabody to the cytosolic side of the plasma membrane. Intrabodies can also be targeted to exert function in the cytosol. For example, cytosolic intrabodies are used to sequester factors within the cytosol, thereby preventing them from being transported to their natural cellular destination.

In one embodiment, intrabodies are used to capture 205P1B5 in the nucleus, thereby preventing its activity within the nucleus. Nuclear targeting signals are engineered into such 205P1B5 intrabodies in order to achieve the desired targeting. Such 205P1B5 intrabodies are designed to bind specifically to a particular 205P1B5 domain. In another embodiment, cytosolic intrabodies that specifically bind to the 205P1B5 protein are used to prevent 205P1B5 from gaining access to the nucleus, thereby preventing it from exerting any biological activity within the nucleus (e.g., preventing 205P1B5 from forming transcription complexes with other factors).

In order to specifically direct the expression of such intrabodies to particular cells, the transcription of the intrabody is placed under the regulatory control of an appropriate tumor-specific promoter and/or enhancer. In order to target intrabody expression specifically to prostate, for example, the PSA promoter and/or promoter/enhancer can be utilized (See, for example, U.S. Pat. No. 5,919,652 issued 6 Jul. 1999).

XII.B.) Inhibition of 205P1B5 with Recombinant Proteins

In another approach, recombinant molecules bind to 205P1B5 and thereby inhibit 205P1B5 function. For example, these recombinant molecules prevent or inhibit 205P1B5 from accessing/binding to its binding partner(s) or associating with other protein(s). Such recombinant molecules can, for example, contain the reactive part(s) of a 205P1B5 specific antibody molecule. In a particular embodiment, the 205P1B5 binding domain of a 205P1B5 binding partner is engineered into a dimeric fusion protein, whereby the fusion protein comprises two 205P1B5 ligand binding domains linked to the Fc portion of a human IgG, such as human IgG1. Such IgG portion can contain, for example, the $C_H2$ and $C_H3$ domains and the hinge region, but not the $C_H1$ domain Such dimeric fusion proteins are administer in soluble form to patients suffering from a cancer associated with the expression of 205P1B5, whereby the dimeric fusion protein specifically binds to 205P1B5 and blocks 205P1B5 interaction with a binding partner. Such dimeric fusion proteins are further combined into multimeric proteins using known antibody linking technologies.

XII.C.) Inhibition of 205P1B5 Transcription or Translation

The present invention also comprises various methods and compositions for inhibiting the transcription of the 205P1B5 gene. Similarly, the invention also provides methods and compositions for inhibiting the translation of 205P1B5 mRNA into protein.

In one approach, a method of inhibiting the transcription of the 205P1B5 gene comprises contacting the 205P1B5 gene with a 205P1B5 antisense polynucleotide. In another approach, a method of inhibiting 205P1B5 mRNA translation comprises contacting the 205P1B5 mRNA with an antisense polynucleotide. In another approach, a 205P1B5 specific ribozyme is used to cleave the 205P1B5 message, thereby inhibiting translation. Such antisense and ribozyme based methods can also be directed to the regulatory regions of the 205P1B5 gene, such as the 205P1B5 promoter and/or enhancer elements. Similarly, proteins capable of inhibiting a 205P1B5 gene transcription factor are used to inhibit 205P1B5 mRNA transcription. The various polynucleotides and compositions useful in the aforementioned methods have been described above. The use of antisense and ribozyme molecules to inhibit transcription and translation is well known in the art.

Other factors that inhibit the transcription of 205P1B5 by interfering with 205P1B5 transcriptional activation are also useful to treat cancers expressing 205P1B5. Similarly, factors that interfere with 205P1B5 processing are useful to treat cancers that express 205P1B5. Cancer treatment methods utilizing such factors are also within the scope of the invention.

XII.D.) General Considerations for Therapeutic Strategies

Gene transfer and gene therapy technologies can be used to deliver therapeutic polynucleotide molecules to tumor cells synthesizing 205P1B5 (i.e., antisense, ribozyme, polynucleotides encoding intrabodies and other 205P1B5 inhibitory molecules). A number of gene therapy approaches are known in the art. Recombinant vectors encoding 205P1B5 antisense polynucleotides, ribozymes, factors capable of interfering with 205P1B5 transcription, and so forth, can be delivered to target tumor cells using such gene therapy approaches.

The above therapeutic approaches can be combined with any one of a wide variety of surgical, chemotherapy or radiation therapy regimens. The therapeutic approaches of the invention can enable the use of reduced dosages of chemotherapy (or other therapies) and/or less frequent administration, an advantage for all patients and particularly for those that do not tolerate the toxicity of the chemotherapeutic agent well.

The anti-tumor activity of a particular composition (e.g., antisense, ribozyme, intrabody), or a combination of such compositions, can be evaluated using various in vitro and in vivo assay systems. In vitro assays that evaluate therapeutic activity include cell growth assays, soft agar assays and other assays indicative of tumor promoting activity, binding assays capable of determining the extent to which a therapeutic composition will inhibit the binding of 205P1B5 to a binding partner, etc.

In vivo, the effect of a 205P1B5 therapeutic composition can be evaluated in a suitable animal model. For example, xenogenic prostate cancer models can be used, wherein human prostate cancer explants or passaged xenograft tissues are introduced into immune compromised animals, such as nude or SCID mice (Klein et al., 1997, Nature Medicine 3: 402408). For example, PCT Patent Application WO98/16628, Sawyers et al., published Apr. 23, 1998, describes various xenograft models of human prostate cancer capable of recapitulating the development of primary tumors, micrometastasis, and the formation of osteoblastic metastases characteristic of late stage disease. Efficacy can be predicted using assays that measure inhibition of tumor formation, tumor regression or metastasis, and the like. In vivo assays that evaluate the promotion of apoptosis are useful in evaluating therapeutic compositions. In one embodiment, xenografts from tumor bearing mice treated with the therapeutic composition can be examined for the presence of apoptotic foci and compared to untreated control xenograft-bearing mice. The extent to which apoptotic foci are found in the tumors of the treated mice provides an indication of the therapeutic efficacy of the composition.

The therapeutic compositions used in the practice of the foregoing methods can be formulated into pharmaceutical compositions comprising a carrier suitable for the desired delivery method. Suitable carriers include any material that when combined with the therapeutic composition retains the anti-tumor function of the therapeutic composition and is generally non-reactive with the patient's immune system. Examples include, but are not limited to, any of a number of standard pharmaceutical carriers such as sterile phosphate buffered saline solutions, bacteriostatic water, and the like (see, generally, Remington's Pharmaceutical Sciences 16$^{th}$ Edition, A. Osal., Ed., 1980).

Therapeutic formulations can be solubilized and administered via any route capable of delivering the therapeutic composition to the tumor site. Potentially effective routes of administration include, but are not limited to, intravenous, parenteral, intraperitoneal, intramuscular, intratumor, intradermal, intraorgan, orthotopic, and the like. A preferred formulation for intravenous injection comprises the therapeutic composition in a solution of preserved bacteriostatic water, sterile unpreserved water, and/or diluted in polyvinylchloride or polyethylene bags containing 0.9% sterile Sodium Chloride for Injection, USP. Therapeutic protein preparations can be lyophilized and stored as sterile powders, preferably under vacuum, and then reconstituted in bacteriostatic water (containing for example, benzyl alcohol preservative) or in sterile water prior to injection.

Dosages and administration protocols for the treatment of cancers using the foregoing methods will vary with the method and the target cancer, and will generally depend on a number of other factors appreciated in the art.

XIII.) Kits

For use in the diagnostic and therapeutic applications described herein, kits are also within the scope of the invention. Such kits can comprise a carrier, package or container that is compartmentalized to receive one or more containers such as vials, tubes, and the like, each of the container(s) comprising one of the separate elements to be used in the method. For example, the container(s) can comprise a probe that is or can be detectably labeled. Such probe can be an antibody or polynucleotide specific for a 205P1B5-related protein or a 205P1B5 gene or message, respectively. Where the method utilizes nucleic acid hybridization to detect the target nucleic acid, the kit can also have containers containing nucleotide(s) for amplification of the target nucleic acid sequence and/or a container comprising a reporter-means, such as a biotin-binding protein, such as avidin or streptavidin, bound to a reporter molecule, such as an enzymatic, florescent, or radioisotope label. The kit can include all or part of the amino acid sequence of FIG. 2 or FIG. 3 or analogs thereof, or a nucleic acid molecules that encodes such amino acid sequences.

The kit of the invention will typically comprise the container described above and one or more other containers comprising materials desirable from a commercial and user standpoint, including buffers, diluents, filters, needles, syringes, and package inserts with instructions for use.

A label can be present on the container to indicate that the composition is used for a specific therapy or non-therapeutic application, and can also indicate directions for either in vivo or in vitro use, such as those described above. Directions and or other information can also be included on an insert which is included with the kit.

EXAMPLES

Various aspects of the invention are further described and illustrated by way of the several examples that follow, none of which are intended to limit the scope of the invention.

Example 1

SSH-Generated Isolation of a cDNA Fragment of the 205P1B5 Gene

To isolate genes that are over-expressed in prostate cancer we used the Suppression Subtractive Hybridization (SSH) procedure using cDNA derived from prostate cancer tissues. The 205P1B5 SSH cDNA sequence was derived from a subtraction consisting of a prostate cancer pool (patients with Gleason scores 6 and 7) minus a mix of cDNAs derived from nine normal tissues (stomach, skeletal muscle, lung, brain, liver, kidney, pancreas, small intestine, and heart). By RT-PCR, the 205P1B5 cDNA was identified as highly expressed in the prostate cancer tissue pool, prostate cancer xenograft pool (LAPC4-AD, LAPC4-AI, LAPC9-AD, LAPC9-AI), and in the metastasis cancer pool with no expression observed in the vital tissue pools consisting of normal liver, kidney, lung, stomach, pancreas, and colon.

The 205P1B5 SSH cDNA sequence of 289 bp matched the Homo sapiens cholinergic receptor, nicotinic, alpha polypeptide 2 (neuronal; CHRNA2) with 221/225 (98%) identities (FIG. 1). The fill length 205P1B5/CHRNA2 cDNA and ORF is described in FIG. 2 with the protein sequence listed in FIG. 3.

Materials and Methods

RNA Isolation:

Tumor tissues were homogenized in Trizol reagent (Life Technologies, Gibco BRL) using 10 ml/g tissue or 10 ml/$10^8$ cells to isolate total RNA. Poly A RNA was purified from total RNA using Qiagen's Oligotex mRNA Mini and Midi kits. Total and mRNA were quantified by spectrophotometric analysis (O.D. 260/280 nm) and analyzed by gel electrophoresis.

Oligonucleotides:

The following HPLC purified oligonucleotides were used.

```
DPNCDN (cDNA synthesis primer):
5'TTTTGATCAAGCTT₃₀3'                                (SEQ ID NO: 714)

Adaptor 1:
5'CTAATACGACTCACTATAGGGCTCGAGCGGCCGCCCGGGCAG3'      (SEQ ID NO: 715)
3'GGCCCGTCCTAG5'                                    (SEQ ID NO: 716)

Adaptor 2:
5'GTAATACGACTCACTATAGGGCAGCGTGGTCGCGGCCGAG3'        (SEQ ID NO: 717)
3'CGGCTCCTAG5'                                      (SEQ ID NO: 708)

PCR primer 1:
5'CTAATACGACTCACTATAGGGC3'                          (SEQ ID NO: 709)

Nested primer (NP)1:
5'TCGAGCGGCCGCCCGGGCAGGA3'                          (SEQ ID NO: 718)

Nested primer (NP)2:
5'AGCGTGGTCGCGGCCGAGGA3'                            (SEQ ID NO: 719)
```

Suppression Subtractive Hybridization:

Suppression Subtractive Hybridization (SSH) was used to identify cDNAs corresponding to genes that may be differentially expressed in prostate cancer. The SSH reaction utilized cDNA from prostate cancer patients with Gleason scores of 6 and 7. The gene 205P1B5 was derived from a prostate cancer pool, Gleason 6, 7 minus nine normal tissues. The SSH DNA sequence (FIG. 1) was identified.

The cDNA derived from nine normal tissues (stomach, skeletal muscle, lung, brain, liver, kidney, pancreas, small intestine, and heart) was used as the source of the "driver" cDNA, while the cDNA from a pool of prostate cancer patients with Gleason scores 6 and 7 was used as the source of the "tester" cDNA. Double stranded cDNAs corresponding to tester and driver cDNAs were synthesized from 2 µg of poly (A)⁺ RNA isolated from the relevant tissue, as described above, using CLONTECH's PCR-Select cDNA Subtraction Kit and 1 ng of oligonucleotide DPNCDN as primer. First- and second-strand synthesis were carried out as described in the Kit's user manual protocol (CLONTECH Protocol No. PT1117-1, Catalog No. K1804-1). The resulting cDNA was digested with Dpn II for 3 hrs at 37° C. Digested cDNA was extracted with phenol/chloroform (1:1) and ethanol precipitated.

Tester cDNA was generated by diluting 1 µl of Dpn II digested cDNA from the relevant tissue source (see above) (400 ng) in 5 µl of water. The diluted cDNA (2 µl, 160 ng) was then ligated to 2 µl of Adaptor 1 and Adaptor 2 (10 µM), in separate ligation reactions, in a total volume of 10 µl at 16° C. overnight, using 400 u of T4 DNA ligase (CLONTECH). Ligation was terminated with 1 µl of 0.2 M EDTA and heating at 72° C. for 5 min.

The first hybridization was performed by adding 1.5 µl (600 ng) of driver cDNA to each of two tubes containing 1.5 µl (20 ng) Adaptor 1- and Adaptor 2-ligated tester cDNA. In a final volume of 4 µl, the samples were overlaid with mineral oil, denatured in an MJ Research thermal cycler at 98° C. for 1.5 minutes, and then were allowed to hybridize for 8 hrs at 68° C. The two hybridizations were then mixed together with an additional 1 µl of fresh denatured driver cDNA and were allowed to hybridize overnight at 68° C. The second hybridization was then diluted in 200 µl of 20 mM Hepes, pH 8.3, 50 mM NaCl, 0.2 mM EDTA, heated at 70° C. for 7 min. and stored at −20° C.

PCR Amplification, Cloning and Sequencing of Gene Fragments Generated from SSH:

To amplify gene fragments resulting from SSH reactions, two PCR amplifications were performed. In the primary PCR reaction 1 µl of the diluted final hybridization mix was added to 1 µl of PCR primer 1 (10 µM), 0.5 µl dNTP mix (10 µM), 2.5 µl 10×reaction buffer (CLONTECH) and 0.5 µl 50×Advantage cDNA polymerase Mix (CLONTECH) in a final volume of 25 µl. PCR 1 was conducted using the following conditions: 75° C. for 5 min., 94° C. for 25 sec., then 27 cycles of 94° C. for 10 sec, 66° C. for 30 sec, 72° C. for 1.5 min. Five separate primary PCR reactions were performed for each experiment. The products were pooled and diluted 1:10 with water. For the secondary PCR reaction, 1 µl from the pooled and diluted primary PCR reaction was added to the same reaction mix as used for PCR 1, except that primers NP1 and NP2 (10 µM) were used instead of PCR primer 1. PCR 2 was performed using 10-12 cycles of 94° C. for 10 sec, 68° C. for 30 sec, and 72° C. for 1.5 minutes. The PCR products were analyzed using 2% agarose gel electrophoresis.

The PCR products were inserted into pCR2.1 using the T/A vector cloning kit (Invitrogen). Transformed E. coli were subjected to blue/white and ampicillin selection. White colonies were picked and arrayed into 96 well plates and were grown in liquid culture overnight. To identify inserts, PCR amplification was performed on 1 ml of bacterial culture using the conditions of PCR1 and NP1 and NP2 as primers. PCR products were analyzed using 2% agarose gel electrophoresis.

Bacterial clones were stored in 20% glycerol in a 96 well format. Plasmid DNA was prepared, sequenced, and subjected to nucleic acid homology searches of the GenBank, dBest, and NCI-CGAP databases.

RT-PCR Expression Analysis:

First strand cDNAs can be generated from 1 µg of mRNA with oligo (dT)12-18 priming using the Gibco-BRL Superscript Preamplification system. The manufacturer's protocol was used which included an incubation for 50 min at 42° C. with reverse transcriptase followed by RNAse H treatment at 37° C. for 20 min. After completing the reaction, the volume can be increased to 200 µl with water prior to normalization. First strand cDNAs from 16 different normal human tissues can be obtained from Clontech.

Normalization of the first strand cDNAs from multiple tissues was performed by using the primers 5'atatcgccgcgctcgtcgtcgacaa3' (SEQ ID NO: 706) and 5'agccacacgcagctcattgtagaagg 3' (SEQ ID NO:707) to amplify β-actin. First strand cDNA (5 µl) were amplified in a total volume of 50 µl containing 0.4 µM primers, 0.2 µM each dNTPs, 1×PCR buffer (Clontech, 10 mM Tris-HCL, 1.5 mM $MgCl_2$, 50 mM KCl, pH8.3) and 1×Klentaq DNA polymerase (Clontech). Five µl of the PCR reaction can be removed at 18, 20, and 22 cycles and used for agarose gel electrophoresis. PCR was performed using an MJ Research thermal cycler under the following conditions: Initial denaturation can be at 94° C. for 15 sec, followed by a 18, 20, and 22 cycles of 94° C. for 15, 65° C. for 2 min, 72° C. for 5 sec. A final extension at 72° C. was carried out for 2 min. After agarose gel electrophoresis, the band intensities of the 283 b.p. β-actin bands from multiple tissues were compared by visual inspection. Dilution factors for the first strand cDNAs were calculated to result in equal β-actin band intensities in all tissues after 22 cycles of PCR. Three rounds of normalization can be required to achieve equal band intensities in all tissues after 22 cycles of PCR.

To determine expression levels of the 205P1B5 gene, 5 µl of normalized first strand cDNA were analyzed by PCR using 26, and 30 cycles of amplification, Semi-quantitative expression analysis can be achieved by comparing the PCR products at cycle numbers that give light band intensities.

A typical RT-PCR expression analysis is shown in FIG. 10. RT-PCR expression analysis was performed on first strand cDNAs generated using pools of tissues from multiple samples. The cDNAs were shown to be normalized using beta-actin PCR.

Example 2

Full Length Cloning of 205P1B5

To isolate genes that are involved in prostate cancer, an experiment was conducted using prostate cancer patients with Gleason scores 6 and 7.

The gene 205P1B5 was derived from a prostate cancer pool minus nine normal tissues subtraction. The SSH DNA sequence (FIG. 1) was designated 205P1B5. cDNA clone 205P1B5-clone 1 consisting of the CHRNA2 ORF was identified from normal prostate cDNA. A single base pair variation was identified at position 760 with an A instead of a G when compared to the CHRNA2 sequence.

Example 3

Chromosomal Localization

Chromosomal localization can implicate genes in disease pathogenesis. Several chromosome mapping approaches are available in the art, including fluorescent in situ hybridization (FISH), human /hamster radiation hybrid (RH) panels (Walter et al., 1994; Nature Genetics 7:22; Research Genetics, Huntsville Ala.), human-rodent somatic cell hybrid panels, such as is available from the Cornell Institute (Camden, N.J.), and genomic viewers utilizing BLAST homologies to sequenced and mapped genomic clones (NCBI, Bethesda, Md.).

205P1B5 maps to chromosome 8p21-8p12, using 205P1B5 sequence and the NCBI BLAST tool: (world wide web URL ncbi.nlm.nih.gov/genome/seq/page.cgi?F=HsBlast.html&&ORG=Hs).

This region has been implicated in prostate cancer (Xu et al., Am J. Hum Genet 2001 August; 69(2):341-350).

Example 4

Expression Analysis of 205P1B5 in Normal Tissues and Patient Specimens

Analysis of 205P1B5 by RT-PCR is shown in FIG. 10. First strand cDNA was prepared from vital pool 1 (VP: liver, lung and kidney), vital pool 2 (VP2: pancreas, colon and stomach), prostate xenograft pool (LAPC-4AD, LAPC4AI, LAPC-9AD, LAPC-9AI), prostate cancer pool, and cancer metastasis pool. Normalization was performed by PCR using primers to actin and GAPDH. Semi-quantitative PCR, using primers to 205P1B5, was performed at 26 and 30 cycles of amplification. Results show expression of 205P1B5 in prostate cancer pool prostate xenograft pool, cancer metastasis pool, but not in VP1 and VP2.

Extensive Northern blot analysis of 205P1B5 in 16 human normal tissues demonstrated that 205P1B5 expression is tissue-restricted (FIG. 11). Two multiple tissue northern blots (Clontech) with 2 µg of mRNA/lane, were probed with 205P1B5 sequence. Size standards in kilobases (kb) are indicated on the side. An approximately 5 kb transcript was detected in prostate and brain but not in any other normal tissues. A larger 205P1B5 transcript of approximately 7.5 kb was only detected in liver.

Expression of 205P1B5 was assayed on a pool of 3 tumors isolated from prostate cancer patients (PCP) and on normal tissues FIG. 12). Northern blots with 10 µg of total RNA/lane were probed with 205P1B5 sequence. Size standards in kilobases (kb) are indicated on the side. 205P1B5 expression was seen in the prostate cancer pool and the normal prostate but not in normal bladder (NB), normal kidney (NK), normal colon (NC). Northern blot analysis on individual prostate cancer patient specimens and prostate cancer xenografts is shown in FIG. 13. RNA was extracted from prostate cancer xenografts (LAPC4AD, LAPC4AI, LAPC-9AD, LAPC-9AI), prostate cancer cell line PC3, normal prostate (N), prostate tumors (T) and normal adjacent tissue (Nat) derived from prostate cancer patients. Northern blot with 10 µg of total RNA/lane was probed with 205P1B5 sequence. Size standards in kilobases (kb) are indicated on the side. Results show expression of 205P1B5 in all prostate tumor specimens tested. Expression is also seen in 3 of the 4 xenografts, but not in the PC3 cell line.

The restricted expression of 205P1B5 in normal tissues and the expression detected in the cancers listed in Table I indicate that 205P1B5 is a therapeutic and prophylactic target and a diagnostic and prognostic marker for human cancer.

FIG. 15 shows expression of 205P1B5 in cancer metastasis patient specimens. RNA was extracted from prostate cancer metastasis to lymph node obtained from two different patients, as well as from normal bladder (NB), normal kidney (NK), normal lung (NL), normal breast (NBr), normal ovary (NO), and normal pancreas (NPa). Northern blots with 10 µg of total RNA/lane were probed with 205P1B5 sequence. Size standards in kilobases (kb) are indicated on the side. The results show expression of 205P1B5 in both cancer metastasis samples but not in the normal tissues tested.

Example 5

Production of Recombinant 205P1B5 in Prokaryotic Systems

To express recombinant 205P1B5 in prokaryotic cells, the full or partial length 205P1B5 cDNA sequences can be cloned into any one of a variety of expression vectors known in the art. One or more of the following regions of 205P1B5 are expressed in these constructs, amino acids 1 to 529; or any 8, 9, 10, 11, 12, 13, 14, 15, 16, 17, 18,.19, 20, 21, 22, 23, 24,25, 26, 27, 28, 29, 30 or more contiguous amino acids from 205P1B5, variants, or analogs thereof.

A. In Vitro Transcription and Translation Constructs:
pCRII:
To generate 205P1B5 sense and anti-sense RNA probes for RNA in situ investigations, pCRII constructs (Invitrogen, Carlsbad Calif.) are generated encoding either all or fragments of the 205P1B5 cDNA. The pCRII vector has Sp6 and T7 promoters flanking the insert to drive the transcription of 205P1B5 RNA for use as probes in RNA in situ hybridization experiments. These probes are used to analyze the cell and tissue expression of 205P1B5 at the RNA level. Transcribed 205P1B5 RNA representing the cDNA amino acid coding region of the 205P1B5 gene is used in in vitro translation systems such as the TnT™ Coupled Reticulolysate System (Promega, Corp., Madison, Wis.) to synthesize 205P1B5 protein.

B. Bacterial Constructs:
pGEX Constructs:
To generate recombinant 205P1B5 proteins in bacteria that are fused to the Glutathione S-transferase (GST) protein, all or parts of the 205P1B5 cDNA protein coding sequence are fused to the GST gene by cloning into pGEX-6P-1 or any other GST-fusion vector of the pGEX family (Amersham Pharmacia Biotech, Piscataway, N.J.). These constructs allow controlled expression of recombinant 205P1B5 protein sequences with GST fused at the amino-terminus and a six histidine epitope (6× His) at the carboxyl-terminus. The GST and 6× His tags permit purification of the recombinant fusion protein from induced bacteria with the appropriate affinity matrix and allow recognition of the fusion protein with anti-GST and anti-His antibodies. The 6× His tag is generated by adding 6 histidine codons to the cloning primer at the 3' end, e.g., of the open reading frame (ORF). A proteolytic cleavage site, such as the PreScission™ recognition site in pGEX-6P-1, may be employed such that it permits cleavage of the GST tag from 205P1B5-related protein. The ampicillin resistance gene and pBR322 origin permits selection and maintenance of the pGEX plasmids in *E. coli*.

pMAL Constructs:
To generate, in bacteria, recombinant 205P1B5 proteins that are fused to maltose-binding protein (MBP), all or parts of the 205P?B5 cDNA protein coding sequence are fused to the MBP gene by cloning into the pMAL-c2X and pMAL-p2X vectors (New England Biolabs, Beverly, Mass.). These constructs allow controlled expression of recombinant 205P1B5 protein sequences with MBP fused at the amino-terminus and a 6× His epitope tag at the carboxyl-terminus. The MBP and 6× His tags permit purification of the recombinant protein from induced bacteria with the appropriate affinity matrix and allow recognition of the fusion protein with anti-MBP and anti-His antibodies. The 6× His epitope tag is generated by adding 6 histidine codons to the 3' cloning primer. A Factor Xa recognition site permits cleavage of the pMAL tag from 205P1B5. The pMAL-c2X and pMAL-p2X vectors are optimized to express the recombinant protein in the cytoplasm or periplasm respectively. Periplasm expression enhances folding of proteins with disulfide bonds.

pET Constructs:
To express 205P1B5 in bacterial cells, all or parts of the 205P1B5 cDNA protein coding sequence are cloned into the pET family of vectors (Novagen, Madison, Wis.). These vectors allow tightly controlled expression of recombinant 205P1B5 protein in bacteria with and without fusion to proteins that enhance solubility, such as NusA and thioredoxin (Trx), and epitope tags, such as 6× His and S-Tag™ that aid purification and detection of the recombinant protein. For example, constructs are made utilizing pET NusA fusion system 43.1 such that regions of the 205P1B5 protein are expressed as amino-terminal fusions to NusA.

C. Yeast Constructs:
pESC Constructs:
To express 205P1B5 in the yeast species *Saccharomyces cerevisiae* for generation of recombinant protein and functional studies, all or parts of the 205P1B5 cDNA protein coding sequence are cloned into the pESC family of vectors each of which contain 1 of 4 selectable markers, HIS3, TRP1, LEU2, and URA3 (Stratagene, La Jolla, Calif.). These vectors allow controlled expression from the same plasmid of up to 2 different genes or cloned sequences containing either Flag™ or Myc epitope tags in the same yeast cell. This system is useful to confirm protein-protein interactions of 205P1B5. In addition, expression in yeast yields similar post-translational modifications, such as glycosylations and phosphorylations, that are found when expressed in eukaryotic cells.

pESP Constructs:
To express 205P1B5 in the yeast species *Saccharomyces pombe*, all or parts of the 205P1B5 cDNA protein coding sequence are cloned into the pESP family of vectors. These vectors allow controlled high level of expression of a 205P1B5 protein sequence that is fused at either the amino terminus or at the carboxyl terminus to GST which aids purification of the recombinant protein. A Flag™ epitope tag allows detection of the recombinant protein with anti-Flag™ antibody.

Example 6

Production of Recombinant 205P1B5 in Eukaryotic Systems

A. Mammalian Constructs:
To express recombinant 205P1B5 in eukaryotic cells, the full or partial length 205P1B5 cDNA sequences can be cloned into any one of a variety of expression vectors known in the art. One or more of the following regions of 205P1B5 are expressed in these constructs, amino acids 1 to 529; or any 8, 9, 10, 11, 12, 13, 14, 15, 16, 17, 18, 19, 20, 21, 22, 23, 24, 25, 26, 27, 28, 29, 30 or more contiguous amino acids from 205P1B5, variants, or analogs thereof.

The constructs can be transfected into any one of a wide variety of mammalian cells such as 293T cells. Transfected 293T cell lysates can be probed with the anti-205P1B5 polyclonal serum, described herein.

pcDNA4/HisMax Constructs:
To express 205P1B5 in mammalian cells, the 205P1B5 ORF, or portions thereof, of 205P1B5 are cloned into pcDNA4/HisMax Version A (Invitrogen, Carlsbad, Calif.). Protein expression is driven from the cytomegalovirus (CMV) promoter and the SP16 translational enhancer. The recombinant protein has Xpress™ and six histidine (6× His) epitopes fused to the amino-terminus. The pcDNA4/HisMax vector also contains the bovine growth hormone (BGH) polyadenylation signal and transcription termination sequence to enhance mRNA stability along with the SV40 origin for episomal replication and simple vector rescue in cell lines expressing the large T antigen. The Zeocin resistance gene allows for selection of mammalian cells expressing the protein and the ampicillin resistance gene and ColE1 origin permits selection and maintenance of the plasmid in E. coli.

pcDNA3.1/MycHis Constructs:

To express 205P1B5 in mammalian cells, the 205P1B5 ORF, or portions thereof, of 205P1B5 with a consensus Kozak translation initiation site are cloned into pcDNA3.1/MycHis Version A (Invitrogen, Carlsbad, Calif.). Protein expression is driven from the cytomegalovirus (CMV) promoter. The recombinant proteins have the myc epitope and 6× His epitope fused to the carboxyl-terminus. The pcDNA3.1/MycHis vector also contains the bovine growth hormone (BGH) polyadenylation signal and transcription termination sequence to enhance mRNA stability, along with the SV40 origin for episomal replication and simple vector rescue in cell lines expressing the large T antigen. The Neomycin resistance gene can be used, as it allows for selection of mammalian cells expressing the protein and the ampicillin resistance gene and ColE1 origin permits selection and maintenance of the plasmid in E. coli.

pcDNA3.1/CT-GFP-TOPO Construct:

To express 205P1B5 in mammalian cells and to allow detection of the recombinant proteins using fluorescence, the 205P1B5 ORF, or portions thereof, of 205P1B5 with a consensus Kozak translation initiation site are cloned into pcDNA3.1/CT-GFP-TOPO (Invitrogen, Calif.). Protein expression is driven from the cytomegalovirus (CMV) promoter. The recombinant proteins have the Green Fluorescent Protein (GFP) fused to the carboxyl-terminus facilitating non-invasive, in vivo detection and cell biology studies. The pcDNA3.1CT-GFP-TOPO vector also contains the bovine growth hormone (BGH) polyadenylation signal and transcription termination sequence to enhance mRNA stability along with the SV40 origin for episomal replication and simple vector rescue in cell lines expressing the large T antigen. The Neomycin resistance gene allows for selection of mammalian cells that express the protein, and the ampicillin resistance gene and ColE1 origin permits selection and maintenance of the plasmid in E. coli. Additional constructs with an amino-terminal GFP fusion are made in pcDNA3.1/NT-GFP-TOPO spanning the entire length of the 205P1B5 proteins.

PAPtap:

The 205P1B5 ORF, or portions thereof, of 205P1B5 are cloned into pAPtag-5 (GenHunter Corp. Nashville, Tenn.). This construct generates an alkaline phosphatase fusion at the carboxyl-terminus of the 205P1B5 proteins while fusing the IgGk signal sequence to the amino-terminus. Constructs are also generated in which alkaline phosphatase with an amino-terminal IgGk signal sequence is fused to the amino-terminus of 205P1B5 proteins. The resulting recombinant 205P1B5 proteins are optimized for secretion into the media of transfected mammalian cells and can be used to identify proteins such as ligands or receptors that interact with the 205P1B5 proteins. Protein expression is driven from the CMV promoter and the recombinant proteins also contain myc and 6× His epitopes fused at the carboxyl-terminus that facilitates detection and purification. The Zeocin resistance gene present in the vector allows for selection of mammalian cells expressing the recombinant protein and the ampicillin resistance gene permits selection of the plasmid in E. coli.

ptag5:

The 205P1B5 ORF, or portions thereof, of 205P1B5 are cloned into pTag-5. This vector is similar to pAPtag but without the alkaline phosphatase fusion. This construct generates 205P1B5 protein with an amino-terminal IgGk signal sequence and myc and 6× His epitope tags at the carboxyl-terminus that facilitate detection and affinity purification. The resulting recombinant 205P1B5 protein is optimized for secretion into the media of transfected mammalian cells, and is used as immunogen or ligand to identify proteins such as ligands or receptors that interact with the 205P1B5 proteins. Protein expression is driven from the CMV promoter. The Zeocin resistance gene present in the vector allows for selection of mammalian cells expressing the protein, and the ampicillin resistance gene permits selection of the plasmid in E. coli.

PsecFe:

The 205P1B5 ORF, or portions thereof, of 205P1B5 are also cloned into psecFc. The psecFc vector was assembled by cloning the human immunoglobulin G1 (IgG) Fc (hinge, CH2, CH3 regions) into pSecTag2 (Invitrogen, Calif.). This construct generates an IgG1 Fc fusion at the carboxyl-terminus of the 205P1B5 proteins, while fusing the IgGK signal sequence to N-terminus. 205P1B5 fusions utilizing the murine IgG1 Fc region are also used. The resulting recombinant 205P1B5 proteins are optimized for secretion into the media of transfected mammalian cells, and can be used as immunogens or to identify proteins such as ligands or receptors that interact with the 205P1B5 protein. Protein expression is driven from the CMV promoter. The hygromycin resistance gene present in the vector allows for selection of mammalian cells that express the recombinant protein, and the ampicillin resistance gene permits selection of the plasmid in E. coli.

pSRα Constructs:

To generate mammalian cell lines that express 205P1B5 constitutively, 205P1B5 ORF, or portions thereof, of 205P1B5 are cloned into pSRα constructs. Amphotropic and ecotropic retroviruses are generated by transfection of pSRα constructs into the 293T-10A1 packaging line or co-transfection of pSRα and a helper plasmid (containing deleted packaging sequences) into the 293 cells, respectively. The retrovirus is used to infect a variety of mammalian cell lines, resulting in the integration of the cloned gene, 205P1B5, into the host cell-lines. Protein expression is driven from a long terminal repeat (LTR). The Neomycin resistance gene present in the vector allows for selection of mammalian cells that express the protein, and the ampicillin resistance gene and ColE1 origin permit selection and maintenance of the plasmid in E. coli. The retroviral vectors can thereafter be used for infection and generation of various cell lines using, for example, PC3, NIH 3T3, TsuPr1, 293 or rat-1 cells.

Additional pSRα constructs are made that fuse an epitope tag such as the FLAG™ tag to the carboxyl-terminus of 205P1B5 sequences to allow detection using anti-Flag antibodies. For example, the FLAG™ sequence 5' gat tac aag gat gac gac gat aag 3' is added to cloning primer at the 3' end of the ORF. Additional pSRα constructs are made to produce both amino-terminal and carboxyl-terminal GFP and myc/6× His fusion proteins of the full-length 205P1B5 proteins.

Additional Viral Vectors:

Additional constructs are made for viral-mediated delivery and expression of 205P1B5. High virus titer leading to high level expression of 205P1B5 is achieved in viral delivery systems such as adenoviral vectors and herpes amplicon vectors. The 205P1B5 coding sequences or fragments thereof are amplified by PCR and subcloned into the AdEasy shuttle vector (Stratagene). Recombination and virus packaging are performed according to the manufacturer's instructions to generate adenoviral vectors. Alternatively, 205P1B5 coding sequences or fragments thereof are cloned into the HSV-1 vector (Imgenex) to generate herpes viral vectors. The viral vectors are thereafter used for infection of various cell lines such as PC3, NIH 3T3, 293 or rat-1 cells.

Regulated Expression Systems:

To control expression of 205P1B5 in mammalian cells, coding sequences of 205P1B5, or portions thereof, are cloned into regulated mammalian expression systems such as the T-Rex System (Invitrogen), the GeneSwitch System (Invitrogen) and the tightly-regulated Ecdysone System (Sratagene). These systems allow the study of the temporal and concentration dependent effects of recombinant 205P1B5. These vectors are thereafter used to control expression of 205P1B5 in various cell lines such as PC3, NIH 3T3, 293 or rat-1 cells.

B. Baculovirus Expression Systems

To generate recombinant 205P1B5 proteins in a baculovirus expression system, 205P1B5 ORF, or portions thereof, are cloned into the baculovirus transfer vector pBlueBac 4.5 (Invitrogen), which provides a His-tag at the N-terminus. Specifically, pBlueBac-205P1B5 is co-transfected with helper plasmid pBac-N-Blue (Invitrogen) into SF9 (*Spodoptera frugiperda*) insect cells to generate recombinant baculovirus (see Invitrogen instruction manual for details). Baculovirus is then collected from cell supernatant and purified by plaque assay.

Recombinant 205P1B5 protein is then generated by infection of HighFive insect cells (Invitrogen) with purified baculovirus. Recombinant 205P1B5 protein can be detected using anti-205P1B5 or anti-His-tag antibody. 205P1B5 protein can be purified and used in various cell-based assays or as immunogen to generate polyclonal and monoclonal antibodies specific for 205P1B5.

Example 7

Antigenicity Profiles and Secondary Structure

FIG. 5, FIG. 6, FIG. 7, FIG. 8, and FIG. 9 depict graphically five amino acid profiles of the 205P1B5 amino acid sequence, each assessment available by accessing the ProtScale website (URL world wide web URL expasy.ch/cgi-bin/protscale.pl) on the ExPasy molecular biology server.

These profiles: FIG. 5, Hydrophilicity, (Hopp T. P., Woods K. R., 1981. Proc. Natl. Acad. Sci. U.S.A. 78:3824-3828); FIG. 6, Hydropathicity, (Kyte J., Doolittle R. F., 1982. J. Mol. Biol. 157:105-132); FIG. 7, Percentage Accessible Residues (Janin J., 1979 Nature 277:491492); FIG. 8, Average Flexibility, (Bhaskaran R., and Ponnuswamy P. K., 1988. Int. J. Pept. Protein Res. 32:242-255); FIG. 9, Beta-turn (Deleage, G., Roux B. 1987 Protein Engineering 1:289-294); and optionally others available in the art, such as on the ProtScale website, were used to identify antigenic regions of the 205P1B5 protein. Each of the above amino acid profiles of 205P1B5 were generated using the following ProtScale parameters for analysis: 1) A window size of 9; 2) 100% weight of the window edges compared to the window center; and, 3) amino acid profile values normalized to he between 0 and 1.

Hydrophilicity (FIG. 5), Hydropathicity (FIG. 6) and Percentage Accessible Residues (FIG. 7) profiles were used to determine stretches of hydrophilic amino acids (i.e., values greater than 0.5 on the Hydrophilicity and Percentage Accessible Residues profile, and values less than 0.5 on the Hydropathicity profile). Such regions are likely to be exposed to the aqueous environment, be present on the surface of the protein, and thus available for immune recognition, such as by antibodies.

Average Flexibility (FIG. 8) and Beta-turn (FIG. 9) profiles determine stretches of amino acids (i.e., values greater than 0.5 on the Beta-turn profile and the Average Flexibility profile) that are not constrained in secondary structures such as beta sheets and alpha helices. Such regions are also more likely to be exposed on the protein and thus accessible to immune recognition, such as by antibodies.

Antigenic sequences of the 205P1B5 protein indicated, e.g., by the profiles set forth in FIG. 5, FIG. 6, FIG. 7, FIG. 8, and/or FIG. 9 are used to prepare immunogens, either peptides or nucleic acids that encode them, to generate therapeutic and diagnostic anti-205P1B5 antibodies. The immunogen can be any 5, 6, 7, 8, 9, 10, 11, 12, 13, 14, 15, 16, 17, 18, 19, 20, 21, 22, 23, 24, 25, 30, 35, 40, 45, 50 or more than 50 contiguous amino acids, or the corresponding nucleic acids that encode them from the 205P1B5 protein. In particular, peptide immunogens of the invention can comprise, a peptide region of at least 5 amino acids of FIG. 2 in any whole number increment up to 529 that includes an amino acid position having a value greater than 0.5 in the Hydrophilicity profile of FIG. 5; a peptide region of at least 5 amino acids of FIG. 2 in any whole number increment up to 529 that includes an amino acid position having a value less than 0.5 in the Hydropathicity profile of FIG. 6; a peptide region of at least 5 amino acids of FIG. 2 in any whole number increment up to 529 that includes an amino acid position having a value greater than 0.5 in the Percent Accessible Residues profile of FIG. 7; a peptide region of at least 5 amino acids of FIG. 2 in any whole number increment up to 529 that includes an amino acid position having a value greater than 0.5 in the Average Flexibility profile on FIG. 8; and, a peptide region of at least 5 amino acids of FIG. 2 in any whole number increment up to 529 that includes an amino acid position having a value greater than 0.5 in the Beta-turn profile of FIG. 9. Peptide immunogens of the invention can also comprise nucleic acids that encode any of the forgoing.

All immunogens of the invention, peptide or nucleic acid, can be embodied in human unit dose form, or comprised by a composition that includes a pharmaceutical excipient compatible with human physiology.

The secondary structure of 205P1B5, namely the predicted presence and location of alpha helices, extended strands, and random coils, is predicted from the primary amino acid sequence using the HNN-Hierarchical Neural Network method (Guermeur, 1997, world wide web URL /pbil.ibcp.fr/cgi-bin/npsa_automat.pl?page=npsa_nn.html), accessed from the ExPasy molecular biology server (world wide web URL: expasy.ch/tools/). The analysis indicates that 205P1B5 is composed 41.40% alpha helix, 12.67% extended strand, and 45.94% random coil (FIG. 14A).

Figure 14B:
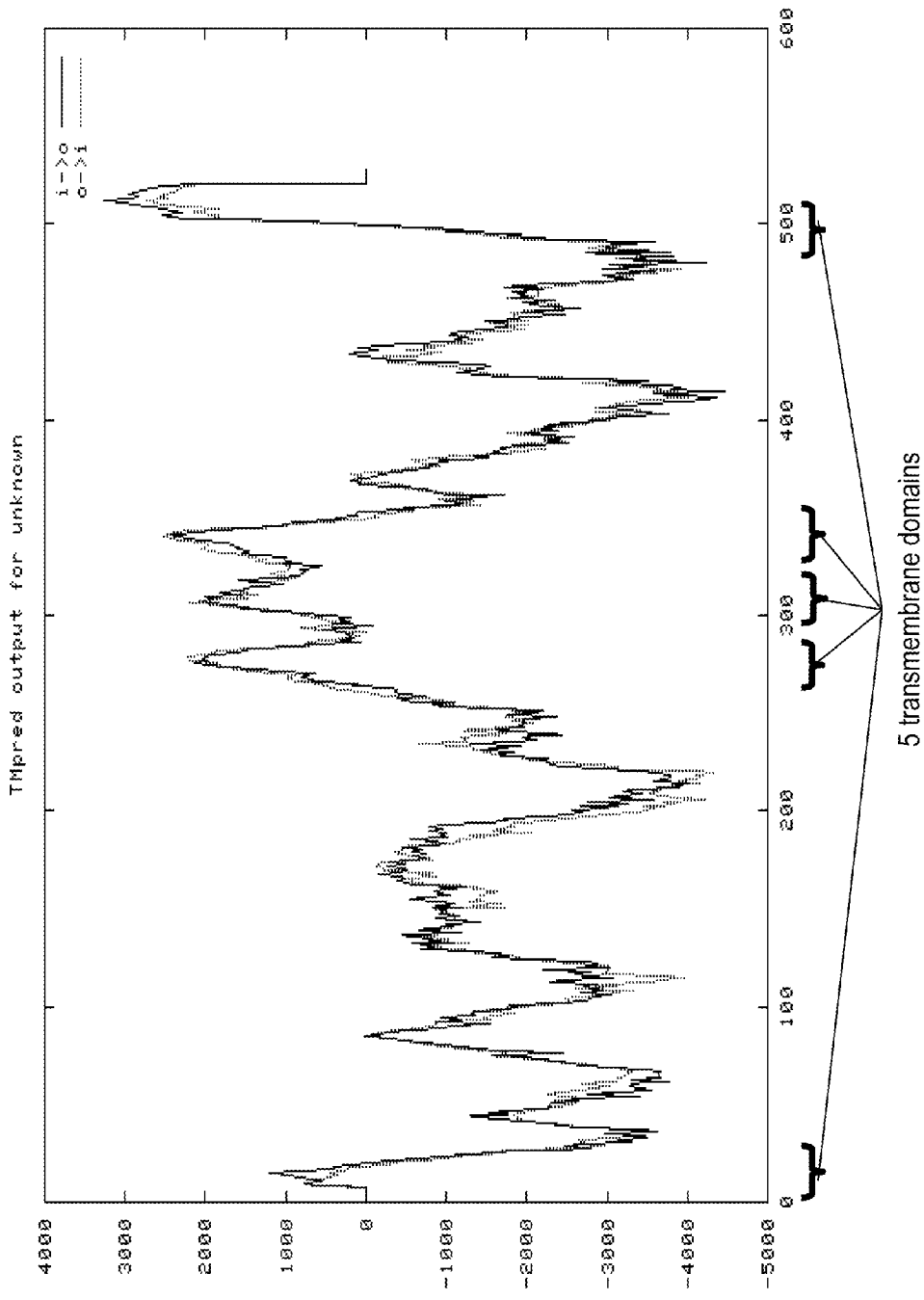
Figure 14C:
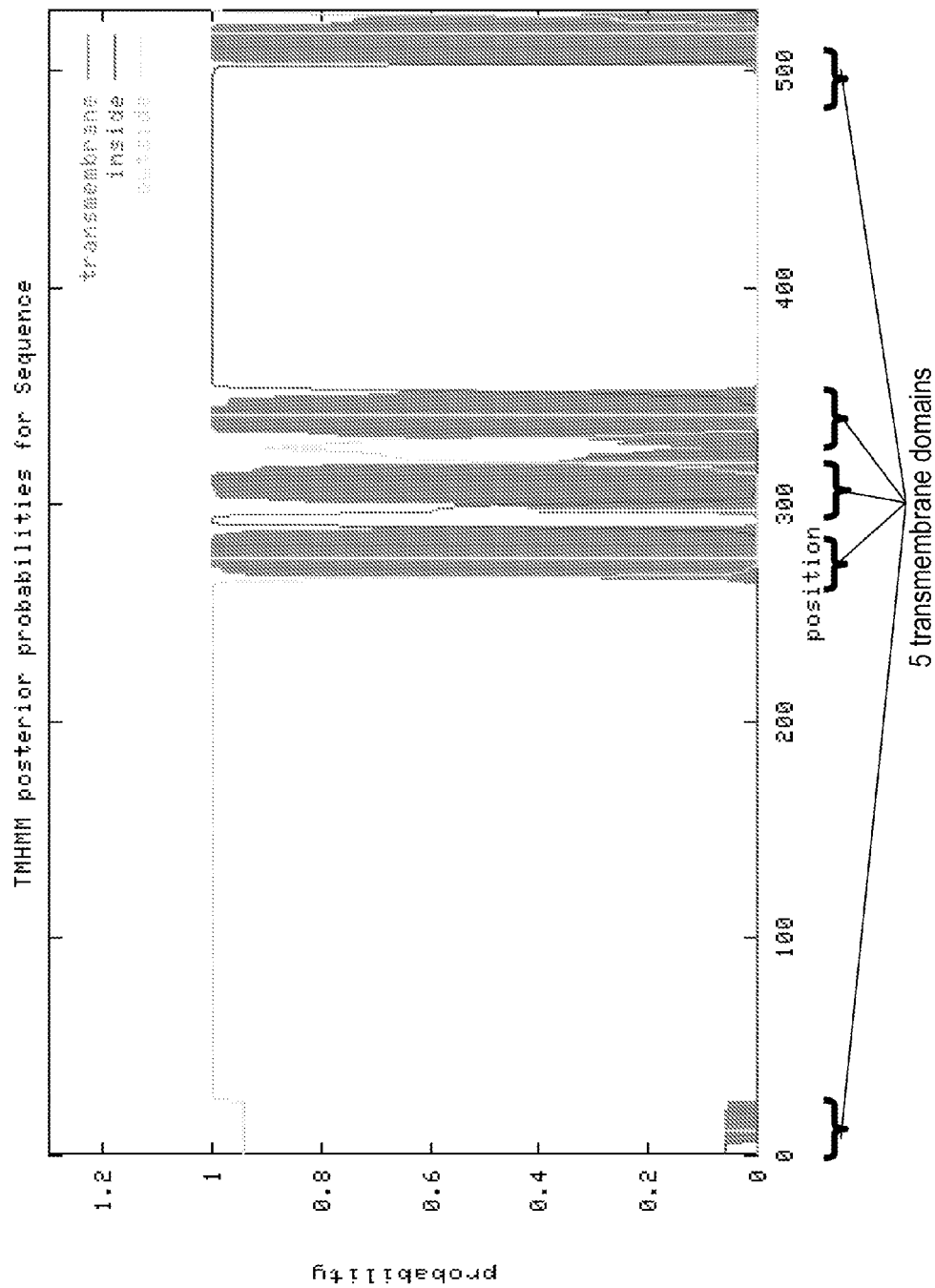

Analysis for the potential presence of transmembrane domains in 205P1B5 was carried out using a variety of transmembrane prediction algorithms accessed from the ExPasy molecular biology server (world wide web URL expasy.ch/tools/). The programs predict the presence of 5 transmembrane domains in 205P1B5, consistent with the structure of a G-protein coupled receptor. Shown graphically in FIG. 14 are the results of analysis using the TMpred (FIG. 14B) and TMHMM (FIG. 14C) prediction programs depicting the location of the 5 transmembrane domains. The results of each program, namely the amino acids encoding the transmembrane domains are summarized in Table XXI.

Example 8

Generation of 205P1B5 Polyclonal Antibodies

Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. In addition to immunizing with the full length 205P1B5 protein, computer algorithms are employed in design of immunogens that, based on amino acid sequence analysis contain characteristics of being antigenic and available for recognition by the immune system of the immunized host (see the Example entitled "Antigenicity Profiles"). Such regions would be predicted to be hydrophilic, flexible, in beta-turn conformations, and be exposed on the surface of the protein (see, e.g., FIG. 5, FIG. 6, FIG. 7, FIG. 8, or FIG. 9 for amino acid profiles that indicate such regions of 205P1B5).

For example, 205P1B5 recombinant bacterial fusion proteins or peptides encoding hydrophilic, flexible, beta-turn regions of the 205P1B5 sequence, such as amino acids 23-63, are used as antigens to generate polyclonal antibodies in New Zealand White rabbits. It is useful to conjugate the immunizing agent to a protein known to be immunogenic in the mammal being immunized. Examples of such immunogenic proteins include, but are not limited to, keyhole limpet hemocyanin (KLH), serum albumin, bovine thyroglobulin, and soybean trypsin inhibitor. In one embodiment, a peptide encoding amino acids 23-63 of 205P1B5 is conjugated to KLH and used to immunize the rabbit. Alternatively the immunizing agent may include all or portions of the 205P1B5 protein, analogs or fusion proteins thereof. For example, the 205P1B5 amino acid sequence can be fused using recombinant DNA techniques to any one of a variety of fusion protein partners that are well known in the art, such as glutathione-S-transferase (GST) and HIS tagged fusion proteins. Such fusion proteins are purified from induced bacteria using the appropriate affinity matrix.

In one embodiment, a GST-fusion protein encoding the predicted second extracellular loop of 205P1B5 (amino acids 27-271) is produced and purified and used as immunogen (see the section entitled "Production of 205P1B5 in Prokaryotic Systems"). Other recombinant bacterial fusion proteins that may be employed include maltose binding protein, LacZ, thioredoxin, NusA, or an immunoglobulin constant region (see the section entitled "Production of 205P1B5 in Prokaryotic Systems" and Current Protocols In Molecular Biology, Volume 2, Unit 16, Frederick M. Ausubul et al. eds., 1995; Linsley, P. S., Brady, W., Urnes, M., Grosmaire, L., Damle, N., and Ledbetter, L.(1991) J. Exp. Med. 174, 561-566).

In addition to bacterial derived fusion proteins, mammalian expressed protein antigens are also used. These antigens are expressed from mammalian expression vectors such as the Tag5 and Fc-fusion vectors (see the section entitled "Production of Recombinant 205P1B5 in Eukaryotic Systems"), and retain post-translational modifications such as glycosylations found in native protein. In one embodiment, amino acids 27-271 is cloned into the Tag5 mammalian secretion vector. The recombinant protein is purified by metal chelate chromatography from tissue culture supernatants of 293T cells stably expressing the recombinant vector. The purified Tag5 205P1B5 protein is then used as immunogen.

During the immunization protocol, it is useful to mix or emulsify the antigen in adjuvants that enhance the immune response of the host animal. Examples of adjuvants include, but are not limited to, complete Freund's adjuvant (CFA) and MPL-TDM adjuvant (monophosphoryl Lipid A, synthetic trehalose dicorynomycolate).

In a typical protocol, rabbits are initially immunized subcutaneously with up to 200 μg, typically 100-200 μg, of fusion protein or peptide conjugated to KLH mixed in complete Freund's adjuvant (CFA). Rabbits are then injected subcutaneously every two weeks with up to 200 μg, typically 100-200 μg, of the immunogen in incomplete Freund's adjuvant (IFA). Test bleeds are taken approximately 7-10 days following each immunization and used to monitor the titer of the antiserum by ELISA.

To test reactivity and specificity of immune serum, such as the rabbit serum derived from immunization with Tag5 205P1B5 encoding amino acids 27-271, the full-length 205P1B5 cDNA is cloned into pCDNA 3.1 myc-his expression vector Invitrogen, see the Example entitled "Production of Recombinant 205P1B5 in Eukaryotic Systems"). After transfection of the constructs into 293T cells, cell lysates are probed with the anti-205P1B5 serum and with anti-His antibody (Santa Cruz Biotechnologies, Santa Cruz, Calif.) to determine specific reactivity to denatured 205P1B5 protein using the Western blot technique. Immunoprecipitation and flow cytometric analyses of 293T and other recombinant 205P1B5-expressing cells determine recognition of native protein by the antiserum. In addition, Western blot, immunoprecipitation, fluorescent microscopy, and flow cytometric techniques using cells that endogenously express 205P1B5 are carried out to test specificity.

The anti-serum from the Tag5 205P1B5 immunized rabbit the serum is affinity purified by passage over a column composed of the Tag5 antigen covalently coupled to Affigel matrix (BioRad, Hercules, Calif.). The serum is then further purified by protein G affinity chromatography to isolate the IgG fraction. Serum from rabbits immunized with fusion proteins, such as GST and MBP fusion proteins, are purified by depletion of antibodies reactive to the fusion partner sequence by passage over an affinity column containing the fusion partner either alone or in the context of an irrelevant fusion protein. Sera from other His-tagged antigens and peptide immunized rabbits as well as fusion partner depleted sera are affinity purified by passage over a column matrix composed of the original protein immunogen or free peptide.

Example 9

Generation of 205P1B5 Monoclonal Antibodies (mAbs)

In one embodiment, therapeutic mAbs to 205P1B5 comprise those that react with epitopes of the protein that would disrupt or modulate the biological function of 205P1B5, for example those that would disrupt its interaction with ligands or proteins that mediate or are involved in its biological activity. Therapeutic mAbs also comprise those that specifically bind epitopes of 205P1B5 exposed on the cell surface and thus are useful in targeting mAb-toxin conjugates. Immunogens for generation of such mAbs include those designed to encode or contain the entire 205P1B5 protein or regions of the 205P1B5 protein predicted to be antigenic from computer analysis of the amino acid sequence (see, e.g., FIG. 5, FIG. 6, FIG. 7, FIG. 8, or FIG. 9, and the Example entitled "Antigenicity Profiles"). Immunogens include peptides, recombinant bacterial proteins, and mammalian expressed Tag 5 proteins and human and murine IgG FC fusion proteins. In addition, cells expressing high levels of 205P1B5, such as 293T-205P1B5 cells, are used to immunize mice.

To generate mAbs to 205P1B5, mice are first immunized intraperitoneally (IP) with, typically, 10-50 µg of protein immunogen or $10^7$ 205P1B5-expressing cells mixed in complete Freund's adjuvant. Mice are then subsequently immunized IP every 2-4 weeks with, typically, 10-50 µg of protein immunogen or $10^7$ cells mixed in incomplete Freund's adjuvant Alternatively, MPL-TDM adjuvant is used in immunizations. In addition to the above protein and cell-based immunization strategies, a DNA-based immunization protocol is employed in which a mammalian expression vector encoding 205P1B5 sequence is used to immunize mice by direct injection of the plasmid DNA. For example, the predicted second extracellular loop of 205P1B5, amino acids 27-271, is cloned into the Tag5 mammalian secretion vector and the recombinant vector is used as immunogen. In another example, amino acids 23-63 (predicted to be antigenic from sequence analysis, see, e.g., FIG. 5, FIG. 6, FIG. 7, FIG. 8 or FIG. 9) is cloned into an Fc-fusion secretion vector in which the 205P1B5 sequence is fused at the amino-terminus to an IgK leader sequence and at the carboxyl-terminus to the coding sequence of the human IgG Fc region. This recombinant vector is then used as immunogen. The plasmid immunization protocols are used in combination with purified proteins expressed from the same vector and with cells expressing 205P1B5.

During the immunization protocol, test bleeds are taken 7-10 days following an injection to monitor titer and specificity of the immune response. Once appropriate reactivity and specificity is obtained as determined by ELISA, Western blotting, immunoprecipitation, fluorescence microscopy, and flow cytometric analyses, fusion and hybridoma generation is then carried out with established procedures well known in the art (see, e.g., Harlow and Lane, 1988).

In one embodiment for generating 205P1B5 monoclonal antibodies, a Tag5 205P1B5 antigen encoding amino acids 27-271 is expressed and purified from stably transfected 293T cells. Balb C mice are initially immunized intraperitoneally with 25 µg of the Tag5 205P1B5 protein mixed in complete Freund's adjuvant Mice are subsequently immunized every two weeks with 25 µg of the antigen mixed in incomplete Freund's adjuvant for a total of three immunizations. ELISA using the Tag5 antigen determines the titer of serum from immunized mice. Reactivity and specificity of serum to full length 205P1B5 protein is monitored by Western blotting, immunoprecipitation and flow cytometry using 293T cells transfected with an expression vector encoding the 205P1B5 cDNA (see e.g., the Example entitled "Production of Recombinant 205P1B5 in Eukaryotic Systems"). Other recombinant 205P1B5-expressing cells or cells endogenously expressing 205P1B5 are also used. Mice showing the strongest reactivity are rested and given a final injection of Tag5 antigen in PBS and then sacrificed four days later. The spleens of the sacrificed mice are harvested and fused to SPO/2 myeloma cells using standard procedures (Harlow and Lane, 1988). Supernatants from HAT selected growth wells are screened by ELISA, Western blot, immunoprecipitation, fluorescent microscopy, and flow cytometry to identify 205P1B5 specific antibody-producing clones.

The binding affinity of a 205P1B5 monoclonal antibody is determined using standard technologies. Affinity measurements quantify the strength of antibody to epitope binding and are used to help define which 205P1B5 monoclonal antibodies preferred for diagnostic or therapeutic use, as appreciated by one of skill in the art. The BIAcore system (Uppsala, Sweden) is a preferred method for determining binding affinity. The BIAcore system uses surface plasmon resonance (SPR, Welford K. 1991, Opt. Quant. Elect. 23:1; Morton and Myszka, 1998, Methods in Enzymology 295: 268) to monitor biomolecular interactions in real time. BIAcore analysis conveniently generates association rate constants, dissociation rate constants, equilibrium dissociation constants, and affinity constants.

Example 10

HLA Class I and Class II Binding Assays

HLA class I and class II binding assays using purified HLA molecules are performed in accordance with disclosed protocols (e.g., PCT publications WO 94/20127 and WO 94/03205; Sidney et al., Current Protocols in Immunology 18.3.1 (1998); Sidney, et al., J. Immunol. 154:247 (1995); Sette, et al., Mol. Immunol. 31:813 (1994)). Briefly, purified MHC molecules (5 to 500 nM) are incubated with various unlabeled peptide inhibitors and 1-10 nM $^{125}$I-radiolabeled probe peptides as described. Following incubation, MHC-peptide complexes are separated from free peptide by gel filtration and the fraction of peptide bound is determined. Typically, in preliminary experiments, each MHC preparation is titered in the presence of fixed amounts of radiolabeled peptides to determine the concentration of HLA molecules necessary to bind 10-20% of the total radioactivity. All subsequent inhibition and direct binding assays are performed using these HLA concentrations.

Since under these conditions [label]<[HLA] and $IC_{50} \geq$ [HLA], the measured $IC_{50}$ values are reasonable approximations of the true $K_D$ values. Peptide inhibitors are typically tested at concentrations ranging from 120 µg/ml to 1.2 ng/ml, and are tested in two to four completely independent experiments. To allow comparison of the data obtained in different experiments, a relative binding figure is calculated for each peptide by dividing the $IC_{50}$ of a positive control for inhibition by the $IC_{50}$ for each tested peptide (typically unlabeled versions of the radiolabeled probe peptide). For database purposes, and inter-experiment comparisons, relative binding values are compiled. These values can subsequently be converted back into $IC_{50}$ nM values by dividing the $IC_{50}$ nM of the positive controls for inhibition by the relative binding of the peptide of interest. This method of data compilation is accurate and consistent for comparing peptides that have been tested on different days, or with different lots of purified MHC.

Binding assays as outlined above may be used to analyze HLA supermotif and/or HLA motif-bearing peptides.

Example 11

Identification of HLA Supermotif- and Motif-Bearing CTL Candidate Epitopes

HLA vaccine compositions of the invention can include multiple epitopes. The multiple epitopes can comprise multiple HLA supermotifs or motifs to achieve broad population coverage. This example illustrates the identification and confirmation of supermotif- and motif-bearing epitopes for the inclusion in such a vaccine composition. Calculation of population coverage is performed using the strategy described below.

Computer Searches and Algorithms for Identification of Supermotif and/or Motif-Bearing Epitopes The searches performed to identify the motif-bearing peptide sequences in the Example entitled "Antigenicity Profiles" and Tables V-XVII employ the protein sequence data from the gene product of 205P1B5 set forth in FIGS. 2 and 3.

Computer searches for epitopes bearing HLA Class I or Class II supermotifs or motifs are performed as follows. All translated 205P1B5 protein sequences are analyzed using a text string search software program to identify potential peptide sequences containing appropriate HLA binding motifs; such programs are readily produced in accordance with information in the art in view of known motif/supermotif disclosures. Furthermore, such calculations can be made mentally.

Identified A2-, A3-, and DR-supermotif sequences are scored using polynomial algorithms to predict their capacity to bind to specific HLA-Class I or Class II molecules. These polynomial algorithms account for the impact of different amino acids at different positions, and are essentially based on the premise that the overall affinity (or $\Delta G$) of peptide-HLA molecule interactions can be approximated as a linear polynomial function of the type:

$$"\Delta G" = a_{1i} \times a_{2i} \times a_{3i} \ldots \times a_{ni}$$

where $a_{ji}$ is a coefficient which represents the effect of the presence of a given amino acid (f) at a given position (i) along the sequence of a peptide of n amino acids. The crucial assumption of this method is that the effects at each position are essentially independent of each other (i.e., independent binding of individual side-chains). When residue j occurs at position i in the peptide, it is assumed to contribute a constant amount $j_i$ to the free energy of binding of the peptide irrespective of the sequence of the rest of the peptide.

The method of derivation of specific algorithm coefficients has been described in Gulukota et al., *J. Mol. Biol.* 267:1258-126, 1997; (see also Sidney et al., *Human. Immunol.* 45:79-93, 1996; and Southwood et al., *J. Immunol.* 160:3363-3373, 1998). Briefly, for all i positions, anchor and non-anchor alike, the geometric mean of the average relative binding (ARB) of all peptides carrying j is calculated relative to the remainder of the group, and used as the estimate of $j_i$. For Class II peptides, if multiple alignments are possible, only the highest scoring alignment is utilized, following an iterative procedure. To calculate an algorithm score of a given peptide in a test set, the ARB values corresponding to the sequence of the peptide are multiplied. If this product exceeds a chosen threshold, the peptide is predicted to bind. Appropriate thresholds are chosen as a function of the degree of stringency of prediction desired.

Selection of HLA-A2 Supertype Cross-Reactive Rentides

Complete protein sequences from 205P1B5 are scanned utilizing motif identification software, to identify 8-, 9-, 10- and 11-mer sequences containing the HLA-A2-supermotif main anchor specificity. Typically, these sequences are then scored using the protocol described above and the peptides corresponding to the positive-scoring sequences are synthesized and tested for their capacity to bind purified HLA-A*0201 molecules in vitro (HLA-A*0201 is considered a prototype A2 supertype molecule).

These peptides are then tested for the capacity to bind to additional A2-supertype molecules (A*0202, A*0203, A*0206, and A*6802). Peptides that bind to at least three of the five A2-supertype alleles tested are typically deemed A2-supertype cross-reactive binders. Preferred peptides bind at an affinity equal to or less than 500 nM to three or more HLA-A2 supertype molecules.

Selection of HA-A3 Supermotif-Bearing Epitopes

The 205P1B5 protein sequence scanned above is also examined for the presence of peptides with the HLA-A3-supermotif primary anchors. Peptides corresponding to the BLA A3 supermotif-bearing sequences are then synthesized and tested for binding to HLA-A*0301 and HLA-A*1101 molecules, the molecules encoded by the two most prevalent A3-supertype alleles. The peptides that bind at least one of the two alleles with binding affinities of<500 nM, often<200 nM, are then tested for binding cross-reactivity to the other common A3-supertype alleles (e.g., A*3101, A*3301, and A*6801) to identify those that can bind at least three of the five HLA-A3-supertype molecules tested.

Selection of HLA-B7 supermotif Bearing Epitopes

The 205P1B5 protein is also analyzed for the presence of 8-, 9-, 10-, or 11-mer peptides with the HLA-B7-supermotif. Corresponding peptides are synthesized and tested for binding to HLA-B*0702, the molecule encoded by the most common B7-supertype allele (i.e., the prototype B7 supertype allele). Peptides binding B*0702 with IC5 of≦500 nM are identified using standard methods. These peptides are then tested for binding to other common B7-supertype molecules (e.g., B*3501, B*5 101, B*5301, and B*5401). Peptides capable of binding to three or more of the five B7-supertype alleles tested are thereby identified.

Selection of A1 and A24 Motif-Bearing Epitopes

To further increase population coverage, HLA-A1 and -A24 epitopes can also be incorporated into vaccine compositions. An analysis of the 205P1B5 protein can also be performed to identify HLA-A1- and A24-motif-containing sequences.

High affinity and/or cross-reactive binding epitopes that bear other motif and/or supermotifs are identified using analogous methodology.

Example 12

Confirmation of Immunogenicity

Cross-reactive candidate CTL A2-supermotif-bearing peptides that are identified as described herein are selected to confirm in vitro immunogenicity. Confirmation is performed using the following methodology:

Target Cell Lines for Cellular Screening:

The 0.221A2.1 cell line, produced by transferring the HLA-A2.1 gene into the HLA-A, -B, -C null mutant human B-lymphoblastoid cell line 721.221, is used as the peptide-loaded target to measure activity of HLA-A2.1-restricted CTL. This cell line is grown in RPMI-1640 medium supplemented with antibiotics, sodium pyruvate, nonessential amino acids and 10% (v/v) heat inactivated FCS. Cells that express an antigen of interest, or transfectants comprising the gene encoding the antigen of interest, can be used as target cells to confirm the ability of peptide-specific CTLs to recognize endogenous antigen.

Primary CTL Induction Cultures:

Generation of Dendritic Cells (DC):

PBMCs are thawed in RPMI with 30 µg/ml DNAse, washed twice and resuspended in complete medium (RPMI-1640 plus 5% AB human serum, nonessential amino acids, sodium pyruvate, L-glutamine and penicillin/streptomycin). The monocytes are purified by plating $10 \times 10^6$ PBMC/well in a 6-well plate. After 2 hours at 37° C., the non-adherent cells are removed by gently shaking the plates and aspirating the supernatants. The wells are washed a total of three times with 3 ml RPMI to remove most of the non-adherent and loosely adherent cells. Three ml of complete medium containing 50 ng/ml of GM-CSF and 1,000 U/ml of IL-4 are then added to each well. TNFα is added to the DCs on day 6 at 75 ng/ml and the cells are used for CTL induction cultures on day 7.

Induction of CTL with DC and Peptide:

CD8+ T-cells are isolated by positive selection with Dynal immunomagnetic beads (Dynabeads® M450) and the detacha-bead® reagent. Typically about 200-250×10$^6$ PBMC are processed to obtain 24×10$^6$ CD8$^+$ T-cells (enough for a 48-well plate culture). Briefly, the PBMCs are thawed in RPMI with 30 μg/ml DNAse, washed once with PBS containing 1% human AB serum and resuspended in PBS/1% AB serum at a concentration of 20×10$^6$cells/ml. The magnetic beads are washed 3 times with PBS/AB serum, added to the cells (140 μl beads/20×10$^6$ cells) and incubated for 1 hour at 4° C. with continuous mixing. The beads and cells are washed 4× with PBS/AB serum to remove the nonadherent cells and resuspended at 100×10$^6$ cells/ml (based on the original cell number) in PBS/AB serum containing 100 μl/ml detacha-bead® reagent and 30 μg/ml DNAse. The mixture is incubated for 1 hour at room temperature with continuous mixing. The beads are washed again with PBS/AB/DNAse to collect the CD8+ T-cells. The DC are collected and centrifuged at 1300 rpm for 5-7 minutes, washed once with PBS with 1% BSA, counted and pulsed with 40 μ/ml of peptide at a cell concentration of 1-2×10$^6$/ml in the presence of 3 μg/ml β$_2$-microglobulin for 4 hours at 20° C. The DC are then irradiated (4,200 rads), washed 1 time with medium and counted again.

Setting Up Induction Cultures:

0.25 ml cytokine-generated DC (at 1×10$^5$ cells/ml) are co-cultured with 0.25 ml of CD8+ T-cells (at 2×10$^6$ cell/ml) in each well of a 48-well plate in the presence of 10 ng/ml of IL7. Recombinant human IL-10 is added the next day at a final concentration of 10 ng/ml and human IL-2 is added 48 hours later at 10 IU/ml.

Restimulation of the Induction Cultures with Peptide-Pulsed Adherent Cells:

Seven and fourteen days after the primary induction, the cells are restimulated with peptide-pulsed adherent cells. The PBMCs are thawed and washed twice with RPMI and DNAse. The cells are resuspended at 5×10$^6$ cells/ml and irradiated at ~4200 rads. The PBMCs are plated at 2×10$^6$ in 0.5 ml complete medium per well and incubated for 2 hours at 37° C. The plates are washed twice with RPMI by tapping the plate gently to remove the nonadherent cells and the adherent cells pulsed with 10 μg/ml of peptide in the presence of 3 μg/ml β$_2$ microglobulin in 0.25 ml RPMI/5% AB per well for 2 hours at 37° C. Peptide solution from each well is aspirated and the wells are washed once with RPMI. Most of the media is aspirated from the induction cultures (CD8+ cells) and brought to 0.5 ml with fresh media. The cells are then transferred to the wells containing the peptide-pulsed adherent cells. Twenty four hours later recombinant human IL-10 is added at a final concentration of 10 ng/ml and recombinant human IL2 is added the next day and again 2-3 days later at 50 IU/ml (Tsai et al., *Critical Reviews in Immunology* 18(1-2): 65-75, 1998). Seven days later, the cultures are assayed for CTL activity in a $^{51}$Cr release assay. In some experiments the cultures are assayed for peptide-specific recognition in the in situ IFNγ ELISA at the time of the second restimulation followed by assay of endogenous recognition 7 days later. After expansion, activity is measured in both assays for a side-by-side comparison.

Measurement of CTL Lytic Activity by $^{51}$Cr Release.

Seven days after the second restimulation, cytotoxicity is determined in a standard (5 hr) $^{51}$Cr release assay by assaying individual wells at a single E:T. Peptide-pulsed targets are prepared by incubating the cells with 10 μg/ml peptide overnight at 37° C.

Adherent target cells are removed from culture flasks with trypsin-EDTA. Target cells are labeled with 200 μCi of $^{51}$Cr sodium chromate (Dupont Wilmington, Del.) for 1 hour at 37° C. Labeled target cells are suspended at 10$^6$ per ml and diluted 1:10 with K562 cells at a concentration of 3.3×10$^6$/ml (an NK-sensitive erythroblastoma cell line used to reduce non-specific lysis). Target cells (100 μl) and effectors (100 μl) are plated in 96 well round-bottomplates and incubated for 5 hours at 37° C. At that time, 100 μl of supernatant are collected from each well and percent lysis is determined according to the formula:

[(cpm of the test sample–cpm of the spontaneous $^{15}$Cr release sample)/(cpm of the maximal $^{51}$Cr release sample–cpm of the spontaneous $^{51}$Cr release sample)]×100.

Maximum and spontaneous release are determined by incubating the labeled targets with 1% Triton X-100 and media alone, respectively. A positive culture is defined as one in which the specific lysis (sample-background) is 10% or higher in the case of individual wells and is 15% or more at the two highest E:T ratios when expanded cultures are assayed.

In Situ Measurement of Human IFNγ Production as an Indicator of Peptide-Specific and Endogenous Recognition Immulon 2 plates are coated with mouse anti-human IFNγ monoclonal antibody (4 μg/ml 0.1M NaHCO$_3$, pH8.2) overnight at 4° C. The plates are washed with Ca$^{2+}$, Mg$^{2+}$-free PBS/0.05% Tween 20 and blocked with PBS/100% FCS for two hours, after which the CTLs (100 μl/well) and targets (100 μl/well) are added to each well, leaving empty wells for the standards and blanks (which received media only). The target cells, either peptide-pulsed or endogenous targets, are used at a concentration of 1×10$^6$ cells/ml. The plates are incubated for 48 hours at 37° C. with 5% CO$_2$.

Recombinant human IFN-gamma is added to the standard wells starting at 400 pg or 1200 pg/100 microliter/well and the plate incubated for two hours at 37° C. The plates are washed and 100 μl of biotinylated mouse anti-human IFN-gamma monoclonal antibody (2 microgram/ml in PBS/3% FCS/0.05% Tween 20) are added and incubated for 2 hours at room temperature. After washing again, 100 microliter HRP-streptavidin (1:4000) are added and the plates incubated for one hour at room temperature. The plates are then washed 6× with wash buffer, 100 microliter/well developing solution (TMB 1:1) are added, and the plates allowed to develop for 5-15 minutes. The reaction is stopped with 50 microliter/well 1M H$_3$PO$_4$ and read at OD450. A culture is considered positive if it measured at least 50 pg of IFN-gamma/well above background and is twice the background level of expression.

CTL Expansion.

Those cultures that demonstrate specific lytic activity against peptide-pulsed targets and/or tumor targets are expanded over a two week period with anti-CD3. Briefly, 5×10$^4$ CD8+ cells are added to a T75 flask containing the following: 1×10$^6$ irradiated (4,200 rad) PBMC (autologous or allogeneic) per ml, 2×10$^5$ irradiated (8,000 rad) EBV-transformed cells per ml, and OKT3 (anti-CD3) at 30 ng per ml in RPMI-1640 containing 10% (v/v) human AB serum, non-essential amino acids, sodium pyruvate, 25 μM 2-mercaptoethanol; L-glutamine and penicillin/streptomycin. Recombinant human IL2 is added 24 hours later at a final concentration of 200 IU/ml and every three days thereafter with fresh media at 50 IU/ml. The cells are split if the cell concentration exceeds 1×10$^6$/ml and the cultures are assayed between days 13 and 15 at E:T ratios of 30, 10, 3 and 1:1 in the $^{51}$Cr release assay or at 1×10$^6$/ml in the in situ IFNγ assay using the same targets as before the expansion.

Cultures are expanded in the absence of anti-CD3$^+$ as follows. Those cultures that demonstrate specific lytic activity against peptide and endogenous targets are selected and 5×10$^4$ CD8$^+$ cells are added to a T25 flask containing the following: 1×10⁶ autologous PBMC per ml which have been peptide-pulsed with 10 µg/ml peptide for two hours at 37° C. and irradiated (4,200 rad); 2×10⁵ irradiated (8,000 rad) EBV-transformed cells per ml RPMI-1640 containing 10%(v/v) human AB serum, non-essential AA, sodium pyruvate, 25 mM 2-ME, L-glutamine and gentamicin.

Immunogenicity of A2 Supermotif-Bearing Peptides

A2-supermotif cross-reactive binding peptides are tested in the cellular assay for the ability to induce peptide-specific CTL in normal individuals. In this analysis, a peptide is typically considered to be an epitope if it induces peptide-specific CTLs in at least individuals, and preferably, also recognizes the endogenously expressed peptide.

Immunogenicity can also be confirmed using PBMCs isolated from patients bearing a tumor that expresses 205P1B5. Briefly, PBMCs are isolated from patients, re-stimulated with peptide-pulsed monocytes and assayed for the ability to recognize peptide-pulsed target cells as well as transfected cells endogenously expressing the antigen.

Evaluation of A*03/A11 Immunogenicity

HLA-A3 supermotif-bearing cross-reactive binding peptides are also evaluated for immunogenicity using methodology analogous for that used to evaluate the immunogenicity of the HLA-A2 supermotif peptides.

Evaluation of B7 Immunogenicity

Immunogenicity screening of the B7-supertype cross-reactive binding peptides identified as set forth herein are confirmed in a manner analogous to the confirmation of A2-and A3-supermotif-bearing peptides.

Peptides bearing other supermotifs/motifs, e.g. HLA-A1, HLA-A24 etc. are also confirmed using similar methodology Example 13

Implementation of the Extended Supermotif to Improve the Binding Capacity of Native Epitopes by Creating Analogs HLA motifs and supermotifs (comprising primary and/or secondary residues) are useful in the identification and preparation of highly cross-reactive native peptides, as demonstrated herein. Moreover, the definition of HLA motifs and supermotifs also allows one to engineer highly cross-reactive epitopes by identifying residues within a native peptide sequence which can be analoged to confer upon the peptide certain characteristics, e.g. greater cross-reactivity within the group of HLA molecules that comprise a supertype, and/or greater binding affinity for some or all of those HLA molecules. Examples of analoging peptides to exhibit modulated binding affinity are set forth in this example.

Analoging at Primary Anchor Residues

Peptide engineering strategies are implemented to further increase the cross-reactivity of the epitopes. For example, the main anchors of A2-supermotif-bearing peptides are altered, for example, to introduce a preferred L, I, V, or M at position 2, and I or V at the C-terminus.

To analyze the cross-reactivity of the analog peptides, each engineered analog is initially tested for binding to the prototype A2 supertype allele A*0201, then, if A*0201 binding capacity is maintained, for A2-supertype cross-reactivity.

Alternatively, a peptide is confirmed as binding one or all supertype members and then analogued to modulate binding affinity to any one (or more) of the supertype members to add population coverage.

The selection of analogs for immunogenicity in a cellular screening analysis is typically further restricted by the capacity of the parent wild type (WT) peptide to bind at least weakly, i.e., bind at an $IC_{50}$ of 5000 nM or less, to three of more A2 supertype alleles. The rationale for this requirement is that the WT peptides must be present endogenously in sufficient quantity to be biologically relevant Analoged peptides have been shown to have increased immunogenicity and cross-reactivity by T cells specific for the parent epitope (see, e.g., Parkhurst et al., *J. Immunol.* 157:2539, 1996; and Pogue et al., *Proc. Natl. Acad. Sci. USA* 92:8166, 1995).

In the cellular screening of these peptide analogs, it is important to confirm that analog-specific CTLs are also able to recognize the wild-type peptide and, when possible, target cells that endogenously express the epitope.

Analoging of HLA-A3 and B7-Supermotif-Bearing Peptides

Analogs of HLA-A3 supermotif-bearing epitopes are generated using strategies similar to those employed in analoging HLA-A2 supermotif-bearing peptides. For example, peptides binding to 3/5 of the A3-supertype molecules are engineered at primary anchor residues to possess a preferred residue (V, S, M, or A) at position 2.

The analog peptides are then tested for the ability to bind A*03 and A*11 (prototype A3 supertype alleles). Those peptides that demonstrate≦500 nM binding capacity are then confirmed as having A3-supertype cross-reactivity.

Similarly to the A2- and A3-motif bearing peptides, peptides binding 3 or more B7-supertype alleles can be improved, where possible, to achieve increased cross-reactive binding or greater binding affinity or binding half life. B7 supermotif-bearing peptides are, for example, engineered to possess a preferred residue (V, I, L, or F) at the C-terminal primary anchor position, as demonstrated by Sidney et al. (*J. Immunol.* 157:3480-3490, 1996).

Analoging at primary anchor residues of other motif and/or supermotif-bearing epitopes is performed in a like manner.

The analog peptides are then be confirmed for immunogenicity, typically in a cellular screening assay. Again, it is generally important to demonstrate that analog-specific CTLs are also able to recognize the wild-type peptide and, when possible, targets that endogenously express the epitope.

Analoging at Secondary Anchor Residues

Moreover, HLA supermotifs are of value in engineering highly cross-reactive peptides and/or peptides that bind HLA molecules with increased affinity by identifying particular residues at secondary anchor positions that are associated with such properties. For example, the binding capacity of a B7 supermotif-bearing peptide with an F residue at position 1 is analyzed. The peptide is then analoged to, for example, substitute L for F at position 1. The analoged peptide is evaluated for increased binding affinity, binding half life and/or increased cross-reactivity. Such a procedure identifies analoged peptides with enhanced properties.

Engineered analogs with sufficiently improved binding capacity or cross-reactivity can also be tested for immunogenicity in HLA-B7-transgenic mice, following for example, IFA immunization or lipopeptide immunization. Analogued peptides are additionally tested for the ability to stimulate a recall response using PBMC from patients with 205P1B5-expressing tumors.

Other Analoging, Strategies

Another form of peptide analoging, unrelated to anchor positions, involves the substitution of a cysteine with α-amino butyric acid. Due to its chemical nature, cysteine has the propensity to form disulfide bridges and sufficiently alter the peptide structurally so as to reduce binding capacity. Substitution of α-amino butyric acid for cysteine not only alleviates this problem, but has been shown to improve binding and crossbinding capabilities in some instances (see, e.g., the review by Sette et al., In: Persistent Viral Infections, Eds. R Ahmed and I. Chen, John Wiley & Sons, England, 1999).

Thus, by the use of single amino acid substitutions, the binding properties and/or cross-reactivity of peptide ligands for HLA supertype molecules can be modulated.

Example 14

Identification and Confirmation of 205P1B5-Derived Sequences with HLA-DR Binding Motifs Peptide epitopes bearing an HLA class II supermotif or motif are identified and confirmed as outlined below using methodology similar to that described for HLA Class I peptides.

Selection of HLA-DR-Supermotif-Bearing Epitopes.

To identify 205P1B5-derived, HLA class II HTL epitopes, the 205P1B5 antigen is analyzed for the presence of sequences bearing an HLA-DR-motif or supermotif. Specifically, 15-mer sequences are selected comprising a DR-supermotif, comprising a 9-mer core, and three-residue N- and C-terminal flanking regions (15 amino acids total).

Protocols for predicting peptide binding to DR molecules have been developed (Southwood et al., *J. Immunol.* 160: 3363-3373, 1998). These protocols, specific for individual DR molecules, allow the scoring, and ranking, of 9-mer core regions. Each protocol not only scores peptide sequences for the presence of DR-supermotif primary anchors (i.e., at position 1 and position 6) within a 9-mer core, but additionally evaluates sequences for the presence of secondary anchors. Using allele-specific selection tables (see, e.g., Southwood et al., ibid.), it has been found that these protocols efficiently select peptide sequences with a high probability of binding a particular DR molecule. Additionally, it has been found that performing these protocols in tandem, specifically those for DR1, DR4w4, and DR7, can efficiently select DR cross-reactive peptides.

The 205P1B5-derived peptides identified above are tested for their binding capacity for various common HLA-DR molecules. All peptides are initially tested for binding to the DR molecules in the primary panel: DR1, DR4w4, and DR7. Peptides binding at least two of these three DR molecules are then tested for binding to DR2w2 β1, DR2w2 β2, DR6w19, and DR9 molecules in secondary assays. Finally, peptides binding at least two of the four secondary panel DR molecules, and thus cumulatively at least four of seven different DR molecules, are screened for binding to DR4w15, DR5w11, and DR8w2 molecules in tertiary assays. Peptides binding at least seven of the ten DR molecules comprising the primary, secondary, and tertiary screening assays are considered cross-reactive DR binders. 205P1B5-derived peptides found to bind common HLA-DR alleles are of particular interest.

Selection of DR3 Motif Peptides

Because HLA-DR3 is an allele that is prevalent in Caucasian, Black, and Hispanic populations, DR3 binding capacity is a relevant criterion in the selection of HTL epitopes. Thus, peptides shown to be candidates may also be assayed for their DR3 binding capacity. However, in view of the binding specificity of the DR3 motif, peptides binding only to DR3 can also be considered as candidates for inclusion in a vaccine formulation.

To efficiently identify peptides that bind DR3, target 205P1B5 antigens are analyzed for sequences carrying one of the two DR3-specific binding motifs reported by Geluk et al. (*J. Immunol.* 152:5742-5748, 1994). The corresponding peptides are then synthesized and confirmed as having the ability to bind DR3 with an affinity of 1 μM or better, i.e., less than 1 μM. Peptides are found that meet this binding criterion and qualify as HLA class II high affinity binders.

DR3 binding epitopes identified in this manner are included in vaccine compositions with DR supermotif-bearing peptide epitopes.

Similarly to the case of HLA class I motif-bearing peptides, the class II motif-bearing peptides are analoged to improve affinity or cross-reactivity. For example, aspartic acid at position 4 of the 9-mer core sequence is an optimal residue for DR3 binding, and substitution for that residue often improves DR 3 binding.

Example 15

Immunogenicity of 20SP1B5 Derived HTL Epitopes

This example determines immunogenic DR supermotif- and DR3 motif-bearing epitopes among those identified using the methodology set forth herein.

Immunogenicity of HTL epitopes are confirmed in a manner analogous to the determination of immunogenicity of CTL epitopes, by assessing the ability to stimulate HTL responses and/or by using appropriate transgenic mouse models. Immunogenicity is determined by screening for: 1.) in vitro primary induction using normal PBMC or 2.) recall responses from patients who have 205P1B5-expressing tumors.

Example 16

Calculation of Phenotypic Frequencies of HLA-Supertypes in Various Ethnic Backgrounds to Determine Breadth of Population Coverage This example illustrates the assessment of the breadth of population coverage of a vaccine composition comprised of multiple epitopes comprising multiple supermotifs and/or motifs.

In order to analyze population coverage, gene frequencies of HLA alleles are determined. Gene frequencies for each HLA allele are calculated from antigen or allele frequencies utilizing the binomial distribution formulae gf=1−(SQRT(1−af)) (see, e.g., Sidney et al. *Human Immunol.* 45:79-93, 1996). To obtain overall phenotypic frequencies, cumulative gene frequencies are calculated, and the cumulative antigen frequencies derived by the use of the inverse formula [af=1−(1−Cgf)$^2$].

Where frequency data is not available at the level of DNA typing, correspondence to the serologically defined antigen frequencies is assumed. To obtain total potential supertype population coverage no linkage disequilibrium is assumed, and only alleles confirmed to belong to each of the supertypes are included (minimal estimates). Estimates of total potential coverage achieved by inter-loci combinations are made by adding to the A coverage the proportion of the non-A covered population that could be expected to be covered by the B alleles considered (e.g., total=A+B*(1−A)). Confirmed members of the A3-like supertype are A3, A11, A31, A*3301, and A*6801. Although the A3-like supertype may also include A34, A66, and A*7401, these alleles were not included in overall frequency calculations. Likewise, confirmed members of the A2-like supertype family are A*0201, A*0202, A*0203, A*0204, A*0205, A*0206, A*0207, A*6802, and A*6901. Finally, the B7-like supertype-confirmed alleles are: B7, B*3501-03, B51, B*5301, B*5401, B*5501-2, B*5601, B*6701, and B*7801 (potentially also B*1401, B*3504-06, B*4201, and B*5602).

Population coverage achieved by combining the A2-, A3- and B7-supertypes is approximately 86% in five major ethnic groups. Coverage may be extended by including peptides bearing the A1 and A24 motifs. On average, A1 is present in 12% and A24 in 29% of the population across five different major ethnic groups (Caucasian, North American Black, Chinese, Japanese, and Hispanic). Together, these alleles are represented with an average frequency of 39% in these same ethnic populations. The total coverage across the major ethnicities when A1 and A24 are combined with the coverage of the A2-, A3- and B7-supertype alleles is>95%. An analogous approach can be used to estimate population coverage achieved with combinations of class II motif-bearing epitopes.

Immunogenicity studies in humans (e.g., Bertoni et al., *J. Clin. Invest.* 100:503, 1997; Doolan et al., *Immunity* 7:97, 1997; and Threlkeld et al., *J. Immunol.* 159:1648, 1997) have shown that highly cross-reactive binding peptides are almost always recognized as epitopes. The use of highly cross-reactive binding peptides is an important selection criterion in identifying candidate epitopes for inclusion in a vaccine that is immunogenic in a diverse population.

With a sufficient number of epitopes (as disclosed herein and from the art), an average population coverage is predicted to be greater than 95% in each of five major ethnic populations. The game theory Monte Carlo simulation analysis, which is known in the art (see e.g., Osborne, M. J. and Rubinstein, A. "A course in game theory" MIT Press, 1994), can be used to estimate what percentage of the individuals in a population comprised of the Caucasian, North American Black, Japanese, Chinese, and Hispanic ethnic groups would recognize the vaccine epitopes described herein. A preferred percentage is 90%. A more preferred percentage is 95%.

Example 17

CTL Recognition of Endogenously Processed Antigens After Priming

This example confirms that CTL induced by native or analoged peptide epitopes identified and selected as described herein recognize endogenously synthesized, i.e., native antigens.

Effector cells isolated from transgenic mice that are immunized with peptide epitopes, for example HLA-A2 supermotif-bearing epitopes, are re-stimulated in vitro using peptide-coated stimulator cells. Six days later, effector cells are assayed for cytotoxicity and the cell lines that contain peptide-specific cytotoxic activity are further re-stimulated. An additional six days later, these cell lines are tested for cytotoxic activity on $^{51}$Cr labeled Jurkat-A2.1/K$^b$ target cells in the absence or presence of peptide, and also tested on $^{51}$Cr labeled target cells bearing the endogenously synthesized antigen, i.e. cells that are stably transfected with 205P1B5 expression vectors.

The results demonstrate that CTL lines obtained from animals primed with peptide epitope recognize endogenously synthesized 205P1B5 antigen. The choice of transgenic mouse model to be used for such an analysis depends upon the epitope(s) that are being evaluated. In addition to HLA-A*0201/K$^b$ transgenic mice, several other transgenic mouse models including mice with human A11, which may also be used to evaluate A3 epitopes, and B7 alleles have been characterized and others (e.g. transgenic mice for HLA-A1 and A24) are being developed. HLA-DR1 and HLA-DR3 mouse models have also been developed, which may be used to evaluate HTL epitopes.

Example 18

Activity of CTL-HTL Conjugated Epitopes in Transgenic Mice

This example illustrates the induction of CTLs and HTLs in transgenic mice, by use of a 205P1B5-derived CTL and HTL peptide vaccine compositions. The vaccine composition used herein comprise peptides to be administered to a patient with a 205P1B5-expressing tumor. The peptide composition can comprise multiple CTL and/or HTL epitopes. The epitopes are identified using methodology as described herein. This example also illustrates that enhanced immunogenicity can be achieved by inclusion of one or more HTL epitopes in a CTL vaccine composition; such a peptide composition can comprise an HTL epitope conjugated to a CTL epitope. The CTL epitope can be one that binds to multiple HLA family members at an affinity of 500 nM or less, or analogs of that epitope. The peptides may be lipidated, if desired.

Immunization procedures:

Immunization of transgenic mice is performed as described (Alexander et al., *J. Immunol.* 159:4753-4761, 1997). For example, A2/K$^b$ mice, which are transgenic for the human HLA A2.1 allele and are used to confirm the immunogenicity of HLA-A*0201 motif- or HLA-A2 supermotif-bearing epitopes, and are primed subcutaneously (base of the tail) with a 0.1 ml of peptide in Incomplete Freund's Adjuvant, or if the peptide composition is a lipidated CTL/HTL conjugate, in DMSO/saline, or if the peptide composition is a polypeptide, in PBS or Incomplete Freund's Adjuvant Seven days after priming, splenocytes obtained from these animals are restimulated with syngenic irradiated LPS-activated lymphoblasts coated with peptide.

Cell Lines:

Target cells for peptide-specific cytotoxicity assays are Jurkat cells transfected with the HLA-A2.1/K$^b$ chimeric gene (e.g., Vitiello et al., *J. Exp. Med* 173:1007, 1991)

In Vitro CTL Activation:

One week after priming, spleen cells ($30 \times 10^6$ cells/flask) are co-cultured at 37° C. with syngeneic, irradiated (3000 rads), peptide coated lymphoblasts ($10 \times 10^6$ cells/flask) in 10 ml of culture medium/T25 flask. After six days, effector cells are harvested and assayed for cytotoxic activity.

Assay for Cytotoxic Activity:

Target cells (1.0 to $1.5 \times 10^6$) are incubated at 37° C. in the presence of 200 µl of $^{51}$Cr. After 60 minutes, cells are washed three times and resuspended in R10 medium. Peptide is added where required at a concentration of 1 µg/ml. For the assay, $10^4$ $^{51}$Cr-labeled target cells are added to different concentrations of effector cells (final volume of 200 µL) in U-bottom 96-well plates. After a six hour incubation period at 37° C., a 0.1 ml aliquot of supernatant is removed from each well and radioactivity is determined in a Micromedic automatic gamma counter. The percent specific lysis is determined by the formula: percent specific release=100×(experimental release−spontaneous release)/(maximum release−spontaneous release). To facilitate comparison between separate CTL assays run under the same conditions, % $^{51}$Cr release data is expressed as lytic units/$10^6$ cells. One lytic unit is arbitrarily defined as the number of effector cells required to achieve 30% lysis of 10,000 target cells in a six hour $^{51}$Cr release assay. To obtain specific lytic units/$10^6$, the lytic units/$10^6$ obtained in the absence of peptide is subtracted from the lytic units/$10^6$ obtained in the presence of peptide. For example, if 30% $^{51}$Cr release is obtained at the effector (E): target (7) ratio of 50:1 (i.e., $5\times10^5$ effector cells for 10,000 targets) in the absence of peptide and 5:1 (i.e., $5\times10^4$ effector cells for 10,000 targets) in the presence of peptide, the specific lytic units would be: $[(1/50,000)-(1/500,000)]\times10^6=18$ LU.

The results are analyzed to assess the magnitude of the CTL responses of animals injected with the immunogenic CTL/HTL conjugate vaccine preparation and are compared to the magnitude of the CTL response achieved using, for example, CTL epitopes as outlined above in the Example entitled "Confirmation of Immunogenicity". Analyses similar to this may be performed to confirm the immunogenicity of peptide conjugates containing multiple CTL epitopes and/or multiple HTL epitopes. In accordance with these procedures, it is found that a CTL response is induced, and concomitantly that an HTL response is induced upon administration of such compositions.

Example 19

Selection of CTL and HTL Epitopes for Inclusion in an 205P1B5-Specific Vaccine

This example illustrates a procedure for selecting peptide epitopes for vaccine compositions of the invention. The peptides in the composition can be in the form of a nucleic acid sequence, either single or one or more sequences (i.e., minigene) that encodes peptide(s), or can be single and/or polyepitopic peptides.

The following principles are utilized when selecting a plurality of epitopes for inclusion in a vaccine composition. Each of the following principles is balanced in order to make the selection.

Epitopes are selected which, upon administration, mimic immune responses that are correlated with 205P1B5 clearance. The number of epitopes used depends on observations of patients who spontaneously clear 205P1B5. For example, if it has been observed that patients who spontaneously clear 205P1B5 generate an immune response to at least three (3) from 205P1B5 antigen, then three or four (3-4) epitopes should be included for HLA class I. A similar rationale is used to determine HLA class II epitopes.

Epitopes are often selected that have a binding affinity of an $IC_{50}$ of 500 nM or less for an HLA class I molecule, or for class II, an $IC_{50}$ of 1000 nM or less; or HLA Class I peptides with high binding scores from the BIMAS web site, at URL bimas.dcrt.nih.gov/.

In order to achieve broad coverage of the vaccine through out a diverse population, sufficient supermotif bearing peptides, or a sufficient array of allele-specific motif bearing peptides, are selected to give broad population coverage. In one embodiment, epitopes are selected to provide at least 80% population coverage. A Monte Carlo analysis, a statistical evaluation known in the art can be employed to assess breadth, or redundancy, of population coverage.

When creating polyepitopic compositions, or a minigene that encodes same, it is typically desirable to generate the smallest peptide possible that encompasses the epitopes of interest. The principles employed are similar, if not the same, as those employed when selecting a peptide comprising nested epitopes. For example, a protein sequence for the vaccine composition is selected because it has maximal number of epitopes contained within the sequence, i.e., it has a high concentration of epitopes. Epitopes maybe nested or overlapping (i.e., frame shifted relative to one another). For example, with overlapping epitopes, two 9-mer epitopes and one 10-mer epitope can be present in a 10 amino acid peptide. Each epitope can be exposed and bound by an HLA molecule upon administration of such a peptide. A multi-epitopic, peptide can be generated synthetically, recombinantly, or via cleavage from the native source. Alternatively, an analog can be made of this native sequence, whereby one or more of the epitopes comprise substitutions that alter the cross-reactivity and/or binding affinity properties of the polyepitopic peptide. Such a vaccine composition is administered for therapeutic or prophylactic purposes. This embodiment provides for the possibility that an as yet undiscovered aspect of immune system processing will apply to the native nested sequence and thereby facilitate the production of therapeutic or prophylactic immune response-inducing vaccine compositions. Additionally such an embodiment provides for the possibility of motif-bearing epitopes for an HLA makeup that is presently unknown. Furthermore, this embodiment (absent the creating of any analogs) directs the immune response to multiple peptide sequences that are actually present in 205P1B5, thus avoiding the need to evaluate any junctional epitopes. Lastly, the embodiment provides an economy of scale when producing nucleic acid vaccine compositions. Related to this embodiment, computer programs can be derived in accordance with principles in the art, which identify in a target sequence, the greatest number of epitopes per sequence length A vaccine composition comprised of selected peptides, when administered, is safe, efficacious, and elicits an immune response similar in magnitude to an immune response that controls or clears cells that bear or overexpress 205P1B5.

Example 20

Construction of "Minigene" Multi-Epitope DNA Plasmids

This example discusses the construction of a minigene expression plasmid. Minigene plasmids may, of course, contain various configurations of B cell CTL and/or HTL epitopes or epitope analogs as described herein.

A minigene expression plasmid typically includes multiple CTL and HTL peptide epitopes. In the present example, HLA-A2, -A3,-B7 supermotif-bearing peptide epitopes and HLA-A1 and -A24 motif-bearing peptide epitopes are used in conjunction with DR supermotif-bearing epitopes and/or DR3 epitopes. HLA class I supermotif or motif-bearing peptide epitopes derived 205P1B5, are selected such that multiple supermotifs/motifs are represented to ensure broad population coverage. Similarly, HLA class II epitopes are selected from 205P1B5 to provide broad population coverage, i.e. both HLA DR-1-4-7 supermotif-bearing epitopes and HLA DR-3 motif-bearing epitopes are selected for inclusion in the minigene construct. The selected CTL and HTL epitopes are then incorporated into a minigene for expression in an expression vector.

Such a construct may additionally include sequences that direct the HTL epitopes to the endoplasmic reticulum. For example, the Ii protein may be fused to one or more HTL epitopes as described in the art, wherein the CLIP sequence of the Ii protein is removed and replaced with an HLA class II epitope sequence so that HLA class II epitope is directed to the endoplasmic reticulum, where the epitope binds to an HLA class H molecules.

This example illustrates the methods to be used for construction of a minigene-bearing expression plasmid. Other expression vectors that may be used for minigene compositions are available and known to those of skill in the art The minigene DNA plasmid of this example contains a consensus Kozak sequence and a consensus murine kappa Ig-light chain signal sequence followed by CTL and/or HTL epitopes selected in accordance with principles disclosed herein. The sequence encodes an open reading frame fused to the Myc and His antibody epitope tag coded for by the pcDNA 3.1 Myc-His vector.

Overlapping oligonucleotides that can, for example, average about 70 nucleotides in length with 15 nucleotide overlaps, are synthesized and HPLC-purified, The oligonucleotides encode the selected peptide epitopes as well as appropriate linker nucleotides, Kozak sequence, and signal sequence. The final multiepitope minigene is assembled by extending the overlapping oligonucleotides in three sets of reactions using PCR A Perkin/Elmer 9600 PCR machine is used and a total of 30 cycles are performed using the following conditions: 95° C. for 15 sec, annealing temperature (5° below the lowest calculated Tm of each primer pair) for 30 sec, and 72° C. for 1 min.

For example, a minigene is prepared as follows. For a first PCR reaction, 5 µg of each of two oligonucleotides are annealed and extended: In an example using eight oligonucleotides, i.e., four pairs of primers, oligonucleotides 1+2, 3+4, 5+6, and 7+8 are combined in 100 µl reactions containing Pfu polymerase buffer (1×=10 mM KCL, 10 mM (NH4)$_2$SO$_4$, 20 mM Tris-chloride, pH 8.75, 2 mM MgSO$_4$, 0.1% Triton X-100, 100 µg/ml BSA), 0.25 mM each dNTP, and 2.5 U of Pfu polymerase. The full-length dimer products are gel-purified, and two reactions containing the product of 1+2 and 3+4, and the product of 5+6 and 7+8 are mixed, annealed, and extended for 10 cycles. Half of the two reactions are then mixed, and 5 cycles of annealing and extension carried out before flanking primers are added to amplify the full length product. The fill-length product is gel-purified and cloned into pCR-blunt (Invitrogen) and individual clones are screened by sequencing.

Example 21

The Plasmid Construct and the Degree to which it Induces Immunogenicity

The degree to which a plasmid construct, for example a plasmid constructed in accordance with the previous Example, is able to induce immunogenicity is confirmed in vitro by determining epitope presentation by APC following transduction or transfection of the APC with an epitope-expressing nucleic acid construct Such a study determines "antigenicity" and allows the use of human APC. The assay determines the ability of the epitope to be presented by the APC in a context that is recognized by a T cell by quantifying the density of epitope-HLA class I complexes on the cell surface. Quantitation can be performed by directly measuring the amount of peptide eluted from the APC (see, e.g., Sijts et al., J. Immunol. 156:683-692, 1996; Demotz et al., Nature 342:682-684, 1989); or the number of peptide-HLA class I complexes can be estimated by measuring the amount of lysis or lympholine release induced by diseased or transfected target cells, and then determining the concentration of peptide necessary to obtain equivalent levels of lysis or lympholine release (see, e.g., Kageyama et al., J. Immunol. 154:567-576, 1995).

Alternatively, immunogenicity is confirmed through in vivo injections into mice and subsequent in vitro assessment of CTL and HTL activity, which are analyzed using cytotoxicity and proliferation assays, respectively, as detailed e.g., in Alexander et al., Immunity 1:751-761, 1994.

For example, to confirm the capacity of a DNA minigene construct containing at least one HLA-A2 supermotif peptide to induce CTLs in vivo, HLA-A$_{2.1}$/K$^b$ transgenic mice, for example, are immunized intramuscularly with 100 µg of naked cDNA. As a means of comparing the level of CTLs induced by cDNA immunization, a control group of animals is also immunized with an actual peptide composition that comprises multiple epitopes synthesized as a single polypeptide as they would be encoded by the minigene.

Splenocytes from immunized animals are stimulated twice with each of the respective compositions (peptide epitopes encoded in the minigene or the polyepitopic peptide), then assayed for peptide-specific cytotoxic activity in a $^{51}$Cr release assay. The results indicate the magnitude of the CTL response directed against the A2-restricted epitope, thus indicating the in vivo immunogenicity of the minigene vaccine and polyepitopic vaccine.

It is, therefore, found that the minigene elicits immune responses directed toward the HLA-A2 supermotif peptide epitopes as does the polyepitopic peptide vaccine. A similar analysis is also performed using other HLA-A3 and HLA-B7 transgenic mouse models to assess CTL induction by HLA-A3 and HLA-B7 motif or supermotif epitopes, whereby it is also found that the minigene elicits appropriate immune responses directed toward the provided epitopes.

To confirm the capacity of a class II epitope-encoding minigene to induce HTLs in vivo, DR transgenic mice, or for those epitopes that cross react with the appropriate mouse MHC molecule, I-A$^b$-restricted mice, for example, are immunized intramuscularly with 100 µg of plasmid DNA. As a means of comparing the level of HTLs induced by DNA immunization, a group of control animals is also immunized with an actual peptide composition emulsified in complete Freund's adjuvant CD4+ T cells, i.e. HTLs, are purified from splenocytes of immunized animals and stimulated with each of the respective compositions (peptides encoded in the minigene). The HTL response is measured using a $^3$H-thymidine incorporation proliferation assay, (see, e.g., Alexander et al. Immunity 1:751-761, 1994). The results indicate the magnitude of the HTL response, thus demonstrating the in vivo immunogenicity of the minigene.

DNA minigenes, constructed as described in the previous Example, can also be confirmed as a vaccine in combination with a boosting agent using a prime boost protocol. The boosting agent can consist of recombinant protein (e.g., Barnett et al., Aids Res. and Human Retroviruses 14, Supplement 3:S299-S309, 1998) or recombinant vaccinia, for example, expressing a minigene or DNA encoding the complete protein of interest (see, e.g., Hanke et al., Vaccine 16:439-445, 1998; Sedegah et al., Proc. Natl. Acad. Sci. USA 95:7648-53, 1998; Hanke and McMichael, Immunol. Letters 66:177-181, 1999; and Robinson et al., Nature Med. 5:526-34, 1999).

For example, the efficacy of the DNA minigene used in a prime boost protocol is initially evaluated in transgenic mice. In this example, A2.1/K$^b$ transgenic mice are immunized IM with 100 µg of a DNA minigene encoding the immunogenic peptides including at least one HLA-A2 supermotif-bearing peptide. After an incubation period (ranging from 3-9 weeks), the mice are boosted IP with 10$^7$ pfu/mouse of a recombinant vaccinia virus expressing the same sequence encoded by the DNA minigene. Control mice are immunized with 100 µg of DNA or recombinant vaccinia without the minigene sequence, or with DNA encoding the minigene, but without the vaccinia boost. After an additional incubation period of two weeks, splenocytes from the mice are immediately assayed for peptide-specific activity in an ELISPOT assay. Additionally, splenocytes are stimulated in vitro with the A2-restricted peptide epitopes encoded in the minigene and recombinant vaccinia, then assayed for peptide-specific activity in an alpha, beta and/or gamma IFN ELISA.

It is found that the minigene utilized in a prime-boost protocol elicits greater immune responses toward the HLA-A2 supermotif peptides than with DNA alone. Such an analysis can also be performed using HLA-A11 or HLA-B7 transgenic mouse models to assess CTL induction by HLA-A3 or HLA-B7 motif or supermotif epitopes. The use of prime boost protocols in humans is described below in the Example entitled "Induction of CTL Responses Using a Prime Boost Protocol."

Example 22

Peptide Composition for Prophylactic Uses

Vaccine compositions of the present invention can be used to prevent 205P1B5 expression in persons who are at risk for tumors that bear this antigen. For example, a polyepitopic peptide epitope composition (or a nucleic acid comprising the same) containing multiple CTL and HTL epitopes such as those selected in the above Examples, which are also selected to target greater than 80% of the population, is administered to individuals at risk for a 205P1B5-associated tumor.

For example, a peptide-based composition is provided as a single polypeptide that encompasses multiple epitopes. The vaccine is typically administered in a physiological solution that comprises an adjuvant, such as Incomplete Freunds Adjuvant. The dose of peptide for the initial immunization is from about 1 to about 50,000 µg, generally 100-5,000 µg, for a 70 kg patient. The initial administration of vaccine is followed by booster dosages at 4 weeks followed by evaluation of the magnitude of the immune response in the patient, by techniques that determine the presence of epitope-specific CTL populations in a PBMC sample. Additional booster doses are administered as required. The composition is found to be both safe and efficacious as a prophylaxis against 205P1B5-associated disease.

Alternatively, a composition typically comprising transfecting agents is used for the administration of a nucleic acid-based vaccine in accordance with methodologies known in the art and disclosed herein.

Example 23

Polyepitopic Vaccine Compositions Derived from Native 205P1B5 Sequences

A native 205P1B5 polyprotein sequence is analyzed, preferably using computer algorithms defined for each class I and/or class II supermotif or motif, to identify "relatively short" regions of the polyprotein that comprise multiple epitopes. The "relatively short" regions are preferably less in length than an entire native antigen. This relatively short sequence that contains multiple distinct or overlapping, "nested" epitopes is selected; it can be used to generate a minigene construct The construct is engineered to express the peptide, which corresponds to the native protein sequence. The "relatively short" peptide is generally less than 250 amino acids in length, often less than 100 amino acids in length, preferably less than 75 amino acids in length, and more preferably less than 50 amino acids in length. The protein sequence of the vaccine composition is selected because it has maximal number of epitopes contained within the sequence, i.e., it has a high concentration of epitopes. As noted herein, epitope motifs may be nested or overlapping (i.e., frame shifted relative to one another). For example, with overlapping epitopes, two 9-mer epitopes and one 10 mer epitope can be present in a 10 amino acid peptide. Such a vaccine composition is administered for therapeutic or prophylactic purposes.

The vaccine composition will include, for example, multiple CTL epitopes from 205P1B5 antigen and at least one HTL epitope. This polyepitopic native sequence is administered either as a peptide or as a nucleic acid sequence which encodes the peptide. Alternatively, an analog can be made of this native sequence, whereby one or more of the epitopes comprise substitutions that alter the cross-reactivity and/or binding affinity properties of the polyepitopic peptide.

The embodiment of this example provides for the possibility that an as yet undiscovered aspect of immune system processing will apply to the native nested sequence and thereby facilitate the production of therapeutic or prophylactic immune response-inducing vaccine compositions. Additionally such an embodiment provides for the possibility of motif-bearing epitopes for an HLA makeup that is presently unknown. Furthermore, this embodiment (excluding an analoged embodiment) directs the immune response to multiple peptide sequences that are actually present in native 205P1B5, thus avoiding the need to evaluate any junctional epitopes. Lastly, the embodiment provides an economy of scale when producing peptide or nucleic acid vaccine compositions.

Related to this embodiment, computer programs are available in the art which can be used to identify in a target sequence, the greatest number of epitopes per sequence length.

Example 24

Polyepitopic Vaccine Compositions from Multiple Antigens

The 205P1B5 peptide epitopes of the present invention are used in conjunction with epitopes from other target tumor-associated antigens, to create a vaccine composition that is useful for the prevention or treatment of cancer that expresses 205P1B5 and such other antigens. For example, a vaccine composition can be provided as a single polypeptide that incorporates multiple epitopes from 205P1B5 as well as tumor-associated antigens that are often expressed with a target cancer associated with 205P1B5 expression, or can be administered as a composition comprising a cocktail of one or more discrete epitopes. Alternatively, the vaccine can be administered as a minigene construct or as dendritic cells which have been loaded with the peptide epitopes in vitro.

Example 25

Use of Peptides to Evaluate an Immune Response

Peptides of the invention may be used to analyze an immune response for the presence of specific antibodies, CTL or HTL directed to 205P1B5. Such an analysis can be performed in a manner described by Ogg et al., Science 279: 2103-2106, 1998. In this Example, peptides in accordance with the invention are used as a reagent for diagnostic or prognostic purposes, not as an immunogen.

In this example highly sensitive human leukocyte antigen tetrameric complexes ("tetrames") are used for a cross-sectional analysis of, for example, 205P1B5 HLA-A*0201-specific CTL frequencies from HLA A*0201-positive individuals at different stages of disease or following immunization comprising an 205P1B5 peptide containing an A*0201 motif. Tetrameric complexes are synthesized as described (Musey et al., *N. Engl. J. Med.* 337:1267, 1997). Briefly, purified HLA heavy chain (A*0201 in this example) and β2-microglobulin are synthesized by means of a prokaryotic expression system. The heavy chain is modified by deletion of the transmembrane-cytosolic tail and COOH-terminal addition of a sequence containing a BirA enzymatic biotinylation site. The heavy chain, β2-microglobulin, and peptide are refolded by dilution. The 45-kD refolded product is isolated by fast protein liquid chromatography and then biotinylated by BirA in the presence of biotin (Sigma, St. Louis, Mo.), adenosine 5' triphosphate and magnesium. Streptavidin-phycoerythrin conjugate is added in a 1:4 molar ratio, and the tetrameric product is concentrated to 1 mg/ml. The resulting product is referred to as tetramer-phycoerythrin.

For the analysis of patient blood samples, approximately one million PBMCs are centrifuged at 300 g for 5 minutes and resuspended in 50 μl of cold phosphate-buffered saline. Tricolor analysis is performed with the tetramer-phycoerythrin, along with anti-CD8-Tricolor, and anti-CD38. The PBMCs are incubated with tetramer and antibodies on ice for 30 to 60 min and then washed twice before formaldehyde fixation. Gates are applied to contain>99.98% of control samples. Controls for the tetramers include both A*0201-negative individuals and A*0201-positive non-diseased donors. The percentage of cells stained with the tetramer is then determined by flow cytometry. The results indicate the number of cells in the PBMC sample that contain epitope-restricted CTLs, thereby readily indicating the extent of immune response to the 205P1B5 epitope, and thus the status of exposure to 205P1B5, or exposure to a vaccine that elicits a protective or therapeutic response.

Example 26

Use of Peptide Epitopes to Evaluate Recall Responses

The peptide epitopes of the invention are used as reagents to evaluate T cell responses, such as acute or recall responses, in patients. Such an analysis may be performed on patients who have recovered from 205P1B5-associated disease or who have been vaccinated with an 205P1B5 vaccine.

For example, the class I restricted CTL response of persons who have been vaccinated may be analyzed. The vaccine may be any 205P1B5 vaccine. PBMC are collected from vaccinated individuals and HLA typed. Appropriate peptide epitopes of the invention that, optimally, bear supermotifs to provide cross-reactivity with multiple HLA supertype family members, are then used for analysis of samples derived from individuals who bear that HLA type.

PBMC from vaccinated individuals are separated on Ficoll-Histopaque density gradients (Sigma Chemical Co., St. Louis, Mo.), washed three times in HBSS (GIBCO Laboratories), resuspended in RPMI-1640 (GIBCO Laboratories) supplemented with L-glutamine (2 nM,) penicillin (50 μ/ml), streptomycin (50 μg/ml), and Hepes (10 mM) containing 10% heat-inactivated human AB serum (complete RPMI) and plated using microculture formats. A synthetic peptide comprising an epitope of the invention is added at 10 μg/ml to each well and HBV core 128-140 epitope is added at 1 μg/ml to each well as a source of T cell help during the first week of stimulation.

In the microculture format, $4 \times 10^5$ PBMC are stimulated with peptide in 8 replicate cultures in 96-well round bottom plate in 100 μl/well of complete RPMI. On days 3 and 10, 100 μl of complete RPMI and 20 U/ml final concentration of rIL-2 are added to each well. On day 7 the cultures are transferred into a 96-well flat-bottom plate and restimulated with peptide, rIL-2 and $10^5$ irradiated (3,000 rad) autologous feeder cells. The cultures are tested for cytotoxic activity on day 14. A positive CTL response requires two or more of the eight replicate cultures to display greater than 10% specific $^{51}$Cr release, based on comparison with non-diseased control subjects as previously described (Rehermann, et al., *Nature Med.* 2:1104,1108, 1996; Rehermann et al., *J. Clin. Invest.* 97:1655-1665, 1996; and Rehermann et al. *J. Clin. Invest.* 98:1432-1440, 1996).

Target cell lines are autologous and allogeneic EBV-transformed B-LCL that are either purchased from the American Society for Histocompatibility and Immunogenetics (ASHI, Boston, Mass.) or established from the pool of patients as described (Guilhot, et al. *J. Virol.* 66:2670-2678, 1992).

Cytotoxicity assays are performed in the following manner. Target cells consist of either allogeneic HLA-matched or autologous EBV-transformed B lymphoblastoid cell lane that are incubated overnight with the synthetic peptide epitope of the invention at 10 μM, and labeled with 100 μCi of $^{51}$Cr (Amersham Corp., Arlington Heights, Ill.) for 1 hour after which they are washed four times with HBSS.

Cytolytic activity is determined in a standard 4-h, split well $^{51}$Cr release assay using U-bottomed 96 well plates containing 3,000 targets/well. Stimulated PBMC are tested at effector/target (E/T) ratios of 20-50:1 on day 14. Percent cytotoxicity is determined from the formula: 100×[(experimental release−spontaneous release)/maximum release−spontaneous release)]. Maximum release is determined by lysis of targets by detergent (2% Triton X-100; Sigma Chemical Co., St. Louis, Mo.). Spontaneous release is<25% of maximum release for all experiments.

The results of such an analysis indicate the extent to which HLA-restricted CTL populations have been stimulated by previous exposure to 205P1B5 or an 205P1B5 vaccine.

Similarly, Class II restricted HTL responses may also be analyzed. Purified PBMC are cultured in a 96-well flat bottom plate at a density of $1.5 \times 10^5$ cells/well and are stimulated with 10 μg/ml synthetic peptide of the invention, whole 205P1B5 antigen, or PHA. Cells are routinely plated in replicates of 4-6 wells for each condition. After seven days of culture, the medium is removed and replaced with fresh medium containing 10 U/ml IL-2. Two days later, 1 μCi $^3$H-thymidine is added to each well and incubation is continued for an additional 18 hours. Cellular DNA is then harvested on glass fiber mats and analyzed for $^3$H-thymidine incorporation. Antigen-specific T cell proliferation is calculated as the ratio of $^3$H-thymidine incorporation in the presence of antigen divided by the $^3$H-thymidine incorporation in the absence of antigen.

Example 27

Induction of Specific CTL Response In Humans

A human clinical trial for an immunogenic composition comprising CTL and HTL epitopes of the invention is set up as an IND Phase I, dose escalation study and carried out as a randomized, double-blind, placebo-controlled trial. Such a trial is designed, for example, as follows:

A total of about 27 individuals are enrolled and divided into 3 groups:

Group I: 3 subjects are injected with placebo and 6 subjects are injected with 5 µg of peptide composition;

Group II: 3 subjects are injected with placebo and 6 subjects are injected with 50 µg peptide composition;

Group III: 3 subjects are injected with placebo and 6 subjects are injected with 500 µg of peptide composition.

After 4 weeks following the first injection, all subjects receive a booster inoculation at the same dosage.

The endpoints measured in this study relate to the safety and tolerability of the peptide composition as well as its immunogenicity. Cellular immune responses to the peptide composition are an index of the intrinsic activity of this the peptide composition, and can therefore be viewed as a measure of biological efficacy. The following summarize the clinical and laboratory data that relate to safety and efficacy endpoints.

Safety:

The incidence of adverse events is monitored in the placebo and drug treatment group and assessed in terms of degree and reversibility.

Evaluation of Vaccine Efficacy:

For evaluation of vaccine efficacy, subjects are bled before and after injection. Peripheral blood mononuclear cells are isolated from fresh heparinized blood by Ficoll-Hypaque density gradient centrifugation, aliquoted in freezing media and stored frozen. Samples are assayed for CTL and HTL activity.

The vaccine is found to be both safe and efficacious.

Example 28

Phase II Trials in Patients Expressing 205P1B5

Phase II trials are performed to study the effect of administering the CTL-HTL peptide compositions to patients having cancer that expresses 205P1B5. The main objectives of the trial are to determine an effective dose and regimen for inducing CTLs in cancer patients that express 205P1B5, to establish the safety of inducing a CTL and HTL response in these patients, and to see to what extent activation of CTLs improves the clinical picture of these patients, as manifested, e.g., by the reduction and/or shrinking of lesions. Such a study is designed, for example, as follows:

The studies are performed in multiple centers. The trial design is an open-label, uncontrolled, dose escalation protocol wherein the peptide composition is administered as a single dose followed six weeks later by a single booster shot of the same dose. The dosages are 50, 500 and 5,000 micrograms per injection. Drug-associated adverse effects (severity and reversibility) are recorded.

There are three patient groupings. The first group is injected with 50 micrograms of the peptide composition and the second and third groups with 500 and 5,000 micrograms of peptide composition, respectively. The patients within each group range in age from 21-65 and represent diverse ethnic backgrounds. All of them have a tumor that expresses 205P1B5.

Clinical manifestations or antigen-specific T-cell responses are monitored to assess the effects of administering the peptide compositions. The vaccine composition is found to be both safe and efficacious in the treatment of 205P1B5-associated disease.

Example 29

Induction of CTL Responses Using a Prime Boost Protocol

A prime boost protocol similar in its underlying principle to that used to confirm the efficacy of a DNA vaccine in transgenic mice, such as described above in the Example entitled "The Plasmid Construct and the Degree to Which It Induces Immunogenicity," can also be used for the administration of the vaccine to humans. Such a vaccine regimen can include an initial administration of, for example, naked DNA followed by a boost using recombinant virus encoding the vaccine, or recombinant protein/polypeptide or a peptide mixture administered in an adjuvant.

For example, the initial immunization may be performed using an expression vector, such as that constructed in the Example entitled "Construction of 'Minigene' Multi-Epitope DNA Plasmids" in the form of naked nucleic acid administered IM (or SC or ID) in the amounts of 0.5-5 mg at multiple sites. The nucleic acid (0.1 to 1000 µg) can also be administered using a gene gun. Following an incubation period of 3-4 weeks, a booster dose is then administered. The booster can be recombinant fowlpox virus administered at a dose of $5–10^7$ to $5 \times 10^9$ pfu. An alternative recombinant virus, such as an MVA, canarypox, adenovirus, or adeno-associated virus, can also be used for the booster, or the polyepitopic protein or a mixture of the peptides can be administered. For evaluation of vaccine efficacy, patient blood samples are obtained before immunization as well as at intervals following administration of the initial vaccine and booster doses of the vaccine. Peripheral blood mononuclear cells are isolated from fresh heparinized blood by Ficoll-Hypaque density gradient centrifugation, aliquoted in freezing media and stored frozen. Samples are assayed for CTL and HTL activity.

Analysis of the results indicates that a magnitude of response sufficient to achieve a therapeutic or protective immunity against 205P1B5 is generated.

Example 30

Administration of Vaccine Compositions Using Dendritic Cells (DC)

Vaccines comprising peptide epitopes of the invention can be administered using APCs, or "professional" APCs such as DC. In this example, peptide-pulsed DC are administered to a patient to stimulate a CTL response in vivo. In this method, dendritic cells are isolated, expanded, and pulsed with a vaccine comprising peptide CTL and HTL epitopes of the invention. The dendritic cells are infused back into the patient to elicit CTL and HTL responses in vivo. The induced CTL and HTL then destroy or facilitate destruction, respectively, of the target cells that bear the 205P1B5 protein from which the epitopes in the vaccine are derived.

For example, a cocktail of epitope-comprising peptides is administered ex vivo to PBMC, or isolated DC therefrom. A pharmaceutical to facilitate harvesting of DC can be used, such as Progenipoietin™ (Monsanto, St. Louis, Mo.) or GM-CSF/IL-4. After pulsing the DC with peptides, and prior to reinfusion into patients, the DC are washed to remove unbound peptides.

As appreciated clinically, and readily determined by one of skill based on clinical outcomes, the number of DC reinfused into the patient can vary (see, e.g., *Nature Med.* 4:328, 1998; *Nature Med.* 2:52, 1996 and *Prostate* 32:272, 1997). Although 2–50×10$^6$ DC per patient are typically administered, larger number of DC, such as 10$^7$ or 10$^8$ can also be provided. Such cell populations typically contain between 50-90% DC.

In some embodiments, peptide-loaded PBMC are injected into patients without purification of the DC. For example, PBMC generated after treatment with an agent such as Progenipoietin™ are injected into patients without purification of the DC. The total number of PBMC that are administered often ranges from 10$^8$ to 10$^{10}$. Generally, the cell doses injected into patients is based on the percentage of DC in the blood of each patient, as determined, for example, by immunofluorescence analysis with specific anti-DC antibodies. Thus, for example, if Progenipoietin™ mobilizes 2% DC in the peripheral blood of a given patient, and that patient is to receive 5×10$^6$ DC, then the patient will be injected with a total of 2.5×10$^8$ peptide-loaded PBMC. The percent DC mobilized by an agent such as Progenipoietin™ is typically estimated to be between 2-10%, but can vary as appreciated by one of skill in the art.

Ex Vivo Activation of CTL/HTL Responses

Alternatively, ex vivo CTL or HTL responses to 205P1B5 antigens can be induced by incubating, in tissue culture, the patient's, or genetically compatible, CTL or HTL precursor cells together with a source of APC, such as DC, and immunogenic peptides. After an appropriate incubation time (typically about 7-28 days), in which the precursor cells are activated and expanded into effector cells, the cells are infused into the patient, where they will destroy (CTL) or facilitate destruction (HTL) of their specific target cells, i.e., tumor cells.

Example 31

An Alternative Method of Identifying and Confirming Motif-Bearing Peptides

Another method of identifying and confirming motif-bearing peptides is to elute them from cells bearing defined MHC molecules. For example, EBV transformed B cell lines used for tissue typing have been extensively characterized to determine which HLA molecules they express. la certain cases these cells express only a single type of HLA molecule. These cells can be transfected with nucleic acids that express the antigen of interest, e.g. 205P1B5. Peptides produced by endogenous antigen processing of peptides produced as a result of transfection will then bind to HLA molecules within the cell and be transported and displayed on the cell's surface. Peptides are then eluted from the HLA molecules by exposure to mild acid conditions and their amino acid sequence determined, e.g., by mass spectral analysis (e.g., Kubo et al., *J. Immunol.* 352:3913, 1994). Because the majority of peptides that bind a particular HLA molecule are motif-bearing, this is an alternative modality for obtaining the motif-bearing peptides correlated with the particular HLA molecule expressed on the cell.

Alternatively, cell lines that do not express endogenous HLA molecules can be transfected with an expression construct encoding a single HLA allele. These cells can then be used as described, i.e., they can then be transfected with nucleic acids that encode 205P1B5 to isolate peptides corresponding to 205P1B5 that have been presented on the cell surface. Peptides obtained from such an analysis will bear motif(s) that correspond to binding to the single HLA allele that is expressed in the cell.

As appreciated by one in the art, one can perform a similar analysis on a cell bearing more than one HLA allele and subsequently determine peptides specific for each HLA allele expressed. Moreover, one of skill would also recognize that means other than transfection, such as loading with a protein antigen, can be used to provide a source of antigen to the cell.

Example 32

Complementary Polynucleotides

Sequences complementary to the 205P1B5-encoding sequences, or any parts thereof, are used to detect, decrease, or inhibit expression of naturally occurring 205P1B5. Although use of oligonucleotides comprising from about 15 to 30 base pairs is described, essentially the same procedure is used with smaller or with larger sequence fragments. Appropriate oligonucleotides are designed using, e.g., OLIGO 4.06 software (National Biosciences) and the coding sequence of 205P1B5. To inhibit transcription, a complementary oligonucleotide is designed from the most unique 5' sequence and used to prevent promoter binding to the coding sequence. To inhibit translation, a complementary oligonucleotide is designed to prevent ribosomal binding to the 205P1B5-encoding transcript.

Example 33

Purification of Naturally-Occurring or Recombinant 205P1B5 Using 205P1B5 Specific Antibodies Naturally occurring or recombinant 205P1B5 is substantially purified by immunoaffinity chromatography using antibodies specific for 205P1B5. An immunoaffinity column is constructed by covalently coupling anti-205P1B5 antibody to an activated chromatographic resin, such as CNBr-activated SEPHAROSE (Amersham Pharmacia Biotech). After the coupling, the resin is blocked and washed according to the manufacturer's instructions.

Media containing 205P1B5 are passed over the immunoaffinity column, and the column is washed under conditions that allow the preferential absorbance of 205P1B5 (e.g., high ionic strength buffers in the presence of detergent). The column is eluted under conditions that disrupt antibody/205P1B5 binding (e.g., a buffer of pH 2 to pH 3, or a high concentration of a chaotrope, such as urea or thiocyanate ion), and GCRP is collected.

Example 34

Identification of Molecules which Interact with 205P1B5

205P1B5, or biologically active fragments thereof, are labeled with 121 1 Bolton-Hunter reagent. (See, e.g., Bolton et al. (1973) *Biochem. J.* 133:529.) Candidate molecules previously arrayed in the wells of a multi-well plate are incubated with the labeled 205P1B5, washed, and any wells with labeled 205P1B5 complex are assayed. Data obtained using different concentrations of 205P1B5 are used to calculate values for the number, affinity, and association of 205P1B5 with the candidate molecules.

Example 35

In Vivo Assay for 205P1B5 Tumor Growth Promotion

The effect of the 205P1B5 protein on tumor cell growth is evaluated in vivo by gene overexpression in tumor-bearing mice. For example, SCID mice are injected subcutaneously on each flank with $1 \times 10^6$ of either PC3, TSUPR1, or DU145 cells containing tkNeo empty vector or 205P1B5. At least two strategies may be used: (1) Constitutive 205P1B5 expression under regulation of a promoter such as a constitutive promoter obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), or from heterologous mammalian promoters, e.g., the actin promoter or an immunoglobulin promoter, provided such promoters are compatible with the host cell systems, and (2) Regulated expression under control of an inducible vector system, such as ecdysone, tet, etc., provided such promoters are compatible with the host cell systems. Tumor volume is then monitored at the appearance of palpable tumors and followed over time to determine if 205P1B5-expressing cells grow at a faster rate and whether tumors produced by 205P1B5-expressing cells demonstrate characteristics of altered aggressiveness (e.g. enhanced metastasis, vascularization, reduced responsiveness to chemotherapeutic drugs).

Additionally, mice can be implanted with $1 \times 10^5$ of the same cells orthotopically to determine if 205P1B5 has an effect on local growth in the prostate or on the ability of the cells to metastasize, specifically to lungs, lymph nodes, and bone marrow.

The assay is also useful to determine the 205P1B5 inhibitory effect of candidate therapeutic compositions, such as for example, 205P1B5 intrabodies, 205P1B5 antisense molecules and ribozymes.

Example 36

205P1B5 Monoclonal Antibody-Mediated Inhibition of Prostate Tumors In Vivo

The significant expression of 205P1B5, in cancer tissues, together with its restrictive expression in normal tissues along with its expected cell surface expression makes 205P1B5 an excellent target for antibody therapy. Similarly, 205P1B5 is a target for T cell-based immunotherapy. Thus, the therapeutic efficacy of anti-205P1B5 mAbs in human prostate cancer xenograft mouse models is evaluated by using androgen-independent LAPC4 and LAPC-9 xenograft (Craft, N., et al., Cancer Res, 1999. 59(19): p. 5030-6) and the androgen independent recombinant cell line PC3-205P1B5 (see, e.g., Kaighn, M E., et al., Invest. Urol, 1979. 17(1): p. 16-23).

Antibody efficacy on tumor growth and metastasis formation is studied, e.g., in a mouse orthotopic prostate cancer xenograft model. The antibodies can be unconjugated, as discussed in this Example, or can be conjugated to a therapeutic modality, as appreciated in the art. Anti-205P1B5 mAbs inhibit formation of both the androgen-dependent LAPC-9 and androgen-independent PC3-205P1B5 tumor xenografts. Anti-205P1B5 mAbs also retard the growth of established orthotopic tumors and prolonged survival of tumor-bearing mice. These results indicate the utility of anti-205P1B5 mAbs in the treatment of local and advanced stages of prostate cancer. (See, e.g., (Saffran, D., et al., PNAS 10:1073-1078 or world wide web URL pnas.org/cgi/doi/10.1073/pnas.051624698)

Administration of the anti-205P1B5 mAbs led to retardation of established orthotopic tumor growth and inhibition of metastasis to distant sites, resulting in a significant prolongation in the survival of tumor-bearing mice. These studies indicate that 205P1B5 as an attractive target for immunotherapy and demonstrate the therapeutic potential of anti-205P1B5 mAbs for the treatment of local and metastatic prostate cancer. This example demonstrates that unconjugated 205P1B5 monoclonal antibodies are effective to inhibit the growth of human prostate tumor xenografts grown in SCID mice; accordingly a combination of such efficacious monoclonal antibodies is also effective.

Tumor Inhibition Using Multiple Unconjugated 205P1B5 mAbs

Materials and Methods

205P1B5 Monoclonal Antibodies:

Monoclonal antibodies are raised against 205P1B5 as described in the Example entitled "Generation of 205P1B5 Monoclonal Antibodies (mAbs)." The antibodies are characterized by ELISA, Western blot, FACS, and immunoprecipitation for their capacity to bind 205P1B5. Epitope mapping data for the anti-205P1B5 mAbs, as determined by ELISA and Western analysis, recognize epitopes on the 205P1B5 protein. Immunohistochemical analysis of prostate cancer tissues and cells with these antibodies is performed.

The monoclonal antibodies are purified from ascites or hybridoma tissue culture supernatants by Protein-G Sepharose chromatography, dialyzed against PBS, filter sterilized, and stored at −20° C. Protein determinations are performed by a Bradford assay (Bio-Rad, Hercules, Calif.). A therapeutic monoclonal antibody or a cocktail comprising a mixture of individual monoclonal antibodies is prepared and used for the treatment of mice receiving subcutaneous or orthotopic injections of LAPC-9 prostate tumor xenografts.

Prostate Cancer Xenografts and Cell Lines

The LAPC-9 xenograft, which expresses a wild-type androgen receptor and produces prostate-specific antigen (PSA), is passaged in 6- to 8-week-old male ICR-severe combined immunodeficient (SCID) mice (Taconic Farms) by s.c. trocar implant (Craft, N., et al., supra). Single-cell suspensions of LAPC-9 tumor cells are prepared as described in Craft, et al. The prostate carcinoma cell line PC3 (American Type Culture Collection) is maintained in DMEM supplemented with L-glutamine and 10% (vol/vol) FBS.

A PC3-205P1B5 cell population is generated by retroviral gene transfer as described in Hubert, R S., et al., STEAP: a prostate-specific cell-surface antigen highly expressed in human prostate tumors. Proc Natl Acad Sci USA, 1999. 96(25): p. 14523-8. Anti-205P1B5 staining is detected by using an FITC-conjugated goat anti-mouse antibody (Southern Biotechnology Associates) followed by analysis on a Coulter Epics-XL f low cytometer.

Xenograft Mouse Models.

Subcutaneous (s.c.) tumors are generated by injection of $1 \times 10^6$ LAPC-9, PC3, or PC3-205P1B5 cells mixed at a 1:1 dilution with Matrigel (Collaborative Research) in the right flank of male SCID mice. To test antibody efficacy on tumor formation, i.p. antibody injections are started on the same day as tumor-cell injections. As a control, mice are injected with either purified mouse IgG (ICN) or PBS; or a purified monoclonal antibody that recognizes an irrelevant antigen not expressed in human cells. In preliminary studies, no difference is found between mouse IgG or PBS on tumor growth. Tumor sizes are determined by vernier caliper measurements, and the tumor volume is calculated as length×width×height. Mice with s.c. tumors greater than 1.5 cm in diameter are sacrificed. PSA levels are determined by using a PSA ELISA kit (Anogen, Mississauga, Ontario). Circulating levels of anti-205P1B5 mAbs are determined by a capture ELISA kit (Bethyl Laboratories, Montgomery, Tex.). (See, e.g., (Saffran, D., et al., PNAS 10: 1073-1078 or world wide web URL pnas.org/cgi/doi/10.1073/pnas.051624698)

Orthotopic injections are performed under anesthesia by using ketamine/xylazine. An incision is made through the abdominal muscles to expose the bladder and seminal vesicles, which then are delivered through the incision to expose the dorsal prostate. LAPC-9 cells ($5\times10^5$) mixed with Matrigel are injected into each dorsal lobe in a 10-μl volume. To monitor tumor growth, mice are bled on a weekly basis for determination of PSA levels. Based on the PSA levels, the mice are segregated into groups for the appropriate treatments. To test the effect of anti-205P1B5 mAbs on established orthotopic tumors, i.p. antibody injections are started when PSA levels reach 2-80 ng/ml.

Anti-205P1B5 mAbs Inhibit Growth of 205P1B5-Expressing Prostate-Cancer Tumors

The effect of anti-205P1B5 mAbs on tumor formation is tested by using the LAPC-9 orthotopic model. As compared with the s.c. tumor model, the orthotopic model, which requires injection of tumor cells directly in the mouse prostate, results in a local tumor growth, development of metastasis in distal sites, deterioration of mouse health, and subsequent death (Saffran, D., et al., PNAS supra; Fu, X., et al., Int J. Cancer, 1992. 52(6): p. 987-90; Kubota, T., J. Cell Biochem, 1994. 56(1): p. 4-8). The features make the orthotopic model more representative of human disease progression and allowed us to follow the therapeutic effect of mAbs on clinically relevant end points.

Accordingly, LAPC-9 tumor cells are injected into the mouse prostate, and 2 days later, the mice are segregated into two groups and treated with either: a) 50-2000 μg, usually 200-500 μg, of anti-205P1B5 Ab, or b) PBS three times per week for two to five weeks. Mice are monitored weekly for circulating PSA levels as an indicator of tumor growth.

A major advantage of the orthotopic prostate-cancer model is the ability to study the development of metastases. Formation of metastasis in mice bearing established orthotopic tumors is studies by IHC analysis on lung sections using an antibody against a prostate-specific cell-surface protein STEAP expressed at high levels in LAPC-9 xenografts (Hubert, R. S., et al., Proc Natl Acad Sci USA, 1999. 96(25): p. 14523-8).

Mice bearing established orthotopic LAPC-9 tumors are administered 1000 μg injections of either anti-205P1B5 mAb or PBS over a 4-week period. Mice in both groups are allowed to establish a high tumor burden (PSA levels greater than 300 ng/ml), to ensure a high frequency of metastasis formation in mouse lungs. Mice then are killed and their prostate and lungs are analyzed for the presence of LAPC-9 cells by anti-STEAP IHC analysis.

These studies demonstrate a broad anti-tumor efficacy of anti-205P1B5 antibodies on initiation and progression of prostate cancer in xenograft mouse models. Anti-205P1B5 antibodies inhibit tumor formation of both androgen-dependent and androgen-independent tumors as well as retarding the growth of already established tumors and prolong the survival of treated mice. Moreover, anti-205P1B5 mAbs demonstrate a dramatic inhibitory effect on the spread of local prostate tumor to distal sites, even in the presence of a large tumor burden. Thus, anti-205P1B5 mAbs are efficacious on major clinically relevant end points/PSA levels (tumor growth), prolongation of survival, and health.

Example 37

Comparison of 205P1B5 to Known Genes

205P1B5 is a 529 amino acid protein with a calculated MW of 59.7 kDa, and pI of 5.69. As shown in FIG. 4, 205P1B5 shows 100% identity to the human cholinergic receptor, nicotinic, alpha polypeptide 2 (gi:12734121). 205P1B5 is predicted to be a cell surface protein that functions as an ion transporter (Vizi E S and Lendvai B. Brain Res Brain Res Rev. 1999, 30:219; Shao Z and Yakel J. L. J. Physiol. 2000, 527: 507). As described by Vizi et Lendvai nicotinic acetylcholine receptors participates in calcium and sodium signaling in both synaptic and non-synaptic locations (Vizi E S and Lendvai B. Brain Res Brain Res Rev. 1999, 30:219). The expression of nicotinic cholinergic receptors has been documented in small cell lung cancer, where they are functionally active and induce calcium flux in response to stimuli (Codignola A et al., FEBS Lett. 1994, 342:286). Thus, substances that modulate the presence or effect of cholinergic receptors are used for diagnosis, prophylaxis, prognosis and/or treatment of a disease condition disclosed herein, such as a cancer listed in Table I.

Example 38

Identification of Potential Signal Transduction Pathways

Many mammalian proteins have been reported to interact with signaling molecules and to participate in, regulating signaling pathways (J Neurochem. 2001; 76:217-223). Using immunoprecipitation and Western blotting techniques, proteins are identified that associate with 205P1B5 and mediate signaling events. Several pathways known to play a role in cancer biology can be regulated by several of these genes, including phospholipid pathways such as P13K, AKT, etc., adhesion and migration pathways, including FAK, Rho, Rac-1, etc., as well as mitogenic/survival cascades such as ERK, p38, etc. (Cell Growth Differ. 2000,11:279; J. Biol. Chem. 1999,274:801; Oncogene 2000, 19:3003,J. Cell Biol. 1997, 138:913.). Using Western blotting techniques, the ability of 205P1B5 to regulate these pathways is examined. Cells expressing 205P1B5 and cells lacking these genes are either left untreated or stimulated with ions, channel activators, or antibodies. Cell lysates are analyzed using anti-phospho-specific antibodies (Cell Signaling, Santa Cruz Biotechnology) in order to detect phosphorylation and regulation of ERK, p38, AKT, P13K, PLC and other signaling molecules, When 205P1B5 plays a role in the regulation of signaling pathways, whether individually or communally, it is used as a target for diagnostic, preventative and therapeutic purposes.

To confirm that 205P1B5 directly or indirectly activates known signal transduction pathways in cells, luciferase (luc) based transcriptional reporter assays are carried out in cells expressing individual genes. These transcriptional reporters contain consensus-binding sites for known transcription factors that lie downstream of well-characterized signal transduction pathways. The reporters and examples of these associated transcription factors, signal transduction pathways, and activation stimuli are listed below.

1. NFkB-luc, NFkB/Rel; Ik-kinase/SAPK; growth/apoptosis/stress
2. SRE-luc, SRF/TCF/ELK1; MAPK/SAPK; growth/differentiation
3. AP-1-luc, FOS/JUN; MAPK/SAPK/PKC; growth/apoptosis/stress
4. ARE-luc, androgen receptor; steroids/MAPK; growth/differentiation/apoptosis
5. p53-luc, p53; SAPK; growth/differentiation/apoptosis
6. CRE-luc, CREB/ATF2; PKA/p38; growth/apoptosis/stress Gene-mediated effects are assayed in cells showing mRNA expression. Luciferase reporter plasmids can be introduced by lipid-mediated transfection (TFX-50, Promega). Luciferase activity, an indicator of relative transcriptional activity, is measured by incubation of cell extracts with luciferin substrate and luminescence of the reaction is monitored in a luminometer. Signaling pathways activated by 205P1B5 are mapped and used for the identification and validation of therapeutic targets. When these genes are involved in cell signaling, they are used as targets for diagnostic, preventative and therapeutic purposes.

Example 39

Involvement in Tumor Progression

205P1B5 can contribute to the growth of cancer cells. The role of 205P1B5 in tumor growth is investigated in a variety of primary and transfected cell lines including prostate, colon, bladder and kidney cell lines as well as NIH 3T3 cells engineered to stably express 205P1B5. Parental cells lacking our 205P1B5 and cells expressing the gene are evaluated for cell growth using a well-documented proliferation assay (Fraser S P, Grimes J. A, Djamgoz M B. Prostate. 2000;44:61, Johnson D E, Ochieng J, Evans S L. Anticancer Drugs. 1996, 7:288). The proliferation of control 3T3 and 3T3-205P1B5 were compared using an Alamar blue assay. Control and 205P1B5 expressing cells were grown in 0.5% or 10% FBS and analyzed after 48 and 72 hours. As shown in FIG. 16, expression of 205P1B5 enhanced the proliferation of NIH 3T3 cells stably expressing 205P1B5. These results indicate that 205P1B5 plays a critical role in tumor cell growth To confirm the role of 205P1B5 in the transformation process, the effect of 205P1B5 in colony forming assays is evaluated. Parental NIH3T3 cells lacking 205P1B5 are compared to NIH-3T3 cells expressing 205P1B5, using a soft agar assay under stringent and more permissive conditions (Song Z. et al. Cancer Res. 2000; 60:6730). It is found that 205P1B5 causes cellular transformation.

To confirm the role of 205P1B5 in invasion and metastasis of cancer cells, a well-established Transwell Insert System assay (Becton Dickinson) (Cancer Res. 1999; 59:6010) is used. Control cells, including prostate, colon, bladder and kidney cell lines lacking 205P1B5 are compared to cells expressing 205P1B5. Cells are loaded with the fluorescent dye, calcein, and plated in the top well of the Transwell insert coated with a basement membrane analog. Invasion is determined by fluorescence of cells in the lower chamber relative to the fluorescence of the entire cell population. It is found that 205P1B5 causes invasion.

205P1B5 can also play a role in cell cycle and apoptosis. Parental cells and cells expressing 205P1B5 are compared for differences in cell cycle regulation using a well-established BrdU assay (Abdel-Malek Z A. J Cell Physiol. 1988, 136:247). In short, cells are grown under both optimal (full serum) and limiting (low serum) conditions are labeled with BrdU and stained with anti-BrdU Ab and propidiumn iodide. Cells are analyzed for entry into the G1, S, and G2M phases of the cell cycle. Alternatively, the effect of stress on apoptosis is evaluated in control parental cells and cells expressing genes under consideration, including normal and tumor prostate, colon and lung cells. Engineered and parental cells are treated with various chemotherapeutic agents, such as etoposide, flutamide, etc., and protein synthesis inhibitors, such as cycloheximide. Cells are stained with annexin V-FITC and cell death is measured by FACS analysis. It is found that 205P1B5 adversely affects cell cycling and apoptosis.

The function of 205P1B5 is evaluated using anti-sense RNA technology coupled to the various functional assays described above, e.g. growth, invasion and migration. Anti-sense RNA oligonucleotides can be introduced into 205P1B5 expressing cells, thereby preventing the expression of 205P1B5. Control and anti-sense containing cells are analyzed for proliferation, invasion, migration, apoptotic and transcriptional potential. The local as well as systemic effects of the loss of 205P1B5 expression are evaluated. It is found that 205P1B5 expression adversely impacts properties such as proliferation, invasion, migration, apoptosis and transcription.

When 205P1B5 plays a role in cell growth, transformation, invasion or apoptosis, it is used as a target for diagnostic, preventative and therapeutic purposes.

Example 40

Regulation of Transcription

Several ion transporters have been shown to play a role in transcriptional regulation of eukaryotic genes. Regulation of gene expression can be evaluated by studying gene expression in cells expressing or lacking 205P1B5. For this purpose, two types of experiments are performed. In the first set of experiments, RNA from parental and gene-expressing cells are extracted and hybridized to commercially available gene arrays (Clontech) (Smid-Koopman, E, et al. Br. J. Cancer 2000 83:246). Resting cells as well as cells treated with ions, FBS or androgen are compared. Differentially expressed genes are identified in accordance with procedures known in the art. The differentially expressed genes are then mapped to biological pathways (see, e.g., Chen K et al. Thyroid. 2001. 11:41.).

In the second set of experiments, specific transcriptional pathway activation is evaluated using commercially available (Stratagene) luciferase reporter constructs including: NFkB-luc, SRE-luc, ELK1-luc, ARE-luc, p53-luc, and CRE-luc. These transcriptional reporters contain consensus binding sites for known transcription factors that lie downstream of well-characterized signal transduction pathways, and represent a good tool to ascertain pathway activation and screen for positive and negative modulators of pathway activation.

Thus, it is found that 205P1B5 adversely impacts gene regulation, and it is used as a target for diagnostic, prognostic, preventative and therapeutic purposes.

Example 41

Subcellular Localization and Cell Binding

Based on bioinformatic analysis and function, 205P1B5 is indicated to be located at the cell surface. The cellular location of 205P1B5 is confirmed using subcellular fractionation techniques widely used in cellular biology (Storrie B, et al. Methods Enzymol. 1990;182:203-25). A variety of cell lines, including prostate, kidney and bladder cell lines can be separated into nuclear, cytosolic and membrane fractions. Gene expression and location in nuclei, heavy membranes (lysosomes, peroxisomes, and mitochondria), light membranes (plasma membrane and endoplasmic reticulum), and soluble protein fractions are tested using Western blotting techniques.

Alternatively, 293T cells are transfected with an expression vector encoding 205P1B5 HIS-tagged (PCDNA 3.1 MYC/HIS, Invitrogen), and the subcellular localization of 205P1B5 is confirmed by immunofluorescence. Alternatively, the location of the HIS-tagged 205P1B5 is followed by Western blotting to confirm the cell surface localization When 205P1B5 is localized to specific subcellular locale, such as the cell surface, it is used as a target for diagnostic, preventative and therapeutic purposes as appreciated by one of ordinary skill in the art.

Example 42

Protein and Ion Transporter Function

Based on bioinformatic analysis, 205P1B5 is indicated to function as a transporter. To confirm that 205P1B5 functions as an ion channel, FACS analysis and electrophysiology techniques are used (Gergely L, Cook L, Agnello V. Clin Diagn Lab Immunol. 1997;4:70; Skryma R. et al. J. Physiol. 2000, 527: 71). Using FACS analysis and commercially available indicators (Molecular Probes), parental cells and cells expressing 205P1B5 are compared for their ability to transport calcium, sodium and potassium. Prostate, colon, bladder and kidney normal and tumor cell lines are used in these studies. For example cells loaded with calcium responsive indicators such as Fluo4 and Fura red are incubated in the presence or absence of ions and analyzed by flow cytometry.

Information derived from these procedures confirms important mechanisms by which cancer cells are regulated by 205P1B5. 205P1B5 regulates prostate cancer growth by regulating intracellular levels of calcium Of note, calcium channel inhibitors have been reported to induce the death of certain cancer cells, including prostate cancer cell lines (Batra S, Popper L D, Hartley-Asp B. Prostate. 1991,19: 299).

Using a modified rhodamine retention assay (Davies J. et al. Science 2000, 290:2295; Leith C et al. Blood 1995, 86:2329) it is confirmed that 205P1B5 functions as a protein transporter. Cell lines, such as prostate, colon, bladder and kidney cancer and normal cells, expressing or lacking 205P1B5 are loaded with Calcein AM (Molecular Probes). Cells are examined over time for dye transport using a fluorescent microscope or fluorometer. Quantitation is performed using a fluorometer (Hollo Z. et al., Biochim Biophys. Acta. 1994. 1191:384). Information obtained from such experiments determines that 205P1B5 serves to extrude chemotherapeutic drugs, such as doxorubicin, paclitaxel, etoposide, etc., from tumor cells, thereby lowering drug content and reducing tumor responsiveness to treatment. Such a system also determines that 205P1B5 functions in transporting small molecules.

When 205P1B5 functions as a transporter, it is used as a target for preventative, prognostic, diagnostic and/or therapeutic purposes as well as drug sensitivity/resistance.

Using electrophysiology, uninjected oocytes and oocytes injected with gene-specific cRNA are compared for ion channel activity. Patch/voltage clamp assays are performed on oocytes in the presence or absence of selected ions, including calcium, potassium sodium, etc. Ion channel activators (such as cAMP/GMP, forskolin, TPA, etc.) and inhibitors (such as calcicludine, conotoxin, TEA, tetrodotoxin, etc.) confirm that 205P1B5 functions as an ion channel (Schweitz H. et al. Proc. Natl. Acad. Sci. 1994. 91:878; Skryma R et al. Prostate. 1997. 33:112). Using similar techniques, it was recently demonstrated that hCaT induces calcium flux in 293T cells (Wissenbach, U., et al. J. Biol. Chem. 2001, 276: 19461). The magnitude of the flux shown in this paper was similar to the one observed in figure A, where hCaT was expressed in prostate cancer cells.

Thus, 205P1B5 functions as an ion channel, and it is used as a target for diagnostic, preventative, prognostic and therapeutic purposes.

Example 43

Involvement in Cell-Cell Communication

Cell-cell communication is essential in maintaining organ integrity and homeostasis, both of which become dysregulated during tumor formation and progression. Intercellular communications can be measured using two types of assays (J. Biol. Chem. 2000, 275:25207). In the first assay, cells loaded with a fluorescent dye are incubated in the presence of unlabeled recipient cells and the cell populations are examined under fluorescent microscopy. This qualitative assay measures the exchange of dye between adjacent cells. In the second assay system, donor and recipient cell populations are treated as above and quantitative measurements of the recipient cell population are performed by FACS analysis. Using these two assay systems, cells expressing or lacking 205P1B5 are compared and it is determined that 205P1B5 adversely impacts cellular communications. This assay also identifies small molecules and/or specific antibodies that modulate cell-cell communication.

Thus, 205P1B5 adversely impacts cell-cell communication, and it is used as a target for diagnostic, prognostics, preventative and therapeutic purposes.

Example 44

Protein-Protein Interaction

Several ion transporters have been shown to interact with other proteins, thereby forming a protein complex that can regulate ion transport, cell division, gene transcription, and cell transformation (Biochem Biophys Res Commun. 2000, 277: 61 1; J Biol Chem. 1999; 274: 20812). Using immunoprecipitation techniques as well as two yeast hybrid systems, proteins that associate with 205P1B5 are identified. Immunoprecipitates from cells expressing 205P1B5 and cells lacking 205P1B5 are compared for specific protein-protein associations. 205P1B5 may also associate with, for example, effector molecules, such as adaptor proteins, SNARE proteins, signaling molecules, syntaxins, ATPase subunits, etc. (3 Biol Chem. 1999; 274: 20812; Proc Natl Acad Sci USA 1998, 95:14523). Studies comparing 205P1B5 positive and 205P1B5 negative cells as well as studies comparing unstimulated/resting cells and cells treated with epithelial cell activators, such as cytokines, growth factors, androgen and anti-integrin Ab reveal unique interactions.

In addition, protein-protein interactions are confirmed using two yeast hybrid methodologies (see, e.g., Curr Opin Chem Biol. 1999, 3:64). A vector carrying a library of proteins fused to the activation domain of a transcription factor is introduced into yeast expressing a 205P1B5-DNA-binding domain fusion protein and a reporter construct. Protein-protein interaction is detected by colorimetric reporter activity. Specific association with effector molecules and transcription factors directs one of skill to the mode of action of 205P1B5, and thus identifies therapeutic, preventative and/or diagnostic targets for cancer. This and similar assays are also used to identify and screen for small molecules that interact with 205P1B5.

Thus, 205P1B5 associates with proteins or small molecules and is used as a target for diagnostic, prognostic, preventative and therapeutic purposes.

Example 45

Transcript Variants of 20SP1B5

Transcript variants are variants of matured mRNA from the same gene by alternative transcription or alternative splicing. Alternative transcripts are transcripts from the same gene but start transcription at different points. Splice variants are mRNA variants spliced differently from the same transcript In eukaryotes, when a multi-exon gene is transcribed from genomic DNA, the initial RNA is spliced to produce functional mRNA, which has only exons and is used for translation into an amino acid sequence. Accordingly, a given gene can have zero to many alternative transcripts and each transcript can have zero to many splice variants. Each transcript variant has a unique exon makeup, and can have different coding and/or non-coding (5' or 3' end) portions, from the original transcript. Transcript variants can code for similar or different proteins with the same or a similar function or may encode proteins with different functions, and may be expressed in the same tissue at the same time, or at different tissue, or at different times, proteins encoded by transcript variants can have similar or different cellular or extracellular localizations, i.e., be secreted.

Transcript variants are identified by a variety of art-accepted methods. For example, alternative transcripts and splice variants are identified in a full-length cloning experiment, or by use of full-length transcript and EST sequences. First, all human ESTs were grouped into clusters which show direct or indirect identity with each other. Second, ESTs in the same cluster were further grouped into sub-clusters and assembled into a consensus sequence. The original gene sequence is compared to the consensus sequence(s) or other full-length sequences. Each consensus sequence is a potential splice variant for that gene (see, e.g., Kan, Z., et al., Gene structure prediction and alternative splicing analysis using genomically aligned ESTs, Genome Research, 2001 May, 11(5):889-900). Even when a variant is identified that is not a full-length clone, that portion of the variant is useful for antigen generation and for further cloning of the full-length splice variant, using techniques known in the art.

Moreover, computer programs are available in the art that identify transcript variants based on genomic sequences. Genomic-based transcript variant identification programs include FgenesH (A. Salamov and V. Solovyev, "Ab initio gene finding in Drosophila genomic DNA," Genome Research. 2000 Apr. 10(4):516-22); Grail (world wide web URL //compbio.ornl.gov/Grail-bin/EmptyGrailForm) and GenScan (world wide web URL//genes.mit.edu/GENSCAN.html). For a general discussion of splice variant identification protocols see., e.g., Southan, C., A genomic perspective on human proteases, FEBS Lett. 2001 Jun. 8; 498(2-3):214-8; de Souza, S. J., et al., Identification of human chromosome 22 transcribed sequences with ORF expressed sequence tags, Proc. Natl Acad Sci USA. 2000 Nov. 7; 97(23):12690-3.

To further confirm the parameters of a transcript variant, a variety of techniques are available in the art, such as full-length cloning, proteomic validation, PCR-based validation, and 5' RACE validation, etc. (see e.g., Proteomic Validation: Brennan, S. O., et al., Albumin banks peninsula: a new termination variant characterized by electrospray mass spectrometry, Biochem Biophys Acta. 1999 Aug. 17;1433(1-2): 321-6; Ferranti P, et al., Differential splicing of pre-messenger RNA produces multiple forms of mature caprine alpha(s1)-casein, Eur J Biochem. 1997 Oct. 1;249(1):1-7. For PCR-based Validation: Wellmann S, et al., Specific reverse transcription-PCR quantification of vascular endothelial growth factor (VEGF) splice variants by LightCycler technology, Clin Chem. 2001 April; 47(4):654-60; Jia, H. P., et al., Discovery of new human beta-defensins using a genomics-based approach, Gene. 2001 Jan. 24; 263(1-2):211-8. For PCR-based and 5' RACE Validation: Brigle, K. E., et al., Organization of the murine reduced folate carrier gene and identification of variant splice forms, Biochem Biophys Acta. 1997 Aug. 7; 1353(2): 191-8).

It is known in the art that genomic regions are modulated in cancers. When the genomic region, to which a gene maps, is modulated in a particular cancer, the alternative transcripts or splice variants of the gene are modulated as well. Disclosed herein is that 205P1B5 has a particular expression profile related to cancer. Alternative transcripts and splice variants of 205P1B5 may also be involved in cancers in the same or different tissues, thus serving as tumor-associated markers/antigens.

Example 46

Singe Nucleotide Polymorphisms of 205P1B5

A Single Nucleotide Polymorphism (SNP) is a single base pair variation in nucleotide sequences. At a specific point of the genome, there are four possible nucleotide base pairs: A/T, C/G, G/C and T/A. Genotype refers to the base pair make-up of one or more spots in the genome of an individual, while haplotype refers to base pair make-up of more than one varied spots on the same DNA molecule (chromosome in higher organism). SNPs that occur on a cDNA are called cSNPs. These cSNPs may change amino acids of the protein encoded by the gene and thus change the functions of the protein. Some SNPs cause inherited diseases and some others, contribute to quantitative variations in phenotype and reactions to environmental factors including diet and drugs among individuals. Therefore, SNPs and/or combinations of alleles (called haplotypes) have many applications including diagnosis of inherited diseases, determination of drug reactions and dosage, identification of genes responsible for diseases and discovery of genetic relationship between individuals (P. Nowotny, 3. M. Kwon and A. M. Goate, "SNP analysis to dissect human traits," Curr. Opin. Neurobiol. 2001 Oct.; 11(5):637-641; M. Pirmohamed and B. K. Park, "Genetic susceptibility to adverse drug reactions," Trends Pharmacol. Sci. 2001 June; 22(6):298-305; J. H. Riley, C. J. Allan, E. Lai and A. Roses, "The use of single nucleotide polymorphisms in the isolation of common disease genes," Pharmacogenomics. 2000 February; 1(1):39-47; R. Judson, J. C. Stephens and A. Windemuth, "The predictive power of haplotypes in clinical response," Pharmacogenomics. 2000 February; 1(1):15-26).

SNPs are identified by a variety of art-accepted methods (P. Bean, "The promising voyage of SNP target discovery," Am. Clin. Lab. 2001 October-November; 20(9):18-20; K. M. Weiss, "In search of human variation," Genome Res. 1998 July; 8(7):691-697; M. M. She, "Enabling large-scale pharmacogenetic studies by high-throughput mutation detection and genotyping technologies," Clin. Chem. 2001 February;

47(2):164-172). For example, SNPs are identified by sequencing DNA fragments that show polymorphism by gel-based methods such as restriction fragment length polymorphism (RFLP) and denaturing gradient gel electrophoresis (DGGE). They can also be discovered by direct sequencing of DNA samples pooled from different individuals or by comparing sequences from different DNA samples. With the rapid accumulation of sequence data in public and private databases, one can discover SNPs by comparing sequences using computer programs (Z. Gu, L. Hillier and P. Y. Kwok, "Single nucleotide polymorphism hunting in cyberspace," Hum. Mutat. 1998; 12(4):221-225). SNPs can be verified and genotype or haplotype of an individual can be determined by a variety of methods including direct sequencing and high throughput microarrays (P. Y. Kwok, "Methods for genotyping single nucleotide polymorphisms,"Annu. Rev. Genomics Hum. Genet. 2001; 2:235-258; M. Kokoris, K. Dix, K. Moynihan, J. Mathis, B. Erwin, P. Grass, B. Hines and A. Duesterhoeft, "High-throughput SNP genotyping with the Masscode system," Mol. Diagn. 2000 December; 5(4):329-340).

Two variants are identified for 205P1B5. These are set forth in FIG. 2 and FIG. 3.

Throughout this application, various website data content, publications, patent applications and patents are referenced. (Websites are referenced by their Uniform Resource Locator, or URL, addresses on the World Wide Web.) The disclosures of each of these references are hereby incorporated by reference herein in their entireties.

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

TABLES

TABLE I: Tissues that Express 205P1B5 When Malignant Prostate

TABLE II

AMINO ACID ABBREVIATIONS

| SINGLE LETTER | THREE LETTER | FULL NAME |
|---|---|---|
| F | Phe | phenylalanine |
| L | Leu | leucine |
| S | Ser | serine |
| Y | Tyr | tyrosine |
| C | Cys | cysteine |
| W | Trp | tryptophan |
| P | Pro | proline |
| H | His | histidine |
| Q | Gln | glutamine |
| R | Arg | arginine |
| I | Ile | isoleucine |
| M | Met | methionine |
| T | Thr | threonine |
| N | Asn | asparagine |
| K | Lys | lysine |
| V | Val | valine |
| A | Ala | alanine |
| D | Asp | aspartic acid |
| E | Glu | glutamic acid |
| G | Gly | glycine |

TABLE III

AMINO ACID SUBSTITUTION MATRIX
Adapted from the GCG Software 9.0 BLOSUM62 amino acid substitution matrix (block substitution matrix). The higher the value, the more likely a substitution is found in related, natural proteins. (See world wide web URL ikp.unibe.ch/manual/blosum62.html)

| A | C | D | E | F | G | H | I | K | L | M | N | P | Q | R | S | T | V | W | Y | . |
|---|---|---|---|---|---|---|---|---|---|---|---|---|---|---|---|---|---|---|---|---|
| 4 | 0 | −2 | −1 | −2 | 0 | −2 | −1 | −1 | −1 | −1 | −2 | −1 | −1 | −1 | 1 | 0 | 0 | −3 | −2 | A |
|  | 9 | −3 | −4 | −2 | −3 | −3 | −1 | −3 | −1 | −1 | −3 | −3 | −3 | −3 | −1 | −1 | −1 | −2 | −2 | C |
|  |  | 6 | 2 | −3 | −1 | −1 | −3 | −1 | −4 | −3 | 1 | −1 | 0 | −2 | 0 | −1 | −3 | −4 | −3 | D |
|  |  |  | 5 | −3 | −2 | 0 | −3 | 1 | −3 | −2 | 0 | −1 | 2 | 0 | 0 | −1 | −2 | −3 | −2 | E |
|  |  |  |  | 6 | −3 | −1 | 0 | −3 | 0 | 0 | −3 | −4 | −3 | −3 | −2 | −2 | −1 | 1 | 3 | F |
|  |  |  |  |  | 6 | −2 | −4 | −2 | −4 | −3 | 0 | −2 | −2 | −2 | 0 | −2 | −3 | −2 | −3 | G |
|  |  |  |  |  |  | 8 | −3 | −1 | −3 | −2 | 1 | −2 | 0 | 0 | −1 | −2 | −3 | −2 | 2 | H |
|  |  |  |  |  |  |  | 4 | −3 | 2 | 1 | −3 | −3 | −3 | −3 | −2 | −1 | 3 | −3 | −1 | I |
|  |  |  |  |  |  |  |  | 5 | −2 | −1 | 0 | −1 | 1 | 2 | 0 | −1 | −2 | −3 | −2 | K |
|  |  |  |  |  |  |  |  |  | 4 | 2 | −3 | −3 | −2 | −2 | −2 | −1 | 1 | −2 | −1 | L |
|  |  |  |  |  |  |  |  |  |  | 5 | −2 | −2 | 0 | −1 | −1 | −1 | 1 | −1 | −1 | M |
|  |  |  |  |  |  |  |  |  |  |  | 6 | −2 | 0 | 0 | 1 | 0 | −3 | −4 | −2 | N |
|  |  |  |  |  |  |  |  |  |  |  |  | 7 | −1 | −2 | −1 | −1 | −2 | −4 | −3 | P |
|  |  |  |  |  |  |  |  |  |  |  |  |  | 5 | 1 | 0 | −1 | −2 | −2 | −1 | Q |
|  |  |  |  |  |  |  |  |  |  |  |  |  |  | 5 | −1 | −1 | −3 | −3 | −2 | R |
|  |  |  |  |  |  |  |  |  |  |  |  |  |  |  | 4 | 1 | −2 | −3 | −2 | S |
|  |  |  |  |  |  |  |  |  |  |  |  |  |  |  |  | 5 | 0 | −2 | −2 | T |
|  |  |  |  |  |  |  |  |  |  |  |  |  |  |  |  |  | 4 | −3 | −1 | V |
|  |  |  |  |  |  |  |  |  |  |  |  |  |  |  |  |  |  | 11 | 2 | W |
|  |  |  |  |  |  |  |  |  |  |  |  |  |  |  |  |  |  |  | 7 | Y |

TABLE IV A

| | POSITION 2 (Primary Anchor) | POSITION 3 (Primary Anchor) | POSITION C Terminus (Primary Anchor) |
|---|---|---|---|
| SUPERMOTIFS | | | |
| A1 | T I*LVMS* | | FWY |
| A2 | LIVM*ATQ* | | IV*MATL* |
| A3 | VSMA*TLI* | | RK |
| A24 | YF*WIVLMT* | | FI*YWLM* |
| B7 | P | | VILF*MWYA* |
| B27 | RHK | | FYL*WMIVA* |
| B44 | E*D* | | FWYLIMVA |
| B58 | ATS | | FWY*LIVMA* |
| B62 | QL*IVMP* | | FWYMIVLA |
| MOTIFS | | | |
| A1 | TSM | | Y |
| A1 | | DE*AS* | Y |
| A2.1 | LM*VQIAT* | | V*LIMAT* |
| A3 | LMVISATF*CGD* | | KYR*HFA* |
| A11 | VTMLISAGN*CDF* | | KR*YH* |
| A24 | YF*WM* | | FLIW |
| A*3101 | MVT*ALIS* | | R*K* |
| A*3301 | MVALF*IST* | | RK |
| A*6801 | AVT*MSLI* | | RK |
| B*0702 | P | | LMF*WYAIV* |
| B*3501 | P | | LMFWY*IVA* |
| B51 | P | | LIVF*WYAM* |
| B*5301 | P | | IMFWY*ALV* |
| B*5401 | P | | ATIV*LMFWY* |

Bolded residues are preferred, italicized residues are less preferred: A peptide is considered motif-bearing if it has primary anchors at each primary anchor position for a motif or supermotif as specified in the above table.

TABLE IV (B)

HLA CLASS II SUPERMOTIF

| 1 | 6 | 9 |
|---|---|---|
| W, F, Y, V, I, L | A, V, I, L, P, C, S, T | A, V, I, L, C, S, T, M, Y |

TABLE IV (C)

HLA Class II Motifs

| MOTIFS | | 1° anchor 1 | 2 | 3 | 4 | 5 | 1° anchor 6 | 7 | 8 | 9 |
|---|---|---|---|---|---|---|---|---|---|---|
| DR4 | preferred | FMY*LIVW* | M | | T | I | VST*CPALIM* | MH | | MH |
| | deleterious | | | | W | | | R | | WDE |
| DR1 | preferred | MF*LIVWY* | | | PAMQ | | VMAT*SPLIC* | M | | AVM |
| | deleterious | | C | CH | FD | CWD | | GDE | D | |
| DR7 | preferred | MF*LIVWY* | M | W | A | | IVMSA*CTPL* | M | | IV |
| | deleterious | | C | | G | | | GRD | N | G |
| DR3 | MOTIFS | 1° anchor 1 | 2 | 3 | 1° anchor 4 | 5 | 1° anchor 6 | | | |
| motif a preferred | | LIVMFY | | | D | | | | | |
| motif b preferred | | LIVMFAY | | | DNQEST | | KRH | | | |
| DR Supermotif | | MF*LIVWY* | | | | | VMSTA*CPLI* | | | |

Italicized residues indicate less preferred or "tolerated" residues.

TABLE IV (D)

HLA Class I Supermotifs

| SUPERMOTIFS | | 1 | 2 | 3 | 4 | 5 | 6 | 7 | 8 | C-terminus |
|---|---|---|---|---|---|---|---|---|---|---|
| A1 | | | 1° Anchor TI*LVMS* | | | | | | | 1° Anchor FWY |
| A2 | | | 1° Anchor LIVM*ATQ* | | | | | | | 1° Anchor LIVMAT |
| A3 | preferred | | 1° Anchor VSMA*TLI* | YFW (4/5) | | | YFW (3/5) | YFW (4/5) | P (4/5) | 1° Anchor RK |
| | deleterious | DE (3/5); P (5/5) | | DE (4/5) | | | | | | |
| A24 | | | 1° Anchor YF*WIVLMT* | | | | | | | 1° Anchor FIY*WLM* |
| B7 | preferred | FWY (5/5) LIVM (3/5) | 1° Anchor P | FWY (4/5) | | | | | FWY (3/5) | 1° Anchor VILF*MWYA* |
| | deleterious | DE (3/5); P (5/5); G (4/5); A (3/5); QN (3/5) | | | | DE (3/5) | G (4/5) | QN (4/5) | DE (4/5) | |
| B27 | | | 1° Anchor RHK | | | | | | | 1° Anchor FYL*WMIVA* |
| B44 | | | 1° Anchor E*D* | | | | | | | 1° Anchor FWYLIMVA |
| B58 | | | 1° Anchor ATS | | | | | | | 1° Anchor FWY*LIVMA* |
| B62 | | | 1° Anchor QL*IVMP* | | | | | | | 1° Anchor FWY*MIVLA* |

Italicized residues indicate less preferred or "tolerated" residues

TABLE IV (E)

HLA Class I Motifs

| | | 1 | 2 | 3 | 4 | 5 | 6 | 7 | 8 | 9 or C-terminus | C-terminus |
|---|---|---|---|---|---|---|---|---|---|---|---|
| A1 9-mer | preferred | GFYW | 1° Anchor STM | DEA | YFW | | P | DEQN | YFW | 1° Anchor Y | |
| | deleterious | DE | | RHKLIVMP | A | G | A | | | | |
| A1 9-mer | preferred | GRHK | ASTCLIVM | 1° Anchor DE*AS* | GSTC | | ASTC | LIVM | DE | 1° Anchor Y | |
| | deleterious | A | RHKDEPYFW | | DE | PQN | RHK | PG | GP | | |
| A1 10-mer | preferred | YFW | 1° Anchor STM | DEAQN | A | YFWQN | | PASTC | GDE | P | 1° Anchor Y |
| | deleterious | GP | | RHKGLIVM | DE | RHK | QNA | RHKYFW | RHK | A | |
| A1 10-mer | preferred | YFW | STCLIVM | 1° Anchor DE*AS* | A | YFW | QNA | PG | G | YFW | 1° Anchor Y |
| | deleterious | RHK | RHKDEPYFW | | | P | G | | PRHK | QN | |
| A2.1 9-mer | preferred | YFW | 1° Anchor LM*IVQAT* | YFW | STC | YFW | | A | P | 1° Anchor V*LIMAT* | |
| | deleterious | DEP | | DERKH | | | RKH | DERKH | | | |

Italicized residues indicate less preferred or "tolerated" residues

TABLE IV (E)

HLA Class I Motifs,

| | | 1 | 2 | 3 | 4 | 5 | 6 | 7 | 8 | 9 | C-terminus |
|---|---|---|---|---|---|---|---|---|---|---|---|
| A2.1 10-mer | preferred | AYFW | 1° Anchor LM*IVQAT* | LVIM | G | | G | | FYWLVIM | | 1° Anchor V*LIMAT* |
| | deleterious | DEP | | DE | RKHA | P | | RKH | DERKH | RKH | |
| A3 | preferred | RHK | 1° Anchor LMVISATFCGD | YFW | PRHKYFW | A | YFW | | P | 1° Anchor KYR*HFA* | |
| | deleterious | DEP | | DE | | | | | | | |

TABLE IV (E)-continued

HLA Class I Motifs,

| | | POSITION: | | | | | | | | | |
|---|---|---|---|---|---|---|---|---|---|---|---|
| | | 1 | 2 | 3 | 4 | 5 | 6 | 7 | 8 | 9 | C-terminus |
| A11 | preferred | A | 1° Anchor VTLMISAGN*CDF* | YFW | YFW | A | YFW | YFW | P | 1° Anchor K*RYH* | |
| | deleterious | DEP | | | | | | A | G | | |
| A24 9-mer | preferred | YFWRHK | 1° Anchor YFW*M* | | STC | | | YFW | YFW | 1° Anchor FLIW | |
| | deleterious | DEG | | DE | G | QNP | DERHK | G | AQN | | |
| A24 10-mer | preferred | | 1° Anchor YFW*M* | | P | YFWP | | P | | | 1° Anchor FLIW |
| | deleterious | | | GDE | QN | RHK | DE | A | QN | DEA | |
| A3101 | preferred | RHK | 1° Anchor MVT*ALIS* | YFW | P | | YFW | YFW | AP | 1° Anchor R*K* | |
| | deleterious | DEP | | DE | | ADE | DE | DE | DE | | |
| A3301 | preferred | | 1° Anchor MVALF*IST* | YFW | | | | AYFW | | 1° Anchor RK | |
| | deleterious | GP | | DE | | | | | | | |

Italicized residues indicate less preferred or "tolerated" residues.

TABLE IV (E)

HLA Class I Motifs,

| | | POSITION: | | | | | | | | | C- |
|---|---|---|---|---|---|---|---|---|---|---|---|
| | | 1 | 2 | 3 | 4 | 5 | 6 | 7 | 8 | 9 | Terminus |
| A6801 | preferred | YFWSTC | 1° Anchor AVT*MSLI* | | | YFWLIVM | | YFW | P | 1° Anchor RK | |
| | deleterious | GP | | DEG | | RHK | | | A | | |
| B0702 | preferred | RHKFWY | 1° Anchor P | RHK | | RHK | RHK | RHK | PA | 1° Anchor LMF*WYAIV* | |
| | deleterious | DEQNP | | DEP | DE | DE | GDE | QN | DE | | |
| B3501 | preferred | FWYLIVM | 1° Anchor P | FWY | | | | FWY | | 1° Anchor LMFW*YIVA* | |
| | deleterious | AGP | | | | G | G | | | | |
| B51 | preferred | LIVMFWY | 1° Anchor P | FWY | STC | FWY | | G | FWY | 1° Anchor LIVF*WYAM* | |
| | deleterious | AGPDERHKSTC | | | | DE | G | DEQN | GDE | | |
| B5301 | preferred | LIVMFWY | 1° Anchor P | FWY | STC | FWY | | LIVMFWY | FWY | 1° Anchor IMFW*YALV* | |
| | deleterious | AGPQN | | | | | G | RHKQN | DE | | |
| B5401 | preferred | FWY | 1° Anchor P | FWYLIVM | | LIVM | | ALIVM | FWYAP | 1° Anchor ATIV*LMFWY* | |
| | deleterious | GPQNDE | | GDESTC | | RHKDE | DE | QNDGE | DE | | |

Italicized residues indicate less preferred or "tolerated" residues. The information in this Table is specific for 9-mers unless otherwise specified.

TABLE V

HLA Peptide Scoring Results - 205P1B5 - A1, 9-mers

| Rank | Start Position | Subsequence Residue Listing | Score (Estimate of Half Time of Disassociation of a Molecule Containing This Subsequence) | Seq. ID# |
|---|---|---|---|---|
| 1 | 184 | SIDVTFFPF | 25.000 | 1. |
| 2 | 55 | HTETEDRLF | 22.500 | 2. |
| 3 | 80 | TSDVVIVRF | 15.000 | 3. |
| 4 | 57 | ETEDRLFKH | 11.250 | 4. |
| 5 | 215 | QMEQTVDLK | 9.000 | 5. |
| 6 | 323 | LVIPLIGEY | 5.000 | 6. |
| 7 | 210 | KIDLEQMEQ | 2.500 | 7. |
| 8 | 314 | ITEIIPSTS | 2.250 | 8. |
| 9 | 386 | PVELCHPLR | 1.800 | 9. |
| 10 | 469 | ALEGVHYIA | 1.800 | 10. |
| 11 | 409 | DAEEREVVV | 1.800 | 11. |
| 12 | 481 | RSEDADSSV | 1.350 | 12. |
| 13 | 244 | KYDCCAEIY | 1.250 | 13. |
| 14 | 79 | NTSDVVIVR | 1.250 | 14. |
| 15 | 255 | VTYAFVIRR | 1.250 | 15. |
| 16 | 328 | IGEYLLFTM | 1.125 | 16. |
| 17 | 280 | SCLTVLVFY | 1.000 | 17. |
| 18 | 150 | NADGEFAVT | 1.000 | 18. |
| 19 | 460 | LLLSPHMQK | 1.000 | 19. |
| 20 | 248 | CAEIYPDVT | 0.900 | 20. |
| 21 | 416 | VVEEEDRWA | 0.900 | 21. |
| 22 | 450 | KAEALLQEG | 0.900 | 22. |
| 23 | 212 | DLEQMEQTV | 0.900 | 23. |
| 24 | 3 | PSCPVFLSF | 0.750 | 24. |

TABLE V-continued

HLA Peptide Scoring Results - 205P1B5 - A1, 9-mers

| Rank | Start Position | Subsequence Residue Listing | Score (Estimate of Half Time of Disassociation of a Molecule Containing This Subsequence) | Seq. ID# |
|---|---|---|---|---|
| 25 | 115 | WSDYKLRWN | 0.750 | 25. |
| 26 | 279 | ISCLTVLVF | 0.750 | 26. |
| 27 | 455 | LQEGELLLS | 0.675 | 27. |
| 28 | 124 | PTDFGNITS | 0.625 | 28. |
| 29 | 232 | AIVNATGTY | 0.500 | 29. |
| 30 | 95 | LIDVDEKNQ | 0.500 | 30. |
| 31 | 389 | LCHPLRLKL | 0.500 | 31. |
| 32 | 407 | NVDAEEREV | 0.500 | 32. |
| 33 | 372 | GCVPRWLLM | 0.500 | 33. |
| 34 | 97 | DVDEKNQMM | 0.500 | 34. |
| 35 | 360 | HTMPHWVRG | 0.500 | 35. |
| 36 | 482 | SEDADSSVK | 0.500 | 36. |
| 37 | 236 | ATGTYNSKK | 0.500 | 37. |
| 38 | 172 | HWVPPAIYK | 0.500 | 38. |
| 39 | 272 | LIIPCLLIS | 0.500 | 39. |
| 40 | 140 | IWIPDIVLY | 0.500 | 40. |
| 41 | 228 | SGEWAIVNA | 0.450 | 41. |
| 42 | 486 | DSSVKEDWK | 0.300 | 42. |
| 43 | 181 | SSCSIDVTF | 0.300 | 43. |
| 44 | 112 | KQEWSDYKL | 0.270 | 44. |
| 45 | 142 | IPDIVLYNN | 0.250 | 45. |
| 46 | 499 | VIDRIFLWL | 0.250 | 46. |
| 47 | 5 | CPVFLSFTK | 0.250 | 47. |
| 48 | 252 | YPDVTYAFV | 0.250 | 48. |
| 49 | 457 | EGELLLSPH | 0.225 | 49. |
| 50 | 152 | DGEFAVTHM | 0.225 | 50. |

TABLE VI

HLA Peptide Scoring Results - 205P1B5 - A1, 10-mers

| Rank | Start Position | Subsequence Residue Listing | Score (Estimate of Half Time of Disassociation of a Molecule Containing This Subsequence) | Seq. ID# |
|---|---|---|---|---|
| 1 | 55 | HTETEDRLFK | 225.000 | 51. |
| 2 | 248 | CAEIYPDVTY | 90.000 | 52. |
| 3 | 481 | RSEDADSSVK | 27.000 | 53. |
| 4 | 97 | DVDEKNQMMT | 2.500 | 54. |
| 5 | 57 | ETEDRLFKHL | 2.250 | 55. |
| 6 | 314 | ITEIIPSTSL | 2.250 | 56. |
| 7 | 250 | EIYPDVTYAF | 2.000 | 57. |
| 8 | 279 | ISCLTVLVFY | 1.500 | 58. |
| 9 | 112 | KQEWSDYKLR | 1.350 | 59. |
| 10 | 236 | ATGTYNSKKY | 1.250 | 60. |
| 11 | 150 | NADGEFAVTH | 1.000 | 61. |
| 12 | 170 | TVHWVPPAIY | 1.000 | 62. |
| 13 | 4 | SCPVFLSFTK | 1.000 | 63. |
| 14 | 459 | ELLLSPHMQK | 1.000 | 64. |
| 15 | 416 | VVEEEDRWAC | 0.900 | 65. |
| 16 | 26 | GEEAKRPPPR | 0.900 | 66. |
| 17 | 486 | DSSVKEDWKY | 0.750 | 67. |
| 18 | 183 | CSIDVTFPPF | 0.750 | 68. |
| 19 | 80 | TSDVVIVRFG | 0.750 | 69. |
| 20 | 252 | YPDVTYAFVI | 0.625 | 70. |
| 21 | 95 | LIDVDEKNQM | 0.500 | 71. |
| 22 | 476 | IADHLRSEDA | 0.500 | 72. |
| 23 | 278 | LISCLTVLVF | 0.500 | 73. |
| 24 | 484 | DADSSVKEDW | 0.500 | 74. |
| 25 | 372 | GCVPRWLLMN | 0.500 | 75. |
| 26 | 322 | SLVIPLIGEY | 0.500 | 76. |
| 27 | 499 | VIDRIFLWLF | 0.500 | 77. |
| 28 | 515 | GTIGLFLPPF | 0.500 | 78. |
| 29 | 254 | DVTYAFVIRR | 0.500 | 79. |
| 30 | 407 | NVDAEEREVV | 0.500 | 80. |
| 31 | 316 | EIIPSTSLVI | 0.500 | 81. |

TABLE VI-continued

HLA Peptide Scoring Results - 205P1B5 - A1, 10-mers

| Rank | Start Position | Subsequence Residue Listing | Score (Estimate of Half Time of Disassociation of a Molecule Containing This Subsequence) | Seq. ID# |
|---|---|---|---|---|
| 32 | 210 | KIDLEQMEQT | 0.500 | 82. |
| 33 | 79 | NTSDVVIVRF | 0.500 | 83. |
| 34 | 219 | TVDLKDYWES | 0.500 | 84. |
| 35 | 272 | LIIPCLLISC | 0.500 | 85. |
| 36 | 231 | WAIVNATGTY | 0.500 | 86. |
| 37 | 21 | LTPAGGEEAK | 0.500 | 87. |
| 38 | 386 | PVELCHPRL | 0.450 | 88. |
| 39 | 457 | EGELLLSPHM | 0.450 | 89. |
| 40 | 469 | ALEGVHYIAD | 0.450 | 90. |
| 41 | 290 | PSDCGEKITL | 0.375 | 91. |
| 42 | 446 | ASGPKAEALL | 0.300 | 92. |
| 43 | 180 | KSSCSIDVTF | 0.300 | 93. |
| 44 | 136 | PSEMIWIPDI | 0.270 | 94. |
| 45 | 360 | HTMPHWVRGA | 0.250 | 95. |
| 46 | 358 | STHTMPHWVR | 0.250 | 96. |
| 47 | 157 | VTHMTKAHLF | 0.250 | 97. |
| 48 | 339 | VTLSIVITVF | 0.250 | 98. |
| 49 | 259 | FVIRRLPLFY | 0.250 | 99. |
| 50 | 228 | SGEWAIVNAT | 0.225 | 100. |

TABLE VII

HLA Peptide Scoring Results - 205P1B5 - A2, 9-mers

| Rank | Start Position | Subsequence Residue Listing | Score (Estimate of Half Time of Disassociation of a Molecule Containing This Subsequence) | Seq. ID# |
|---|---|---|---|---|
| 1 | 331 | YLLFTMIFV | 14974.754 | 101. |
| 2 | 506 | WLFIIVCFL | 4599.389 | 102. |
| 3 | 281 | CLTVLVFYL | 1567.359 | 103. |
| 4 | 303 | VLLSLTVFL | 739.032 | 104. |
| 5 | 504 | FLWLFIIVC | 679.693 | 105. |
| 6 | 396 | KLSPSYHWL | 616.839 | 106. |
| 7 | 513 | FLGTIGLFL | 540.469 | 107. |
| 8 | 304 | LLSLTVFLL | 484.457 | 108. |
| 9 | 103 | QMMTTNVWL | 313.968 | 109. |
| 10 | 276 | CLLISCLTV | 257.342 | 110. |
| 11 | 332 | LLFTMIFVT | 256.368 | 111. |
| 12 | 520 | FLPPFLAGM | 199.733 | 112. |
| 13 | 454 | LLQEGELLL | 148.896 | 113. |
| 14 | 344 | VITVFVLNV | 142.093 | 114. |
| 15 | 13 | KLSLWWLLL | 127.106 | 115. |
| 16 | 518 | GLFLPPFLA | 106.613 | 116. |
| 17 | 8 | FLSFTKLSL | 98.267 | 117. |
| 18 | 468 | KALEGVHYI | 97.322 | 118. |
| 19 | 306 | SLTVFLLLI | 91.183 | 119. |
| 20 | 327 | LIGEYLLFT | 90.344 | 120. |
| 21 | 379 | LMNRPPPPV | 85.394 | 121. |
| 22 | 497 | AMVIDRIFL | 84.856 | 122. |
| 23 | 336 | MIFVTLSIV | 56.725 | 123. |
| 24 | 370 | LLGCVPRWL | 39.948 | 124. |
| 25 | 453 | ALLQEGELL | 38.730 | 125. |
| 26 | 310 | FLLLITEII | 35.673 | 126. |
| 27 | 277 | LLISCLTVL | 34.246 | 127. |
| 28 | 502 | RIFLWLFII | 29.030 | 128. |
| 29 | 166 | FSTGTVHWV | 26.419 | 129. |
| 30 | 499 | VIDRIFLWL | 20.873 | 130. |
| 31 | 461 | LLSPHMQKA | 19.425 | 131. |
| 32 | 139 | MIWIPDIVL | 16.993 | 132. |
| 33 | 313 | LITEIIPST | 16.426 | 133. |
| 34 | 278 | LISCLTVLV | 16.258 | 134. |
| 35 | 342 | SIVITVFVL | 16.065 | 135. |
| 36 | 339 | VTLSIVITV | 13.975 | 136. |
| 37 | 324 | VIPLIGEYL | 13.457 | 137. |
| 38 | 134 | RVPSEMIWI | 11.548 | 138. |

TABLE VII-continued

HLA Peptide Scoring Results - 205P1B5 - A2, 9-mers

| Rank | Start Position | Subsequence Residue Listing | Score (Estimate of Half Time of Disassociation of a Molecule Containing This Subsequence) | Seq. ID# |
|---|---|---|---|---|
| 39 | 149 | NNADGEFAV | 10.797 | 139. |
| 40 | 271 | NLIIPCLLI | 10.433 | 140. |
| 41 | 296 | KITLCISVL | 9.695 | 141. |
| 42 | 84 | VIVRFGLSI | 9.267 | 142. |
| 43 | 508 | FIIVCFLGT | 8.955 | 143. |
| 44 | 488 | SVKEDWKYV | 8.165 | 144. |
| 45 | 335 | TMIFVTLSI | 7.535 | 145. |
| 46 | 48 | ALPQGGSHT | 7.452 | 146. |
| 47 | 252 | YPDVTYAFV | 6.892 | 147. |
| 48 | 269 | TINLIIPCL | 6.756 | 148. |
| 49 | 358 | STHTMPHWV | 5.313 | 149. |
| 50 | 517 | IGLFLPPFL | 4.824 | 150. |

TABLE VIII

HLA Peptide Scoring Results - 205P1B5 - A2, 10-mers

| Rank | Start Position | Subsequence Residue Listing | Score (Estimate of Half Time of Disassociation of a Molecule Containing This Subsequence) | Seq. ID# |
|---|---|---|---|---|
| 1 | 303 | VLLSLTVFLL | 1792.489 | 151. |
| 2 | 331 | YLLFTMIFVT | 693.701 | 152. |
| 3 | 378 | LLMNRPPPPV | 437.482 | 153. |
| 4 | 340 | TLSIVITVFV | 382.536 | 154. |
| 5 | 370 | LLGCVPRWLL | 272.371 | 155. |
| 6 | 332 | LLFTMIFVTL | 255.302 | 156. |
| 7 | 89 | GLSIAQLIDV | 159.970 | 157. |
| 8 | 498 | MVIDRIFLWL | 136.147 | 158. |
| 9 | 277 | LLISCLTVLV | 118.238 | 159. |
| 10 | 15 | SLWWLLLTPA | 94.839 | 160. |
| 11 | 343 | IVITVFVLNV | 90.423 | 161. |
| 12 | 369 | ALLGCVPRWL | 86.945 | 162. |
| 13 | 453 | ALLQEGELLL | 79.041 | 163. |
| 14 | 276 | CLLISCLTVL | 74.536 | 164. |
| 15 | 460 | LLLSPHMQKA | 71.872 | 165. |
| 16 | 304 | LLSLTVFLLL | 69.001 | 166. |
| 17 | 338 | FVTLSIVITV | 64.388 | 167. |
| 18 | 327 | LIGEYLLFTM | 63.515 | 168. |
| 19 | 13 | KLSLWWLLLT | 59.989 | 169. |
| 20 | 298 | TLCISVLLSL | 49.134 | 170. |
| 21 | 335 | TMIFVTLSIV | 47.369 | 171. |
| 22 | 102 | NQMMTTNVWL | 44.076 | 172. |
| 23 | 302 | SVLLSLTVFL | 38.038 | 173. |
| 24 | 280 | SCLTVLVFYL | 37.856 | 174. |
| 25 | 461 | LLSPHMQKAL | 36.316 | 175. |
| 26 | 312 | LLITEIIPST | 29.137 | 176. |
| 27 | 502 | RIFLWLFIIV | 27.565 | 177. |
| 28 | 288 | YLPSDCGEKI | 23.516 | 178. |
| 29 | 263 | RLPLFYTINL | 21.362 | 179. |
| 30 | 204 | WTYDKAKIDL | 17.906 | 180. |
| 31 | 516 | TIGLFLPPFL | 16.155 | 181. |
| 32 | 148 | YNNADGEFAV | 12.113 | 182. |
| 33 | 273 | IIPCLLISCL | 11.485 | 183. |
| 34 | 296 | KITLCISVLL | 10.281 | 184. |
| 35 | 496 | VAMVIDRIFL | 10.264 | 185. |
| 36 | 260 | VIRRLPLFYT | 9.713 | 186. |
| 37 | 300 | CISVLLSLTV | 9.563 | 187. |
| 38 | 323 | LVIPLIGEYL | 8.564 | 188. |
| 39 | 284 | VLVFYLPSDC | 8.446 | 189. |
| 40 | 308 | TVFLLLITEI | 7.769 | 190. |
| 41 | 508 | FIIVCFLGTI | 7.497 | 191. |
| 42 | 506 | WLFIIVCFLG | 7.356 | 192. |
| 43 | 306 | SLTVFLLLIT | 7.027 | 193. |
| 44 | 504 | FLWLFIIVCF | 6.544 | 194. |
| 45 | 520 | FLPPFLAGMI | 6.239 | 195. |
| 46 | 83 | VVIVRFGLSI | 5.897 | 196. |
| 47 | 257 | YAFVIRRLPL | 5.050 | 197. |
| 48 | 324 | VIPLIGEYLL | 4.993 | 198. |
| 49 | 490 | KEDWKYVAMV | 4.355 | 199. |
| 50 | 487 | SSVKEDWKYV | 4.245 | 200. |

TABLE IX

HLA Peptide Scoring Results - 205P1B5 - A3, 9-mers

| Rank | Start Position | Subsequence Residue Listing | Score (Estimate of Half Time of Disassociation of a Molecule Containing This Subsequence) | Seq. ID# |
|---|---|---|---|---|
| 1 | 104 | MMTTNVWLK | 180.000 | 201. |
| 2 | 460 | LLLSPHMQK | 90.000 | 202. |
| 3 | 215 | QMEQTVDLK | 60.000 | 203. |
| 4 | 198 | KMKFGSWTY | 36.000 | 204. |
| 5 | 255 | VTYAFVIRR | 18.000 | 205. |
| 6 | 506 | WLFIIVCFL | 13.500 | 206. |
| 7 | 518 | GLFLPPFLA | 13.500 | 207. |
| 8 | 13 | KLSLWWLLL | 10.800 | 208. |
| 9 | 504 | FLWLFIIVC | 9.000 | 209. |
| 10 | 288 | YLPSDCGEK | 6.000 | 210. |
| 11 | 119 | KLRWNPTDF | 6.000 | 211. |
| 12 | 281 | CLTVLVFYL | 5.400 | 212. |
| 13 | 306 | SLTVFLLLI | 5.400 | 213. |
| 14 | 304 | LLSLTVFLL | 5.400 | 214. |
| 15 | 340 | TLSIVITVF | 4.500 | 215. |
| 16 | 502 | RIFLWLFII | 4.050 | 216. |
| 17 | 110 | WLKQEWSDY | 4.000 | 217. |
| 18 | 236 | ATGTYNSKK | 3.000 | 218. |
| 19 | 396 | KLSPSYHWL | 2.700 | 219. |
| 20 | 93 | AQLIDVDEK | 2.700 | 220. |
| 21 | 271 | NLIIPCLLI | 2.700 | 221. |
| 22 | 335 | TMIFVTLSI | 2.700 | 222. |
| 23 | 202 | GSWTYDKAK | 2.250 | 223. |
| 24 | 332 | LLFTMIFVT | 2.250 | 224. |
| 25 | 79 | NTSDVVIVR | 1.800 | 225. |
| 26 | 184 | SIDVTFFPF | 1.800 | 226. |
| 27 | 454 | LLQEGELLL | 1.800 | 227. |
| 28 | 497 | AMVIDRIFL | 1.800 | 228. |
| 29 | 513 | FLGTIGLFL | 1.800 | 229. |
| 30 | 310 | FLLLITEII | 1.350 | 230. |
| 31 | 277 | LLISCLTVL | 1.350 | 231. |
| 32 | 388 | ELCHPLRLK | 1.350 | 232. |
| 33 | 369 | ALLGCVPRW | 1.350 | 233. |
| 34 | 469 | ALEGVHYIA | 1.350 | 234. |
| 35 | 520 | FLPPFLAGM | 1.350 | 235. |
| 36 | 8 | FLSFTKLSL | 1.200 | 236. |
| 37 | 164 | HLFSTGTVH | 1.000 | 237. |
| 38 | 190 | FPFDQQNCK | 1.000 | 238. |
| 39 | 65 | HLFRGYNRW | 1.000 | 239. |
| 40 | 453 | ALLQEGELL | 0.900 | 240. |
| 41 | 516 | TIGLFLPPF | 0.900 | 241. |
| 42 | 132 | SLRVPSEMI | 0.900 | 242. |
| 43 | 5 | CPVFLSFTK | 0.900 | 243. |
| 44 | 139 | MIWIPDIVL | 0.900 | 244. |
| 45 | 103 | QMMTTNVWL | 0.900 | 245. |
| 46 | 331 | YLLFTMIFV | 0.900 | 246. |
| 47 | 303 | VLLSLTVFL | 0.900 | 247. |
| 48 | 326 | PLIGEYLLF | 0.900 | 248. |
| 49 | 342 | SIVITVFVL | 0.810 | 249. |
| 50 | 260 | VIRRLPLFY | 0.800 | 250. |

TABLE X

HLA Peptide Scoring Results - 205P1B5 - A3, 10-mers

| Rank | Start Position | Subsequence Residue Listing | Score (Estimate of Half Time of Disassociation of a Molecule Containing This Subsequence) | Seq. ID# |
|---|---|---|---|---|
| 1 | 103 | QMMTTNVWLK | 270.000 | 251. |
| 2 | 110 | WLKQEWSDYK | 60.000 | 252. |
| 3 | 459 | ELLLSPHMQK | 27.000 | 253. |
| 4 | 504 | FLWLFIIVCF | 22.500 | 254. |
| 5 | 332 | LLFTMIFVTL | 13.500 | 255. |
| 6 | 303 | VLLSLTVFLL | 8.100 | 256. |
| 7 | 61 | RLFKHLFRGY | 6.000 | 257. |
| 8 | 441 | HLHSGASGPK | 6.000 | 258. |
| 9 | 346 | TVFVLNVHHR | 6.000 | 259. |
| 10 | 304 | LLSLTVFLLL | 5.400 | 260. |
| 11 | 263 | RLPLFYTINL | 3.600 | 261. |
| 12 | 515 | GTIGLFLPPF | 3.038 | 262. |
| 13 | 146 | VLYNNADGEF | 3.000 | 263. |
| 14 | 139 | MIWIPDIVLY | 3.000 | 264. |
| 15 | 370 | LLGCVPRWLL | 2.700 | 265. |
| 16 | 298 | TLCISVLLSL | 2.700 | 266. |
| 17 | 499 | VIDRIFLWLF | 2.700 | 267. |
| 18 | 13 | KLSLWWLLLT | 2.700 | 268. |
| 19 | 518 | GLFLPPFLAG | 2.700 | 269. |
| 20 | 322 | SLVIPLIGEY | 2.700 | 270. |
| 21 | 254 | DVTYAFVIRR | 2.160 | 271. |
| 22 | 250 | EIYPDVTYAF | 2.025 | 272. |
| 23 | 55 | HTETEDRLFK | 2.000 | 273. |
| 24 | 453 | ALLQEGELLL | 1.800 | 274. |
| 25 | 89 | GLSIAQLIDV | 1.800 | 275. |
| 26 | 153 | GEFAVTHMTK | 1.800 | 276. |
| 27 | 15 | SLWWLLLTPA | 1.500 | 277. |
| 28 | 276 | CLLISCLTVL | 1.350 | 278. |
| 29 | 199 | MKFGSWTYDK | 1.350 | 279. |
| 30 | 497 | AMVIDRIFLW | 1.350 | 280. |
| 31 | 214 | EQMEQTVDLK | 1.215 | 281. |
| 32 | 472 | GVHYIADHLR | 1.200 | 282. |
| 33 | 259 | FVIRRLPLFY | 1.200 | 283. |
| 34 | 373 | CVPRWLLMNR | 1.200 | 284. |
| 35 | 278 | LISCLTVLVF | 1.200 | 285. |
| 36 | 21 | LTPAGGEEAK | 1.000 | 286. |
| 37 | 164 | HLFSTGTVHW | 1.000 | 287. |
| 38 | 358 | STHTMPHWVR | 0.900 | 288. |
| 39 | 235 | NATGTYNSKK | 0.900 | 289. |
| 40 | 265 | PLFYTINLII | 0.900 | 290. |
| 41 | 394 | RLKLSPSYHW | 0.900 | 291. |
| 42 | 138 | EMIWIPDIVL | 0.810 | 292. |
| 43 | 396 | KLSPSYHWLE | 0.810 | 293. |
| 44 | 498 | MVIDRIFLWL | 0.810 | 294. |
| 45 | 331 | YLLFTMIFVT | 0.675 | 295. |
| 46 | 336 | MIFVTLSIVI | 0.600 | 296. |
| 47 | 502 | RIFLWLFIIV | 0.600 | 297. |
| 48 | 288 | YLPSDCGEKI | 0.600 | 298. |
| 49 | 92 | IAQLIDVDEK | 0.600 | 299. |
| 50 | 170 | TVHWVPPAIY | 0.600 | 300. |

TABLE XI

HLA Peptide Scoring Results - 205P1B5 - A11, 9-mers

| Rank | Start Position | Subsequence Residue Listing | Score (Estimate of Half Time of Disassociation of a Molecule Containing This Subsequence) | Seq. ID# |
|---|---|---|---|---|
| 1 | 460 | LLLSPHMQK | 1.200 | 301. |
| 2 | 200 | KFGSWTYDK | 1.200 | 302. |
| 3 | 236 | ATGTYNSKK | 1.000 | 303. |
| 4 | 5 | CPVFLSFTK | 0.900 | 304. |
| 5 | 93 | AQLIDVDEK | 0.900 | 305. |
| 6 | 255 | VTYAFVIRR | 0.800 | 306. |
| 7 | 104 | MMTTNVWLK | 0.800 | 307. |
| 8 | 494 | KYVAMVIDR | 0.720 | 308. |
| 9 | 190 | FPFDQQNCK | 0.400 | 309. |
| 10 | 288 | YLPSDCGEK | 0.400 | 310. |
| 11 | 215 | QMEQTVDLK | 0.400 | 311. |
| 12 | 79 | NTSDVVIVR | 0.400 | 312. |
| 13 | 22 | TPAGGEEAK | 0.200 | 313. |
| 14 | 235 | NATGTYNSK | 0.200 | 314. |
| 15 | 368 | GALLGCVPR | 0.180 | 315. |
| 16 | 414 | EVVVEEEDR | 0.180 | 316. |
| 17 | 154 | EFAVTHMTK | 0.120 | 317. |
| 18 | 254 | DVTYAFVIR | 0.120 | 318. |
| 19 | 56 | TETEDRLFK | 0.120 | 319. |
| 20 | 134 | RVPSEMIWI | 0.120 | 320. |
| 21 | 498 | MVIDRIFLW | 0.090 | 321. |
| 22 | 374 | VPRWLLMNR | 0.080 | 322. |
| 23 | 518 | GLFLPPFLA | 0.072 | 323. |
| 24 | 502 | RIFLWLFII | 0.072 | 324. |
| 25 | 202 | GSWTYDKAK | 0.060 | 325. |
| 26 | 172 | HWVPPAIYK | 0.060 | 326. |
| 27 | 472 | GVHYIADHL | 0.060 | 327. |
| 28 | 482 | SEDADSSVK | 0.060 | 328. |
| 29 | 347 | VFVLNVHHR | 0.060 | 329. |
| 30 | 434 | GTLCSHGHL | 0.045 | 330. |
| 31 | 169 | GTVHWVPPA | 0.045 | 331. |
| 32 | 346 | TVFVLNVHH | 0.040 | 332. |
| 33 | 386 | PVELCHPLR | 0.040 | 333. |
| 34 | 64 | KHLFRGYNR | 0.036 | 334. |
| 35 | 112 | KQEWSDYKL | 0.036 | 335. |
| 36 | 415 | VVVEEEDRW | 0.030 | 336. |
| 37 | 323 | LVIPLIGEY | 0.030 | 337. |
| 38 | 339 | VTLSIVITV | 0.030 | 338. |
| 39 | 259 | FVIRRLPLF | 0.030 | 339. |
| 40 | 302 | SVLLSLTVF | 0.030 | 340. |
| 41 | 82 | DVVIVRFGL | 0.027 | 341. |
| 42 | 198 | KMKFGSWTY | 0.024 | 342. |
| 43 | 13 | KLSLWWLLL | 0.024 | 343. |
| 44 | 11 | FTKLSLWWL | 0.020 | 344. |
| 45 | 495 | YVAMVIDRI | 0.020 | 345. |
| 46 | 442 | LHSGASGPK | 0.020 | 346. |
| 47 | 170 | TVHWVPPAI | 0.020 | 347. |
| 48 | 111 | LKQEWSDYK | 0.020 | 348. |
| 49 | 428 | HVAPSVGTL | 0.020 | 349. |
| 50 | 85 | IVRFGLSIA | 0.020 | 350. |

TABLE XII

HLA Peptide Scoring Results - 205P1B5 - A11, 10-mers

| Rank | Start Position | Subsequence Residue Listing | Score (Estimate of Half Time of Disassociation of a Molecule Containing This Subsequence) | Seq. ID# |
|---|---|---|---|---|
| 1 | 55 | HTETEDRLFK | 2.000 | 351. |
| 2 | 103 | QMMTTNVWLK | 1.600 | 352. |
| 3 | 472 | GVHYIADHLR | 1.200 | 353. |
| 4 | 21 | LTPAGGEEAK | 1.000 | 354. |
| 5 | 346 | TVFVLNVHHR | 0.800 | 355. |
| 6 | 373 | CVPRWLLMNR | 0.800 | 356. |
| 7 | 153 | GEFAVTHMTK | 0.720 | 357. |
| 8 | 287 | FYLPSDCGEK | 0.600 | 358. |
| 9 | 4 | SCPVFLSFTK | 0.600 | 359. |
| 10 | 110 | WLKQEWSDYK | 0.400 | 360. |
| 11 | 358 | STHTMPHWVR | 0.400 | 361. |
| 12 | 441 | HLHSGASGPK | 0.400 | 362. |
| 13 | 214 | EQMEQTVDLK | 0.360 | 363. |
| 14 | 459 | ELLLSPHMQK | 0.360 | 364. |

TABLE XII-continued

HLA Peptide Scoring Results - 205P1B5 - A11, 10-mers

| Rank | Start Position | Subsequence Residue Listing | Score (Estimate of Half Time of Disassociation of a Molecule Containing This Subsequence) | Seq. ID# |
|---|---|---|---|---|
| 15 | 254 | DVTYAFVIRR | 0.240 | 365. |
| 16 | 189 | FPPFDQQNCK | 0.200 | 366. |
| 17 | 235 | NATGTYNSKK | 0.200 | 367. |
| 18 | 92 | IAQLIDVDEK | 0.200 | 368. |
| 19 | 112 | KQEWSDYKLR | 0.180 | 369. |
| 20 | 199 | MKFGSWTYDK | 0.080 | 370. |
| 21 | 171 | VHWVPPAIYK | 0.080 | 371. |
| 22 | 66 | LFRGYNRWAR | 0.080 | 372. |
| 23 | 481 | RSEDADSSVK | 0.060 | 373. |
| 24 | 343 | IVITVFVLNV | 0.060 | 374. |
| 25 | 259 | FVIRRLPLFY | 0.060 | 375. |
| 26 | 498 | MVIDRIFLWL | 0.060 | 376. |
| 27 | 83 | VVIVRFGLSI | 0.060 | 377. |
| 28 | 413 | REVVVEEEDR | 0.054 | 378. |
| 29 | 502 | RIFLWLFIIV | 0.048 | 379. |
| 30 | 515 | GTIGLFLPPF | 0.045 | 380. |
| 31 | 169 | GTVHWVPPAI | 0.045 | 381. |
| 32 | 434 | GTLCSHGHLH | 0.045 | 382. |
| 33 | 204 | WTYDKAKIDL | 0.040 | 383. |
| 34 | 510 | IVCFLGTIGL | 0.040 | 384. |
| 35 | 308 | TVFLLLITEI | 0.040 | 385. |
| 36 | 234 | VNATGTYNSK | 0.040 | 386. |
| 37 | 338 | FVTLSIVITV | 0.040 | 387. |
| 38 | 22 | TPAGGEEAKR | 0.040 | 388. |
| 39 | 488 | SVKEDWKYVA | 0.040 | 389. |
| 40 | 334 | FTMIFVTLSI | 0.040 | 390. |
| 41 | 26 | GEEAKRPPPR | 0.036 | 391. |
| 42 | 323 | LVIPLIGEYL | 0.030 | 392. |
| 43 | 302 | SVLLSLTVFL | 0.030 | 393. |
| 44 | 89 | GLSIAQLIDV | 0.024 | 394. |
| 45 | 263 | RLPLFYTINL | 0.024 | 395. |
| 46 | 394 | RLKLSPSYHW | 0.024 | 396. |
| 47 | 351 | NVHHRSPSTH | 0.020 | 397. |
| 48 | 11 | FTKLSLWWLL | 0.020 | 398. |
| 49 | 365 | WVRGALLGCV | 0.020 | 399. |
| 50 | 407 | NVDAEEREVV | 0.020 | 400. |

TABLE XIII

HLA Peptide Scoring Results - 205P1B5 - A24, 9-mers

| Rank | Start Position | Subsequence Residue Listing | Score (Estimate of Half Time of Disassociation of a Molecule Containing This Subsequence) | Seq. ID# |
|---|---|---|---|---|
| 1 | 256 | TYAFVIRRL | 280.000 | 401. |
| 2 | 251 | IYPDVTYAF | 252.000 | 402. |
| 3 | 205 | TYDKAKIDL | 200.000 | 403. |
| 4 | 147 | LYNNADGEF | 165.000 | 404. |
| 5 | 330 | EYLLFTMIF | 150.000 | 405. |
| 6 | 87 | RFGLSIAQL | 40.000 | 406. |
| 7 | 333 | LFTMIFVTL | 33.600 | 407. |
| 8 | 258 | AFVIRRLPL | 30.000 | 408. |
| 9 | 512 | CFLGTIGLF | 15.000 | 409. |
| 10 | 112 | KQEWSDYKL | 13.200 | 410. |
| 11 | 305 | LSLTVFLLL | 10.080 | 411. |
| 12 | 244 | KYDCCAEIY | 10.000 | 412. |
| 13 | 309 | VFLLLITEI | 9.900 | 413. |
| 14 | 396 | KLSPSYHWL | 9.600 | 414. |
| 15 | 337 | IFVTLSIVI | 9.000 | 415. |
| 16 | 82 | DVVIVRFGL | 8.400 | 416. |
| 17 | 270 | INLIIPCLL | 8.400 | 417. |
| 18 | 324 | VIPLIGEYL | 8.400 | 418. |
| 19 | 269 | TINLIIPCL | 8.400 | 419. |
| 20 | 297 | ITLCISVLL | 8.400 | 420. |
| 21 | 299 | LCISVLLSL | 8.400 | 421. |

TABLE XIII-continued

HLA Peptide Scoring Results - 205P1B5 - A24, 9-mers

| Rank | Start Position | Subsequence Residue Listing | Score (Estimate of Half Time of Disassociation of a Molecule Containing This Subsequence) | Seq. ID# |
|---|---|---|---|---|
| 22 | 296 | KITLCISVL | 8.000 | 422. |
| 23 | 13 | KLSLWWLLL | 8.000 | 423. |
| 24 | 474 | HYIADHLRS | 7.500 | 424. |
| 25 | 69 | GYNRWARPV | 7.500 | 425. |
| 26 | 239 | TYNSKKYDC | 7.500 | 426. |
| 27 | 303 | VLLSLTVFL | 7.200 | 427. |
| 28 | 214 | EQMEQTVDL | 7.200 | 428. |
| 29 | 517 | IGLFLPPFL | 7.200 | 429. |
| 30 | 454 | LLQEGELLL | 7.200 | 430. |
| 31 | 266 | LFYTINLII | 7.000 | 431. |
| 32 | 499 | VIDRIFLWL | 6.720 | 432. |
| 33 | 452 | EALLQEGEL | 6.600 | 433. |
| 34 | 389 | LCHPLRLKL | 6.336 | 434. |
| 35 | 434 | GTLCSHGHL | 6.000 | 435. |
| 36 | 342 | SIVITVFVL | 6.000 | 436. |
| 37 | 1 | MGPSCPVFL | 6.000 | 437. |
| 38 | 447 | SGPKAEALL | 6.000 | 438. |
| 39 | 462 | LSPHMQKAL | 6.000 | 439. |
| 40 | 453 | ALLQEGELL | 6.000 | 440. |
| 41 | 497 | AMVIDRIFL | 6.000 | 441. |
| 42 | 264 | LPLFYTINL | 6.000 | 442. |
| 43 | 400 | SYHWLESNV | 6.000 | 443. |
| 44 | 117 | DYKLRWNPT | 6.000 | 444. |
| 45 | 325 | IPLIGEYLL | 6.000 | 445. |
| 46 | 224 | DYWESGEWA | 6.000 | 446. |
| 47 | 277 | LLISCLTVL | 6.000 | 447. |
| 48 | 103 | QMMTTNVWL | 6.000 | 448. |
| 49 | 472 | GVHYIADHL | 5.600 | 449. |
| 50 | 513 | FLGTIGLFL | 5.600 | 450. |

TABLE XIV

HLA Peptide Scoring Results - 205P1B5 - A24, 10-mers

| Rank | Start Position | Subsequence Residue Listing | Score (Estimate of Half Time of Disassociation of a Molecule Containing This Subsequence) | Seq. ID# |
|---|---|---|---|---|
| 1 | 494 | KYVAMVIDRI | 210.000 | 451. |
| 2 | 224 | DYWESGEWAI | 60.000 | 452. |
| 3 | 512 | CFLGTIGLFL | 42.000 | 453. |
| 4 | 7 | VFLSFTKLSL | 30.000 | 454. |
| 5 | 10 | SFTKLSLWWL | 20.000 | 455. |
| 6 | 87 | RFGLSIAQLI | 16.800 | 456. |
| 7 | 258 | AFVIRRLPLF | 15.000 | 457. |
| 8 | 498 | MVIDRIFLWL | 12.096 | 458. |
| 9 | 263 | RLPLFYTINL | 12.000 | 459. |
| 10 | 296 | KITLCISVLL | 11.200 | 460. |
| 11 | 309 | VFLLLITEII | 10.500 | 461. |
| 12 | 57 | ETEDRLFKHL | 10.368 | 462. |
| 13 | 323 | LVIPLIGEYL | 10.080 | 463. |
| 14 | 251 | IYPDVTYAFV | 9.000 | 464. |
| 15 | 369 | ALLGCVPRWL | 8.400 | 465. |
| 16 | 361 | TMPHWVRGAL | 8.400 | 466. |
| 17 | 268 | YTINLIIPCL | 8.400 | 467. |
| 18 | 471 | EGVHYIADHL | 8.400 | 468. |
| 19 | 269 | TINLIIPCLL | 8.400 | 469. |
| 20 | 505 | LWLFIIVCFL | 8.400 | 470. |
| 21 | 5 | CPVFLSFTKL | 7.920 | 471. |
| 22 | 239 | TYNSKKYDCC | 7.500 | 472. |
| 23 | 147 | LYNNADGEFA | 7.500 | 473. |
| 24 | 330 | EYLLFTMIFV | 7.500 | 474. |
| 25 | 273 | IIPCLLISCL | 7.200 | 475. |
| 26 | 302 | SVLLSLTVFL | 7.200 | 476. |
| 27 | 280 | SCLTVLFYL | 7.200 | 477. |
| 28 | 304 | LLSLTVFLLL | 6.720 | 478. |

TABLE XIV-continued

HLA Peptide Scoring Results - 205P1B5 - A24, 10-mers

| Rank | Start Position | Subsequence Residue Listing | Score (Estimate of Half Time of Disassociation of a Molecule Containing This Subsequence) | Seq. ID# |
|---|---|---|---|---|
| 29 | 332 | LLFTMIFVTL | 6.720 | 479. |
| 30 | 267 | FYTINLIIPC | 6.000 | 480. |
| 31 | 324 | VIPLIGEYLL | 6.000 | 481. |
| 32 | 453 | ALLQEGELLL | 6.000 | 482. |
| 33 | 452 | EALLQEGELL | 6.000 | 483. |
| 34 | 138 | EMIWIPDIVL | 6.000 | 484. |
| 35 | 102 | NQMMTTNVWL | 6.000 | 485. |
| 36 | 341 | LSIVITVFVL | 6.000 | 486. |
| 37 | 496 | VAMVIDRIFL | 6.000 | 487. |
| 38 | 276 | CLLISCLTVL | 6.000 | 488. |
| 39 | 314 | ITEIIPSTSL | 6.000 | 489. |
| 40 | 303 | VLLSLTVFLL | 6.000 | 490. |
| 41 | 255 | VTYAFVIRRL | 5.600 | 491. |
| 42 | 180 | KSSCSIDVTF | 5.600 | 492. |
| 43 | 298 | TLCISVLLSL | 5.600 | 493. |
| 44 | 388 | ELCHPLRLKL | 5.280 | 494. |
| 45 | 380 | MNRPPPPVEL | 5.280 | 495. |
| 46 | 178 | IYKSSCSIDV | 5.000 | 496. |
| 47 | 446 | ASGPKAEALL | 4.800 | 497. |
| 48 | 318 | IPSTSLVIPL | 4.800 | 498. |
| 49 | 11 | FTKLSLWWLL | 4.800 | 499. |
| 50 | 516 | TIGLFLPPFL | 4.800 | 500. |

TABLE XV

HLA Peptide Scoring Results - 205P1B5 - B7, 9-mers

| Rank | Start Position | Subsequence Residue Listing | Score (Estimate of Half Time of Disassociation of a Molecule Containing This Subsequence) | Seq. ID# |
|---|---|---|---|---|
| 1 | 362 | MPHWVRGAL | 120.000 | 501. |
| 2 | 33 | PPRAPGDPL | 120.000 | 502. |
| 3 | 325 | IPLIGEYLL | 80.000 | 503. |
| 4 | 274 | IPCLLISCL | 80.000 | 504. |
| 5 | 264 | LPLFYTINL | 80.000 | 505. |
| 6 | 82 | DVVIVRFGL | 30.000 | 506. |
| 7 | 472 | GVHYIADHL | 20.000 | 507. |
| 8 | 428 | HVAPSVGTL | 20.000 | 508. |
| 9 | 497 | AMVIDRIFL | 18.000 | 509. |
| 10 | 453 | ALLQEGELL | 12.000 | 510. |
| 11 | 103 | QMMTTNVWL | 12.000 | 511. |
| 12 | 446 | ASGPKAEAL | 12.000 | 512. |
| 13 | 214 | EQMEQTVDL | 12.000 | 513. |
| 14 | 452 | EALLQEGEL | 12.000 | 514. |
| 15 | 371 | LGCVPRWLL | 9.000 | 515. |
| 16 | 385 | PPVELCHPL | 8.000 | 516. |
| 17 | 289 | LPSDCGEKI | 8.000 | 517. |
| 18 | 521 | LPPFLAGMI | 8.000 | 518. |
| 19 | 77 | VPNTSDVVI | 8.000 | 519. |
| 20 | 139 | MIWIPDIVL | 6.000 | 520. |
| 21 | 389 | LCHPLRLKL | 6.000 | 521. |
| 22 | 132 | SLRVPSEMI | 6.000 | 522. |
| 23 | 365 | WVRGALLGC | 5.000 | 523. |
| 24 | 85 | IVRFGLSIA | 5.000 | 524. |
| 25 | 396 | KLSPSYHWL | 4.000 | 525. |
| 26 | 297 | ITLCISVLL | 4.000 | 526. |
| 27 | 511 | VCFLGTIGL | 4.000 | 527. |
| 28 | 13 | KLSLWWLLL | 4.000 | 528. |
| 29 | 281 | CLTVLVFYL | 4.000 | 529. |
| 30 | 277 | LLISCLTVL | 4.000 | 530. |
| 31 | 157 | VTHMTKAHL | 4.000 | 531. |
| 32 | 324 | VIPLIGEYL | 4.000 | 532. |
| 33 | 370 | LLGCVPRWL | 4.000 | 533. |
| 34 | 11 | FTKLSLWWL | 4.000 | 534. |
| 35 | 296 | KITLCISVL | 4.000 | 535. |

TABLE XV-continued

HLA Peptide Scoring Results - 205P1B5 - B7, 9-mers

| Rank | Start Position | Subsequence Residue Listing | Score (Estimate of Half Time of Disassociation of a Molecule Containing This Subsequence) | Seq. ID# |
|---|---|---|---|---|
| 36 | 1 | MGPSCPVFL | 4.000 | 536. |
| 37 | 299 | LCISVLLSL | 4.000 | 537. |
| 38 | 517 | IGLFLPPFL | 4.000 | 538. |
| 39 | 506 | WLFIIVCFL | 4.000 | 539. |
| 40 | 270 | INLIIPCLL | 4.000 | 540. |
| 41 | 8 | FLSFTKLSL | 4.000 | 541. |
| 42 | 304 | LLSLTVFLL | 4.000 | 542. |
| 43 | 434 | GTLCSHGHL | 4.000 | 543. |
| 44 | 342 | SIVITVFVL | 4.000 | 544. |
| 45 | 305 | LSLTVFLLL | 4.000 | 545. |
| 46 | 447 | SGPKAEALL | 4.000 | 546. |
| 47 | 75 | RPVPNTSDV | 4.000 | 547. |
| 48 | 41 | LSSPSPTAL | 4.000 | 548. |
| 49 | 454 | LLQEGELLL | 4.000 | 549. |
| 50 | 462 | LSPHMQKAL | 4.000 | 550. |

TABLE XVI

HLA Peptide Scoring Results - 205P1B5 - B7, 10-mers

| Rank | Start Position | Subsequence Residue Listing | Score (Estimate of Half Time of Disassociation of a Molecule Containing This Subsequence) | Seq. ID# |
|---|---|---|---|---|
| 1 | 362 | MPHWVRGALL | 80.000 | 551. |
| 2 | 318 | IPSTSLVIPL | 80.000 | 552. |
| 3 | 5 | CPVFLSFTKL | 80.000 | 553. |
| 4 | 380 | MNRPPPPVEL | 60.000 | 554. |
| 5 | 156 | AVTHMTKAHL | 60.000 | 555. |
| 6 | 496 | VAMVIDRIFL | 54.000 | 556. |
| 7 | 190 | FPFDQQNCKM | 20.000 | 557. |
| 8 | 498 | MVIDRIFLWL | 20.000 | 558. |
| 9 | 302 | SVLLSLTVFL | 20.000 | 559. |
| 10 | 510 | IVCFLGTIGL | 20.000 | 560. |
| 11 | 323 | LVIPLIGEYL | 20.000 | 561. |
| 12 | 257 | YAFVIRRLPL | 18.000 | 562. |
| 13 | 453 | ALLQEGELLL | 12.000 | 563. |
| 14 | 445 | GASGPKAEAL | 12.000 | 564. |
| 15 | 32 | PPPRAPGDPL | 12.000 | 565. |
| 16 | 369 | ALLGCVPRWL | 12.000 | 566. |
| 17 | 452 | EALLQEGELL | 12.000 | 567. |
| 18 | 446 | ASGPKAEALL | 12.000 | 568. |
| 19 | 102 | NQMMTTNVWL | 12.000 | 569. |
| 20 | 365 | WVRGALLGCV | 10.000 | 570. |
| 21 | 370 | LLGCVPRWLL | 9.000 | 571. |
| 22 | 384 | PPPVELCHPL | 8.000 | 572. |
| 23 | 264 | LPLFYTINLI | 8.000 | 573. |
| 24 | 138 | EMIWIPDIVL | 6.000 | 574. |
| 25 | 388 | ELCHPLRLKL | 6.000 | 575. |
| 26 | 361 | TMPHWVRGAL | 6.000 | 576. |
| 27 | 280 | SCLTVLVFYL | 4.000 | 577. |
| 28 | 273 | IIPCLLISCL | 4.000 | 578. |
| 29 | 324 | VIPLIGEYLL | 4.000 | 579. |
| 30 | 276 | CLLISCLTVL | 4.000 | 580. |
| 31 | 77 | VPNTSDVVIV | 4.000 | 581. |
| 32 | 471 | EGVHYIADHL | 4.000 | 582. |
| 33 | 298 | TLCISVLLSL | 4.000 | 583. |
| 34 | 461 | LLSPHMQKAL | 4.000 | 584. |
| 35 | 204 | WTYDKAKIDL | 4.000 | 585. |
| 36 | 516 | TIGLFLPPFL | 4.000 | 586. |
| 37 | 296 | KITLCISVL | 4.000 | 587. |
| 38 | 304 | LLSLTVFLLL | 4.000 | 588. |
| 39 | 332 | LLFTMIFVTL | 4.000 | 589. |
| 40 | 303 | VLLSLTVFLL | 4.000 | 590. |
| 41 | 269 | TINLIIPCLL | 4.000 | 591. |
| 42 | 268 | YTINLIIPCL | 4.000 | 592. |

TABLE XVI-continued

HLA Peptide Scoring Results - 205P1B5 - B7, 10-mers

| Rank | Start Position | Subsequence Residue Listing | Score (Estimate of Half Time of Disassociation of a Molecule Containing This Subsequence) | Seq. ID# |
|---|---|---|---|---|
| 43 | 263 | RLPLFYTINL | 4.000 | 593. |
| 44 | 433 | VGTLCSHGHL | 4.000 | 594. |
| 45 | 75 | RPVPNTSDVV | 4.000 | 595. |
| 46 | 11 | FTKLSLWWLL | 4.000 | 596. |
| 47 | 255 | VTYAFVIRRL | 4.000 | 597. |
| 48 | 53 | GSHTETEDRL | 4.000 | 598. |
| 49 | 341 | LSIVITVFVL | 4.000 | 599. |
| 50 | 39 | DPLSSPSPTA | 3.000 | 600. |

TABLE XVII

HLA Peptide Scoring Results - 205P1B5 - B35, 9-mers

| Rank | Start Position | Subsequence Residue Listing | Score (Estimate of Half Time of Disassociation of a Molecule Containing This Subsequence) | Seq. ID# |
|---|---|---|---|---|
| 1 | 208 | KAKIDLEQM | 54.000 | 601. |
| 2 | 362 | MPHWVRGAL | 20.000 | 602. |
| 3 | 325 | IPLIGEYLL | 20.000 | 603. |
| 4 | 274 | IPCLLISCL | 20.000 | 604. |
| 5 | 264 | LPLFYTINL | 20.000 | 605. |
| 6 | 289 | LPSDCGEKI | 16.000 | 606. |
| 7 | 487 | SSVKEDWKY | 15.000 | 607. |
| 8 | 198 | KMKFGSWTY | 12.000 | 608. |
| 9 | 131 | TSLRVPSEM | 10.000 | 609. |
| 10 | 110 | WLKQEWSDY | 9.000 | 610. |
| 11 | 75 | RPVPNTSDV | 8.000 | 611. |
| 12 | 77 | VPNTSDVVI | 8.000 | 612. |
| 13 | 521 | LPPFLAGMI | 8.000 | 613. |
| 14 | 33 | PPRAPGDPL | 6.000 | 614. |
| 15 | 260 | VIRRLPLFY | 6.000 | 615. |
| 16 | 119 | KLRWNPTDF | 6.000 | 616. |
| 17 | 305 | LSLTVFLLL | 5.000 | 617. |
| 18 | 181 | SSCSIDVTF | 5.000 | 618. |
| 19 | 41 | LSSPSPTAL | 5.000 | 619. |
| 20 | 279 | ISCLTVLVF | 5.000 | 620. |
| 21 | 462 | LSPHMQKAL | 5.000 | 621. |
| 22 | 446 | ASGPKAEAL | 5.000 | 622. |
| 23 | 468 | KALEGVHYI | 4.800 | 623. |
| 24 | 385 | PPVELCHPL | 4.000 | 624. |
| 25 | 123 | NPTDFGNIT | 4.000 | 625. |
| 26 | 382 | RPPPPVELC | 4.000 | 626. |
| 27 | 452 | EALLQEGEL | 3.000 | 627. |
| 28 | 11 | FTKLSLWWL | 3.000 | 628. |
| 29 | 217 | EQTVDLKDY | 3.000 | 629. |
| 30 | 496 | VAMVIDRIF | 3.000 | 630. |
| 31 | 9 | LSFTKLSLW | 2.500 | 631. |
| 32 | 396 | KLSPSYHWL | 2.000 | 632. |
| 33 | 430 | APSVGTLCS | 2.000 | 633. |
| 34 | 372 | GCVPRWLLM | 2.000 | 634. |
| 35 | 520 | FLPPFLAGM | 2.000 | 635. |
| 36 | 280 | SCLTVLVFY | 2.000 | 636. |
| 37 | 323 | LVIPLIGEY | 2.000 | 637. |
| 38 | 398 | SPSYHWLES | 2.000 | 638. |
| 39 | 214 | EQMEQTVDL | 2.000 | 639. |
| 40 | 237 | TGTYNSKKY | 2.000 | 640. |
| 41 | 296 | KITLCISVL | 2.000 | 641. |
| 42 | 2 | GPSCPVFLS | 2.000 | 642. |
| 43 | 174 | VPPAIYKSS | 2.000 | 643. |
| 44 | 454 | LLQEGELLL | 2.000 | 644. |
| 45 | 13 | KLSLWWLLL | 2.000 | 645. |
| 46 | 39 | DPLSSPSPT | 2.000 | 646. |
| 47 | 232 | AIVNATGTY | 2.000 | 647. |
| 48 | 488 | SVKEDWKYV | 1.800 | 648. |
| 49 | 415 | VVVEEEDRW | 1.500 | 649. |
| 50 | 80 | TSDVVIVRF | 1.500 | 650. |

TABLE XVIII

HLA Peptide Scoring Results - 205P1B5 - B35, 10-mers

| Rank | Start Position | Subsequence Residue Listing | Score (Estimate of Half Time of Disassociation of a Molecule Containing This Subsequence) | Seq. ID# |
|---|---|---|---|---|
| 1 | 190 | FPFDQQNCKM | 80.000 | 651. |
| 2 | 325 | IPLIGEYLLF | 30.000 | 652. |
| 3 | 362 | MPHWVRGALL | 20.000 | 653. |
| 4 | 318 | IPSTSLVIPL | 20.000 | 654. |
| 5 | 2 | GPSCPVFLSF | 20.000 | 655. |
| 6 | 5 | CPVFLSFTKL | 20.000 | 656. |
| 7 | 486 | DSSVKEDWKY | 15.000 | 657. |
| 8 | 180 | KSSCSIDVTF | 10.000 | 658. |
| 9 | 356 | SPSTHTMPHW | 10.000 | 659. |
| 10 | 183 | CSIDVTFFPF | 10.000 | 660. |
| 11 | 279 | ISCLTVLVFY | 10.000 | 661. |
| 12 | 466 | MQKALEGVHY | 9.000 | 662. |
| 13 | 75 | RPVPNTSDVV | 8.000 | 663. |
| 14 | 264 | LPLFYTINLI | 8.000 | 664. |
| 15 | 181 | SSCSIDVTFF | 7.500 | 665. |
| 16 | 77 | VPNTSDVVIV | 6.000 | 666. |
| 17 | 231 | WAIVNATGTY | 6.000 | 667. |
| 18 | 341 | LSIVITVFVL | 5.000 | 668. |
| 19 | 301 | ISVLLSLTVF | 5.000 | 669. |
| 20 | 53 | GSHTETEDRL | 5.000 | 670. |
| 21 | 446 | ASGPKAEALL | 5.000 | 671. |
| 22 | 452 | EALLQEGELL | 4.500 | 672. |
| 23 | 496 | VAMVIDRIFL | 4.500 | 673. |
| 24 | 61 | RLFKHLFRGY | 4.000 | 674. |
| 25 | 327 | LIGEYLLFTM | 4.000 | 675. |
| 26 | 36 | APGDPLSSPS | 4.000 | 676. |
| 27 | 123 | NPTDFGNITS | 4.000 | 677. |
| 28 | 289 | LPSDCGEKIT | 4.000 | 678. |
| 29 | 445 | GASGPKAEAL | 3.000 | 679. |
| 30 | 394 | RLKLSPSYHW | 3.000 | 680. |
| 31 | 380 | MNRPPPPVEL | 3.000 | 681. |
| 32 | 202 | GSWTYDKAKI | 3.000 | 682. |
| 33 | 257 | YAFVIRRLPL | 3.000 | 683. |
| 34 | 139 | MIWIPDIVLY | 3.000 | 684. |
| 35 | 11 | FTKLSLWWLL | 3.000 | 685. |
| 36 | 9 | LSFTKLSLWW | 2.500 | 686. |
| 37 | 252 | YPDVTYAFVI | 2.400 | 687. |
| 38 | 391 | HPLRLKLSPS | 2.000 | 688. |
| 39 | 263 | RLPLFYTINL | 2.000 | 689. |
| 40 | 498 | MVIDRIFLWL | 2.000 | 690. |
| 41 | 79 | NTSDVVIVRF | 2.000 | 691. |
| 42 | 174 | VPPAIYKSSC | 2.000 | 692. |
| 43 | 398 | SPSYHWLESN | 2.000 | 693. |
| 44 | 204 | WTYDKAKIDL | 2.000 | 694. |
| 45 | 236 | ATGTYNSKKY | 2.000 | 695. |
| 46 | 130 | ITSLRVPSEM | 2.000 | 696. |
| 47 | 371 | LGCVPRWLLM | 2.000 | 697. |
| 48 | 32 | PPPRAPGDPL | 2.000 | 698. |
| 49 | 45 | SPTALPQGGS | 2.000 | 699. |
| 50 | 259 | FVIRRLPLFY | 2.000 | 700. |

TABLE XIX

Motifs and Post-translational Modifications of 205P1B5

N-glycosylation site
Number of matches: 3

1. 79-82 NTSD (SEQ ID NO.: 720)
2. 129-132 NITS (SEQ ID NO.: 721)
3. 235-238 NATG (SEQ ID NO.: 722)

Protein kinase C phosphorylation site
Number of matches: 3

1. 132-134 SLR
2. 242-244 SKK
3. 488-490 SVK

Casein kinase II phosphorylation site
Number of matches: 4

1. 54-57 SHTE (SEQ ID NO.: 723)
2. 56-59 TETE (SEQ ID NO.: 724)
3. 406-409 SNVD (SEQ ID NO.: 725)
4. 488-491 SVKE (SEQ ID NO.: 726)

Tyrosine kinase phosphorylation site 468-475 KALEGVHY (SEQ ID NO.: 727)

N-myristoylation site
Number of matches: 7

1. 25-30 GGEEAK (SEQ ID NO.: 728)
2. 52-57 GGSHTE (SEQ ID NO.: 729)
3. 89-94 GLSIAQ (SEQ ID NO.: 730)
4. 128-133 GNITSL (SEQ ID NO.: 731)
5. 238-243 GTYNSK (SEQ ID NO.: 732)
6. 368-373 GALLGC (SEQ ID NO.: 733)
7. 434-439 GTLCSH (SEQ ID NO.: 734)

Neurotransmitter-gated ion-channels signature 183-197 CSIDVTFFPFDQQNC (SEQ ID NO.: 735)

BLOCKS

Neurotransmitter-gated ion-channel between aa 168-206
Neurotransmitter-gated ion-channel between aa 252-296

PRINTS

Nicotinic acetylcholine receptor signature between aa 163-181-
Nicotinic acetylcholine receptor signature between aa 93-109

Pfam

Neurotransmitter-gated ion-channel ligand binding domain between aa 59-265
Neurotransmitter-gated ion-channel transmembrane region between aa 272-520

TABLE XX

Frequently Occurring Motifs

| Name | avrg. % identity | Description | Potential Function |
|---|---|---|---|
| zf-C2H2 | 34% | Zinc finger, C2H2 type | Nucleic acid-binding protein functions as transcription factor, nuclear location probable |
| cytochrome_b_N | 68% | Cytochrome b(N-terminal)/b6/petB | membrane bound oxidase, generate superoxide |
| ig | 19% | Immunoglobulin domain | domains are one hundred amino acids long and include a conserved intradomain disulfide bond. |
| WD40 | 18% | WD domain, G-beta repeat | tandem repeats of about 40 residues, each containing a Trp-Asp motif. Function in signal transduction and protein interaction |
| PDZ | 23% | PDZ domain | may function in targeting signaling molecules to sub-membranous sites |
| LRR | 28% | Leucine Rich Repeat | short sequence motifs involved in protein-protein interactions |
| pkinase | 23% | Protein kinase domain | conserved catalytic core common to both serine/threonine and tyrosine protein kinases containing an ATP binding site and a catalytic site |
| PH | 16% | PH domain | pleckstrin homology involved in intracellular signaling or as constituents of the cytoskeleton |
| EGF | 34% | EGF-like domain | 30-40 amino-acid long found in the extracellular domain of membrane-bound proteins or in secreted proteins |
| rvt | 49% | Reverse transcriptase (RNA-dependent DNA polymerase) | |
| ank | 25% | Ank repeat | Cytoplasmic protein, associates integral membrane proteins to the cytoskeleton |
| oxidored_q1 | 32% | NADH-Ubiquinone/plastoquinone (complex I), various chains | membrane associated. Involved in proton translocation across the membrane |
| efhand | 24% | EF hand | calcium-binding domain, consists of a12 residue loop flanked on both sides by a 12 residue alpha-helical domain |
| rvp | 79% | Retroviral aspartyl protease | Aspartyl or acid proteases, centered on a catalytic aspartyl residue |

TABLE XX-continued

Frequently Occurring Motifs

| Name | avrg. % identity | Description | Potential Function |
|---|---|---|---|
| Collagen | 42% | Collagen triple helix repeat (20 copies) | extracellular structural proteins involved in formation of connective tissue. The sequence consists of the G-X-Y and the polypeptide chains forms a triple helix. |
| fn3 | 20% | Fibronectin type III domain | Located in the extracellular ligand-binding region of receptors and is about 200 amino acid residues long with two pairs of cysteines involved in disulfide bonds |
| 7tm_1 | 19% | 7 transmembrane receptor (rhodopsin family) | seven hydrophobic transmembrane regions, with the N-terminus located extracellularly while the C-terminus is cytoplasmic. Signal through G proteins |

TABLE XXI

Properties of 205P1B5

| Feature | Bioinformatic Program | World wide web URL | Outcome |
|---|---|---|---|
| ORF (includes stop codon) | ORF finder | ncbi.nlm.nih.gov/ | See FIG. 2; 555-2144 |
| # of amino acids | | | 529 amino acids |
| Transmembrane region | TM Pred | ch.embnet.org/ | 5 transmembrane domains |
| | HMMTop | enzim.hu/hmmtop/ | 4 transmembrane domains |
| | Sosui | genome.ad.jp/SOSui/ | 5 transmembrane domains |
| | TMHMM | cbs.dtu.dk/services/TMHMM | 5 transmembrane domains |
| Signal Peptide | Signal P | cbs.dtu.dk/services/SignalP/ | Signal sequence aa 1-26 |
| pI | pI/MW tool | expasy.ch/tools/ | pI 5.69 |
| Molecular weight | pI/MW tool | expasy.ch/tools/ | 59.76 kDa |
| Localization | PSORT | psort.nibb.ac.jp/ | plasma membrane 0.600 mitochondrial membrane 0.400 |
| | PSORT II | psort.nibb.ac.jp/ | Plasma membrane 22.2% endoplasmic reticulum 33.3% |
| Motifs | Pfam | sanger.ac.uk/Pfam/ | Neurotransmitter-gated ion-channel |
| | Prints | biochem.ucl.ac.uk/ | Nicotinic acetylcholine receptor signature |
| | Blocks | blocks.fhcrc.org/ | Neurotransmitter-gated ion-channel |
| | Prosite | genome.ad.jp/ | Neurotransmitter-gated ion-channels |

The invention claimed is:

1. An isolated polynucleotide that encodes a protein comprising SEQ ID NO: 702.

2. The polynucleotide of claim 1, wherein the polynucleotide comprises SEQ ID NO:701 from residue 555 to 2144.

3. A pharmaceutical composition comprising the polynucleotide of claim 1 and a pharmaceutically acceptable carrier.

4. The polynucleotide of claim 1, wherein the polynucleotide further comprises an expression vector.

5. The polynucleotide of claim 4, wherein the expression vector is a viral vector.

6. The polynucleotide of claim 5, wherein the viral expression vector is selected from the group consisting of vaccinia virus, fowlpox virus, canarypox virus, adenovirus, influenza virus, poliovirus, adeno-associated virus, lentivirus, and sindbis virus.

7. An isolated host cell that contains an expression vector of claim 4.

8. A process for producing a 205P1B5 protein comprising culturing a host cell of claim 7 under conditions sufficient for the production of the protein, and recovering the protein comprising SEQ ID NO: 702 from the culture.

* * * * *